US008742090B2

(12) United States Patent
Rabbani et al.

(10) Patent No.: US 8,742,090 B2
(45) Date of Patent: *Jun. 3, 2014

(54) PROPERTY EFFECTING AND/OR PROPERTY EXHIBITING COMPOSITIONS FOR THERAPEUTIC AND DIAGNOSTIC USES

(75) Inventors: Elazar Rabbani, New York, NY (US); Jannis G. Stavrianopoulos, Bay Shore, NY (US); James J. Donegan, Long Beach, NY (US); Dakai Liu, Bethpage, NY (US); Norman E. Kelker, New York, NY (US); Dean L. Engelhardt, New York, NY (US)

(73) Assignee: Enzo Biochem, Inc., New York, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 08/978,632

(22) Filed: Nov. 25, 1997

(65) Prior Publication Data

US 2001/0007767 A1    Jul. 12, 2001

Related U.S. Application Data

(63) Continuation of application No. 08/574,443, filed on Dec. 15, 1995, now abandoned.

(51) Int. Cl.
*C07H 21/04* (2006.01)

(52) U.S. Cl.
USPC ........ 536/24.5; 435/320.1; 435/325; 435/375

(58) Field of Classification Search
USPC ........... 435/91.1, 91.4, 325, 320.1, 6; 514/44; 536/23.1, 24.3, 24.5
See application file for complete search history.

(56) References Cited

U.S. PATENT DOCUMENTS

| | | | |
|---|---|---|---|
| 4,687,732 A | 8/1987 | Ward | |
| 4,707,440 A | 11/1987 | Stavrianopoulos | |
| 4,711,955 A | 12/1987 | Ward | |
| 4,716,112 A | 12/1987 | Panayotatos | |
| 4,795,706 A * | 1/1989 | Hsiung et al. | 435/172.3 |
| 4,843,122 A | 6/1989 | Stavrianopoulos | |
| 4,847,240 A | 7/1989 | Ryser | |
| 5,108,921 A * | 4/1992 | Low et al. | 435/375 |
| 5,128,256 A | 7/1992 | Huse | |
| 5,166,320 A | 11/1992 | Wu | |
| 5,241,060 A | 8/1993 | Engelhardt | |
| 5,260,433 A | 11/1993 | Engelhardt | |
| 5,288,609 A | 2/1994 | Engelhardt | |
| 5,413,999 A | 5/1995 | Vacca | |
| 5,438,040 A | 8/1995 | Ekwuribe | |
| 5,480,792 A | 1/1996 | Buechler | |
| 5,547,932 A | 8/1996 | Curiel | |
| 5,561,043 A * | 10/1996 | Cantor et al. | 435/6.16 |
| 5,574,142 A * | 11/1996 | Meyer, Jr. et al. | 536/23.1 |
| 5,583,020 A | 12/1996 | Sullivan | |
| 5,587,308 A * | 12/1996 | Carter et al. | 435/240.2 |
| 5,591,601 A | 1/1997 | Wagner | |
| 5,604,118 A | 2/1997 | Giri | |
| 5,610,067 A | 3/1997 | Saito | |
| 5,633,152 A | 5/1997 | McKnight | |
| 5,646,032 A | 7/1997 | ter Meulen | |
| 5,648,243 A | 7/1997 | Hurwitz | |
| 5,683,869 A * | 11/1997 | Ramsay Shaw et al. | 435/6 |
| 5,693,463 A | 12/1997 | Edwards | |
| 5,712,384 A | 1/1998 | Symonds | |
| 5,734,039 A | 3/1998 | Calabretta | |
| 5,736,387 A | 4/1998 | Paul | |
| 5,766,902 A * | 6/1998 | Craig et al. | 435/461 |
| 5,814,500 A | 9/1998 | Dietz | |
| 5,821,046 A | 10/1998 | Karn | |
| 5,827,935 A | 10/1998 | Rossi | |
| 5,854,038 A | 12/1998 | Sullenger | |
| 6,503,755 B1 * | 1/2003 | Keating et al. | 435/455 |
| 6,538,107 B1 | 3/2003 | Hinuma | |

FOREIGN PATENT DOCUMENTS

| | | | | |
|---|---|---|---|---|
| EP | 0 273 085 | * | 6/1988 | |
| EP | 0285057 | | 10/1988 | |
| EP | 0547920 | | 6/1993 | |
| WO | WO9420079 | | 9/1994 | |
| WO | WO 9420079 | | 9/1994 | |
| WO | WO 95/06129 | * | 3/1995 | 514/44 |
| WO | WO9508635 | | 3/1995 | |
| WO | WO9519428 | | 7/1995 | |
| WO | WO 9519428 | | 7/1995 | |
| WO | WO9526200 | | 10/1995 | |
| WO | WO 9528494 | | 10/1995 | |
| WO | WO9528494 | | 10/1995 | |
| WO | WO9531566 | | 11/1995 | |
| WO | WO 9531566 | | 11/1995 | |
| WO | WO9532225 | | 11/1995 | |
| WO | WO 9532225 | | 11/1995 | |

OTHER PUBLICATIONS

Branch, TIBS (23), pp. 45-50, Feb. 1998.*
Flanagan et al., Nature Biotech. (17), pp. 48-52, Jan. 1999.*
Vos et al.. Mol. Cell. Biol. 1989, 9(7)2897-2905.*
Pardridge et al., Vector-mediated delivery of a polyamide ("peptide") nucleic acid analogue through the blood-brain barrier in vivo, Jun. 1995, Proc. Natl. Acad. Sci., Pharmacology, vol. 92, pp. 5592-5596.*

(Continued)

*Primary Examiner* — Kimberly Chong
(74) *Attorney, Agent, or Firm* — Anna D. DiGabriele Petti, Esq.

(57) ABSTRACT

The present invention provides an array of compositions useful for effecting and/or exhibiting changes in biological functioning and processing within cells and in biological systems containing such cells. In effect, these compositions combine chemical modifications and/or ligand additions with biological functions. The chemical modifications and/or ligand additions provide additional characteristics to the compositions without interfering substantially with their biological function. Such additional characteristics include nuclease resistance, targeting specific cells or specific cell receptors localizing to specific sites within cells and augmenting interactions between the compositions and target cells of interest as well as decreasing such interactions when desired. Also provided by the present invention are processes and kits.

18 Claims, 51 Drawing Sheets

(56) References Cited

OTHER PUBLICATIONS

Putney et al. (1981) Proc. Natl. Acad. Sci. 78:7350-7354.*
Bos et al. (1992) Hybridoma 11:41-51.*
Hirsch et al. (1993) Transplantation Proceedings 25:138-139.*
Olsen et al. (1990) Proc. Natl. Acad. Sci. 87:1451-1455.*
Smith-Ravin et al. (1989) Int. J. Radiat. Biol. 56:951-961.*
Perales et al. Eur. J. Biochem. vol. 226, 1994: 255-266.*
Chang, H-K, et al, "Block of HIV-1 infection by combination of antisense tat RNA and TAR decoys: a strategy for control of HIV-1," *Gene Therapy*, vol. 1(3):208-216 (1994).
Cohli, H., et al, "Inhibition of HIV-1 multiplication in a human CD4 lymphocytic cell line expressing antisense and sense RNA molecules containing HIV-1 packaging signal and rev response element(s)," *Antisense Research and Development*, vol. 4:19-26 (1994).
Michael, W.M., et al, "Signal sequences that target nuclear import and nuclear export of pre-mRNA-binding proteins," *Cold Spring Harbor Symposia on Quantitative Biology*, vol. 60:663-668 (1995).
McBride, K.E., et al, "Controlled expression of plastid transgenes in plants based on a nuclear DNA-encoded and plastid-targeted T7 RNA polymerase," *Proc. Natl. Acad. Sci. USA*, vol. 91:7301-7305 (1994).
Afione, S.A., et al, "Gene therapy vectors as drug delivery system," *Clin. Pharmacokinet*, vol. 28(3):181-189 (1995).
Wagner, E., et al, "Coupling of adenovirus to transferring-polylysine/DNA complexes greatly enhances receptor-mediated gene delivery and expression of transfected genes," *Proc. Natl. Acad. Sci. USA*, vol. 89:6099-6103 (1992).
Chatterjee, S., et al,"Dual-target inhibition of HIV-1 in vitro by means of an adeno-associated virus antisense vector," *Science*, vol. 258:1485-1488 (1992).
Teem, J.L., et al, "Expression of a beta-galactosidase gene containing the ribosomal protein 51 intron is sensitive to the rna2 mutation of yeast," *Proc. Natl. Acad. Sci.*, vol. 80(14): 4403-4407 (1983).
U.S. Appl. No. 08/978,639 Non-final rejection Jan. 11, 2000.
U.S. Appl. No. 08/978,639 Non-final rejection Jan. 4, 1999.
U.S. Appl. No. 08/978,638 Final Rejection Oct. 4, 2007.
U.S. Appl. No. 08/978,638 Non-Final Rejection Jan. 3, 2007.
U.S. Appl. No. 08/978,638 Non-Final Rejection May 4, 2005.
U.S. Appl. No. 08/978,638 Final Rejection Dec. 19, 2003.
U.S. Appl. No. 08/978,638 Non-Final Rejection Mar. 25, 2003.
U.S. Appl. No. 08/978,638 Final Rejection Jan. 17, 2001.
U.S. Appl. No. 08/978,638 Final Rejection Jun. 20, 2000.
U.S. Appl. No. 08/978,638 Final Rejection Nov. 23, 1999.
U.S. Appl. No. 08/978,638 Non-Final Rejection.
U.S. Appl. No. 08/978,637 Non-Final Rejection Apr. 4, 2007.
U.S. Appl. No. 08/978,637 Final Rejection Apr. 21, 2006.
U.S. Appl. No. 08/978,637 Final Rejection Jul. 29, 2005.
U.S. Appl. No. 08/978,637 Final Rejection Feb. 11, 2004.
U.S. Appl. No. 08/978,637 Non-Final Rejection May 1, 2003.
U.S. Appl. No. 08/978,637 Final Rejection Dec. 19, 2000.
U.S. Appl. No. 08/978,637 Final Rejection Jun. 5, 2000.
U.S. Appl. No. 08/978,637 Final Rejection Nov. 9, 1999.
U.S. Appl. No. 08/978,637 Non-Final Rejection Feb. 17, 1999.
U.S. Appl. No. 08/978,635 Non-Final Rejection Apr. 1, 2003.
U.S. Appl. No. 08/978,635 Final Rejection Jan. 17, 2001.
U.S. Appl. No. 08/978,635 Final Rejection Jun. 21, 2000.
U.S. Appl. No. 08/978,635 Final Rejection Nov. 24, 1999.
U.S. Appl. No. 08/978,635 Non-Final Rejection Feb. 16, 1999.
U.S. Appl. No. 08/978,636 Final Rejection Dec. 26, 2007.
U.S. Appl. No. 08/978,636 Non-Final Rejection Apr. 4, 2007.
U.S. Appl. No. 08/978,636 Final Rejection Jun. 27, 2006.
U.S. Appl. No. 08/978,636 Non-Final Rejection May 31, 2005.
U.S. Appl. No. 08/978,636 Final Rejection Jul. 15, 2004.
U.S. Appl. No. 08/978,636 Non-Final Rejection Apr. 9, 2003.
U.S. Appl. No. 08/978,636 Final Rejection Dec. 19, 2000.
U.S. Appl. No. 08/978,636 Final Rejection Jun. 5, 2000.
U.S. Appl. No. 08/978,636 Final Rejection Nov. 10, 1999.
U.S. Appl. No. 08/978,636 Non-Final Rejection Feb. 18, 1999.
U.S. Appl. No. 08/978,634 Non-Final Rejection Jan. 7, 2006.
U.S. Appl. No. 08/978,634 Final Rejection Oct. 21, 2005.
U.S. Appl. No. 08/978,634 Non-Final Rejection Mar. 25, 2003.
U.S. Appl. No. 08/978,634 Final Rejection Dec. 19, 2000.
U.S. Appl. No. 08/978,634 Final Rejection Jun. 5, 2000.
U.S. Appl. No. 08/978,634 Final Rejection Nov. 9, 1999.
U.S. Appl. No. 08/978,634 Non-Final Rejection Feb. 17, 1999.
U.S. Appl. No. 08/978,633 Non-Final Rejection Apr. 8, 2003.
U.S. Appl. No. 08/978,633 Final Rejection Dec. 18, 2000.
U.S. Appl. No. 08/978,633 Final Rejection Jun. 5, 2000.
U.S. Appl. No. 08/978,633 Final Rejection Nov. 9, 1999.
U.S. Appl. No. 08/978,633 Non-Final Rejection Feb. 16, 1999.
U.S. Appl. No. 08/574,443 Non-Final Rejection Feb. 19, 1999.
U.S. Appl. No. 08/574,443 Non-Final Rejection Nov. 25, 1996.
Wyatt et al. "Replication-deficient Vaccinia virus encoding bacteriophage T7 RNA polymerase for transient gene expression in mammalian cells" Virology 210: 202-205. 1995.
Mansky et al. "Lower In Vivo Mutation Rate of Human Immunodeficiency Virus Type 1 than That Predicted from the Fidelity of Purified Reverse Transcriptase" J. Virol. 69: 5087-5094. 1995.
Junker et al. "Genetic instability of a MoMLV-based antisense double-copy retroviral vector designed for HIV-1 gene therapy" Gene Therapy 2: 639-645. 1995.
Wolfe et al. "The effect of sodium ion concentration on intrastrand base-pairing in single-stranded DNA" Nucleic Acids Res. 22: 3147-3150. 1994.
Buchholz et al. "The Carboxy-terminal domain of Sendai virus nucleocapsid protein is involved in complex formation between phosphoprotein and nucleocapsid-like particles" Virology 204: 770-776. 1994.
Ho et al. "Expression in animal cells of the 5-HT1A receptor by a vaccinia virus vector system" FEBS 278: 229-233. 1992.
Pattnaik et al."Cells that express all five proteins of vesicular stomatitis virus from cloned cDNAs support replication, assembly, and budding of defective interfering particles" Proc. Natl. Acad. Sci. USA 88: 1379-1383. 1991.
Karschin et al., "K + channel expression in primary cell cultures mediated by vaccinia virus" FEBS 278: 229-233. 1991.
Sullenger et al. "Expression of Chimeric tRNA-Driven Antisense Transcripts Renders NIH 3T3 Cells Highly Resistant to Moloney Murine Leukemia Virus Replication" Mol. Cell. Biol. 10: 6512-6523. 1990.
Moss et al. "Product Review: New Mammalian Expression Vectors" Nature 348: 91-92. 1990.
Elroy-Stein "Cytoplasmic expression system based on constitutive synthesis of bacteriophage T7 RNA polymerase in mammalian cells" Proc. Natl. Acad. Sci. USA 87: 6743-6747. 1990.
Buonocore et al. "Prevention of HIV-1 glycoprotein transport by soluble CD4 retained in the endoplasmic reticulum" Nature 345: 625-628. 1990.
Brakel et al. U.S. Appl. No. 07/446,235, filed Dec. 4, 1989.
Edlind et al. "Intrastrand Base Pairing in Single-Stranded Deoxyribonucleic Acid from ColEI-Derived Plasmid pCR1" J. Bacteriol. 145: 1436-1441. 1981.
Verma et al. "Gene therapy—promises, problems and prospects" Nature 389: 239-242. 1997.
Fisher "Neural precursor cells: applications for the study and repair of the central nervous system" Neurobiology of Disease 4: 1-22. 1997.
Datta et al. "Mitotic crossovers between diverged sequences are regulated by mismatch repair proteins in *Saccaromyces cerevisiae*" Mol. Cell Biol. 16: 1085-1093. 1996.
Bennet et al. "Pharmacology of antisense therapeutic agents" ch 2 in Methods in Molecular Medicine: Antisense Therapeutics Ed. S. Agrawal, Humana Press, Inc. Totowa, NJ 1996.
Wang et al., "Delivery of antisense oligodeoxyribonucleotides against the human epidermal growth factor receptor into cultured KB cells with liposomes conjugated to folate via polyethylene glycol" Proc. Natl. Acad. Sci. USA 92: 3318-3322. 1995.
Thimme et al., "Mx1 but not MxA confers resistance against tick-borne Dhori virus in mice" Virology 211: 296-301. 1995.

(56) References Cited

OTHER PUBLICATIONS

Sun et al. "Resistance to human immunodeficiency virus type 1 infection conferred by transdution of human peripheral blood lymphocytes with ribozyme, antisense, or polymeric trans-activation response element constructs" Proc. Natl, Acad. Sci. USA 92: 7272-7276. 1995.
Rossi, "Controlled, targeted, intracellular expression of ribozymes: progress and problems" Trends Biotechnol. 13: 301-306. 1995.
Ramirez et al., "Transcriptional inhibition of the Parvovirus Minute virus of mice by constitutive expression of an antisense RNA targeted against the NS-1 transactivator protein" Virology 206: 57-68. 1995.
Miller et al. "Targeted vectors for gene therapy" FASEB J. 9: 190-199. 1995.
Michael et al., "Signal sequences that target nuclear import and nuclear export of pre-mRNA binding proteins" Cold Spring Harbor Symposia on Quantitative Biology 60: 663-668. 1995.
Limjoco et al. "Resistance to retroviral infection in transgenic and bone marrow chimeric mice contaiing Fv4-env-expression hematopoietic cells" Virology 208: 75-83. 1995.
Lever "Gene therapy for HIV infection" British Medical Bulletin 51: 149-166. 1995.
Lau et al. Retroviral gene transfer into the intestinal epitheLAU et al. "Retroviral gene transfer into the intestinal epithelium" Hum Gene Ther. 6: 1145-1151. 1995.
Binkley et al. "RNA ligands to human nerve growth factor" Nucleic Acids Res. 23: 3198-3205. 1995.
Ally et al. "Prevention of autoimmune disease by retroviral-mediated gene therapy" J. Immunol. 155: 5404-5408. 1995.
Agrawal et al. "Absorption, tissue distribution and in vivo stability in rates of a hybrid antisense oligonucleotide following oral administration" Biochem. Pharmacol. 50: 571-576. 1995.
Afione et al., "Gene therapy vectors as drug delivery system" Clin. Pharmacokinet. 28: 181-189. 1995.
Zhou et al. "Inhibition of HIV-1 in human T-lymphocytes by retrovirally transduced anti-tat and rev hammerhead ribozymes" Gene 149: 33-39. 1994.
Yu et al. "Progress towards gene therapy for HIV infection" Gene Therapy 1: 13-16 1994.
Vieillard et al. "Blocking of rteroviral infection at a step prior to reverse transcription in cells transformed to constitutively express interferon beta" Proc. Natl. Acad. Sci. USA 91: 2689-2693 1994.
Nichols et al. "A universal nucleoside for use at ambiguous sites in DNA primers" Nature 369: 492-493. 1994.
McBride et al., Controlled expression of plastid transgenes in plants based on a nuclear DNA-encoded and plastid-targeted t& RNA polymerase: Proc. Natl. Acad. Sci. USA 91: 7301-7305. 1994.
Lewin, in Genes V, pp. 914-915. 1994.
Junker et al. "Reduction in replication of the human immunodeficiency virus type 1 in human T cell lines by polymerase III-drive transcription of chimeric tRNA-antisense RNA genes" Antisense Res. Dev. 4: 165-172. 1994.
Gruber et al. "Efficient tumor cell lysis mediated by a bispecific single chain antibody expressed in *Escherichia coli*" J. Immunol. 152: 5368-5372. 1994.
DeYoung et al. "Functional characterization of ribozymes expressed using U1 and T7 vectors for the intracellular cleavage of ANF mRNA" Biochemistry 33: 12127-12138. 1994.
Crooke "Progress in evaluation of the potential of antisense therapy" Antisense Res. and Development 4: 145-146. 1994.
Cohli et al., "Inhibition of HIV-1 multiplication in a human CD4 lymphocytic cell line expressing antisense and sense RNA molecules containing HIV-1 packaging signal and rev response elements(s)" Antisense Research and Development 4: 19-26. 1994.
Chang et al. "Block of HIV-1 infection by a combination of antisense tat RNA and TAR decoys: a stategy for control of HIV-1" Gene Therapy 1: 208-216. 1994.
Vlassov et al., "Penetration of oligonucleotides into mouse organism through mucosa and skin" FEBS Lett. 327: 271-274. 1993.

Schwartz et al. "Construction of a retrotransposition indicator sequence using a neomycin resistance-encoding gene containing a functional intron" Gene 127: 233-236. 1993.
Sandig et al. "A phage T7 class-III promoter functions as a polymerase II promoter in mammalian cells" Gene 131: 255-259. 1993.
Palsson et al. "Expansion of human bone marrow progenitor cells in a high cell density continuous perfusion system" Biotechnology (NY) 11: 368-372. 1993.
Lisziewicz et al. "Inhibition of human immunodeficiency virus type 1 replication by regulated expression of a polymeric Tat activation response RNA decoy as a strategy for gene therapy in AIDS" Proc. Natl. Acad. Sci. USA 90: 8000-8004 1993.
Lieber et al. "Stable high-level gene expression in mammalian cells by T7 phage RNA polymerase" Methods Enzymol. 217: 47-66 1993.
Koller et al. "Large-scale expansion of human stem and progenitor cells from bone marrow mononuclear cells in continuous perfusion cultures" Blood 82: 378-384. 1993.
Koller et al. "Expansion of primitive human hematopoietic progenitors in a perfusion bioreactor system with IL-3, IL-6, and stem cell factor" BioTechnology (NY) 11: 358-363. 1993.
Holliger et al. ""Diabodies": small bivalent and bispecific antibody fragments" Proc. Natl. Acad. Sci. USA 90: 6444-6448. 1993.
Fischer et al. "Nucleo-cytoplasmic transport of U snRNPs: definition of a nuclear location signal in the Sm core domain that binds a transport receptor independently of the m3G cap" EMBO J. 12: 573-583. 1993.
Cristiano et al. "Hepatic gene therapy: adenovirus enhancement of receptor-mediated gene delivery and expression in primary hepatocytes" Proc. Natl. Acad. Sci. USA 90: 2122-2126. 1993.
Cox et al. "Effect of resistance on combination chemotherapy for human immunodeficiency virus infection" Adv. Enzyme Regul. 33: 27-36. 1993.
Balvay et al. "Pre-mRNA secondary structure and the regulation of splicing" BioEssays 15: 165-169. 1993.
Allaway et al. "Synergistic inhibition of HIV-1 envelope-mediated cell fusion by CD4-based molecules in combination with antibodies to gp120 or gp41" AIDS Res. Human Retroviruses 9: 581-587. 1993.
Zaia et al., "Status of ribozyme and antisense-based developmental approaches for anti-HIV-1 therapy" Annals of the NY Acad Sci 660: 95-106. 1992.
Wagner et al. "Influenza virus hemagglutinin HA-2 N-terminal fusogenic peptides augment gene transfer by transferrin-polylysine-DNA complexes: toward a synthetic virus-like gene-transfer vehicle" Proc. Natl. Acad. Sci. USA 89: 7934-7938. 1992.
Wagner et al., "Coupling of adenovirus to transferring-polylysine/DNA complexes greatly enhances receptor-mediated gene delivery and expression of transfected genes" Proc. Natl. Acad. Sci. USA 89: 6099-6103. 1992.
Tani et al., "Activity of chimeric RNAs of U6 snRNA and (-) sTRSV in the cleavage of a substrate RNA" Nucleic Acids Res. 20: 2991-2996. 1992.
Takeda et al. "Thermodynamics of Cro protein-DNA interactions" Proc. Natl. Acad. Sci USA 89: 8180-8184. 1992.
Sczakiel "Tat- and Rev-directed antisense RNA expression inhibits and abolishes replication of human immunodeficiency virus type 1: a temporal analysis" J. Virol. 66: 5576-5581. 1992.
Muzyczka "Use of adeno-associated virus as a general transduction vector for mammalian cells" Curr Top Microbiol and Immunol 158: 97-129. 1992.
Izant "Chimeric Antisense RNAs" in Gene Regulation: Biology of Antisense RNA and DNA pp. 183-195. Raven Press, Ltd. New York 1992.
Husson et al. "Phase I study of continuous-infusion soluble CD4 as a single agent and in combination with oral dideoxyinosine therapy in children with symptomatic human immunodeficiency virus infection" J. Pediatrics 121: 627-633. 1992.
Harrison et al. "Inhibition of human immunodeficiency virus-1 production resulting from transduction with a retrovirus containing an HIV-regulated diphtheria toxin A chain gene" Human Gene Therapy 3: 461-469. 1992.
Fanger et al. "Bispecific antibodies" Crit Rev Immunol 12: 101-124 .1992.

(56) References Cited

OTHER PUBLICATIONS

Dumontet et al. "[Chemotherapy for human immunodeficiency virus infection. Current status and perspectives]" La Revue de Medecine Intern. 13: 460-464. 1992.
Chen et al. "Inhibition of HIV-1 replication by novel multitarget ribozymes" in Antisense Strategies, Annals NY Acad. Sci. 660: 271-273. 1992.
Chatterjee et al., "Dual-target inhibition of HIV-1 in vitro by means of an adeno-associated virus antisense vector" Science 258: 1485-1488. 1992.
Burkly et al., "Inhibition of HIV infection by a novel CD4 domain 2-specific monoclonal antibody. Dissecting the basis for its inhibitory effect on HIV-induced cell fusion" J. Immunol. 149: 1779-1787. 1992.
Sczakiel et al., "Inhibition of human immunodeficiency virus type 1 replication in human T cells stably expressing antisense RNA" J. Virol 65: 468-472. 1991.
Pilch et al. "Expression of histone-U1 snRNA chimeric genes: U1 promoters are compatible with histone 3' end formation" Gene Expression 1:41-53. 1991.
McBurney et al., "The mouse Pgk-1 gene promoter contains an upstream activator sequence" Nucleic Acids Res. 19: 5755-5761. 1991.
Laurence et al. "Induction of chronic human immunodeficiency virus infection is blocked in vitro by a methylphosphonate oligodeoxynucleoside targeted to a U3 enhancer element" J. Virol. 65: 213-219. 1991.
Joshi et al., "Inhibition of human immunodeficiency virus type 1 multiplication by antisense and sense RNA expression" J. Virol. 65: 5524-5530. 1991.
Faruqi et al., "Replication-defective missense mutations within the terminal protein and spacer/intron regions of the polymerase gene of human hepatitis B virus" Virology 183: 764-768. 1991.
Dubendorff et al., "Creation of a T7 autogene. Cloning and expression of the gene for bacteriophage T7 RNA polymerase under control of its cognate promoter" J. Mol. Biol. 219: 61-68. 1991.
Curiel et al. "Adenovirus enhancement of transferrin-polylysine-mediated gene delivery" Proc. Natl. Acad. Sci. USA 88: 8850-8854. 1991.
Zieve et al. "Cell biology of the snRNP particles" Crit Rev Biochem Mol Biol 25: 1-46. 1990.
Yamashita et al. "Comparison of human lymphotoxin gene expression in CHO cells directed by genomic DNA or cDNA sequences" Agric. Biol. Chem. 54: 2801-2809. 1990.
Sczakiel et al., "Specific inhibition of human immunodeficiency virus type 1 replication by RNA transcribed in sense and antisense orientation from the 5'-leader/gag region" Biochem Biophys Res Commun 169: 643-651. 1990.
Mayeda et al. "Beta-globin transcripts carrying a single intron with three adjacent nucleotides of 5' exon are efficiently spliced in vitro irrespective of intron position or surrounding exon sequences" Nucleic Acids Res. 18: 4671-4676. 1990.
Kessler et al. "Detection of nucleic acids by enzyme-linked immunosorbent assay (ELISA) technique: An example for the development of a novel nonradioactive labeling and detection system with high sensitivity" in Advances in Mutagenic Research. Springer Verlag 1: 105-152. 1990.
Horton et al. "Gene splicing by overlap extension: tailor-made genes using the polymerase chain reaction" BioTechniques 8: 528-535. 1990.
Fischer et al. "An essential signaling role for the m3G cap in the transport of U1 snRNP to the nucleus" Science 249: 786-790. 1990.
Yuo et al. "A U1 small nuclear ribonucleoprotein particle with altered specificity induces alternative splicing of an adenovirus E1A mRNA precursor" Mol. Cell. Biol. 9: 3429-3437. 1989.
Yoshimatsu et al. "Control of gene expression by artificial introns in Saccharomyces cerevisiae" Science 244: 1346-1348. 1989.
Wu et al. "Targeting genes: delivery and persistent expression of a foreign gene driven by mammalian regulatory elements in vivo" J. Biol. Chem. 269: 16985-16987. 1989.
Nitta et al. "Bispecific F (ab')2 monomer prepared with anti-CD3 and anti-tumor monoclonal antibodies is most potent in induction of cytolysis of human T cells" Eur. J. Immunol. 19: 1437-1441. 1989.
Lieber et al. "High level gene expression in mammalian cells by a nuclear T7-phase RNA polymerase" Nucleic Acids Res. 17: 8485-8493. 1989.
Horton et al. "Engineering hybrid genes without the use of restriction enzymes: gene splicing by overlap extension" Gene 77: 61-68. 1989.
Gatermann et al. "Introduction of functional artificial introns into the naturally intronless ura4 gene of Schizosaccharomyces pombe"Mol. Cell Biol. 9: 1526-1535. 1989.
Neuman De Vegvar "Initiation and termination of human U1 RNA transcription requires the concerted action of multiple flanking elements"Nucleic Acids Res. 17: 9305-9318. 1989.
Cotten et al., "Ribozyme mediated destruction of RNA in vivo" EMBO J 8: 3861-3866. 1989.
Bebenek et al. "Specificity and mechanism of error-prone replication by human immunodeficiency virus-1 reverse transcriptase"J. Biol. Chem. 264: 16948-16956. 1989.
Saiki et al. "Primer-directed enzymatic amplification of DNA with a thermostable DNA polymerase." Science 239: 487-491. 1988.
Leibold et al. "Cytoplasmic protein binds in vitro to a highly conserved sequence in the 5' untranslated region of ferritin heavy- and light-subunit mRNAs" Proc. Natl. Acad. Sci. USA 85: 2171-2175. 1988.
Izant et al. "Antisense inhibition of RNA splicing" in Current Communications in Molecular Biology, Cold Spring Harbor Laboratory pp. 141-149. 1988.
Dunn et al. "Targeting bacteriophage T7 RNA polymerase to the mammalian cell nucleus" Gene 68: 259-266. 1988.
Dahlberg et al. "The Genes and Transcription of the Major Small Nuclear RNAs" in Structure and Function of Major and Minor Small Nuclear Ribonucleoprotein Particles Birnstiel, ed. Springer Verlag, Heidelberg, pp. 38-70. 1988.
Cook "Synthesis and hybridization of a series of biotinylated oligonucleotides" et al. Nucleic Acids Res. 16: 4077-4095. 1988.
Lear et al. "Membrane binding and conformational properties of peptides representing the NH2 terminus of influenza HA-2" J. Biol. Chem. 262: 6500-6505. 1987.
Kotani et al. "Nucleotide sequence and expression of the cloned gene of bacteriophage SP6 RNA polymerase" Nucleic Acids Res. 15: 2653-2664. 1987.
Staerz et al. "Hybrid hybridoma producing a bispecific monoclonal antibody that can focus effector T-cell activity" Proc. Natl. Acad. Sci. USA 83: 1453-1457. 1986.
Scharf et al. "Direct cloning and sequence analysis of enzymatically amplified genomic sequences" Science 233: 1076-1078. 1986.
Old et al. "Principles of Gene Manipulation" Blackwell Scientific Publications, London, 1986.
Morris et al. "Cloning and expression of the bacteriophage T3 RNA polymerase gene" Gene 41: 193-200. 1986.
Kozak "Point mutations define a sequence flanking the AUG initiator codon that modulates translation by eukaryotic ribosomes" Cell 44: 283-292. 1986.
Jablonski et al. "Preparation of oligodeoxynucleotide-alkaline phosphatase conjugates and their use as hybridization probes" Nucleic Acids Res. 14: 6115-6128. 1986.
Fuerst, et al., Eukaryotic transient-expression system based on recombinant vaccinia virus that synthesizes bacteriophage T7 RNA poymerase: Proc. Natl. Acad. Sci. USA 83: 8122-8126. 1986.
Eritja et al. "Synthesis and properties of oligonucleotides containing 2'-deoxynebularine and 2'-deoxyxanthosine" Nucleic Acids Res 14: 8135-8153. 1986.
Davis et al., "Basic Methods in Molecular Biology" Elsevier, NY 1986.
Argos et al. "The integrase family of site-specific recombinases: regional similarities and global diversity" EMBO J. 5: 433-440. 1986.
Agrawal et al. "Efficient methods for attaching non-radioactive labels to the 5' ends of synthetic oligodeoxyribonucleotides" Nucleic Acids Res. 14: 6227-6245. 1986.

(56) References Cited

OTHER PUBLICATIONS

Saiki et al., "Enzymatic amplification of beta-globin genomic sequences and restriction site analysis for diagnosis of sickle cell anemia" Science 230: 1350-1354. 1985.
Chu et al. "In vitro expression of the intron-containing gene for T4 phage thymidylate synthase" J. Biol. Chem. 260: 10680-10688. 1985.
Perbal, "A Practical Guide to Molecular Cloning" John Wiley & Sons, New York, 1984.
Melton "Efficient in vitro synthesis of biologically active RNA and RNA hybridization probes from plasmids containing a bacteriophage SP6 promoter" et al. Nucleic Acids Res. 12: 7035-7056. 1984.
Kalderon et al., "A short amino acid sequence able to specify nuclear location." Cell 39: 499-509. 1984.
Davanloo et al. "Cloning and expression of the gene for bacteriophage T7 RNA polymerase" Proc. Natl. Acad. Sci. USA 81: 2035-2039. 1984.
Chu et al. "Intervening sequence in the thymidylate synthase gene of bacteriophage T4" Proc. Natl. Acad. Sci. USA 81: 3049-3053. 1984.
Teem et al., "Expression of a beta-galactosidase gene containing the ribosomal protein S1 intron is sensitive to the rna2 mutation of yeast" Proc. Natl. Acad. Sci. USA 80: 4403-4407. 1983.
Dunn et al., "Complete nucleotide sequence of bacteriophage T7 DNA and the locations of T7 genetic elements" J. Mol. Biol. 166: 477-535. 1983.
Mount "A catalogue of splice junction sequences" Nucleic Acids Res. 10: 459-472. 1982.
Manser et al., Human U1 loci: genes for human U1 RNA have dramatically similar genomic environments Cell: 29: 257-264. 1982.
Maniatis et al. Molecular Cloning, A Laboratory Manual, Cold Spring Harbor Laboratory Press, 1982.
Ruoslahti et al. "Alignment of biologically active domains in the fibronectin molecule" J. Biol. Chem. 256: 7277-7281. 1981.
Anderson et al. "Structure of the cro repressor from bacteriophage lambda and its interaction with DNA" Nature 290: 754-758. 1981.
Roychoudhury et al. "Influence of nucleotide sequence adjacent to duplex DNA termini on 3' terminal labeling by terminal transferase" Nucleic Acids Res. 6: 1323-1333. 1979.
Rigby et al. "Labeling deoxyribonucleic acid to high specific activity in vitro by nick translation with DNA polymerase I" J. Mol. Biol. 113: 237-251. 1977.
Rafestin et al. "Purification of N-acetyl D-glucosamine-binding proteins by affinity chromatography" FEBS Letters 40: 62-66. 1974.
Stavrianopoulos et al. "Mechanism of DNA replication by highly purified DNA polymerase of chicken embryo" Proc. Natl. Acad. Sci. USA 69: 2609-2613. 1972.
Soeiro et al. "Competition hybridization by "pre-saturation" of HeLa cell DNA" J. Mol. Biol. 44: 551-562. 1969.
Definitions for "compound", "polymer", "monomer" on Oct. 19, 2005 from www.cancerweb.ncl.ac.uk.
U.S. Appl. No. 08/978,633 Final Rejection Feb. 25, 2008.
U.S. Appl. No. 08/978,634 Final Rejection May 28, 2008.
U.S. Appl. No. 08/978,637 Final Rejection Apr. 16, 2008.
Ferkol et al. "Immunologic responses to gene transfer into mice via the polymeric immunoglobulin receptor." Gene Therapy 3: 669-678. 1996.
Ferkol et al. "Gene transfer into the airway epithelium of animals by targeting the polymeric immunoglobulin receptor" J. Clin. Invest. 95-493. 1995.
Gao et al. "Direct in vivo gene transfer to airway epithelium employing adenovirus-polylysine-DNA complexes." Human Gene Ther. 4:17-24. 1993.
Hirsch et al. "Antifection: a new method for targeted gene transfection." Transplantation Proceedings 25: 138-139. 1993.
Johansen "Intron insertion facilitates amplification of cloned virus cDNA in *Escherichia coli* while biological activity is reestablished after transcription in vivo" Proc. Natl. Acad. Sci. USA 93: 12400-12405. 1996.
Wu et al. "Receptor-meidated gene delivery and expression in vivo." J. Biol. Chem. 263: 14621-16624. 1988.
Wu et al "Incorporation of adenovirus into a ligand-based DNA carrier system results in retention of original receptor specificity and enhances targeted gene expression." J. Biol. Chem. 269: 11542-11546. 1994.

\* cited by examiner

Figure I
Attachment of Ligands Through Primer Region

Attachment of Ligands by Incorporation of
Modified Nucleotide Precursors

Incorporation of Ligands through Modified Ribonucleotides

Attachment of Ligands through a 3' tail

Preparation of Gapped Circle

Attachment of Ligands through hybridization to a 3' tail

RNA with Ligands on Primer (Continued in Figure 8)

RNA with Ligands on Primer (Continued)

RNA with Ligands on Multiple Primers

RNA with Ligands on Multiple Primers (Continued)

Single-stranded DNA with attached Ligands

Single-stranded DNA with attached Ligands (continued)

Linear Double-stranded DNA with attached Moieties on each strand

Enhanced Delivery of Retroviral Vector to Haematopoeitic Stem Cell

Enhanced Delivery of Vector
DNA to Haematopoeitic Stem Cell

Covalent Attachment of vector DNA to Dimeric Antibody

Covalent attachment of Modified DNA
to a Monovalent Antibody

Modified DNA used as a Binder

Synthetic Steps for Creation of Antibodies
With Nucleic Acid Moieties Attached

Continuation of Synthetic Steps

Enhanced Binding of Antibodies to Antigens by Multimerization

High Affinity Multi-Insulin Soluble Complex

Multimerization of Insulin molecules by hybridization to discrete Sequences

Fusion of Intron into T7 RNA Polymerase Coding Sequence

Construction of T7 Expression Vector

A) Synthesis of pieces

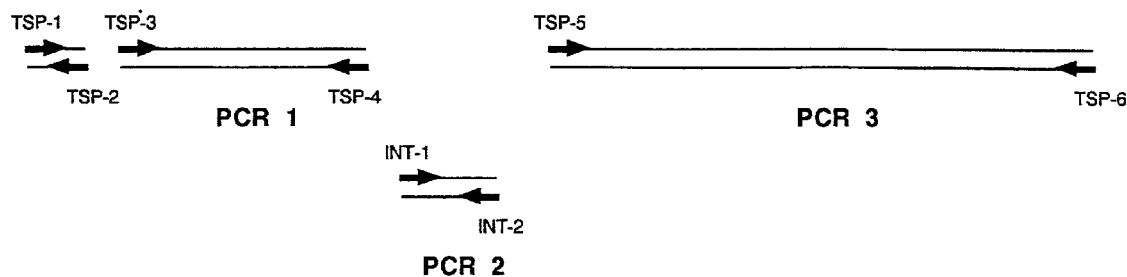

B) Oligomers used for synthesis

TSP-1   GGA ATT CGT CTC GAG CTC TGA TCA CCA CCA TGG ACA CGA TTA ACA TCG C

TSP-2   GAC TAG TTG GTC TCG TCT CTT TTT TGG AGG AGT GTC GTT CTT AGC GAT GTT AAT C

TSP-3   GGA ATT CGT CTC GGA GAA AGG TAA AAT TCT CTG ACA TCG AAC TGG C

TSP-4   GAC TAG TGG TCT CCC CTT AGA GAG CAT GTC AGC

TSP-5   GGA ATT CGG TCT CGG GTC TAC TCG GTG GCG AGG

TSP-6   GAC TAG TCG TTA CGC GAA CGC AAA GTC

INT-1   GGA ATT CGT CTC TAA GGT AAA TAT AAA ATT TTT AAG

INT-2   GAC TAG TCG TCT CTG ACC CTA AAA TAC ACA AAC AAT TAG A

Figure 26

Synthesis of Pieces for Construction of
T7 RNA Polymerase with Intron

Formation of Nuclear Localisation Signal by Fusion of TSP1/TSP2 Product to Clone with PCR #1 product

Annealing of TSP1 with TSP2

TSP1

```
5' GG AAT TCG TCT CGA GCT CTG ATC ACC ACC ATG GAC ACG ATT AAC ATC GC    3'
                                              3' C TAA TTG TAG CGA TTC TTG CTG TGA GGA GGT TTT TTC TCT GCT CTG GTT GAT CAG  5'
```

TSP2

Extension of TSP1/TSP2 by polymerase

```
5' GG AAT TCG TCT CGA GCT CTG ATC ACC ACC ATG GAC ACG ATT AAC ATC GCT AAG AAC GAC ACT CCT CCA AAA AAG AGA CGA GAC CAA CTA GTC  3'
3' CC TTA AGC AGA GCT CGA GAC GTA TGG TGG TAC CTG TGC TAA TTG TAG CGA TTC TTG CTG TGA GGA GGT TTT TTC TCT GCT CTG GTT GAT CAG  5'
```

Bsa I

Digestion of TSP1/TSP2 product with Bsa I

```
5' GG AAT TCG TCT CGA GCT CTG ATC ACC ACC ATG GAC ACG ATT AAC ATC GCT AAG AAC GAC ACT CCT CCA AAA AA
3' CC TTA AGC AGA GCT CGA GAC GTA TGG TGG TAC CTG TGC TAA TTG TAG CGA TTC TTG CTG TGA GGA GGT TTT TTC TCT
```

Digestion of PCR #1 clone (pL-1) with BsmB I

Bsm B1

```
5' GGA ATT CGT CTC G        GAGA AAG GTA AAA TTC TCT GAC ATC GAA CTG GC---------
   CCT TAA GCA GAG CCTCT         TTC CAT TTT AAG AGA CTG TAG CTT GAC CG---------
```

Ligation of Bsa I digested TS1/TS2 product to BsmB I digested PCR#1 clone

```
5' GG AAT TCG TCT CGA GCT CTG ATC ACC ACC ATG GAC ACG ATT AAC ATC GCT AAG AAC GAC ACT CCT CCA AAA AAG AGA AAG GTA AAA TTC
3' CC TTA AGC AGA GCT CGA GAC GTA TGG TGG TAC CTG TGC TAA TTG TAG CGA TTC TTG CTG TGA GGA GGT TTT TTC TCT TTC CAT TTT AAG

TCT GAC ATC GAA CTG GC---------
AGA CTG TAG CTT GAC CG---------
```

Figure 27

Comparison of the 5' ends of the Nucleotide Sequences of Wild Type and Modified T7 RNA Polymerase Wild Type T7 nucleic and amino acid sequence

```
ATG GAC ACG ATT AAC ATC GCT AAG AAC GAC TTC TCT GAC ATC GAA CTG GC-------
TAC CTG TGC TAA TTG TAG CGA TTC TTG CTG AAG AGA CTG TAG CTT GAC CG-------
 1   2   3   4   5   6   7   8   9  10  11  12  13  14  15  16
```

Modified T7 nucleic and amino acid sequence with Nuclear Localisation Signal (NLS) insertion

```
ATG GAC ACG ATT AAC ATC GCT AAG AAC GAC ACT CCT CCA AAA AAG AGA AAG GTA AAA TTC TCT GAC ATC GAA CTG GC-------
TAC CTG TGC TAA TTG TAG CGA TTC TTG CTG TGA GGA GGT TTT TTC TCT TTC CAT TTT AAG AGA CTG TAG CTT GAC CG-------
 1   2   3   4   5   6   7   8   9  10                                      11  12  13  14  15  16
```

Figure 28

Fusion of PCR Pieces to Construct
T7 RNA Polymerase with an Intron (A) Oligomers HTA-1  GAT CAT TAG ACC AGA TCT GAG CCT GGG AGC TCT CTG GCT AAC TAG GGA ACC CAC TGC TTA AGC CTC AAG
HTA-2  GAT CCT TGA GGC TTA AGC AGT GGG TTC CCT AGT TAG CCA GAG AGC TCC CAG GCT CAG ATC TGG TCT AAT HTB-1  GAT CAC CTT AGG CTC TCC TAT GGC AGG AAG AAG CGG AGA CAG CGA CGA AGA CCT CCT CAA G
HTB-2  GAT CCT TGA GGA GGT CTT CGT CGC TGT CTC CGC TTC TTC CTG CCA TAG GAG AGC CTA AGG T HTC-1  GAT CAT AGT GAA TAG AGT TAG GCA GGG ATA CTC ACC ATT ATC GTT TCA GAC CCA CCT CCC AG
HTC-2  GAT CCT GGG AGG TGG GTC TGA AAC GAT AAT GGT GAG TAT CCC TGC CTA ACT CTA TTC ACT AT TER-1  AAT CTA GAG CTA ACA AAG CCC GAA AGG AAG
TER-2  TTC TGC AGA TAT AGT TCC TCC TTT CAG C

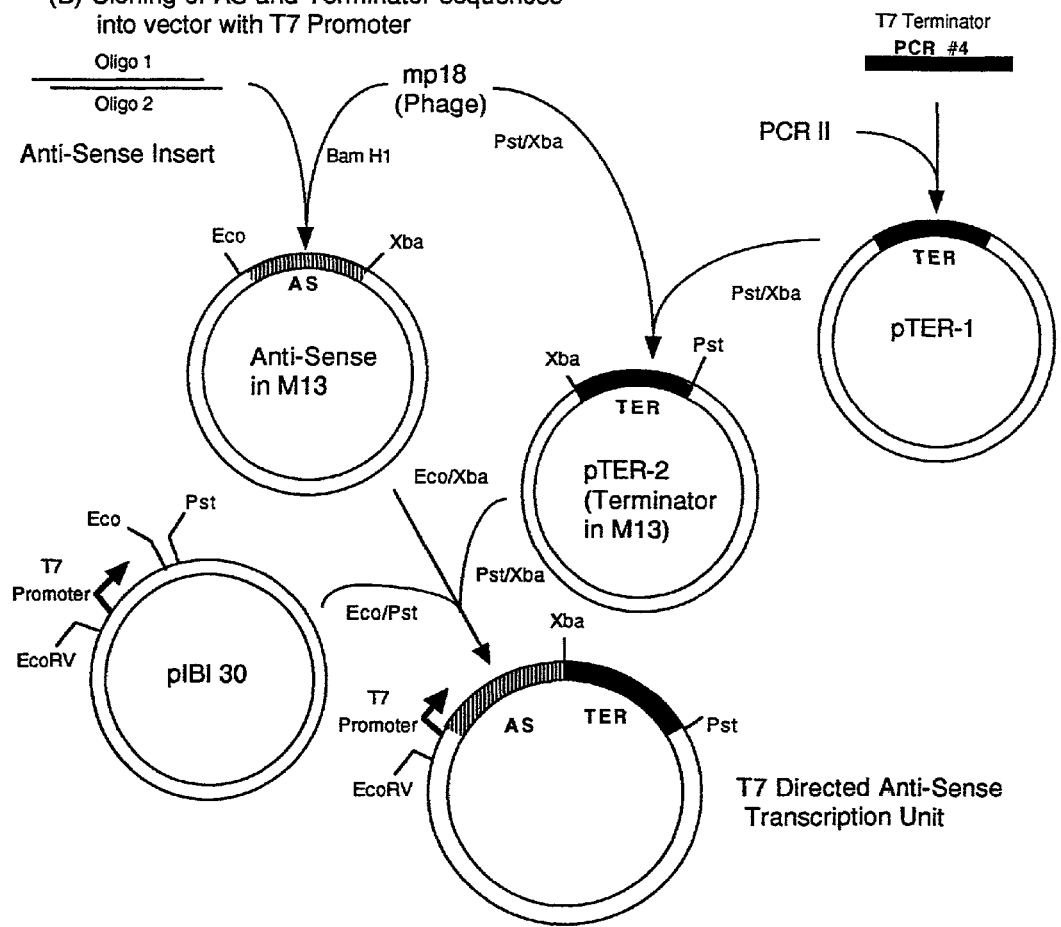

Figure 30
Insertion of Anti-Sense Sequences into
T7 Directed Transcription Units Construct with T7 RNA polymerase and
Anti-Sense directed from a T7 Promoter A) Oligomers for introduction of T7 signals and polylinker PL-1  TCG AGC CAT GGC TTA AGG ATC CGT ACG TCC GGA GCT AGC GGG CCC ATC GAT ACT
      AGT TAA ATG CAG ATC T PL-2  CTA GAG ATC TGC ATT AAC TA GTA TCG ATG GCC CCG CTA GCT CCG GAC GTA CGG
      ATC CTT AAG CCA TGG C Introduction of Poly-Linker for Creation of Protein Expression Vector Final steps for construction of Expression Vector Construct that produces single-stranded Anti-Sense DNA Continued from Figure 34
(Structure 34e)
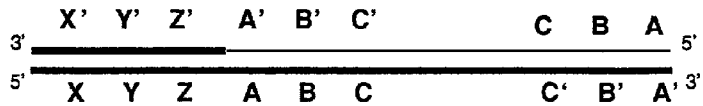
↓ Nicking by RNase H
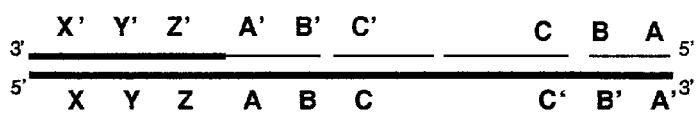
↓ Extension by RT and digestion by RNase H
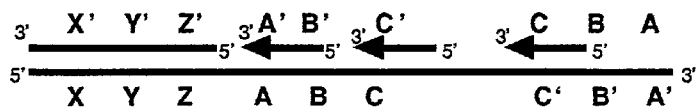
(Structure 35h)
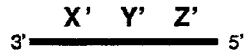
(Structure 35i)
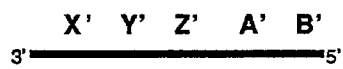
(Structure 35j)
Extension by RT and displacement generates Single-Stranded DNA and a mostly Double-stranded DNA molecule
(Structure 35k)
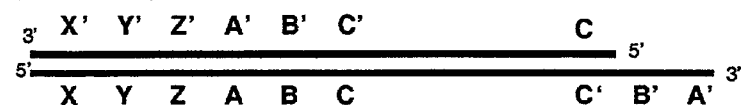
Figure 35
Continuation of Process from Figure 34

Construct that produces RNA that is Reverse Transcribed to create Secondary DNA Constructs capable of directing transcription Construct which Propagates a Double Hairpin Production Center Continuation of process from Figure 37

Construct which propagates a Production Center capable of Inducible Suicide

Use of tRNA primers to create a DNA construct for secondary production of transcripts Excision of Sequences from U1 Transcript Region and Replacement with Novel Sequences Insertion of Anti-Sense Sequences into U1Operons Predicted Secondary structures for U1 Transcripts with Anti-sense Substitutions Construction of U1 Multiple Operon Clone Construction of T7 Triple Operon pNDU1(A,B,C)
Triple U1 Operon Construct with HIV Anti-Sense
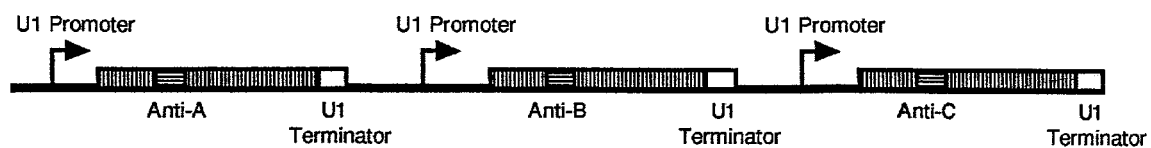
TRI 101
Triple T7 Operon Construct with HIV Anti-Sense
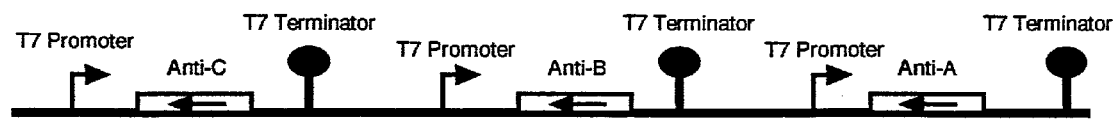
Figure 46
Structures of Triple Operon Constructs from Figures 44 and 45

Construction of Multiple T7 Operons in Vector coding for T7 RNA Polymerse

Flow cytometry data measuring binding of
anti-CD4+ antibody to HIV resistant U037 cells PCR amplification of gag region
indicating absence of HIV in
viral resistant cell line (2.10.16)
after challenge Clone with target-lacZ fusion will have reduced expression of lacZ after transfection by HIV Anti-sense construct

|  | Enzyme activity as expressed by $A_{420}$ readings in extracts prepared from | | |
|---|---|---|---|
|  | $2.5 \times 10^4$ cells | $5 \times 10^4$ cells | $1.0 \times 10^5$ cells |
| U 937 [untransfected] | 0.018 | 0.023 | 0.034 |
| U 937 [ HIV A clone ] | 0.154 | 0.277 | 0.566 |
| U937 [ HIV A / Anti-A] | 0.010 | 0.017 | 0.027 |
| U 937 [ HIV A/Anti-ABC] | 0.013 | 0.021 | 0.035 |
| U 937 [ HIV A / Null DNA] | 0.120 | 0.212 | 0.337 |

[ B] Expression of Beta-galactosidase activity by *In situ* assay :

U 937 [ untransfected ]   no blue spots in cells

U 937 [ HIV A clone ]   blue spots in cells

U 937 [ HIV A/Anti A ]   no blue spots in cells

U 937 [ HIV A/Anti ABC]   no blue spots in cells

U 937 [ HIV A / Null DNA]   blue spots in cells

Figure 51

Expression of Beta-galactosidase activity in extracts

```
                            SEQUENCE LISTING

<160> NUMBER OF SEQ ID NOS: 63

<210> SEQ ID NO 1
<211> LENGTH: 20
<212> TYPE: PRT
<213> ORGANISM: Influenza B virus

<400> SEQUENCE: 1

Gly Phe Phe Gly Ala Ile Ala Gly Phe Leu Glu Gly Gly Trp Glu Gly
  1               5                  10                  15

Met Ile Ala Gly
            20

<210> SEQ ID NO 2
<211> LENGTH: 20
<212> TYPE: DNA
<213> ORGANISM: Bacteriophage T7

<400> SEQUENCE: 2
tgctctctaa gggtctactc                                              20

<210> SEQ ID NO 3
<211> LENGTH: 15
<212> TYPE: DNA
<213> ORGANISM: Simian virus 40

<400> SEQUENCE: 3
ctctaaggta aatat                                                   15

<210> SEQ ID NO 4
<211> LENGTH: 16
<212> TYPE: DNA
<213> ORGANISM: Simian virus 40

<400> SEQUENCE: 4
tgtattttag attcaa                                                  16

<210> SEQ ID NO 5
<211> LENGTH: 19
<212> TYPE: DNA
<213> ORGANISM: Simian virus 40

<400> SEQUENCE: 5
tgctctctaa ggtaaatat                                               19

<210> SEQ ID NO 6
<211> LENGTH: 19
<212> TYPE: DNA
<213> ORGANISM: Simian virus 40

<400> SEQUENCE: 6
tgtattttag ggtctactc                                               19
```

```
<210> SEQ ID NO 7
<211> LENGTH: 19
<212> TYPE: RNA
<213> ORGANISM: Bacteriophage T7

<400> SEQUENCE: 7
ugcucucuaa gguaaauau                                                  19

<210> SEQ ID NO 8
<211> LENGTH: 19
<212> TYPE: RNA
<213> ORGANISM: Bacteriophage T7

<400> SEQUENCE: 8
uguauuuuag ggucuacuc                                                  19

<210> SEQ ID NO 9
<211> LENGTH: 20
<212> TYPE: RNA
<213> ORGANISM: Bacteriophage T7

<400> SEQUENCE: 9
ugcucucuaa gggucuacuc                                                 20

<210> SEQ ID NO 10
<211> LENGTH: 49
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 10
ggaattcgtc tcgagctctg atcaccacca tggacacgat taacatcgc                 49

<210> SEQ ID NO 11
<211> LENGTH: 55
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 11
gactagttgg tctcgtctct tttttggagg agtgtcgttc ttagcgatgt taatc          55

<210> SEQ ID NO 12
<211> LENGTH: 46
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 12
ggaattcgtc tcggagaaag gtaaaattct ctgacatcga actggc                    46

<210> SEQ ID NO 13
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 13
gactagtggt ctcccttag agagcatgtc agc                                   33
```

<210> SEQ ID NO 14
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 14
ggaattcggt ctcgggtcta ctcggtggcg agg                              33

<210> SEQ ID NO 15
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 15
gactagtcgt tacgcgaacg caaagtc                                     27

<210> SEQ ID NO 16
<211> LENGTH: 36
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 16
ggaattcgtc tctaaggtaa atataaaatt tttaag                           36

<210> SEQ ID NO 17
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 17
gactagtcgt ctctgaccct aaaatacaca aacaattaga                       40

<210> SEQ ID NO 18
<211> LENGTH: 92
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 18
ggaattcgtc tcgagctctg atcaccacca tggacacgat taacatcgct aagaacgaca    60
ctcctccaaa aaagagacga gaccaactag tc                               92

<210> SEQ ID NO 19
<211> LENGTH: 92
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 19
gactagttgg ctcgtctctt ttttggagg agggggcgttc ttagcgatgt taatcgtgtc    60
catggtggta tgcagagctc gagacgaatt cc                               92

```
<210> SEQ ID NO 20
<211> LENGTH: 73
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 20
ggaattcgtc gcgagctctg atcaccacca tggacacgat taacatcgct aagaacgaca        60
ctcctccaaa aaa                                                           73

<210> SEQ ID NO 21
<211> LENGTH: 77
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 21
tctctttttt ggaggagtgt cgttcttagc gatgttaatc gtgtccatgg tggtatgcag        60
agctcgagac gaattcc                                                       77

<210> SEQ ID NO 22
<211> LENGTH: 13
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 22
ggaattcgtc tcg                                                           13

<210> SEQ ID NO 23
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 23
gagaaaggta aaattctctg acatcgaact ggc                                     33

<210> SEQ ID NO 24
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 24
tctccgagac gaattcc                                                       17

<210> SEQ ID NO 25
<211> LENGTH: 29
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 25
ttccatttta agagactgta gcttgaccg                                          29
```

```
<210> SEQ ID NO 26
<211> LENGTH: 106
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 26
ggaattcgtc tcgagctctg atcaccacca tggacacgat taacatcgct aagaacgaca       60
ctcctccaaa aaagagaaag gtaaaattct ctgacatcga actggc                     106

<210> SEQ ID NO 27
<211> LENGTH: 106
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 27
gccagttcga tgtcagagaa ttttaccttt ctcttttttg gaggagtgtc gttcttagcg       60
atgttaatcg tgtccatggt ggtagtcaga gctcgagacg aattcc                     106

<210> SEQ ID NO 28
<211> LENGTH: 50
<212> TYPE: DNA
<213> ORGANISM: Bacteriophage T7

<400> SEQUENCE: 28
atggacacga ttaacatcgc taagaacgac ttctctgaca tcgaactggc                  50

<210> SEQ ID NO 29
<211> LENGTH: 50
<212> TYPE: DNA
<213> ORGANISM: Bacteriophage T7

<400> SEQUENCE: 29
gccagttcga tgtcagagaa gtcgttctta gcgatgttaa tcgtgtccat                  50

<210> SEQ ID NO 30
<211> LENGTH: 77
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 30
atggacacga ttaacatcgc taagaacgac actcctccaa aaaagagaaa ggtaaaattc       60
tctgacatcg aactggc                                                      77

<210> SEQ ID NO 31
<211> LENGTH: 77
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 31
gccagttcga tgtcagagaa ttttaccttt ctcttttttg gaggagtgtc gttcttagcg       60
atgttaatcg tgtccat                                                      77
```

```
<210> SEQ ID NO 32
<211> LENGTH: 69
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 32
gatcattaga ccagatctga gcctgggagc tctctggcta actagggaac ccactgctta    60
agcctcaag                                                            69

<210> SEQ ID NO 33
<211> LENGTH: 69
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 33
gatccttgag gcttaagcag tgggttccct agttagccag agagctccca ggctcagatc    60
tggtctaat                                                            69

<210> SEQ ID NO 34
<211> LENGTH: 61
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 34
gatcacctta ggctctccta tggcaggaag aagcggagac agcgacgaag acctcctcaa    60
g                                                                    61

<210> SEQ ID NO 35
<211> LENGTH: 61
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 35
gatccttgag gaggtcttcg tcgctgtctc cgcttcttcc tgccatagga gagcctaagg    60
t                                                                    61

<210> SEQ ID NO 36
<211> LENGTH: 62
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 36
gatcatagtg aatagagtta ggcagggata ctcaccatta tcgtttcaga cccacctccc    60
ag                                                                   62

<210> SEQ ID NO 37
<211> LENGTH: 62
<212> TYPE: DNA
<213> ORGANISM: Artificial Sequence
```

```
<220> FEATURE:
<223> OTHER INFORMATION: Description of Artificial Sequence: Synthetic
      oligonucleotide

<400> SEQUENCE: 37
gatcctggga ggtgggtctg aaacgataat ggtgagtatc cctgcctaac tctattcact        60
at                                                                       62

<210> SEQ ID NO 38
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 38
aatctagagc taacaaagcc cgaaaggaag                                          30

<210> SEQ ID NO 39
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 39
ttctgcagat atagttcctc ctttcagc                                            28

<210> SEQ ID NO 40
<211> LENGTH: 70
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 40
tcgagccatg gcttaaggat ccgtacgtcc ggagctagcg ggcccatcga tactagttaa        60
atgcagatct                                                               70

<210> SEQ ID NO 41
<211> LENGTH: 70
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 41
ctagagatct gcatttaact agtatcgatg ggcccgctag ctccggacgt acggatcctt        60
aagccatggc                                                               70

<210> SEQ ID NO 42
<211> LENGTH: 29
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 42
catgaaatta attcgactca ctatacgga                                           29
```

```
<210> SEQ ID NO 43
<211> LENGTH: 29
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 43
gatctccgta tagtgagtcg aattaattt                                          29

<210> SEQ ID NO 44
<211> LENGTH: 72
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 44
gatccggatt gaggcttaag cagtgggttc cctagttagc cagagagctc ccaggctcag        60
atctggtcta at                                                            72

<210> SEQ ID NO 45
<211> LENGTH: 72
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 45
ccggattaga ccagatctga gcctgggagc tctctggcta actagggaac ccactgctta        60
agcctcaatc cg                                                            72

<210> SEQ ID NO 46
<211> LENGTH: 66
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 46
gatccggacc ttgaggaggt cttcgtcgct gtctccgctt cttcctgcca taggagagcc        60
taaggt                                                                   66

<210> SEQ ID NO 47
<211> LENGTH: 66
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 47
ccggacctta ggctctccta tggcaggaag aagcggagac agcgacgaag acctcctcaa        60
ggtccg                                                                   66

<210> SEQ ID NO 48
<211> LENGTH: 65
<212> TYPE: DNA
<213> ORGANISM: Artificial Sequence
<220> FEATURE:
<223> OTHER INFORMATION: Description of Artificial Sequence: Synthetic
      oligonucleotide
```

```
<400> SEQUENCE: 48
gatccggatg ggaggtgggt ctgaaacgat aatggtgagt atccctgcct aactctattc    60
actat                                                               65

<210> SEQ ID NO 49
<211> LENGTH: 65
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 49
ccggatagtg aatagagtta ggcagggata ctcaccatta tcgtttcaga cccacctccc    60
atccg                                                               65

<210> SEQ ID NO 50
<211> LENGTH: 67
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 50
gatcagcatg cctgcaggtc gactctagac ccgggtaccg agctcgccct atagtgagtc    60
gtattat                                                             67

<210> SEQ ID NO 51
<211> LENGTH: 67
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 51
ccggataata cgactcacta tagggcgagc tcggtacccg gtctagagt cgacctgcag    60 gcatgct                                                             67

<210> SEQ ID NO 52
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 52
tttttttttt tt                                                       12

<210> SEQ ID NO 53
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 53
aaaaaaaaaa aaaaa                                                    15
```

```
<210> SEQ ID NO 54
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 54 ttttttttttt ttttt                                                      15

<210> SEQ ID NO 55
<211> LENGTH: 20
<212> TYPE: DNA
<213> ORGANISM: Simian virus 40

<400> SEQUENCE: 55
gagtagaccc ttagagagca                                                  20

<210> SEQ ID NO 56
<211> LENGTH: 15
<212> TYPE: DNA
<213> ORGANISM: Simian virus 40

<400> SEQUENCE: 56
gagattccat ttata                                                       15

<210> SEQ ID NO 57
<211> LENGTH: 17
<212> TYPE: DNA
<213> ORGANISM: Simian virus 40

<400> SEQUENCE: 57
acataaaaat ctaagtt                                                     17

<210> SEQ ID NO 58
<211> LENGTH: 19
<212> TYPE: DNA
<213> ORGANISM: Simian virus 40

<400> SEQUENCE: 58
tataaatgga atctctcgt                                                   19

<210> SEQ ID NO 59
<211> LENGTH: 19
<212> TYPE: DNA
<213> ORGANISM: Simian virus 40

<400> SEQUENCE: 59
ctcatctggg attttatgt                                                   19

<210> SEQ ID NO 60
<211> LENGTH: 164
<212> TYPE: DNA
<213> ORGANISM: Homo sapiens

<400> SEQUENCE: 60
atacttacct ggcaggggag ataccatgat cacgaaggtg gttttcccag ggcgaggctt      60
atccattgca ctccggatgt gctgacccct gcgatttcgc caaatgtggg aaactcgact    120 gcataaattttg tggtagtggg ggactgcgtt cgcgctttcc cctg                    164
```

```
<210> SEQ ID NO 61
<211> LENGTH: 191
<212> TYPE: DNA
<213> ORGANISM: Artificial Sequence
<220> FEATURE:
<223> OTHER INFORMATION: Description of Artificial Sequence: Synthetic
      U1 construct with Anti-A

<400> SEQUENCE: 61
atacttacct ggcaggggag ataccatgat ccggattgag gcttaagcag tgggttccct      60
agttagccag agagctccca ggctcagatc tggtgtaatc cggatgtgct gacccctgcg     120
atttccccaa atgtgggaaa ctcgactgca taatttgagg tagtggggga ctgcgttcgc     180
gctttcccct g                                                         191

<210> SEQ ID NO 62
<211> LENGTH: 181
<212> TYPE: DNA
<213> ORGANISM: Artificial Sequence
<220> FEATURE:
<223> OTHER INFORMATION: Description of Artificial Sequence: Synthetic
      U1 construct with Anti-B

<400> SEQUENCE: 62
atacttacct ggcaggggag ataccatcgg accttgagga ggtcttcgtc gctgtctccg      60
cttcttcctg cgataggaga gcctaaggtc cggatgtgct gacccctgcg atttccccaa     120
atgtgggaaa ctcgactgca taatttgagg tagtggggga ctgcgttcgc gctttccct     180 g                                                                    181

<210> SEQ ID NO 63
<211> LENGTH: 178
<212> TYPE: DNA
<213> ORGANISM: Artificial Sequence
<220> FEATURE:
<223> OTHER INFORMATION: Description of Artificial Sequence: Synthetic
      U1 construct with Anti-C

<400> SEQUENCE: 63
atacttacct ggcaggggag ataccatgat aatgggaggt gggtctgaaa cgataatggt      60
gagtatccct gcctaagtct attcactatc atgtgctgac ccctgcgagt tccccaaatg     120
tgggaaactc gactgcataa tttgtggtag tgggggactg cgtccgcgct ttcccctg      178
```

PROPERTY EFFECTING AND/OR PROPERTY EXHIBITING COMPOSITIONS FOR THERAPEUTIC AND DIAGNOSTIC USES

This application is a continuation of application Ser. No. 08/574,443 filed Dec. 15, 1995, now abandoned, the contents of which are incorporated herein by reference.

FIELD OF THE INVENTION

This invention relates to compositions including nucleic acid constructs, conjugates, and vectors which are capable of effecting and exhibiting biological function within a cell or cell containing biological system.

All patents, patent publications, scientific articles cited or identified in this application are hereby incorporated by reference in their entirety in order to describe more fully the state of the art to which the present invention pertains.

BACKGROUND OF THE INVENTION

An alternative to viral mediated gene delivery is direct delivery of nucleic acid. This approach has several limitations including low efficiency of transfer, low stability and lack of cell specificity. In order to overcome some of these limitations other approaches have been made. These include non-specific ionic complexes with polycations such as polylysine (Wu and Wu, U.S. Pat. No. 5,166,320, contents of which are incorporated herein by reference) and histone. These bind non-specifically with the nucleic acid construct through polycations or basic proteins, such as histones. However, the resulting complexes still suffer some limitations including lack of uniformity of the complexes, lack of specificity with respect to polycation binding to specific regions of the nucleic acid construct, potential interference of complexes with nucleic acid and possible untimely dissassociation of the complex or lack of timely disassociation of the complex leading to a lack of stability of these nucleic acid polycation or nucleic polypeptide complexes.

Nucleic acid transfer to cells can take place by various methods. Such methods can utilize free nucleic acid, nucleic acid constructs or nucleic acid as part of the genome of a virus or bacteriophage vector.

Wu et al., U.S. Pat. No. 5,166,320, utilized a polynucleotide in a nonspecific association with the polycation polylysine. These complexes suffer limitations including lack of consistency of composition, lack of specificity with respect to polycation binding to specific regions of the nucleic acid construct, potential interference of complexes with nucleic acid and possible untimely dissassociation of the complex or lack of timely disassociation of the complex leading to a lack of stability of these nucleic acid or histone polycation or nucleic polypeptide complexes. This procedure does not provide for delivery of virus vectors. Furthermore, cell transformation efficiencies are still low.

Methods for retrovirus mediated gene transfer to hematopoietic cells ex vivo has been attempted in the presence of fibronectin or fibronectin fragments. Fibronectin binds to retroviruses but not to any other viruses, nucleic acids or nucleic acid constructs. Williams and Patel, WO 95/26200 (the contents of which are incorporated herein by reference), have transformed hematopoietic cells with retroviruses in the presence of fibronectin. The use of fibronectin in this way is limited only to use with some retrovirus vectors and not with other virus vectors or with nucleic acids.

It is desirable to form multimeric complexes for two primary reasons. The formation of such complexes results in an additive effect such that one can obtain collective activity of the monomeric units within a complex or these complexes could provide enhanced binding properties compared to the individual compounds or monomeric units, either through cooperative binding effects or through neighboring effects which produce higher localized concentrations. Polyligands usually exhibit higher binding affinities in the polymeric form than in the monomeric form as seen by the binding of polynucleotide sequences to their complementary sequences when compared to the binding of the monomeric units.

Multimeric complexes have been formed either by crosslinking of monomeric compounds directly or through a matrix or through the formation of noncovalent linkages. Examples of multimeric complexes formed by the crosslinking of a given compound such as enzymes, either directly or through a matrix are described in U.S. Pat. No. 4,687,732 (contents of which are incorporated herein by reference), whereby a visualization polymer composed of multiple units of a visualization monomer is linked together covalently by coupling agents which bond to chemical groups of the monomer. Examples of multimeric complexes made through the formation of noncovalent linkages such as ligand-receptor systems are the PAP (peroxidase-anti-peroxidase) complexes and APAAP (alkaline phosphatase-anti-alkaline phosphatase) complexes in common use as immunological reagents and the streptavidin-biotinylated enzyme complexes used for detection of biotinylated entities.

In the case of complexes formed by crosslinking or non-covalent binding, there are limitations with respect to the spacing and the chemical milieu of the monomeric unit within the complex which may affect the function and activity of the monomeric unit and as the size of the complex grows, solubility may be affected.

Efforts to regulate expression of procaryotic genes by eucaryotic processes have been attempted by Schwartz et al. (1993 Gene 127: 233) (also incorporated herein by reference) who introduced an intron sequence from a eucaryotic gene into a procaryotic gene. However, when introduced into a cell capable of mRNA processing, the gene expressed an altered protein in which additional amino acids were present due to the presence of flanking exon sequences associated with the inserted intron. This limitation is inherent in this approach since this method of intron isolation requires the a priori presence of inherent restriction sites in the exon regions flanking the intron, and intron insertion requires the presence of appropriate restriction sites in the gene receiving the intron. Therefore, even after the excision of the intron from the RNA, the flanking exon sequences remain as part of the coding sequence of the mature RNA molecules. Furthermore, the number of sites for intron insertion on the receiving gene is severely limited by the availability of appropriate restriction sites.

The alteration of the gene product by this approach may have unpredictable effects on the function of the gene product and severely limits the applicability of this method to specific instances. In the example of Schwartz et al. the additional amino acids had no apparent effect on the activity of the protein synthesized in the capable cell, but this is not always a predictable quality since it depends upon the site where the additional amino acids are incorporated. For instance, a short sequence coding for a small peptide introduced into the amino end of T7 RNA polymerase by Dunn et al. (1988 Gene 68: 259) (also incorporated herein by reference) had no apparent effect on enzyme activity. However introduction of the same sequence into a site near the carboxy terminus resulted in nearly complete loss of enzyme activity. Thus, the incorporation of extra amino acids as a result of introducing an exon into a coding sequence by the method of Schwartz et al. could have a drastic mutagenic effect.

Systems derived from procaryotic elements can produce functional products in mammalian cells. T7 RNA polymerase, an enzyme derived from an *E. coli* bacteriophage, has been expressed both transiently and stably in mammalian systems (Fuerst et al., 1986 Proc. Nat. Acad. Sci. U.S.A. 83: 8122, the contents of which are herein incorporated by reference). When synthesized in a mammalian environment, it is capable of acting upon genes under the control of a T7 promoter to produce transcripts that can be translated to provide a functional gene product. Large amounts of RNA can be transcribed from the T7 promoter (comprising up to 30,000 RNA molecules per cell, Lieber et al. 1993, also incorporated by reference).

In eucaryotic systems success has only been achieved by the use of a binary system with the polymerase on one construct and the T7 promoter on a separate construct, In this way either sequential transfections (Lieber et al. 1989 Nucleic Acids Res 17, 8485) (also incorporated by reference) or co-transfections with separate plasmids (Lieber et al. 1993 Methods Enzym. 217, 47) (incorporated by reference) or transfection with a plasmid containing a T7 promoter followed by infection with a recombinant vaccinia virus coding for T7 RNA polymerase (Fuerst et al. 1986 Proc. Nat. Acad. Sci. U.S.A. 83, 8122) must be done. Since T7 RNA polymerase can be cloned only free of a T7 promoter sequence (Davenloo et al. 1984 Proc. Nat. Acad. Sci. U.S.A. 81: 2035) (incorporated herein by reference), it appears that attempts to clone both elements in a single construct fail due to an event where synthesis of the T7 RNA polymerase-initiated transcription from the downstream promoter continues around the plasmid to direct more synthesis of T7 RNA polymerase leading to a cytocidal autocatalytic cascade. A similar strategy of elimination of cognate promoters has been described for the cloning of the bacteriophage T3 (Morris et al. 1986 Gene 41: 193) and SP6 (Kotani et al. 1987 Nucl. Acids Res. 15: 2653) (both publications incorporated herein by reference) RNA polymerases. However, compatibility of these elements has been achieved by the addition of two modifications to the construct, i.e., inhibition of the T7 RNA polymerase by the presence of T7 lysozyme and the use of a repressible T7 lac promoter (Dubendorff and Studier 1991 J. Mol. Biol. 219: 61, 1991, incorporated herein by reference). Both of these limitations are required in order to obtain a construct.

The introduction of genetic material into cells can be done by two methods. One method is the exogenous application of nucleic acids which act directly on cellular processes but which themselves are unable to replicate or produce any nucleic acid. The intracellular concentrations of these molecules that must be achieved in order to affect cellular processes is dependent on the exogenous supply. Another method for nucleic acid delivery is the introduction into cells of Primary Nucleic Acid Constructs which themselves do not act on cellular processes but which produce single stranded nucleic acid in the cell which acts on cellular processes. In this case the introduced Primary Nucleic Acid Construct can integrate into cellular nucleic acid or it can exist in an extrachromosomal state, and it can propagate copies of itself in either the integrated or the extrachromosomal state. The nucleic acid construct can produce, from promoter sequences in the Primary Nucleic Acid Construct, single stranded nucleic acids which affect cellular processes of gene expression and gene replication. Such nucleic acids include antisense nucleic acids, sense nucleic acids and transcripts that can be translated into protein. The intracellular concentrantions of such nucleic acids are limited to promoter-dependent synthesis.

The effectiveness of single stranded nucleic acids produced from primary nucleic acid constructs is dependent on their concentration, the stability and the duration of production in the cell. Current methods for achieving intracellular concentrations are limited by a dependence on promoter directed synthesis.

The effectiveness of antisense therapy depends in large part on three major factors: a) the rate of transcription of antisense RNA, b) the cellular location of the RNA and c) the stability of the RNA molecules. While previous studies have addressed each of these factors, all three have not been addressed in a single approach. The present invention utilizes AS sequences substituted for nucleotide sequences in the U1 and other hnRNAs to achieve high nuclear concentrations of stable antisense RNA sequences.

U1, U2 and other snRNAs are nuclear-localized RNA molecules complexed with protein molecules. (Dahlberg and Lund 1988 in Structure and Function of Major and Minor Small Nuclear Ribonucleoprotein Particles, M. Birnstiel, Ed., Springer Verlag, Heidelberg, p 38: Zieve and Sautereau 1990 Biochemistry and Molecular Biology 25; 1, all of which are incorporated herein by reference).

The various promoters for U1, U2 and other snRNA operons are very strong and produce large amounts of RNA. U1 and other snRNAs have signals for export to the cytoplasm where specific proteins are complexed before reimportation to the cytoplasm as snRNPs (FIG. 41). snRNAs are very stable molecules. They form very highly ordered stem and loop structures (FIG. 43) which, when complexed with specific proteins, form snRNP, or splicesomes.

Antisense and other nucleic acid molecules which affect gene expression by acting on and altering RNA transcripts can derive certain advantages by confinement to the nucleus. Higher concentrations can be maintained in the smaller volume of the nucleus, interactions with target RNA can occur prior to their being used for expression and there would be no competition with messenger binding ribosomes.

Addition of antisense sequence to U2 RNA (Izant and Sardelli 1988 in Current Communications in Molecular Biology, Cold Spring Harbor, p 141, incorporated herein by reference) as a means of delivering antisense sequences altered the properties of normal U2 transcripts. Hybrid U2 molecules formed by insertion of antisense sequences into a restriction site in the 5' end of the U2 transcript region showed decreasing antisense effectiveness with increasing insert size. Inserts longer than 250 bases substantially reduced antisense effectiveness. Furthermore, hybrids did not accumulate in the nucleus as efficiently as their wild type counterparts with the fraction of hybrids in the nucleus decreasing as insert length increased.

Yu and Weiner (1988 in Current Communications in Molecular Biology, Cold Spring Harbor, p 141, contents incorporated by reference) substituted 9 base antisense sequences directed at target sequences surrounding splice sites in mRNA. The antisense substitutions were made at the 5'end of U1 RNA. None of the antisense substitutions affected the level of targeted species of mature cytoplasmic RNA.

Constructs have been designed to increase antisense effectiveness by the inclusion of more than one targeting element in a single transcriptional unit. Multivalent constructs prepared in this way can produce numerous target directed entities acting on multiple target sites in nucleic acids. (Chen et al. 1992 in Antisense Strategies, Annals of the New York Academy of Sciences 660; 271: Zhow et al. Gene 1994 149; 33, both publications incorporated herein by reference). Different approaches to inhibition can be incorporated into a multivalent transcript as shown by Lisziewicz et al. (1993 Proc Natl Acad Sci USA 90, 8000, also incorporated by reference) who combined multiple copies of the HIV TAR with an antisense sequence to HIV gag on the same transcript.

The use of multivalent targeting by the inclusion of more than one targeting element on the same transcript provides a method for counteracting the high mutation rate of viruses such as HIV due to the unlikely event of simultaneous mutation of multiple target sequences. However, the common means of accomplishing these designs is the inclusion of the product entities on a single transcript. This approach suffers from the following limitations:

a) The total number of RNA molecules available as effective entities is limited by the strength of the single promoter;

b) During stable transformation of a cell, the integration event can disrupt the nucleic acid template sequence responsible for expression of the antisense sequence;

c) The use of multivalent transcripts is not favorable when one product entity present on the transcript acts on targets present in one cellular locale and another product entity present on the same multivalent transcript acts on targets present in a different cellular locale. This was the approach reported by Lisziewicz et al. (1993) where multiple TAR sequences, which act to bind the HIV tat protein in the cytoplasm, were present on the same transcript with antisense sequences for the HIV gag RNA, which are most effective in the nucleus.

Although there have been major efforts to find effective antiviral treatments, at the present time the only success has been in a diminution of virus growth rather than elimination of the virus. Among the efforts that have been pursued are attempts to prevent initiation of the virus replication cycle by preventing the virus from entering the cell by immunization or by treatment with antibodies or with proteins that interfere with virus recognition of a cell by interacting with the virus or the virus receptor site on the cell. These include unsuccessful treatment with high levels of soluble CD4 (Husson et al., 1992, incorporated by reference). In addition, efforts have been made to combat HIV infection after virus entry into a cell using protease inhibitors for preventing processing of viral polypeptides into functional proteins and varied nucleoside analogues which can block replication of the virus by inhibiting the activity of the virally encoded reverse transcriptase and other functions necessary for virus propagation. Stages of the processes of viral infection and viral replication cycle have been examined for the possibility of pharmacological or immunological intervention of the disease process. However, as independent and effective therapeutic agents, both immunological and small molecule inhibitors have failed to stem the progression of AIDS, and major problems remain in terms of effectiveness and the rise of viruses resistant to small molecule therapeutic agents. Even the application of combinations of immunological and small molecule agents has not been successful.

The introduction of genetic information into cells either to replace a function or to introduce a new function has provided an effective means for the treatment of viral infection. Genetic therapy approaches have been used to impart cell resistance to viruses by mechanisms which act intracellularly on the viral replication process (see Yu et al., Gene Therapy 1, 13-16 [1994, incorporated by reference). A result of these studies is that, in vitro, the effectiveness of genetic therapies is sensitive to virus concentration. Experiments in vitro that showed substantial levels of resistance at low ratios of virus to cells, at higher ratios showed a "breakthrough" phenomenon characterized by a period of seeming effectiveness followed by a surge in the virus production (Sczakiel et al. 1992 J. Virol 66; 5576: Scakiel and Pawlita 1990 J. Virol. 65; 468, all of which are incorporated by reference). Thus in vitro, at lower virus:cell ratios some genetically treated cells demonstrate longer survival times that at higher virus:cell ratios.

Compartmentalization of function is critical to regulated processes in eucaryotic cells. For example, the major part of cellular DNA is organized into chromosomes located in the nucleus where transcription of genetic information takes place. The major part of RNA synthesized in the nucleus is transported to the cytoplasm where it is translated. Other subcellular compartments for localized function include the Golgi apparatus, endoplasmic reticulum, nucleolus, mitochondria, chloroplast and the cellular membrane. Thus, a variety of mechanisms exist either to retain macromolecules in specific cellular compartments or to transport macromolecules from one cellular compartment to another. For example, in the directed exit of mature mRNA out of the nucleus into the cytoplasm, the presence of a 5' cap, removal of introns and addition of a poly A sequence are all believed to contribute to the signal that directs the relocation (reference).

Some RNAs, such as small nuclear RNAs (snRNAs) involved in splicesome assembly, are relocated by sequential transportation (Dahlberg and Lund, 1988, in Structure and Function of Major and Minor Small Ribonuclear Particles, M. Birnstiel, ed., Springer Verlag, Heidelberg, pg. 38, incorporated by reference). After transcription in the nucleus, the presence of the 5' cap and the processed 3' terminus generate a bipartite signal for transport of U1 RNA into the cytoplasm. At this point there is further processing of the RNA by excision of a few nucleotides and hypermethylation of the 5' cap. The binding of splicesome proteins present in the cytoplasm to the Sm region of the U1 RNA in combination with the hypermethylation is believed to generate a signal for the reimportation of the RNA back into the nucleus.

In contrast to most mRNA, most proteins do not need to be transported from their site of synthesis in the cytoplasm. However, some proteins that function in transcription, replication or other nuclear maintenance functions need to be present in the nucleus to function properly. In this case a polypeptide signal sequence present in the protein directs the transport of the protein from the cytoplasm into the nucleus. Still other proteins are not functional in the cytoplasm or in the nucleus but are required to be present in the membrane of the cell thereby requiring the presence of leader and lipophilic sequences.

The directing of target molecules as an approach to genetic therapy has been studied by attempts at localization for the express purpose of putting an active agent such as antisense RNA in proximity to the target in a particular cellular locale For example, some workers have designed nucleic acid constructs to express anti-sense RNA that would be retained in the nucleus in order to block newly transcribed target RNA from functioning (Izant and Sardelli, 1988, Current Communications in Molecular Biology, D. Melton, ed., Cold Spring Harbor Laboratory; Cotten and Birnstiel, 1989, EMBO Journal 8, 3861, incorporated by reference). The opposite effect has also been achieved by designing the transcript to include a signal for enhancing transport into the cytoplasm in order to block the translation of RNA that may be present there (Liszeiwicz et al. 1993, incorporated by reference).

SUMMARY OF THE INVENTION

The present invention overcomes the above-described limitations in the prior art by providing compositions which retain their biological function within cells or biological systems containing such cells upon chemical modification which may add further useful biological functions in addition to those which are retained.

The present invention relates to nucleic acid constructs capable of biological function and processing within a cell. These constructs may contain chemically modified biological or synthetic compounds. These constructs retain their biological function within a cell, but may also be able to exhibit additional properties by virtue of the chemical modification. The constructs combine chemical modifications and biological functions integrated within the construct.

The invention relates to novel constructs that have either incorporated unique biological elements or have incorporated chemical entities that introduce new properties to the construct, or both.

Unique biological elements are either synthetic, non-native heterologous or artificial elements in the construct that when in the cell provide novel capabilities (non-native) or novel products (artificial). Novel capabilities are provided by but are not limited to the introduction of such elements as heterologous processing elements that allow the construct to function in compatable cells, signaling elements for localization within the cell and multi-independent production cassettes.

Chemical modifications provide added characteristics to the constructs without interfering substantially with its biological function. Such added characteristics can be, but are not limited to nuclease resistance, the capability of targeting specific cells or specific receptors on cells, the capability of localization to specific sites within a cell, or the ability to enhance the interaction between the construct (or virus or vector) and the target cell in a general manner or too prevent or interfere with such interaction when desired.

The invention combines biological elements and chemical modification either to create a construct that defines its function, its location within a cell and its fate, or to modulate the interaction of the virus, vector or construct and cell prior to the entry of the virus, vector or construct into the cell.

Furthermore, the present invention relates to methods and constructs that provide for general interactions between target cells and a nucleic acid entity and compositions of multimeric complexes useful in vivo and in vitro.

Among the compositions provided by this invention is a construct which when present in a cell produces a product. The construct comprises at least one modified nucleotide, a nucleotide analog or a non-nucleic acid entity, or a combination of any of the foregoing. Another composition is a construct bound non-ionically to an entity comprising a chemical modification or a ligand. When present in a cell, such a construct produces a product. Another composition provided by this invention is a construct bound non-ionically to an entity comprising a chemical modification or a ligand. When present in a cell, such a construct also produces a product.

This invention provides a composition comprising (a) a non-natural entity which comprises at least one domain to a nucleic acid component; and at least one domain to a cell of interest; and optionally, (b) the nucleic acid component, and optionally, (c) the cell of interest, or both (b) and (c). In this composition, the domain or domains to the nucleic acid component are different from the domain or domains to the cell. A kit is provided for introducing a nucleic acid component into a cell of interest. This kit comprises in packaged containers or combination one element and three optional elements. The first element is a non-natural entity which comprises at least one domain to the nucleic acid component, and a domain to the cell of interest. Optional elements include the nucleic acid component, the cell of interest, and buffers and instructions.

Another composition provided by this invention comprises an entity which comprises at least one domain to a cell of interest, such domain or domains being attached to a nucleic acid component which is in non-double stranded form. A kit is also provided for introducing a nucleic acid component into a cell of interest. The kit comprises in packaged containers or combination an entity which comprises a domain to the cell of interest, the domain being attached to a nucleic acid component which is in non-double stranded form. Optionally provided are buffers and instructions.

Also provided is a composition comprising an entity which comprises a domain to a nucleic acid component, the domain being attached to a cell of interest. A kit is provided for introducing a nucleic acid component into a cell of interest. In packaged containers or combination, the kit comprises an entity which comprises a domain to the nucleic acid component, the domain being attached to the cell of interest. Buffers and instructions may also be optionally included.

Further provided is a multimeric complex composition comprising more than one monomeric unit attached by means of one or more interactions. Thus, the monomeric units may be attached to each other through polymeric interactions, or to a binding matrix through polymeric interactions, or a combination of both kinds of interactions.

Also provided is a multimeric composition comprising more than one component attached to a charged polymer. In this composition, the charged polymer is selected from a polycationic polymer, a polyionic polymer, a polynucleotide, a modified polynucleotide and a polynucleotide analog, or any combination of the foregoing elements.

The present invention provides a nucleic acid construct which when introduced into a cell codes for and expresses a non-native polymerase. The non-native polymerase is capable of producing more than one copy of a nucleic acid sequence from the construct. Also provided is a nucleic acid construct which when introduced into a cell produces a nucleic acid product comprising a non-native processing element. When contained in a compatible cell, the processing element is substantially removed during processing.

This invention also provides a process for selectively expressing a nucleic acid product in a cell, the product requires processing for functioning. The process comprises first, providing a nucleic acid construct which when introduced into a cell produces a nucleic acid product comprising a non-native processing element, which is substantially removed during processing when contained in a compatible cell, and second, introducing the construct into the cell.

Another composition comprises a primary nucleic acid component which upon introduction into a cell produces a secondary nucleic acid component which is capable of producing a nucleic acid product, or a tertiary nucleic acid component, or both. Neither the secondary nucleic acid component, the tertiary nucleic acid component, nor the nucleic acid product are capable of producing the primary nucleic acid component.

Also provided herein is a process for localizing a nucleic acid product in a eukaryotic cell. This localizing process comprises first, providing a composition of matter comprising a nucleic acid component which when present in a cell produces a non-natural nucleic acid product. The non-natural nucleic acid product comprises a portion of a localizing entity, and a nucleic acid sequence of interest. In the second step of the process, the composition is introduced into a eukaryotic cell or into a biological system containing a eukaryotic cell.

Additionally provided by this invention is a nucleic acid component which upon introduction into a cell is capable of producing more than one specific nucleic acid sequence. Each such specific sequence so produced is substantially nonhomologous with each other and are either complementary with a specific portion of a single-stranded nucleic acid of interest in a cell or capable of binding to a specific protein of interest in a cell.

This invention further provides a process for increasing cellular resistance to a virus of interest. The process comprises first, providing transformed cells phenotypically resistant to the virus; and a reagent capable of binding to the virus or to a virus-specific site on the cells. Second, the process comprises administering the aforementioned reagent to a biological system containing the cells to increase the resistance of the cells to the virus of interest.

Further provided is a nucleic acid construct which when introduced into a cell produces a non-natural product. The non-natural product comprises two components: first, a binding component capable of binding to a cellular component, and second, a localization component capable of dislocating the cellular component when it is bound to the non-natural product.

Also contemplated by the present invention is a process for dislocating a cellular component in a cell. Here, the process comprises, comprises first, providing a nucleic acid construct which when introduced into a cell produces a non-natural product, the product itself comprising two components: a binding component capable of binding to a cellular component, and a localization component capable of dislocating the cellular component when it is bound to the non-natural product. In the second step of the process, the nucleic acid construct is introduced into a cell of interest or a biological system containing the cell or cells of interest.

BRIEF DESCRIPTION OF THE DRAWINGS

FIG. 26 shows the oligomers (SEQ ID NOS 10-17, respectively, in order of appearance) and their products used for the synthesis of the SV40 intron containing T7 RNA polymerase coding sequence.

FIG. 27 depicts the process for the introduction of nucleotide sequences (SEQ ID NOS 10-11, 18-27, respectively, in order of appearance) for the nuclear localization signal.

FIG. 28 is a comparison of the 5' ends of the nucleotide sequence for the normal T7 RNA polymerase (SEQ ID NOS 28-29) and a T7 RNA polymerase with sequences inserted for a nuclear localization signal (SEQ ID NOS 30-31).

FIG. 30 shows the sequences for HIV antisense sequences (SEQ ID NOS 32-39, respectively, in order of appearance) and the process for their cloning into T7 directed transcription units.

FIGS. 34 AND 35 depicts the design of a primary nucleic acid construct that will function as a production center to generate single stranded antisense DNA.

FIG. 46 shows the final structures of the multiple operon constructs described in FIGS. 44 and 45.

FIG. 51 is a table of data demonstrating the effect of the HIV antisense sequence upon beta-galactosidase activity by enzyme assays as well as in situ assays.

DETAILED DESCRIPTION OF THE INVENTION

Definitions

Figure 1:
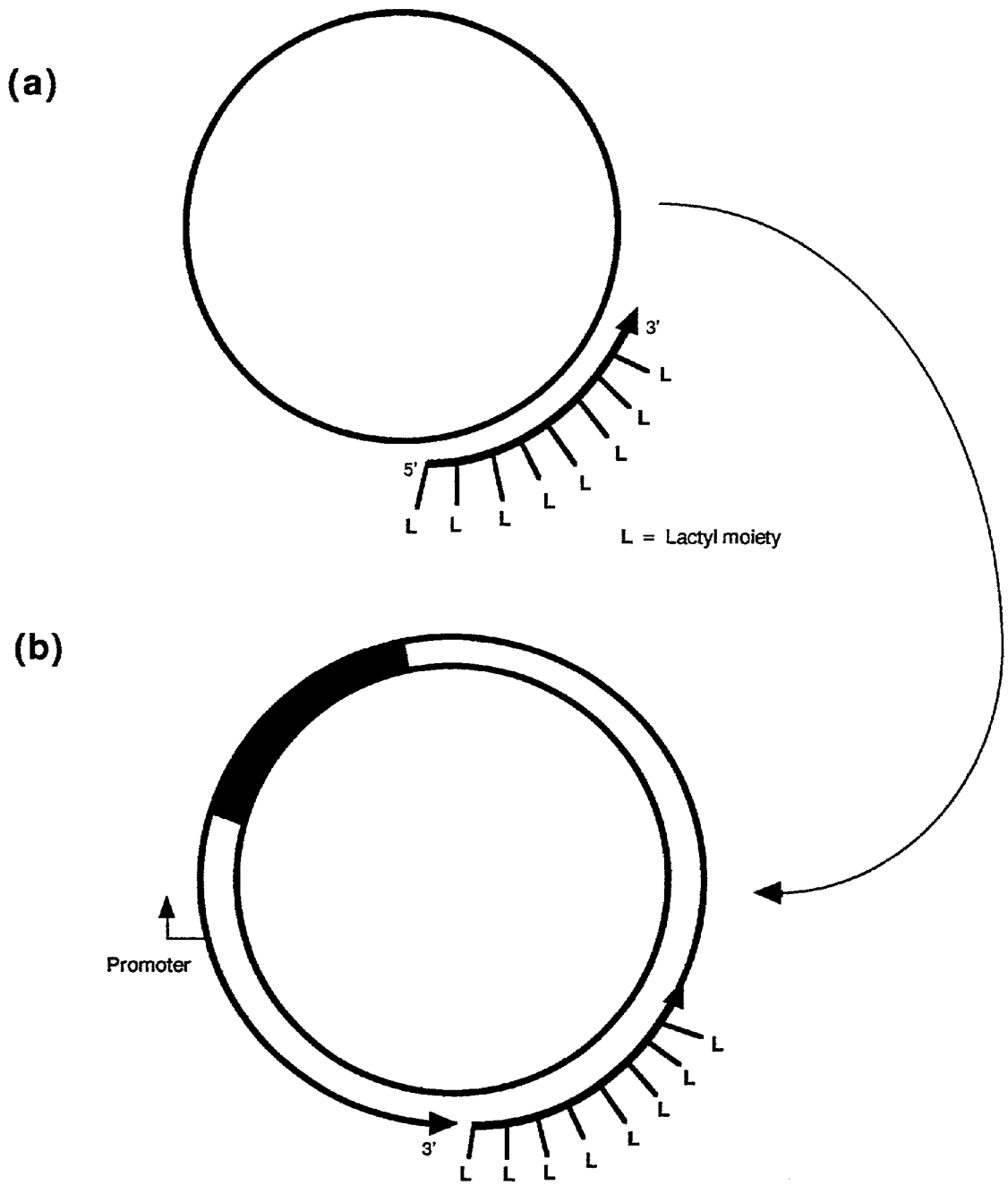
FIG. 1 depicts the localized attachment of ligands and other moieties to a nucleic acid construct by incorporation into a nucleic acid primer.

Some definitions for the terminology used in the art and/or in the present invention might be in order.

Primary Nucleic Acid Construct. A composition consisting of nucleic acid which in a cell propagates Production Centers.

Production Center. A nucleic acid molecule derived from a Primary Nucleic Acid Construct which in a cell is able to propagate other Production Centers or to produce single stranded nucleic acid.

Propagation. The generation or formation of a Production Center from a Primary Nucleic Acid Construct or the generation or formation of a Production Center from another Production Center.

Production. The generation of a single stranded nucleic molecules from a Production Center.

Inherent Cellular Systems. Cellular processes and components present in cells which can be utilized for the Production and Propagation as well as the function of single stranded Nucleic Acid Products. Such processes and components can be native to the cell, or be introduced to the cell by artificial means or by infection by, for example, a virus.

1. Gene Transfer Mediated by Ligands

The present invention is a defined chemically modified nucleic acid construct (CHENAC) which, upon introduction into a cell, is capable of biological function, i.e., production of a nucleic acid, production of a protein in a cell or interaction with a nucleic acid or protein in a cell. The said chemical modification directly or indirectly renders the construct capable of one or more of the following properties: a) binding to a target cell b) nuclease resistance c) providing a mechanism for introduction of the nucleic acid into cells d) providing nuclease resistance within the cytoplasm e) facilitating transfer of the nucleic acid from the cytoplasm to the nucleus f) providing a longer lifetime within the cell g) providing a signal for integration into cellular DNA. In the present invention, one or more of the above properties is capable of being provided without substantially interfering with the biological function of said nucleic acid. The present invention uses chemical modification of nucleic acid to attach directly or indirectly one or more ligands or chemical modifications or other moieties to a nucleic acid construct. A construct modified by the addition of ligands or chemical modifications could further complex with other moieties, those moieties being natural or unnatural, modified or unmodified oligo- or polypeptides; polycations; natural or unnatural, modified or unmodified oligo- or polysaccharides; multimolecular complexes; inactivated viruses; and any chemical binding, attachment or conjugation capable of complexing with the ligand or chemical moiety. The Modified Nucleic Acid Constructs of the present invention provide for the delivery of nucleic acid to eucaryotic cells including the cells of plants, humans and other mammals and to procaryotic cells.

The present invention provides the capability to localize chemical modifications to regions of the CHENAC. This permits construction of compositions in which the segment of the CHENAC responsible for the biological function can be segregated from modified region(s) responsible for the properties listed above in cases where the addition of ligands or chemical modifications could be disruptive to biological function. In cases where ligands or chemical modifications can interfere with biological activity, chemically modified segments of the CHENAC could be segregated from the construct subsequent to introduction into the cell by displacement or loss of modified segments.

In one aspect, this invention provides a construct which when present in a cell produces a product, the construct comprising at least one modified nucleotide, a nucleotide analog and a non-nucleic acid entity, or a combination of the foregoing. The modified nucleotide may be chemically modified as described further below. When present in the construct, at least one of the nucleotide analog or analogs may also be modified either on the backbone or the side chain or on both positions. With respect to the non-nucleic acid entity this element may also be attached to a single strand or both strands of the construct when the latter is double stranded.

The non-nucleic acid entity or entities may take any number of diverse forms. These include natural polymers, synthetic polymers, natural ligands and synthetic ligands, as well as combinations of any and all of the foregoing. When the non-nucleic acid entity or entities take the form of a natural polymer, suitable members may be modified or unmodified. Natural polymers can be selected from a polypeptide, a protein, a polysaccharide, a fatty acid, and a fatty acid ester as well as any and all combinations of the foregoing.

When the present invention contemplates the use of a synthetic polymer for the non-nucleic acid entity or entities, homopolymers and heteropolymers may be employed. Such homopolymers and heteropolymers are in many ways preferred when they carry a net negative charge or a net positive charge.

It is significant that the above-described construct of the present invention can be designed to exhibit a further and additional biological activity which is usefully imparted by incorporating at least one or more modified nucleotides, nucleotide analogs, nucleic acid entities, ligands or a combination of any or all of these. Such biological activity may itself take a number of forms, including nuclease resistance, cell recognition, cell binding, and cellular (citoplasmic) or nuclear localization.

The nucleic acid of the CHENAC can be DNA, RNA, a combination of RNA and DNA, e.g., a DNA-RNA hybrid or a chimeric nucleic acid, such as a DNA-RNA chimera. The nucleic acid components of the CHENAC can be single-stranded or double-stranded. The nucleic acid component can be all or in part a modified nucleic acid or a nucleic acid analogue. Modified nucleic acids are polymers capable of binding to complementary regions of nulceic acids and which contain chemical modifications of the sugar, base or phosphate moieties.

Nucleic acid analogues are polymers capable of binding to a complementary nucleic acid and in which these polymer backbones are other than ribo- and deoxyribose sugars and phosphate groups or in which side chain groups are other than natural or modified bases. Examples of nucleic acid analogue polymers include peptide nucleic acids or which have side chains containing such non-discriminatory base analogues, or universal bases, as 1-(2'-deoxy-β-D-ribofuranosyl)-3-nitropyrrole (Nichols et al. 1994 Nature 369; 492,) or 2'-deoxynebularine and 2'-deoxyxanthosine (Eritja et al. 1986 Nucleic Acids Research 14; 8135), both publications being incorporated herein by reference.

Modified nucleic acids, nucleic acid analogues and other polymers with a net negative charge and/or a functional amino group(s) may facilitate the practice of this invention, since these properties provide for solubility, specificity, enzyme function and binding. It may be preferred that some of the functional sequences of nucleic acid may be natural or modified nucleic acid sequences such as promoter sequences, terminator sequences or priming binding sequences.

Figure 3:
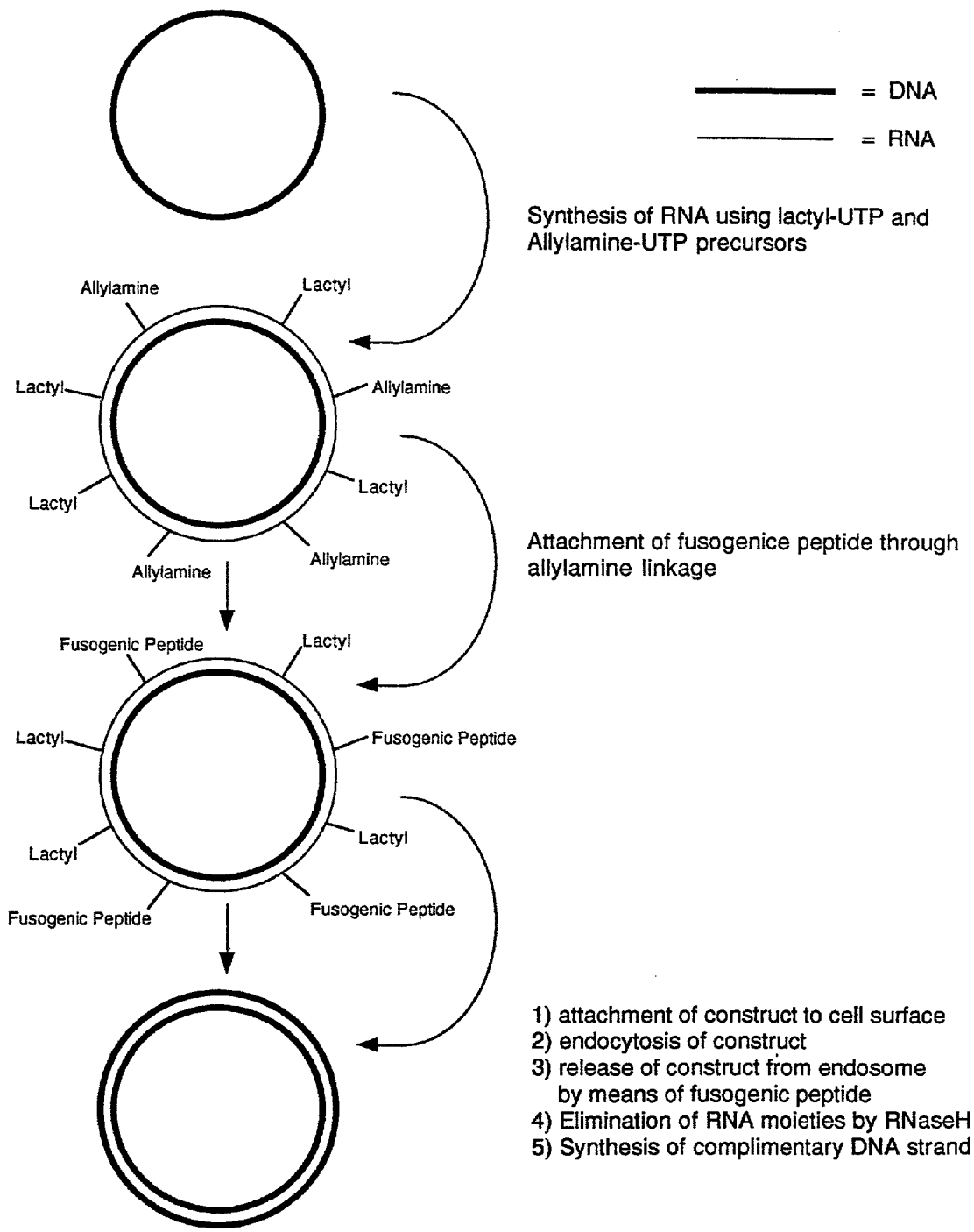
FIG. 3 illustrates the dispersed attachment of ligands to a nucleic acid construct by synthesis of a complementary RNA strand that utilizes modified ribonucleotide precursors.

The nucleic acid component of the CHENAC can be single stranded, double stranded, partially double stranded or even triple stranded. Further, such component can be circular or linear or branched, and may take the form of any DNA or RNA. It can contain both double stranded and single stranded regions and it can contain an non-complementary region, e.g., a tail. Such a tail region could further be bound to complementary nucleic acid. For example, single stranded nucleic acid can be present as one or more regions of single stranded DNA as a gap between otherwise continuous double stranded structure (see FIG. 3, Gap 2). Alternatively, linear single stranded nucleic acid can be present as tails, or linear single stranded nucleic acids in which one end is bound to the CHENAC and the other end is free (See FIGS. 4 and 6a). Gaps and tails can be single stranded RNA or DNA or a variety of other polymers both natural and synthetic, including modified nucleic acids, nucleic acid analogues, polysaccharides, proteins and other natural and synthetic polymers. Such single stranded regions can serve as a means to segregate biological function from other functions and as regions of complementarity for the binding of nucleic acids (as in Example 6b).

The nucleic acid components can contain one or more nicks in which 3'-5' phosphodiester linkage between constituent bases is disrupted (See FIGS. 1b and 2b)

Ligands or chemical modifications can be attached to the nucleic acid, modified nucleic acid or nucleic acid analogue by modification of the sugar, base and phosphate moeities of the constituent nucleotides (Engelhardt et al., U.S. Pat. No. 5,260,433, fully incorporated herein by reference) or to a non nucleic acid segment of the CHENAC such as polysaccharide, polypeptide and other polymers both natural and synthetic. Modifications of sugar and phosphate moieties can be preferred sites for terminal binding of ligands or chemical modifications and other moieties. Modifications of the base moieties can be utilized for both internal or terminal binding of ligands or chemical modifications and other moieties. Modifications which are non-disruptive for biological function such as specific modifications at the 5 positions of pyrimidines (Ward et al. U.S. Pat. No. 4,711,955, and related divisionals) and the 8 and 7 positions of purines (Engelhardt et al., U.S. Pat. No. 5,241,060 and related divisionals; Stavrianopoulos, U.S. Pat. No. 4,707,440 and related divisionals) may be preferred. The contents of each of the aforementioned U.S. patents and their related divisionals are incorporated herein by reference.

Chemical modification can be limited to a specific segment of the construct such as a tail or a gap, or dispersed throughout the CHENAC. Thus, the construct may contain at least one terminus, such a terminus comprising, for example, a polynucleotide tail. Such a modified nucleic acid, subsequently introduced into a cell, could be displaced and/or replaced.

In a further embodiment the present invention provides the construct, described above, further comprising at least one ligand attached covalently or noncovalently to one or more of the modified nucleotide analogs, nonnucleic acid entities (or combinations of the foregoing). Such ligands and chemical modifications can be added directly to the CHENAC through covalent and non-covalent interactions. Covalent additions can be made by chemical methods (Engelhardt et al.) and enzymatic incorporation. Non-covalent additions can be made through nucleic acid-nucleic acid interaction, antigen-antibody interaction, hydrophobic interaction and other interactions based on nucleic acid sequence, nucleic acid structure, protein structure. Indirect additions to the CHENAC can be made by these same methods and interactions. When included in the present invention, such ligand or ligands are attached to any portion or any form of the present construct. Thus the ligand or ligands can be attached to a single stranded segment, a double stranded segment, a single stranded construct tail, a sequence complementary to a construct tail or to any combinations of these portions or forms.

Ligands or chemical modifications, being any chemical entity, natural or synthetic, which can be utilized in this invention include macromolecules greater than 20,000 m.w. as well as small molecules less that 20,000 m.w. The ligand or ligands can include both macromolecules and small molecules. Macromolecules which can be utilized include a variety of natural and synthetic polymers including peptides and proteins, nucleic acids, polysaccharides, lipids, synthetic polymers including polyanions, polycations, and mixed polymers. Small molecules include oligopeptides, oligonucleotides, monosaccharides, oligosaccharides and synthetic polymers including polyanions, polycations, lipids and mixed polymers. Small molecules include mononucleotides, oligonucleotides, oligopeptides, oligosaccharides, monosaccharides, lipids, sugars, and other natural and synthetic entities.

Ligands and chemical modifications provide useful properties for nucleic acid transfer such as 1) cell targeting entities, 2) entities which facilitate cellular uptake, 3) entities specifying intracellular localization, 4) entities which facilitate incorporation into cellular nucleic acid and 5) entities which impart nuclease resistance.

1) Cell targeting entities which can be utilized include:
   a) antibodies to cellular surface components and epitopes
   b) viruses, virus components or fragments of virus components which have affinity for cellular surface components. These include such proteins as the gp120 protein of HIV which binds to the CD4 receptor of T4 lymphocytes (Lever 1995 British Medical Bulletin 51; 149, incorporated herein by reference).
   c) ligands which have affinity for cell surfaces. These include hormones, lectins, proteins, oligosaccharides and polysaccharides. Asialoorosomucoid, for example, binds to the cellular asialoglycoprotein receptor (Wu et al. 1989 J Biol Chem 269; 1698 5, incorporated herein by reference) and transferrin binds to transferrin cellular receptors (Wagner et al. 1992 89; 6099, also incorporated herein by reference).
   d) polycations such as polylysine that bind nonspecifically to cell surfaces (Wu and Wu)
   e) Matrix proteins such as fibronectin that bind to hematopoietic cells and other cells (Ruoslahti et al. 1981 J. Biol. Chem. 256; 7277, incorporated by reference),
   f) lectins which bind to cell surface components.

Entities which facilitate cellular uptake include inactivated viruses such as adenovirus (Cristiano et al. 1993 Proc Natl Acad Sci USA 90; 2122; Curiel et al. 1991 Proc Natl Acad Sci USA 88; 8850, all of which are incorporated by reference); virus components such as the hemaglutinating protein of influenza virus and a peptide fragment from it, the hemagglutinin HA-2 N-terminal fusogenic peptide (Wagner et al. 1992 Proc Natl Acal USA 89; 7934, also incorporated herein by reference).

Entities which specify cellular location include:
   a) nuclear proteins such as histones
   b) nucleic acid species such as the snRNAs U1 and U2 which associate with cytoplasmic proteins and localize in the nucleus (Zieve and Sautereauj 1990 Biochemistry and Molecular Biology 25; 1, incorporated by reference)

4) entities which facilitate incorporation into cellular nucleic acid include:
   a) proteins which function in integration of nucleic acid into DNA. These include integrase site specific recombinases (Argos et al. 1986 EMBO Journ 5; 433, incorporated by reference); and
   b) homologous nucleotide sequences to cellular DNA to promote site specific integration.

5) Entities which impart nuclease resistance modifications of constituent nucleotides including addition of halogen atoms groups to the 2' position of deoxynucleotide sugars. (Braket et al., U.S. patent application Ser. No. 07/446,235, filed on Dec. 4, 1989, incorporated by reference).

Ligands or chemical modifications can be introduced into CHENACs either a) directly by conjugation, b) by enzymatic incorporation of modified nucleoside triphosphates c) by reaction with reactive groups present in constituent nucleotides and d) by incorporation of modified segments. These processes include both chemical and enzymatic methods. Enzymatic methods include primer extension, RNA and DNA ligation, random priming (Kessler et al. 1990 Advances in Mutagenic Research, Vol. 1, Springer Verlag, pp 105-152), nick translation (Rigby et al., 1977, J. Mol. Biol. 113, 237), polymerase chain reaction (Saiki et al., 1985 Science 239, 487), RNA labeling methods utilizing T7, T3 and SP6 polymerases, (Melton et al. 1984 Nucleic Acids Research 12, 7035; Morris et al. 1986 Gene 41, 193), terminal addition by terminal transferase (Roychoudhury et al. 1979 Nucleic Acids Research 6, 1323). Chemical methods (described in Kricka, 1995 Nonisotopic Probing, Blotting and Sequencing, Academic Press) include direct attachment of ligands or chemical modifications to activated groups in the nucleic acid such as allylamine, bromo, thio and amino; incorporation of chemically modified nucleotides during chemical synthesis of nucleic acid (Cook et al. 1988 Nucleic Acids Research 16, 4077; Stavrianopoulos U.S. Pat. No. 4,707,440 and related divisionals), chemical end labeling (Agrawal et al. 1986 Nucleic Acids Research 14, 6777); labelling of nucleic acid with enzymes (Jablonski et al., 1986 Nucleic Acids Research 14, 6115). All of the above-listed publications and U.S. patent are herein incorporated by reference.

CHENACs can be prepared by the incorporation of nucleic acid segments modified by ligands or chemical modifications. Constructs can also be prepared by the incorporation of unmodified nucleic acid segments together with other segments. Segments incorporated into constructs can be single stranded or double stranded or composed of both single and double stranded regions. Such segments can be composed of DNA, RNA, a combination of DNA and RNA, or chimeric nucleic acids. All or part of a segment can be composed of modified nucleic acid or nucleic acid analogue. All or part of a segment can contain natural or synthetic polymers. A segment can be prepared by any of the chemical methods and enzymatic methods listed above.

The present invention provides for choice of localization of ligands or chemical modifications. In order that such ligands or chemical modifications do not interfere with biological activity segments with biological activity can be isolated from modified segments in the CHENAC. Also, modifications can be confined to a region of a segment. For example, a specific primer labeled with Ligands or chemical modifications of choice can be hybridized to a defined region of the construct, and polymerization can be done in the presence unmodified nucleotides in order to confine the ligands or chemical modifications to a defined area of the primer. Alternatively, an unmodified primer can be used to synthesize in the presence of modified nucleotides to confine the ligands or chemical modifications to the non-primer region of the strand. Alternatively, by using a primer containing ligands or chemical modifications, labeling can done be throughout the strand or through complementarity to a tail.

Regions of biological activity in constructs can specify coding for RNA (such as antisense RNA or ribozymes as described in this patent, Example 26) or for RNA which in translated into protein or for DNA. Regions of biological activity in CHENACs can contain sequences for hybridization with intracellular nucleic acid sequences, integration into cellular DNA, termination sequences, primer sites, promoter sites and processing signals and sequences.

In one preferred embodiment the construct of the present invention carries a net positive charge or a net negative charge. Further, the construct can be neutral or even hydrophobic. It should not be overlooked that the construct may comprise unmodified nucleotides and at least one other member or element selected from one or more nucleotide analogs and non-nucleic acid entities, or both.

Another significant embodiment of the present invention is a construct which when present in a cell produces a product, the construct being bound non-ionically to an entity comprising either a chemical modification or a ligand addition, or both. As in the case of the other above-described construct, this construct may also comprise at least one terminus, such terminus comprising a polynucleotide tail. The polynucleotide tail is hybridizable or hybridized to a complementary polynucleotide sequence. An antibody to a double stranded nucleic acid can be directed and thus bound to such hybridized polynucleotide tail sequences. The antibody can comprise a polyclonal antibody or a monoclonal antibody.

2. Universal Gene Delivery

Other useful terms and definitions include the following:

Nucleic Acid Component: a compound or composition in a cell capable of producing a product. The composition comprises a nucleic acid sequence desired to be delivered to a cell including polynucleotide, modified nucleic acid and nucleic acid analogues which can be single stranded or double stranded RNA or DNA, RNA/DNA hybrid molecules and chimeric nucleic acids; nucleic acid construct and chemically modified nucleic acid constructs (See Examples 1 through 13); viruses including animal viruses such as adenovirus, adeno associated virus. retrovirus and plant viruses and bacteriophages; plasmids including the Ti plasmid; or plasmid derivatives that have encapsidated into viral particles by virtue of packaging signals. Nucleic Acid Components can be produced in vivo or assembled in vitro or produced chemically or produced by the techniques of recombinant DNA. The product produced from the Nucleic Acid Component in the cell could be a polynucleotide including mRNA, antisense RNA or DNA, ribozymes or it could be a protein or a protein product.

Domain: A Domain is an entity that has a segment that binds non covalently either to a cell or to a Nucleic Acid Component.

Binder: A Binder is a carrier or matrix that includes at least one Domain.

The present invention overcomes the limitations of prior art by providing a composition and method for universal and efficient nucleic acid transfer. The nucleic acid, whether in a virus vector, in a nucleic acid construct or as polynucleotide, can be introduce into a wide variety of cell types. Furthermore, the use of virus vectors in this invention is not limited to a specific or a unique viruses but a wide variety of virus vectors can be used. This invention is universal in two respects: 1) any Nucleic Acid Component can be applied either in vivo or in vitro and 2) any target cell can be used.

In the practice of this invention it is possible to:
1) bring into close proximity the Nucleic Acid Component and the target cell; and
2) provide specificity between the Nucleic Acid Component and the target cell.
3) enhance nucleic acid transfer to the cell by providing Competence Factors which enhance nucleic acid transfer through enhancing cell growth, cellular uptake of nucleic acid, cellular localization of nucleic acid and integration of nucleic into cellular DNA.

The present invention provides materials and methods for the delivery of nucleic acids to cells. The specificity and/or proximity are provided through an intermediate, a Binder which consists of at least one Domain. If the Binder has at least one Domain to the target cell, then the Binder is attached to a Nucleic Acid Component. If the Binder has at least one Domain to a Nucleic Acid Component, then the Binder is attached to a target cell. If the Binder has at least one Domain to both the Nucleic Acid Component and the target cell the Domain to the cell is different from the Domain to the Nucleic Acid Component.

One of the significant embodiments of the present invention is a composition comprising a non-natural entity which in turn comprises at least one domain to a nucleic acid component; and at least one domain to a cell of interest. The domain or domains to the nucleic acid component are different from the domain or domains to said cell. Optional elements may be added to this composition or non natural entity including the nucleic acid component, the cells of interest, or both such nucleic acid component and such cells.

The entity can, of course, comprise a binder. Further, the binder and the domain in the non natural entity can be the same or they can be different.

A Binder is a support or matrix that is composed of at least one Domain. A Binder can be natural or synthetic, such as a polymer, support, matrix or carrier (or combination of these). The binder comprises at least one Domain to a Nucleic Acid Component or to a cell of interest or to both. As such, the Binder can be a monofunctional or bifunctional entity. In the case of a monofunctional Binder, only one Domain is present, either to the Nucleic Acid Component or the cell of interest. In the case of a bifunctional binder, at least two domains are present, one to the Nucleic Acid Component and the other to the cell of interest. Where two domains are present in the binder, i.e., a bifunctional binder, the domain to the Nucleic Acid Component is different from the Domain to the cell of interest. In some cases Domains and Binders can be the same entity, such as an antibody that has a segment (an Fab region) that binds to an epitope and has an Fc segment that can function as a support for attachment.

A Domain is an entity that has a segment that binds either to a cell or to a Nucleic Acid Component. Domains can be natural or synthetic polymers including oligopeptides, polypeptides, oligosaccharides, polysaccharides, oligonucleotides and polynucleotides. These include monoclonal antibodies, polyclonal antibodies, polycations such as polyamines, ligands to cell surface proteins, extracellular matrix proteins and ligands and their binding partners. These can be produced in vivo or assembled in vitro or produced chemically or produced by recombinant DNA techniques.

Domains provide binding to cells or to NA Entities through specific or non-specific binding through a variety of interactions including nucleic acid-nucleic acid interaction, antigen-antibody interaction, receptor-ligand interaction, hydrophobic interaction, polyionic interaction and other interactions based on nucleic acid specificity, nucleic acid sequence and proteins capable of specifically binding to such sequences or secondary structures or combinations thereof. Interactions between ligand binding pairs and between complementary nucleic acid sequences may be preferred for the application of this invention. These include a nucleotide sequence recognized by a complementary sequence, an antigen by an antibody, a lectin recognized by its cognate sugar, a hormone recognized by its receptor, an inhibitor recognized by an enzyme, a cofactor recognized by its cofactor enzyme binding site, a binding ligand recognized by its substrate and combinations of the foregoing.

Antibodies provide useful Domains. Monoclonal and polyclonal antibodies and fragments of these can be used. Antibodies can be obtained from sera, from hybridomas and by recombinant DNA methods. Bispecific antibodies which have the capability to bind to two different epitopes can also be useful. These can be hybrid hybridomas (Staerz and Bevan 1986 Proc Natl Acad Sci USA 83; 1453), heteroantibodies produced by chemical conjugation of antibodies, or fragments of antibodies, of different specificities (Fanger et al. 1992 Critical Rev Immunol. 12; 101), bispecific single chain antibodies (Gruber et al. 1994 Journ Immunol 152; 5368) produced by genetic engineering and diabodies (Holliger et al. 1993 Proc Natl Acad Sci USA 90; 6444) produced by genetic engineering. All of the foregoing publications are incorporated herein by reference.

Useful Domains with non-specific cell binding properties include molecules with polyionic properties such as polycations including polylysine, protamine, histones or segments or fragments thereof.

Useful Domains with specific cell binding properties include:

1) those with binding affinity for a natural cell component, epitope or ligand. Such cell binding domains include ligands specific to cell receptors such as hormones, mono- and oligosaccharides, viral proteins which recognize cell receptor sites, extracellular matrix proteins such as fibronectin and fragments thereof, antibodies to cell proteins and fragments thereof.
2) those with binding affinity for a non-naturally introduced ligand where a) the ligand is attached to a cell by chemical means such as by reaction with a tyrosine or amino group of a cellular surface protein or b) the ligand is indirectly attached to a cell non-specifically.

Useful Domains with non-specific Nucleic Acid Component binding properties include those which bind non-covalently and not through a ligand/receptor system. Examples are polycations such as polylysine and histones that bind to nucleic acid.

Useful Domains with specific Nucleic Acid Component binding properties include:

1) those with binding affinity for a natural component of a Nucleic Acid Component, epitope or ligand. These include:
   a) antibodies to nucleic acid including antibodies to double stranded and single stranded DNA, to double and single stranded RNA or to RNA/DNA hybrids; proteins with nucleic acid binding properties such as the Cro protein of bacteriophage lambda which binds to a sequence of 17 base pairs (Anderson et al. 1981 Nature 290; 754, incorporated by reference).
   b) antibodies to an epitope or receptors for a ligand of a Nucleic Acid Component. These include antibodies to viral proteins, cellular receptors and virus binding proteins, such as the CD4 protein of lymphocytes.
2) artificial specific binding systems (Domains) can be formed by chemically introducing a ligand to the Nucleic Acid Component where said ligand has a corresponding receptor. Such specific ligands or epitopes can be artificially introduced by chemical modification of a tyrosine or amino group of, for example, a vector virus protein.

Binders possessing two Domains can exist naturally or they can be prepared synthetically or artificially. For example, a Binder which possesses one Domain with cell binding capabilities can be associated with a Domain with Nucleic Acid Component binding capabilities to form a bifunctional Binder. This association can occur by 1) by covalent attachment 2) by specific non-covalent attachment and 3) by non-specific non-covalent attachment or 4) as a fusion peptide prepared by recombinant DNA techniques.

In the above-described composition of this invention the nucleic acid component can take a number of different forms including a nucleic acid, a nucleic acid construct, a virus, a viral fragment, a viral vector, a viroid, a phage, a plasmid, a plasmid vector, a bacterium, and a bacterial fragment as well as combinations of these. The cell of interest can be prokaryotic or eukaryotic. As described elsewhere in this disclosure the domains can be attached noncovalently or through a binder or through combinations of these. Where noncovalent binding is used, ionic interactions and/or hydrophobic interactions are preferred. In addition the noncovalent binding can comprise a specific complex, e.g., a specific complex mediated by a ligand binding receptor. The ligand binding receptor can itself take a number of forms. Suitable but not necessarily limited to these members are a polynucleotide sequence to be recognized by its complementary sequence; an antigen to be recognized by its corresponding monoclonal or polyclonal antibody, an antibody to be recognized by its corresponding antigen; a lectin to be recognized by its corresponding sugar; a hormone to be recognized by its receptor; a receptor to be recognized by its hormone; an inhibitor to be recognized by its enzyme; an enzyme to be recognized by its inhibitor; a cofactor to be recognized by its cofactor enzyme binding site; a cofactor enzyme binding site to be recognized by its cofactor; a binding ligand to be recognized by its substrate; or a combination of the foregoing.

Another aspect of the present invention concerns the composition, described above, wherein the domain to the nucleic acid component and the domain to the cell of interest are natural, and the binder is attached to the nucleic acid component by means other than a natural binding site. Here, as in other embodiments, the binder can comprise modified fibronectin or modified polylysine or both.

Cells of interest containing or associated with the above-described compositions may be contained within a biological system, such as an organism.

Also provided are methods for introducing a nucleic acid component, as described above, into a cell. Essentially the method comprises providing any of the above-described compositions and administering these to an appropriate biological system. Administration can be carried out in vivo or ex vivo.

This invention also contemplates kits which are useful for introducing a nucleic acid component into a cell of interest. These kits comprise in packaged containers or combination a non-natural entity which comprises at least one domain to a nucleic acid component, and at least one domain to the cell of interest. Optionally included in such kits are the nucleic acid components, the cells of interest and buffers and instructions.

Another significant embodiment is a composition comprising an entity which comprises at least one domain to a cell of interest, wherein the domain or domains are attached to a nucleic acid component which is in non double stranded form. As elsewhere, the entity can comprise a binder, and the binder in the domain can be the same or they can be different. Among others the binder can comprise a polymer, a matrix, a support or a combination of these. The cell of interest can be prokaryotic or eukaryotic. As also described above, the nucleic acid component can take a number of forms including but not limited to a nucleic acid, a nucleic acid construct, nucleic acid conjugate, a virus, a viral fragment, a viral vector, a viroid, a phage, a plasmid, a plasmid vector, a bacterium, and a bacterial fragment or combinations of these. The domain can comprise covalent bonding or noncovalent binding, or both. Preferred as noncovalent binding are ionic interactions and hydrophobic interactions (or both), and a specific complex e.g., a specific complex mediated by a ligand binding receptor. Such ligand binding receptors have been described above. The cell of interest which is part of the composition may be contained within an organism. This last described composition can likewise be usefully employed in a method for introducing a nucleic acid component into a cell. This process has also been described above.

Kits for introducing a nucleic acid component into a cell of interest can be fashioned from this composition. Such a kit comprises in packaged containers or combinations an entity which comprises a domain to a cell of interest, wherein the domain is attached to a nucleic acid component which is in non-double stranded form. Buffers and instructions may be optionally included.

This invention also provides a composition comprising an entity which comprises a domain to a nucleic acid component wherein the domain is attached to a cell of interest. As further embodiments of this just described composition are the entity, the binder, the domain, nucleic acid component, the cell of interest, the covalent bonding and noncovalent binding of the domain, the ionic and hydrophobic interactions, the specific complex (including its mediation by a ligand binding receptor), the ligand binding receptor, as well as organisms, methods and kits for introducing nucleic acid components into cells containing the cell of interest are all as variously described above.

Attachment of Nucleic Acid Components to Monofunctional Binders

1) Covalent Attachment of a Nucleic Acid Component to a monofunctional Binder which Possesses a Domain to a Cell.

Covalent attachment can occur by direct coupling between reactive groups inherent to a Domain or Binder or by the use of a bifunctional crosslinker. Also, reactive groups can be introduced into Domains and Binders in order to facilitate such covalent attachment. Attachment to proteins, for example, can occur through reactive amino groups or tyrosine residues. Attachment can be made by protein-protein conjugation. Covalent attachment can also be made to polysaccharides and to polynucleotides. Covalent attachment to a nucleic acid, modified nucleic acid or nucleic acid analogue can be made through modification of the sugar, base or phosphate moieties of the constituent nucleotides (Engelhardt et al., U.S. Pat. No. 5,260,433, incorporated by reference). Also, nucleotide analogues can be introduced into nucleic acid to provide reactive groups, e.g., allylamine groups (Ward et al. U.S. Pat. No. 4,711,955 and divisionals, also incorporated herein by reference) and proteins can be covalently attached to these as described below using N-maleimido tri(aminocaproic) acid N-hydroxysuccinimide ester as a bifunctional coupler. Modifications of sugar and phosphate moieties can be preferred sites for terminal attachment of ligands and other moieties. Modifications of the base moieties can be utilized for both internal or terminal attachment of ligands and other moieties. Modifications can include those which are non-disruptive for hybridization such as specific modifications at the 5 positions of pyrimidines (Ward et al., U.S. Pat. No. 4,711,955 and related divisionals). Modifications of the 8 and 7 positions of purines (Englhardt et al. U.S. Pat. No. 5,241,060 and related divisionals) and Stavrianopoulos, U.S. Pat. No. 4,707,440 and related divisionals) may be preferred. In one embodiment, the chemical modification in the construct or construct components may be effected to a moiety independently selected from a base, a sugar, and a phosphate, or a combination of any or all three.

Direct covalent attachment of a Nucleic Acid Component to a Monofunctional Binder can be illustrated by attachment of a double stranded DNA molecule (the Nucleic Acid Component) to an antibody which binds to a cell surface component (a monofunctional Binder). For example, an antibody which binds to the CD4 component of lymphocytes can be covalently attached to a double stranded DNA (a Nucleic Acid Component) which has been modified by the incorporation of nucleotides containing allylamine in order to provide a primary amine as a reactive group. The covalent attachment can be made as described below using N-maleimido tri(aminocaproic) acid N-hydroxysuccinimide ester as a bifunctional coupler.

Fibronectin can also be used for the covalent attachment of a Nucleic Acid Component for delivery of nucleic acid to cells. For example, fibronectin, a fibronectin fragment or fibronectin containing compounds can be attached to either a polynucleotide or to a virus vector. For example, fibronectin can be covalently attached to an allylamine group of a Nucleic Acid Component. A virus vector Nucleic Acid Component, such as adenovirus, can also be covalently bound to fibronectin by protein-protein conjugation. The covalent attachment can be made as described below using N-maleimido tri(aminocaproic) acid N-hydroxysuccinimide ester.

2) Specific Non-Covalent Attachment of a Nucleic Acid Component to a Monofunctional Binder which Possesses a Domain to a Cell.

Non-covalent attachment of a Nucleic Acid Component can occur through complementary nucleic acid binding. A Binder composed of an antibody to a cell surface protein can be covalently coupled to a single stranded DNA by allylamine groups incorporated into the DNA as described below using N-maleimido triaminocaproic acid N-hydroxysuccinimide ester as a bifunctional coupler. The single stranded DNA is attached through complementarity to a tail sequence of a Nucleic Acid Component. For example, an antibody to a CD4 cell receptor can be covalently attached to a single stranded DNA molecule which is complementary to the single stranded tail of a construct (such as the one described in Example 6) to deliver nucleic acid to CD4+ cells.

Fibronectin can be modified to provide for the non-covalent attachment of a Nucleic Acid Component. Fibronectin can be covalently attached to an antibody which has binding specificity for a virus vector such as adenovirus. Fibronectin and anti-adenovirus antibody are covalently attached by the use N-maleimido tri(aminocaproic) acid N-hydroxysuccinimide ester as a bifunctional coupler as described below.

3) Non-Specific Non-Covalent Attachment of a Nucleic Acid Component to a Monofunctional Binder which Possesses a Domain to a Cell.

This can be achieved by the non-covalent attachment of a Domain, such as polylysine which binds to polynucleotides (Nucleic Acid Component). Polylysine can attach to a monofunctional Binder composed of a DNA oligomer modified by the covalent addition of trilactyl lysyl lysine (Domain to a cell) as described in Example 1 of this patent. The resulting entity can deliver nucleic acid specifically to liver cells.

Attachment of Cells to Monofunctional Binders with Domains to a Nucleic Acid Component.

1) Covalent Attachment of a Cell to a Monofunctional Binder which Possesses a Domain to a Nucleic Acid Component A Binder with a Domain for a Nucleic Acid Component can be covalently attached to a cell. For example, a monoclonal antibody to adenovirus can be covalently attached to a cell to provide adenovirus binding sites on the cell surface. Covalent attachment of the antibody can be made by the use of N-maleimido tri(aminocaproic) acid N-hydroxysuccinimide ester as a bifunctional coupler.

Synthesis of the bifunctional coupler and its use for covalent attachment of proteins is described. Tri(aminocaproic) acid is reacted with a threefold excess of 3-maleimidopropionic acid N-hydroxysuccinimide ester at a pH 7.8 for 30 minutes at room temperature. The pH is adjusted to 4.0 with acetic acid and the solution is freeze dried. The solid is triturated with ethanol to remove unreacted 3-maleimidopropionic acid active ester and traces of ethanol are removed in vacuum. The solid residue is dissolved in dimethylformamide and filtered from the insoluble salts and reacted with 1.1 equivalents of dicyclohexyl carbosuccinimide at room temperature overnight. The hydroxyurea is removed by filtration and the dimethylformamide is removed in high vacuum at 35° C. The semisolid residue is triturated with isopropanol to remove unreacted dicyclohexylcarbodiimide and N-hydroxysuccinimide. The solid residue is washed with absolute ether and the ether traces are removed by vacuum leaving N-maleimido tri(aminocaproic) acid N-hydroxysuccinimide ester (Compound 1).

Cells are treated with Ellman's reagent to block reversibly thiol groups on the cell surface. The amino groups on the cell surface are reacted with Compound I in isotonic phosphate buffer at pH 7.8 for 30 minutes. Excess Component I is removed by centrifugation of the cells at 1000×g at room temperature for 5 minutes and decanting the supernatant fluid. The cells are resuspended in phosphate buffered isotonic saline and reacted for one hour at room temperature with an antibody to which thiol groups have been added. Thiol groups are added to the antibody by reaction with homocysteine thiolactone at pH 9.0.

At the end of the reaction the cells are reacted with 0.5 mM cysteine in phosphate buffered saline to reconstitute any blocked thiol residues on the cell surface, and the cells are washed by centrifugation in phosphated buffered saline.

2) Specific Non-Covalent Attachment of a Cell to a Monofunctional Binder Which Possesses a Domain to a Nucleic Acid Component.

This can be accomplished by the covalent attachment of biotin to cell surface proteins using an N-hydroxysuccinimide ester of biotin (Enzotin, Enzo Biochem, Inc.). A binder composed of an antibody to adenovirus covalently attached (by the Fc portion) to avidin will bind to biotin molecules on the cell surface to provide adenovirus binding to the cell surface.

3) Non-Specific Non-Covalent Attachment of a Cell to a Monofunctional Binder With a Domain for a Nucleic Acid Component.

Polylysine can be covalently attached to the Fc portion of an antibody to adenovirus. The polylysine/anti-adenovirus antibody will bind to the cell surfaces to provide attachment sites for an adenovirus vector.

Binding of Cells to Nucleic Acid Components Through Bifunctional Binder Mediation Such bifunctional Binders can be formed by the attachment of two Domains either directly or through a binder or a matrix. The attachment can be covalent, non-covalent, non-specific non-covalent or specific non-covalent. Specific attachment of cells to Nucleic Acid Components can be accomplished by the use of a bifunctional Binder. Such a Binder can be prepared by the association of a domain for a Nucleic Acid Component with a Domain for a cell. For example, an antibody to adenovirus can be covalently attached by the Fc portion to polylysine. An antibody to a cell surface protein such as CD4 can also be covalently attached to the polylysine to produce a bifunctional Binder.

A bifunctional Binder can also be prepared by non-covalent binding through hybridization of complementary nucleic acid strands that have been attached to two different antibodies. The Fab fragment of an antibody to adenovirus can be modified by the addition of a homopolymer such as polythymidilic acid (poly T). The Fab fragment of an antibody to a cell surface marker, such as CD4, also be modified by the addition of a homopolymer such as, in this case, polyadenylic acid (poly A). The two modified Fab fragments can be joined by A:T base pairing to provide for the delivery of adenovirus to CD4+ cells (See Example 16 for the attachment of Fab fragments to homopolymeric polynucleotides.

In addition to Domains and Binders, other entities can be provided to enhance nucleic acid transfer. There can be directly or indirectly attached to a Nucleic Acid Component, to a Binder or to a Domain. Attachment can be made by the methods described above for the covalent and non-covalent attachment of Nucleic Acid Components to Binders and Domains. These entities include;

1) entities which enhance cell growth. These include extracellular matrix protein's such as fibronectin, which enhance the growth and the transformation efficiency of cells.
2) entities which facilitate cellular uptake. These include inactivated viruses such as adenovirus (Cristiano et al. 1993 Proc Natl Acad Sci USA 90; 2122: Curiel et al. 1991 Proc Natl Acad Sci USA 88; 8850, all of which are incorporated herein by reference), virus components such as the hemaglutinating protein of influenza virus and a peptide fragment from it, the hemagglutinin HA-2 N-terminal fusogenic peptide (Wagner et al. 1992 Proc Natl Acal USA 89; 7934, incorporated by reference).
3) entities which facilitate incorporation of nucleic acid into cellular nucleic acid. These include integrase site specific recombinases (Argos et al. 1986 EMBO Journal 5; 433, also incorporated by reference).
4) entities which function in cellular localization of nucleic acid.

These include nuclear proteins such as histones and nucleic acid species such as the snRNAs U1 and U2 which associate with cytoplasmic proteins and localize in the nucleus (Zieve and Sautereauj 1990 Biochemistry and Molecular Biology 25; 1, incorporated by reference).

Factors unattached to a Nucleic Acid Construct, a Binder or a Domain can also facilitate nucleic acid transfer by increasing the competence of cells for nucleic acid transfer. These include factors which act to promote cell growth and are be added to target cells during, before or after the process of gene transfer in vivo or ex vivo. These include:

1) growth factors such as IL-3, IL-6, GM-CSF, Epo and SCF which stimulate cell growth (Paisson et al., 1993 Biotechnology 11; 368: Koller et al. 1993 Biotechnology 11; 358: Koller et al. 1993 Blood 82; 378, both of which are incorporated by reference) and
2) entities such as matrix proteins, their fragments or compounds containing these moieties, e.g., fibronectin, which form a cell binding matrix which promotes cell growth.

The present invention provides one or more of such effects in vivo or ex vivo. Such in vivo or ex vivo effects include the following:

1) bringing a Nucleic Acid Component and a target cell into close proximity
2) providing specificity for the interaction between the Nucleic Acid Component and the target cell.
3) facilitating introduction of the Nucleic Acid Component to the target cell.

4) enhancing the cells capability to be transformed, i.e., the competence of the cell, by providing growth factors, matrix support and other factors.
5) providing for localization, integration and stability of the Nucleic Acid Component and derivatives of the Nucleic Acid Component in the cell.
6) providing a Nucleic Acid Component or a derivative of it which in the cell is capable of producing one or more products which include antisense RNA, antisense DNA, sense RNA, ribozymes, decoys, mRNA and proteins.

3. Multimeric Complexes

The present invention provides novel methods and compositions to form multimeric complexes in which the individual components enjoy retention of their monomeric activity while also maintaining solubility after being joined together. Such a multimeric complex consists of more than one monomeric unit, either bound to each other noncovalently through a polymeric interaction or noncovalently bound to a matrix by a polymeric interaction.

The present invention provides a multimeric complex composition comprising more than one monomeric unit attached to each other through polymeric interactions or attached to a binding matrix through polymeric interactions or a combination of both interactions. The polymer or oligomer of the monomeric unit can be linear or branched, and it can comprise a homopolymer or a heteropolymer. The monomeric unit can comprise an analyte-specific moiety such as one which is capable of recognizing a component in a biological system, e.g., a virus, a phage, a bacterium, a cell or cellular material, a tissue, an organ or an organism, or combinations thereof.

The analyte-specific moiety can take a number of forms including its derivation or selection from a protein, a polysaccharide, a fatty acid or fatty acid ester and a polynucleotide (linear or circular or single stranded) or a combination of these. As an analyte-specific moiety such a protein can comprise an antibody (polyclonal or monoclonal), a hormone, a growth factor, a lymphokine or a cytosine, and a cellular matrix protein, or a combination of these.

A monomeric unit is an entity comprised of two elements. Said first element is a compound. Said second element is a polymer (or oligomer) capable of noncovalently binding, complexing or hybridizing either to the polymer or oligomeric element of a second monomeric unit or to the polymer or oligomer that makes up a binding matrix. Among others, the monomeric unit can be selected from a naturally occurring compound, a modified natural compound, a synthetic compound and a recombinately produced compound or combinations of such compounds.

Said compound may be an analyte specific moiety that is capable of recognizing and binding to a component in a biological system in vivo or in vitro. A biological system can be comprised of cells, cellular components, viruses, viral components, circulating material, extracellular binding matrices or combinations thereof. The compound could be naturally occurring, a modified natural compound, a synthetic compound or a recombinant product. It could be a polyclonal or monoclonal antibody, complete protein chains or f(ab) fragments, from human or other species; it could be a lymphokine, cytokine, hormone (e.g., insulin), or growth factor (e.g., erythropoietin) or a cellular matrix protein (e.g. fibronectin); it could be a ligand, vector, bacterium, or virus; it could be a monosaccharide, oligosaccharide, polysaccharide, polynucleotide, protein, or lipid.

The polymers can be attached to the compounds either covalently or noncovalently. The compounds could be covalently attached to the polymers through conjugation of reactive groups on the compound and the polymer. Either the compound or the polymer or both could be chemically modified such that conjugation could be facilitated. Either the compound or the polymer could be modified such that a ligand such as biotin could be introduced to one and a receptor for the ligand such as avidin introduced to the other.

It is preferred that the polynucleotide segment that is attached to a given compound does not bind to itself or hybridize together or is not substantially self-complementary. In the multimeric construct, the component could be homogeneous or heterogeneous, as long as the polymer segment on the homogeneous component or heterogeneous mixture or compounds can bind or hybridize to the same binding polymer or polynucleotide in the binding matrix.

Polymers that are attached to the compounds to form the monomeric units may be selected from the same group of polymers that comprise the binding matrices with the proviso that they should be able to bind together noncovalently.

The binding matrix is an entity comprised of a linear or branched polymeric compound that has more than one portion of a linear segment that is capable of noncovalent binding to a linear segment of a polymer of a monomeric unit.

The linear segment could be comprised of a homopolymer, heteropolymer or co-polymer, a synthetic polymer, a natural polymer, a polynucleotide, modified polynucleotide, or polynucleotide analog or polyionic compound. Thus the binding matrix can comprise or take its selection from a polypeptide, a polynucleotide and a polysaccharide or any combination.

The binding matrix itself may or may not be attached to a compound or an entity. In instances when the binding matrix does attach to a compound or ligand, it is preferred that the binding matrix have reactive groups for such attachment either, directly (covalently) or indirectly (noncovalently) to the compound. The preferred polymers that are contained within the binding matrix or that are attached to the compound are those with a monomeric backbone containing a charged group, such as the phosphate backbone of polynucleotides. The hydrogen bonding or ionic state of these polymers could be further changed by the chemical modification of appropriate groups of the side chains or backbone of such polymers, such as the introduction of chelator groups described in U.S. Pat. No. 4,843,122 or EP 0 285 057 B1 or amine groups described in U.S. Pat. No. 4,711,955. All of the contents of these aforementioned U.S. and foreign patents are incorporated by reference into this disclosure.

The polymer attached to the compound and the polymer of the binding matrix could bind to each other noncovalently through either ionic interactions, hydrogen bonding, complementarity or polar interactions, including dipole-dipole interactions.

When the binding is through ionic interaction, if the monomeric unit contains polycationic segments, then the corresponding binding matrix should have polyanionic segments. If the monomeric unit has polyanionic segments, then the corresponding binding matrix should contain polycationic segments.

Examples of positively charged polymers could be protamine or polylysine; soluble DEAE (diethylaminoethyl) cellulose, or DEAE dextran (a branched polysaccharide).

Examples of negatively charged polymers are techoic acids (polymeric chains of glycerol or ribitol molecules linked to each other by phosphodiester bridges), polyglutamic acid, carboxymethyl cellulose, dextran sulfate (a branched polysaccharide with 3 negatively charged sulfate groups), and polyacrylic acid.

When the binding is through hydrogen bonding or complementarity, if the monomeric unit has a polynucleotide sequence attached, the corresponding binding matrix should have the complementary nucleic acid sequence.

Binding matrix polymers preferentially have net ionic charges or sufficient polarity to be soluble and have the capability of noncovalent binding to another polymer of opposite polarity, charge, or complementarity Such a polymer could be single or double stranded polynucleotide, RNA or DNA, modified or unmodified; polynucleic acid analogs or any other synthetic polymer that exhibits such properties.

Double stranded nucleic acid can also act as a polyanionic binding matrix. In this case the monomeric unit is attached to a polycationic entity such as polylysine or polyamine.

Another way of constructing such complexes is through protein-nucleic acid interactions. Polypeptides that exhibit high affinity levels for nucleic acids can be attached to desirable compounds to form monomeric units that can then be complexed together by binding to a nucleic acid polymer. The sequence of the nucleic acid polymer can be made up of multimers of binding sequences in the cases where the monomeric units are derived from sequence specific binding proteins such as the HIV TAR protein. However, the choice of the sequence of the nucleic acid polymer can be completely unrestricted in cases where the monomeric units are derived from sequence independent DNA binding proteins such as histone.

One can optimize a given multicomplex compound by adjusting the number of monomeric unites in a given binding matrix such that one obtains the maximum number of compounds on a given binding matrix, while maintaining solubility and avoiding stearic hindrance to assure maximal functioning of the multicomplex construct.

When the binding of a monomeric unit to the binding matrix is through ionic interaction of two oppositely charged polymers, the ratio of the monomeric unit to the binding matrix has to be adjusted such that the net charge or the charge distribution of the multicomplex construct is sufficient to maintains solubility.

Such multimeric complexes are formed by introducing a polymer to an individual compound that can bind either to another polymer and/or can bind to a polymer of another compound. In the case of polynucleotides, the binding could be through complementary sequences. The polymers could be homopolymers or heteropolymers, sufficient in length to form a stable bond. In a stable bond formed by polynucleotides, the polymer could be from approximately 5 to several thousand nucleotides in length.

One aspect of these multicomplex units is the formation of complexes with high affinity for the target entity. A multi-antibody complex of this invention will exhibit a much higher avidity for the target antigen than a single antibody. Such a complex will be useful therapeutically and for in vitro diagnosis. In vivo such complexes could be used as more effective immunologic reagents, including antiviral, antibacterial and antitumor agents. In the case of in vivo use of such a multimeric complex, the preferred polymers are polynucleotides or modified polynucleotides since nucleic acids are better tolerated immunologically. For in vitro diagnostics, such multicomplexes could be used to develop more sensitive assay systems. The sensitivity of any diagnostic system depends on two factors, the sensitivity of the signal and the affinity between the analyte and analyte specific moiety. If the affinity is not high enough there could be practical or theoretical limits as to how much one could increase saturated binding in the system with the target entity.

Furthermore, such complexes could be used for efficient gene transformation both in vivo or in vitro (as discussed in the disclosure).

A certain concentration of the binding partner is required in order to obtain a certain level of binding in vivo as well as in vitro. A multimeric complex of biological binding elements, which upon binding to a cell can trigger biological effects in the cell, would have a much higher binding affinity to a target cell than the corresponding monomeric unit. Consequently much lower quantities of such a multicomplex compared to the monomeric unit would be needed to achieve the same physiological effect. Examples of such biological complexes are hormones, cytokines, lymphokines, growth factors, ligands. A multicomplex of insulin could be useful in that manner in diabetic treatment In addition to being used to form more potent biological effectors, multimeric complexes or polymeric units of this invention can be used to form multimeric complexes or polymeric units of compounds which bind to etiological agents, such as viruses, bacteria and fungi, or to toxic compounds. These binding compounds could be polyclonal or monoclonal antibodies, complete protein chains or F(ab) fragments, from human or other species; or the receptor protein of the etiological agent or toxic compound. The binding of such polymers or complexes to the target is stronger than the binding of the monomers and these polymers or complexes can recognize and bind to low concentrations of the etiological agent or the toxic compound. These compositions can be applied, therefore, for more effective therapeutic use against infection and toxicity. These products can be adminstered to patients in vivo or could be used ex vivo for neutralization of potentially infected or toxic blood.

In preparing such complexes, one would modify a compound, such that the binding of the compound does not interfere with its biological function or effects. The preferred attachment of reactive groups or oligomers or polymers covalently or through a complex would be via non-disruptive chemistry. Binding is through reactive groups in the compound that are not within the active site, binding site or functional groups and binding is such as to allow maximal freedom with the least amount of disruption to the molecule.

Figure 23:
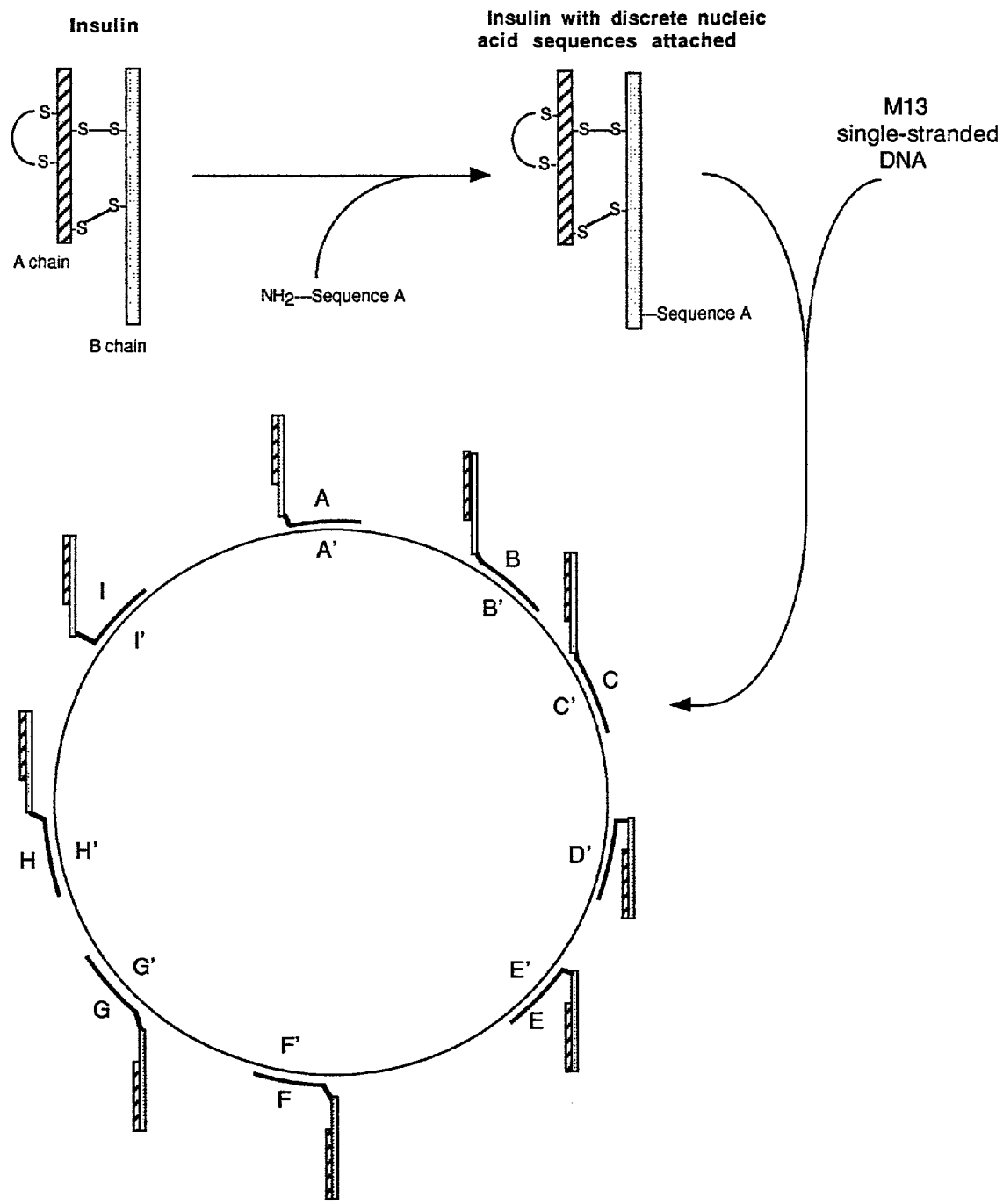
FIG. 23 depicts a process for multimerization of insulin molecules by hybridization of nucleic acid heteropolymers with a binding matrix.

If desired, the spacing of the monomeric units can be predetermined by defining the nature of the region that the monomeric units are bound to the matrix to optimize their spacing so as to provide proper co-operative binding and also to reduce potential stearic hindrance. An example of this type of disposition of the monomeric units is shown in FIG. 23 from Example 18 where each monomeric unit has been joined to a specific unique sequence that is complimentary to different portions of the M13 binding matrix.

These multicomplex compounds could further contain many other entities as ligands, receptors, chemical modifications that either enhance their biological function, increase their solubility, provide further cooperative overall binding or provide capability to bind to desired cells in vitro and in vivo. Thus another aspect of this invention is the composition, described above, further comprising an entity attached to the binding matrix. Such an entity can comprise a ligand or a compound which increases the binding of the binding matrix. Examples of such entities are the cellular matrix proteins (fibronectin), lectins, polysaccharides, and polycationic polymers such as polylysine and histones.

Any of the above-described compositions can be formulated as homogeneous forms or compositions or heterogeneous forms or compositions.

The above-described multimeric complex composition (and its various embodiments) can be usefully employed in a process for delivering a cell effector to a cell. In such a process one would provide the multimeric complex composition wherein the monomeric unit of the composition comprises a cell effector and administer the composition either in vivo or ex vivo. In addition the multimeric complex composition can be employed in a process for delivering a gene or a gene fragment to a cell. Here, one would provide the multimeric complex composition wherein the monomeric unit comprises the gene or gene fragment to be delivered and would administer such composition either in vivo or ex vivo as the case may be.

Another useful multimeric composition comprises more than one component attached to a charged polymer. The charged polymer is selected from a polycationic polymer, a polyionic polymer, a polynucleotide, a modified polynucleotide and a polynucleotide analog as well as combinations of the foregoing. Such a component can comprise a protein, e.g., an antibody (polyclonal or monoclonal), an F(ab')$_2$ fragment or both. The antibody can be further complexed with a target comprising an enzyme.

4. Intron Inactivation

The present invention provides (1) a universal composition for conditional nucleic acid processing by the introduction of a processing element into a nucleic acid sequence produced from a construct introduced into a cell. Said produced nucleic acid is processed in a compatible cell, i.e., a cell capable of processing RNA by removal of the processing element. Said RNA is not processed in an incompatible cell, i.e., a cell capable of processing RNA by removal of the processing element and (2) a binary biological function in which a single nucleic acid construct bearing at least two operons or transcriptional units non-native to a cell when introduced into said cell results in the protein gene product of one of the operons impacting the protein gene product(s).

The present invention provides a novel method and constructs for capability for the conditional inactivation of a gene by the use of a non-native, or heterologous, processing element which only permits gene expression in compatible cells. The method utilizes the introduction of a heterologous processing element into the coding region of a desired gene resulting in inactivation of the gene when present in a non-compatible cell. The intron can be inserted at a number sites in most genes. The heterologous processing element carries no flanking sequences, and thus introduces no additional sequences upon insertion. In a preferred embodiment, the gene product either is absent or inactive in an incompatible cell, but when introduced into a compatible cell yields a functional mRNA molecule which, upon translation, the gene yields an unaltered protein.

Among the significant embodiments is a nucleic acid construct which when introduced into a cell expresses a non native polymerase, the polymerase being capable of producing more than one copy of a nucleic acid sequence from the construct. This construct can further comprise a recognition site for the non native polymerase. Such a recognition site can be complementary to a primer for the non native polymerase. The primer preferably comprises transfer RNA (tRNA).

In certain embodiments the non native polymerase comprises a member selected from DNA polymerase, RNA polymerase and reverse transcriptase as well as any combination of the foregoing enzymes. The RNA polymerase preferably comprises a bacteriophage RNA polymerase, e.g., T3, T7, and SP6, or combinations thereof. Furthermore, the above-described construct can comprise a promoter for the RNA polymerase.

The nucleic acid produced from the construct can take a number of forms including but not limited to DNA, RNA, a DNA-RNA hybrid and a DNA-RNA chimera, or combinations thereof. The DNA or RNA can comprise sense or antisense, or both.

Another significant aspect of this invention concerns a nucleic acid construct which when introduced into a cell produces a nucleic acid product comprising a non native processing element which when in a compatible cell, the processing element is substantially removed during processing. The processing element can comprise an RNA processing element including but not limited to an intron, a polyadenylation signal and a capping element, or combinations of the foregoing.

The nucleic acid product can be single stranded and it can comprise any of antisense RNA, antisense DNA, sense RNA, sense DNA, a ribozyme and a protein binding nucleic acid sequence, as well as combinations of any of these. The protein binding nucleic acid sequence preferably comprises a decoy that binds a protein required for viral assembly or viral replication.

Also provided by this invention is a process for selectively expressing a nucleic acid product in a cell, the product being such that further processing is required for its functioning. The process comprises as its first step providing a nucleic acid construct which when introduced into a cell produces a nucleic acid product comprising a non-native processing element, which when in a compatible cell, the processing element being substantially removed during processing. The second step comprises introducing this construct into the cell. The processing element, e.g., an RNA processing element, the nucleic acid product and the steps of introducing the construct in vivo and ex vivo are all as described previously. Significantly, in this process, the construct can be introduced into a biological system containing the cell. This biological system can comprise, an organism, an organ, a tissue and a culture (cell or tissue) as well as combinations of these.

The present invention provides a universal method for utilizing processing elements, including heterologous elements, for conditional gene inactivation. Rather than a restriction enzyme site, the frequently occurring sequence (C/A)AGG post splice junction sequence is used as the insertion site. This site results from the consensus sequence resulting from an excision of an intron. The consensus splice sequence for splice donors is (C/A)AG*GU and the consensus sequence for splice acceptors is (U/C)$_n$N(C/U)AG*G where * represents the splice site (Mount 1982 Nucl. Acids Res. 10, 459). The frequent occurrence of this sequence provides numerous potential sites for the insertion of processing elements. Insertion at any of these sites in a gene coding region should not affect subsequent removal of the processing element in a compatible cell. Proteins produced from processed mRNA should demonstrate no change in amino sequence or enzyme activity since only processing element sequences free of flanking exon sequences are introduced thereby allowing the processing event to regenerate the original coding sequence.

Furthermore, the site of insertion for a processing element does not appear to affect gene expression. Mayeda and Oshima (1990 Nucl. Acids Res. 18: 4671, incorporated by reference) showed that a native intron, isolated as a restriction fragment of DNA containing the β-globin intron with the conserved bases of the 3' end of the donor exon attached, could be introduced into various sites of a cDNA copy of β-globin and subsequently be spliced out normally, irrespective of intron location in the β-globin coding sequence. This is consistent with the consensus sequences that have been identified for splice donors and splice acceptors and that there are no particular requirements for a specific sequence at the 5' end of the acceptor exon.

It is possible that insertion of a heterologous processing element may not in all cases inactivate a gene when present in an incompatible cell. Although splicing has been observed in procaryotic systems for bacteriophage T4 (Chu et al. 1984 Proc. Nat. Acad. Sci. USA 81: 3049, incorporated by reference), it is in this case due to a self-splicing intron (Chu et al., 1985 J. Biol. Chem. 260: 10680, incorporated by reference) and thus independent of processes employed in compatible cells. Therefore, in a procaryotic environment, the intron should remain in the mRNA as long as a self-splicing intron is not used. In addition, if the number of bases in the intron is a multiple of 3, the reading frame remains the same and a fusion protein with additional amino acids derived from the intron sequence could potentially be produced. These extra bases may or may not change the activity of the target protein depending upon the nature of the extra amino acids and the insertion site within the protein coding sequence. A preferred mode of inactivation is the use a heterologous processing element that introduces a frame shift mutation and/or a stop codon(s).

The present invention also provides for the introduction of genes not native to a cell into said cell wherein the protein products of such introduced gene(s) interact with and impact other proteins produced from introduced non-native gene(s).

The non-native protein gene products resulting from an introduced non-native gene(s) can impact another non-native protein by a variety of processes including polymerization; activation; facilitating transport; competitive inhibition; allosteric interaction; chemical modification including phosphorylation, dephosphorylation, methylation, demethylation, proteolysis, nuclease activity, glycosylation; and others.

Non-native genes can be introduced into cells as RNA, DNA or both DNA and RNA. Non-native genes can be introduced into a cell linked together on a single nucleic acid construct or introduced separately on distinct constructs. Introduction of non-native genes into cells can be done by any of a variety of methods for gene delivery (reference).

The present invention provides the following benefits:
a) This invention has utility for the conditional inactivation of genes when such genes would be lethal to the host cell or when such genes present in a host cell introduce a danger. Thus, genes which would be impossible to clone, such as those which code for enzymes which destroy bacterial cell walls, can be inactivated by intron insertion and thus cloned in this form in a bacterium. Genes coding for toxic products, including tetanus toxin, risin, pseudomonas toxin, *E. coli* enterotoxins, cholera toxin and other plant, animal and microbial toxins, can be inactivated and maintained stably and safely in an incompatible cell and activated to produce an unaltered gene product in a compatible cell. This has special application to cell killing gene therapy.
b) The present invention provides utility for the inactivation, in incompatible cells, of the expression of polymerase catalysts whose expression can be realized in compatible cells. This has application to expression of a variety of gene products, either RNA or protein, under control of promoters of a variety of polymerases. Polymerases, native and non-native to the cell, that could be used in this way include RNA polymerases from T3, T7 and SP6.
c) This invention provides for normally incompatible genes to be cloned together on the same nucleic acid construct. For example, a single construct can be designed containing sequences for the production of T7 promoter directed transcript(s) of choice and T7 RNA polymerase. The ability to clone such genes on the same nucleic acid construct rather than as separate constructs provides the following benefits:
   i) The efficiency of cotransfection of the two genes is 100%.
   ii) In the case of T7 RNA polymerase and a nucleic acid sequence for T7-directed transcript of choice, the entire functional unit is sufficiently compact that it can be cloned into a vector which can only accept inserts below a certain size limit as, for example, adeno associated virus which can only accept inserts of 4.7 kilobases or below and remain functional (Muzyczka 1992 in Current Topics in Microbiology and Immunology, Springer Verlag, Heidelberg, 158; 97, incorporated by reference)
d) Another application of this invention provides for the interaction of non-native gene or its protein products in a cell where the interaction of the introduced genes and/or their gene products can yield useful intracellular processes for gene therapy applications.

In an application of the present invention, an intron is introduced into the coding sequence of T7 RNA polymerase in a construct that also contains a T7 promoter directing the transcription of a useful gene product. As discussed earlier, the use of T7 polymerase for synthesis of a gene under control of a T7 promoter has been accomplished in compatible cells, but always in the context of placing the two entities on separate constructs, i.e., the T7 RNA polymerase and the gene under the control of a T7 promoter are used as a two-part system. The present invention (see Examples) describes the conditional inactivation of a gene (that normally does not a contain a processing element) by the precise introduction of an intron between the last two G's of a site that has the post splice junction sequence (C/A)AGG. The introduction of an intron into sites with this sequence creates a functional splice donor and a functional splice acceptor. Therefore, a construct with this modification should lack any expression of T7 RNA polymerase in an *E. coli* cell, but the normal coding sequence can be restored from transcripts after introduction into a compatible cell. This allows the construction of a single construct that contains both the T7 RNA polymerase and, for example, antisense directed by a T7 promoter, with lethality to an incompatible cell being avoided by introduction of the heterologous processing element into the polymerase coding sequence. In a compatible cell, normal expression of the polymerase will occur but lethality should be negated by the nature of its environment. First, the autocatalytic cascade, due to transcription around the circular plasmid, believed to be responsible for lethality of *E. coli*, would not occur in stably transformed mammalian cells formed by integration into the chromosomal DNA. Second, in the presence of concatameric integration of the construct, runoff transcription from the T7 promoter past a T7 terminator sequence into the coding sequence for the polymerase should produce RNA that would be translated with very low efficiency due to the lack of appropriate signals for processing, transport and translation.

The same advantages of this invention that are enjoyed for the production of T7 directed RNA, such as antisense RNA, can be applied to the T7 RNA polymerase directed production of protein.

5. Hairpin Construct

The introduction of genetic material into cells can be done by two methods. One method is the exogenous application of nucleic acids which act directly on cellular processes but which themselves are unable to replicate or produce any nucleic acid. The intracellular concentrations of these molecules that must be achieved in order to affect cellular processes is dependent on the exogenous supply. Another method for nucleic acid delivery is the introduction into cells of Primary Nucleic Acid Constructs which themselves do not act on cellular processes but which produce single stranded nucleic acid in the cell which acts on cellular processes. In this case the introduced Primary Nucleic Acid Construct can integrate into cellular nucleic acid or it can exist in an extrachromosomal state, and it can propagate copies of itself in either the integrated or the extrachromosomal state. The nucleic acid construct can produce, from promoter sequences in the Primary Nucleic Acid Construct, single stranded nucleic acids which affect cellular processes of gene expression and gene replication. Such nucleic acids include antisense nucleic acids, sense nucleic acids and transcripts that can be translated into protein. The intracellular concentrantions of such nucleic acids are limited to promoter-dependent synthesis.

Definitions

Primary Nucleic Acid Construct. A composition consisting of nucleic acid which in a cell propagates Production Centers.

Production Center. A nucleic acid molecule derived from a Primary Nucleic Acid Construct which in a cell is able to propagate other Production Centers or to produce single stranded nucleic acid. As used herein, the term production center is intended to cover secondary nucleic acid components which can be produced from a primary nucleic acid construct. Also covered are a tertiary nucleic acid component which could be produced from the secondary nucleic acid component, as well as any nucleic acid product which may be produced from the secondary nucleic acid component.

Propagation. The generation or formation of a Production Center from a Primary Nucleic Acid Construct or the generation or formation of a Production Center from another Production Center. However, production centers cannot produce a Primary Nucleic Acid Construct.

Production. The generation of a single stranded nucleic molecules from a Production Center.

Inherent Cellular Systems. Cellular processes and components present in cells which can be utilized for the Production and Propagation as well as the function of single stranded Nucleic Acid Products. Such processes and components can be native to the cell, or be introduced to the cell by artificial means or by infection by, for example, a virus.

The effectiveness of single stranded nucleic acids produced from Primary Nucleic Acid Constructs is dependent on their concentration, the stability and the duration of production in the cell. Current methods for achieving intracellular concentrations are limited by a dependence on promoter directed synthesis.

The present invention provides a novel composition construct and method whereby single stranded nucleic acid is produced in the cell from templates which are formed in the cell and derived from Primary Nucleic Acid Constructs in said cell. This invention further provides for a Primary Nucleic Acid Construct which, when introduced into a cell Propagates one or more Production Centers each of which in the cell is capable of Production of single stranded nucleic acid product.

One aspect of the present invention provides a means to attain high intracellular levels of single stranded nucleic acid through amplification. Such amplification occurs by the Propagation from a Primary Nucleic Acid Construct of more than one Production Center and from each Production Center one or more single stranded nucleic acids. However, Production Centers are not capable of producing Primary Nucleic Acid Constructs.

Thus, a significant embodiment of this invention concerns a composition comprising a primary nucleic acid component which upon introduction into a cell produces a secondary nucleic acid component which is capable of producing a nucleic acid product, or a tertiary nucleic acid component, or both. The secondary and tertiary nucleic acid components and the nucleic acid product are incapable of producing the primary nucleic acid component. In this composition the cell can of course be eukaryotic or prokaryotic.

In the present composition, the primary nucleic acid component can comprise a nucleic acid, a nucleic acid construct, a nucleic acid conjugate, a virus, a viral fragment, a viral vector, a viroid, a phage, a phage vector, a plasmid, a plasmid vector, a bacterium, and a bacterial fragment or combinations of any of these.

Primary Nucleic Acid Constructs consist of single or double stranded nucleic acid (or even partially double stranded) or composed of both single and double stranded nucleic acid, and the nucleic acid can be RNA, DNA or a combination of RNA and DNA. The nucleic acid can be unmodified or it can be modified to provide desirable properties. For example, modified bases can be incorporated to provide nuclease resistance, interaction with Inherent Cellular Systems, cellular localization and other properties for nucleic acid constructs as described in this disclosure. Furthermore, the primary nucleic acid component can comprise nucleic acid analogs which likewise can be used in combination with DNA, RNA, or both.

Primary Nucleic Acid Constructs can reside in the cell integrated into chromosomal DNA or as extrachromosomal entities. The Primary Nucleic Acid Construct, as an integral part of a chromosome, can be replicated concomitant with chromosomal DNA during cell division processes or it can be replicated as part of an extrachromsomal element containing DNA replication elements, such as sequences for origin of replication and others.

Primary Nucleic Acid Constructs contain sequence information for the Propagation of Production Centers and for the subsequent Production of single stranded product. Thus, for this purpose, a variety of desirable elements can be encoded in a Primary Nucleic Acid Construct. Production Centers and Primary Nucleic Acid Constructs may contain one or all of these elements. These include regulatory elements such as promoters and enhancers; primer binding sites; processing elements such as intron sequences, poly A sequences, sequences specifying capping and termination sequences; sequences specifying cellular localization signal sequences with affinity for cellular proteins. Primary Nucleic Acid Constructs can also contain sequences for the synthesis of proteins which act to propagate Production Centers. For example, sequences for a nucleic acid polymerase which acts to propagate a Production Center can be present in a Primary Nucleic Acid Construct (See Example 20 of this patent).

Primary Nucleic Acid Constructs can propagate Production Centers through the activity of nucleic acid polymerizing catalysts present as Inherent Cellular Systems. Production Centers can be RNA, DNA or a combination of RNA and DNA. They can be single stranded, double stranded or contain both single and double stranded regions. Production Centers can propagate other Production Centers and/or produce single stranded nucleic acid product with biological activity directly or through the activity of Inherent Cellular Systems.

Production Centers can produce a variety of single stranded nucleic acids such as antisense RNA sequences, antisense DNA sequences, ribozyme sequences and mRNAs which can be translated into proteins can all be produced. Desirable properties to enhance biological activity can also be incorporated. Thus, RNA processing signals, sequences specifying cellular location, sequences for binding cellular proteins and other functions can be incorporated into single stranded nucleic acids products.

As production centers, the secondary nucleic acid component and the tertiary nucleic acid component (as well as other subsequent components, e.g., a quaternary nucleic acid component, can comprise DNA, RNA, a DNA-RNA hybrid, and a DNA-RNA chimera or a combination of the foregoing.

When the above-described compositions further comprise a signal processing sequence, such sequences can be selected from a promoter, an initiator, a terminator, an intron, and a cellular localization element or a combination of these. Such signal processing sequences can be contained in any of the elements of the composition including those selected from the primary nucleic acid component, the secondary nucleic acid component, the nucleic acid product and the tertiary nucleic acid or a combination of these. The nucleic acid product can of course be single stranded as well as comprising antisense RNA, antisense DNA, a ribozyme and a protein binding nucleic acid sequence or combinations of these. Preferred as a protein binding nucleic acid sequence is a decoy that binds a protein required for viral assembly or viral replication.

In these above-described compositions, production of any component or nucleic acid product can be mediated by a vector, preferred vectors comprise viral vectors, phage vectors, plasmid vectors, as well as combinations of these.

The present composition can be incorporated into a cell which is eukaryotic or prokaryotic. The composition can be introduced either in vivo or ex vivo into such a cell.

Also contemplated by the present invention are production centers including the secondary or tertiary nucleic acid components or the nucleic acid product which can be produced from the composition.

The Propagation of Production Centers from Primary Nucleic Acid Constructs, the Propagation of Production Centers from other Production Centers and the Production of single stranded nucleic acid from Production Centers can proceed by a variety of processes which derive from sequences present in these structures (as described above) and from Inherent Cellular Systems. Inherent Cellular Systems involved in these processes include RNA polymerases, RNA processing enzymes, DNA polymerases, Reverse Transcriptases, Ribonuclease H, endonucleases, exonucleases including ribozymes, enzymes involved in nucleic acid repair, nucleic acid ligases, cellular nucleic acids acting as primers, and entities involved in nucleic acid replication, transcription, translation, localization of nucleic acid in the cell, transport of nucleic acid, integration of nucleic acid into cellular nucleic acid and others.

Elements for Propagation and Production include: 1) single or multiple promoters, 2) self priming processes, 3) one or more primer binding sites, and 4) multiple priming.

1) Promoters for Propagation and Production can be present in one or more copies in a Production Center or in a Primary Nucleic Acid Construct. Such promoter sequences can be present in a preexisting and functional form, as, for example, in a double stranded DNA Primary Nucleic Acid Construct introduced into a cell. Functional promoter sequences can also form subsequent to introduction of a Primary Nucleic Acid Construct into a cell. For example, a single stranded RNA Primary Nucleic Acid Construct containing promoter sequenceses which are non-functional (since they are present as single stranded ribonucleic acid) can be converted to functional promoter sequences by propagation in the cell to a double stranded DNA Production Center from said Primary Nucleic Acid Construct. This Propagation can be achieved by the presence in the Primary Nucleic Acid Construct of primer binding sites, such as the HIV primer binding site for which lysyl tRNA acts as a primer, and reverse transcriptase as an Inherent Cellular Element. The generation of double stranded DNA in this way forms a functional promoter.

Functional promoter sequences can also be generated by the formation of double stranded regions from self complementary formation in a single stranded Primary Nucleic Acid Construct. For example, the presence of both the sense and antisense sequences for a promoter and a coding sequence under its control can be present in a single stranded DNA Nucleic Acid Product or Production Center. Self hybridization of these regions of the same molecule can generate a functional promoter in the formed double stranded region of this single stranded molecule.

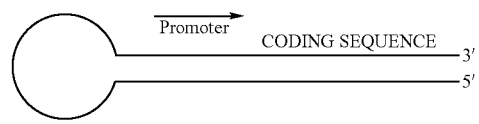

2) A single stranded Primary Nucleic Acid Construct can Propagate or a linear single stranded Production Center can Propagate or Produce nucleic acids by a self priming process. In this process, the 3' end of such a molecule can hybridize with complementary regions located elsewhere in the molecule and act as a primer for the synthesis of complementary nucleic acid. For example, the 3'end of a linear single stranded RNA can act as a primer for a polymerase such as reverse transcriptase.

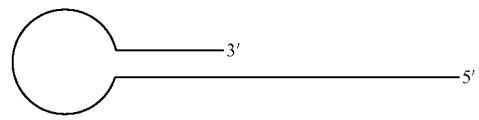

3) One or more primer site sequences can be included in a Primary Nucleic Acid Construct or in a Product Center. Sequences for the primer binding site of a retrovirus, such as HIV, which utilizes lysyl tRNA as a primer, can be included in one or more copies in a single stranded RNA Primary Nucleic Acid Construct or Production Center. Lysyl tRNA is supplied as an inherent cellular system. In the presence of reverse transcriptase, Propagation and Production of complementary DNA proceeds from the primer site.

4) Multiple priming processes can be utilized for Production and Propagation. For example, a double stranded Primary Nucleic Acid Construct composed of one DNA strand and one RNA strand can be acted upon by nucleases to generate limited endonucleolytic cleavage in the RNA strand. The resulting fragments can act as primers the production and propagation of DNA synthesis as catalyzed by inherent cellular processes such as reverse transcriptase.

6. U1 Antisense System

This invention provides a composition of matter comprising a nucleic acid component which when present in a cell produces a non-natural nucleic acid product, the product comprising two elements: a portion of a localizing entity and a nucleic acid of sequence. The portion of the localizing entity is preferably sufficient to permit localization of the non natural nucleic acid product. Furthermore, the portion of the localizing entity preferably comprises a cytoplasmic or nuclear localization signaling sequence.

The nucleic acid sequence of interest can comprise various forms of nucleic acid including but not limited to DNA, RNA, a DNA-RNA hybrid and a DNA-RNA chimera or combinations of these. When comprising RNA, the nucleic acid of sequence preferably comprises a nuclear localized RNA which may be complexed with protein molecules. Among such nuclear localized RNA are the so called snRNAs. Preferred as snRNA's are U1, or U2, or both.

The non natural nucleic acid product can be of course single stranded and it may comprise various members or forms including those selected from antisense RNA, antisense DNA, sense RNA, sense DNA, a ribozyme, and a protein binding nucleic acid sequence. As described elsewhere, such a protein binding nucleic acid sequence preferably comprises a decoy that binds a protein involved or required for viral assembly or replication. In another aspect of the present composition, the non natural nucleic acid product comprises antisense RNA or antisense DNA and the portion of the localizing entity comprises a nuclear localization signalling sequence. In yet another aspect of the composition, the non-natural nucleic acid product comprises antisense RNA or antisense DNA and the portion of the localizing entity comprises a cytoplasmic localization signalling sequence. Still yet another aspect concerns the composition wherein the non-natural nucleic acid product comprises sense RNA or sense DNA and the portion of a localizing entity comprises a cytoplasmic localization signalling sequences As described elsewhere the nucleic acid component can take various forms, e.g., a nucleic acid, a nucleic acid construct, a nucleic acid conjugate, a virus, or fragment, a viroid, a phage, a plasmid, a vector, a bacterium, or fragment, as well as any combination of these. Such nucleic acid can comprise DNA, RNA, a DNA-RNA hybrid and a DNA-RNA chimera and combinations thereof. The nucleic acid can be modified; the cell can be eukaryotic or prokaryotic. The production of nucleic acid product is mediated by a vector such as a viral vector, a phage vector, or a plasmid vector or such combinations.

As described elsewhere the present combination can be incorporated or delivered into a cell which can be eukaryotic or prokaryotic. Introduction into the cell can be ex vivo or in vivo. The present invention also contemplates biological systems (an organism, an organ, a tissue, a culture) containing the cell into which the composition has been introduced.

The present invention further contemplates a process for localizing a nucleic acid product in a eukaryotic cell. In this process, the above-described composition of matter would be provided and appropriately introduced into a eukaryotic cell or a biological system containing such cell. The characteristics of the localizing entity portion, the nucleic acid product, methods, ex vivo and in vivo introduction in this process are all as described above.

The present invention describes a method and composition for utilising snRNAs as carriers for antisense RNA while retaining the advantageous features of snRNA for nuclear localization. The present invention utilizes removal of sequences from snRNA and their replacement with desirable sequences such as antisense or sense sequences.

Figure 41:
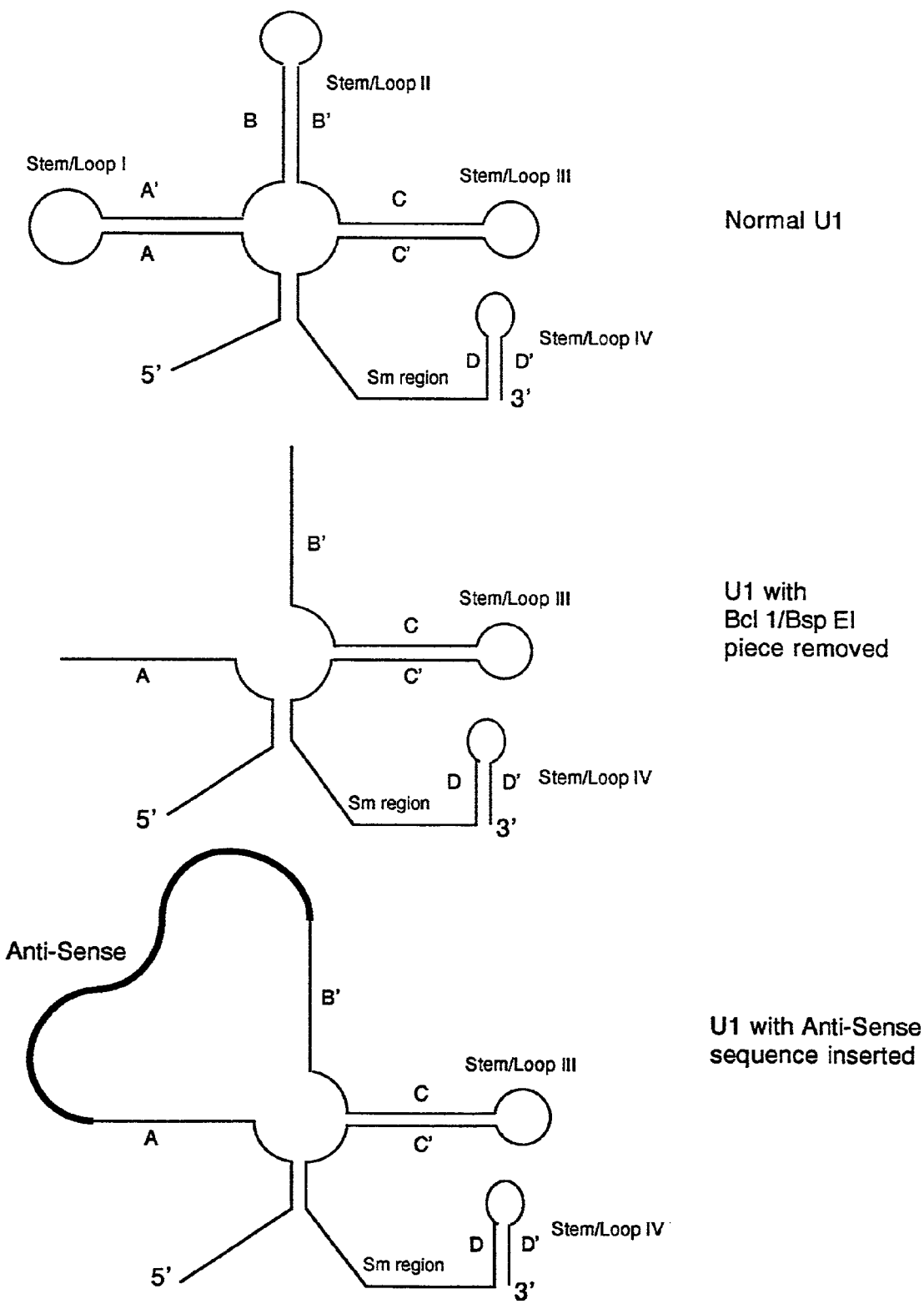
FIG. 41 depicts the process of excision of normal sequences from a U1 transcript region and replacement with novel sequences.

The correct choice of the site for replacement of a portion of the snRNA sequence should not alter the stability and nuclear reimportation features. Digestion of a clone of the human U1 operon with Bcl I and Bsp E II (FIG. 41) eliminates a sequence of 49 bases involved in the formation of the A and B loops formed by U1 RNA (FIG. 41). Removal of this sequence thus both makes room for the addition of foreign sequence and eliminates binding of some snRNP proteins thus enabling the foreign sequence to be available for antisense inhibition free of potential steric hindrance by bound proteins. Elimination of the A and B loops should still allow formation of the C and D loops which are important for maintaining the re-importation signal (FIG. 41). The continued presence of this secondary structure at the 3'end as well as binding of splicesome proteins should also have the effect of maintaining the stability of the RNA.

This invention should be applicable to other species of snRNA including U2.

U1 constructs prepared as described for this invention can be delivered to cells as all or part of nucleic acid constructs by any of several methods applicable to gene delivery.

7. Multi-Cassette Constructs

The present invention, which has application to gene therapy, is a Nucleic Acid Entity which, when introduced into a cell, directs the synthesis of more than one specific entity from a separate functional unit, or cassette. The synthesis of each product entity is initiated from its own initiator signal in a cassette. Multi-targeting can be achieved by inclusion of independent cassettes in a single Multi-Cassette Construct. The advantages of a Multi-Cassette are:

a) Each entity is formed independently from other entities and the total number of product entities will be a summation of the products generated in the cell by each initiation site.

b) Interaction with a target by an independently generated product entity should have no effect upon the activity of other independently generated product entities.

c) An integration event that disrupts expression from one cassette should have no effect upon other cassettes in the construct.

d) Each product entity present in a construct can be directed to a different intracellular locus by use of appropriate signals for either nuclear or cytoplasmic localization. In situations where product entities acting in the nucleus are combined in the same construct with entities acting in the cytoplasm, the application of Multi-Cassette Constructs allows independent synthesis of the two entities, thereby allowing each to accumulate at its most effective site of action.

This invention provides a nucleic acid component which upon introduction into a cell is capable of producing more than one specific nucleic acid sequence. Each such specific sequence so produced are substantially nonhomologous with each other and are either complementary with a specific portion of a single-stranded nucleic acid of interest in a cell or are capable of binding to a specific protein of interest in a cell.

In this component, the single stranded nucleic acids of interest can be part of the same polynucleotide sequence or part of different polynucleotide sequences. The single stranded nucleic acids of interest can comprise viral sequences. The present nucleic acid component can be derived or selected from any of nucleic acids, nucleic acid constructs, nucleic acid conjugates, a virus or fragment, a phage, a plasmid, a bacterium, or fragment, a vector (viral, phage, plasmid), as well as any combinations of these. The nucleic acid can comprise DNA, RNA, and nucleic acid analogs (or combinations thereof). The DNA and RNA can be modified.

In addition, the nucleic acid component can comprise either more than one promoter or more than one initiator, or both. Furthermore, the specific nucleic acid sequence products can be produced independently from either different promoters, different initiators, or combinations of both. Still further, the specific nucleic acid sequence products can be either complementary to a viral or cellular RNA or bind to a viral or cellular protein or a combination of such things. The complementary specific nucleic acid sequence products can be capable of acting as antisense. The viral or cellular protein can comprise a localizing protein or a decoy protein which are described elsewhere. Such localizing proteins preferably comprise a nuclear localizing protein or a cytoplasmic localizing protein. Specific nucleic acid sequence products can comprise antisense RNA, antisense DNA, a ribozyme, and a protein binding nucleic acid sequence or a combination of the foregoing.

The nucleic acid component can further comprise a means for delivering the component to a cell containing the nucleic acid of interest or the specific; protein of interest. Such delivering means are known in the art as well as described elsewhere in the disclosure.

The Multi-Cassette Constructs can be prepared as RNA or DNA. The nucleic acid can be delivered to the cells as modified or unmodified nucleic acid or as modified or unmodified RNA or DNA complexed to proteins, lipids or other molecules or as modified or unmodified RNA or DNA as components of pseudo virions, bacteriophage or other viral delivery systems.

Multi-Cassette constructs can be delivered to target cells by methods commonly used for gene transfer as described in this application.

The presence of independent synthesis units, i.e., cassettes, in a Multi-Cassette Construct provides versatility for the presentation of product entities to the cell through the choice of product entities, synthesis initiator signals and other elements. A Multi-Cassette Construct can be designed to code for a variety of product entities. Thus, cassettes can be designed to code for synthesis of RNA, DNA or protein and such cassettes can be assembled in various combinations in a single Multi-Cassette Construct.

Elements can be incorporated into each cassette to regulate the independently and differentially, if desirable the synthesis, character and nature and activity of the product entity in the cell. Such elements include the type of promoter, enhancer sequences, RNA processing elements such as introns, cellular localization elements such as nuclear or cytoplasmic localization signals and poly A addition signals to provide for addition of poly-A to mRNA.

Useful product entities produced by each cassette include antisense RNA, sense RNA, ribozymes antisense DNA, nucleic acid sequences which bind protein molecules such as decoys which bind proteins required for virus replication: enzymes; toxin molecules; proteins which act in cellular localization of RNA and protein molecules; DNA polymerases; reverse transcriptases; RNA polymerases and nucleic acid sequences under control of cognate promoters for such RNA polymerases; proteins which impart viral resistance to a cell (such as interferons); antibodies and/or fragments thereof; proteins which arrest cell division; proteins which localize in the cell membrane including cellular receptors for viruses, hormones, growth factors and other agents which interact at the cell surface;

Intracellar synthesis of product entities can be controlled by the choice of promoter or initiating element. Thus, a cassette can be designed which contains sequences for a product entity whose synthesis is under control of an inducible promoter providing for temporal synthesis of product entities. This provides advantages to applications wherein, for example, constant production of the product entity would have deleterious effects for the host cell or organism, but whose short term effects are beneficial. For example, induction of a product entity which arrests cell division processes can impart to the cell virus resistance where virus replication is dependent on such cellular processes. In order to restore the cellular processes at a later time, induction can be terminated. Induction can be mediated by use of promoters which can be induced by small molecules such as antibiotics, hormones and heavy metals such as zinc. Alternatively, in cases where constant production of a product entity or entities is beneficial, a promoter not subject to induction can be utilized.

Promoters can also be chosen on the basis of their efficiency. In cases where high levels of product entities are required promoters which initiate transcription at a high frequency can be utilized. Alternatively, when lower levels of product entities are desirable less efficient promoters can be used. Independently synthesized product entities produced from the same Multi-Cassette Construct can act at the same target site. For example, in order to increase effectiveness, a series of antisense RNA product entities directed at a viral nucleic acid target site which demonstrates sequence variability, such as one of the highly variable regions of the nucleic acid of HIV, can be designed to include the predominantly occurring sequences encountered in the wild type HIV population.

Independently synthesized product entities produced from the same Multi-Cassette Construct can also act at separate target sites. For example, an RNA antisense transcript can be directed at mRNA coding for a particular gene product and a different antisense transcript can be directed against an mRNA coding for another gene product.

8. Virus Resistance

The present invention involves the use of agents that in vivo act to increase resistance to viruses by gene therapy by interfering with virus-cell interaction and thus enhancing antiviral gene therapy in the cell. The interaction of regions on viruses with specific sites on the cell surface, i.e., virus-cell interaction, and the susceptibility of extracellular virus to immunological agents provide the basis for supplemental treatment. Agents that act by these means to decrease the effective levels of virus would provide benefit for gene therapy treatments utilizing antisense.

As a supplement to gene therapy, the above agents can be administered to the patient either prior to, concurrently or after a gene therapy procedure by intramuscular, intravenous, intraperitoneal, by inhalation or other appropriate means.

Examples of agents that can interfere with the interaction of a virus and a target cell include:
  a) agents such as antibodies to viral epitopes and cellular proteins which bind viruses. An example of the latter are cellular receptors recognized by viruses, as, for instance the CD4 receptor that is recognized by HIV.
  b) agents that stimulate the production of entities that complex with viruses. These include adjuvants that enhance immunological responses which can be used as a general stimulant and viral antigens that can be used to induce a specific response;
  c) agents that bind to a target cell and compete with or otherwise slow the entry of a virus into a cell. Viral proteins, such as the gp124 protein for HIV, that are involved in cell binding could be used in this way. Antibodies to viral proteins can also act in this way.

In the practice of this invention, additional enhancement can be achieved by the further administration of small molecules such as protease inhibitors or nucleoside analogues. The additional treatment can be either applied prior to, after or concurrently with application of the present invention. The current invention has application to the treatment of virus infections and infections by other intracellular pathogens.

Thus, the present invention provides a process for increasing cellular resistance to a virus of interest. The process comprises two steps. First are provided transformed cells phenotypically resistant to the virus; and a reagent capable of binding to the virus or to a virus-specific site on the cells. Second, the reagent is administered to a biological system containing the cells to increase the resistance of the cells to the virus of interest.

The biological system can comprise an organism, an organ, and a tissue or combinations thereof, viral resistant cells can be eukaryotic or prokaryotic. Such cells can further comprise a nucleic acid sequence selected from antisense RNA, antisense DNA, sense RNA, sense DNA, a ribozyme, and a protein binding nucleic acid sequence or combinations thereof.

The virus binding reagent can take various forms including but not limited to an antibody, a virus binding protein, a cell receptor protein and an agent capable of stimulating the production of a virus binding protein or combinations thereof. The antibody can comprise of course a polyclonal or monoclonal antibody which can be specific to an epitope of the virus of interest. The virus binding protein preferably comprises a CD4 receptor; the cell receptor protein preferably comprises a gp24 protein. In addition the production stimulating agent is selectable from an immunological response enhancing adjuvant and a viral antigen or both.

The reagent can be administered in vivo or ex vivo to the cells. Moreover, the process of the instant invention can further comprise administering an additional viral resistance enhancing agent, e.g., a protease inhibitor, a nucleoside analog, or both.

In carrying out the present process the additional viral resistance enhancing agent can be administered before, after, or at about the same time that the binding reagent is administered.

Also contemplated by this invention are biological systems with increased viral resistance, such resistance having been obtained by any of the processes described above.

9. Dislocation

The present invention is a novel method of altering the concentration of cellular products in a cellular location by the introduction of a construct that produces a product, the dislocation agent, which acts to transport cellular entities from one cellular locale to another. The dislocation agent contains a specificity or affinity domain by which the dislocation agent binds the cellular entity. Dislocation of the cellular entity is mediated by the bound dislocation agent. The resulting co-localization transports the cellular entity to a cellular location that is different from its functional location.

In contrast to previous work (Izant and Sardelli, 1988, Cotten and Birnatiel, 1989, the contents of both publications incorporated herein by reference), which sought to localize the genetic products of their constructs to a cellular location favorable for antisense activity, the present invention acts to disrupt a viral or cellular process by dislocation of macromolecules involved in the viral or cellular processes. Thus, due to the presence of an affinity domain on the dislocation agent, a target molecule will be bound and then transported to a cellular location determined by the dislocation agent.

The application of this invention is through the introduction into cells of nucleic acid constructs which contain sequences for the expression of RNA. The RNA, acting as the dislocation agent, can itself contain sequences for an affinity domain and can transport cellular nucleic acid molecules or proteins to cellular localizations where they are not normally present. Alternatively, the RNA can bind a target RNA molecule and chaperone it to another cellular location where it can't function by the binding of a protein which transports the RNA dislocation agent and its hybridized target RNA to an unnatural cellular location. Also the RNA can contain a sequence that when translated yields a protein dislocation agent with an affinity domain.

In the current invention, active steps are taken upon the interaction of the target with the dislocation agent. Examples of where this might be useful are RNA molecules that contain signals specifying transport from the cytoplasm into the nucleus. Binding of such an RNA dislocation agent to a cytoplasmic RNA or protein would lead to co-localisation of the target into the nucleus. These transported entities would be unable to function due to their presence in an unnatural cellular location. In a similar way, a protein dislocation agent with an affinity domain for a particular RNA sequence or for another protein can be designed such that it also has a nuclear localisation signal present in its sequence. In this way a target entity, normally present in the cytoplasm, would be localised in the nucleus.

This invention provides a nucleic acid construct which when introduced into a cell produces a non-natural product. The non natural nucleic acid product comprises two components: a binding component capable of binding to a cellular component; and a localization component capable of dislocating the cellular component when bound to the product. The product from this construct can comprise a protein or a nucleic acid or both. The protein can comprise an antibody, e.g., a polyclonal or monoclonal antibody, such as one directed to a cellular component inside the cell. Such cellular components can comprise any of the following including but not limited to a nucleic acid, a protein, a virus, a phage, a product from another construct, a metabolite and an allostearic compound, or combinations thereof. When comprising a protein the cellular component can comprise a viral or non-viral enzyme, a gene suppressor, a phosphorylated protein, e.g., an oncogene, or combinations thereof.

The binding component of the product produced from the present construct is selectable from a nucleic acid, a protein and a binding entity or combinations thereof. The nucleic acid can comprise a sequence selected from a complementary sequence to the cellular component and a sequence to a nucleic acid binding protein or combinations of both. The protein is selectable from an antibody, a receptor and a nucleic acid binding protein or combinations thereof. The binding entity is capable of binding metabolites.

The localization component is selectable from a nuclear localizing entity, a cytoplasmic localizing entity, and a cell membrane localizing entity or a combination thereof. The localizing component in the present construct can comprise a member selected from a nucleic acid sequence, a nucleic acid structure, e.g., a stem and loop structure and a peptide or oligopeptide, or combinations of the foregoing.

The present invention further provides a process for dislocating a cellular component in a cell. In this process there are provided a nucleic acid construct which when introduced into a cell produces a non-natural product, which product comprises two components. First, there is a binding component capable of binding to a cellular component; and second, a localization component capable of dislocating the cellular component when bound to the product. The nucleic acid construct is introduced into a cell of interest or a biological system containing the cell or cells of interest.

The following is a list or summary of candidate pairs offered for illustration if not by way of limitation. Potential pairs of relocation agents and their targets are presented.

An application of the present invention for the dislocation of cellular macromolecules is the use of a nucleic acid construct that contains a nucleic sequence for a U1 snRNA molecule in which a portion of the U1 sequence has been substituted with a sequence unique to a portion of the HIV genome (described previously). In this case the U1 RNA in association with snRNP proteins acts as the dislocation agent and the HIV anti-sense sequence represents the affinity domain. The return of U1 to the nucleus, as part of normal cellular processing of U1, while hybridized to target HIV mRNA dislocates the HIV RNA and makes it unavailable for translation in the cytoplasm.

Another application of this invention utilizing U1 RNA is the substitution of HIV packaging signal sequences for a portion of the U1 sequence. Introduction of the substituted U1 as part of a nucleic acid construct used to transfect cells, provides for the synthesis of a dislocation agent containing the U1 RNA sequences and the HIV packaging sequence signals as the affinity signal. The dislocation agent in this case binds to essential HIV proteins responsible for forming virions and transports them from the cytoplasm to the nucleus, thereby inhibiting the packaging of viral RNA.

Another application of present invention is the use of a nucleic construct which produces an RNA molecule which contains sequences specific for splice junctions of HIV RNA as the affinity domain and sequences for the Rev Responsive Element (RRE) of HIV as an affinity domain for binding to HIV Rev protein molecules which acts as the dislocation agent. In HIV-infected cells, the Rev protein dislocation agent binds to RRE sequences on the RNA which is in turn bound to the splice junction of the HIV RNA. The complex would be transported by the Rev protein to the cytoplasm where the unspliced HIV mRNA would be non-functional.

Another application of the present invention is the use of RNA signals for the dislocation of proteins essential for virus replication. The HIV Rev protein is found principally in the nucleolus. However, in the presence of RNA containing RRE sequences, the Rev protein is found principally in the cytoplasm. Therefore, the presence of a nucleic acid construct containing sequences for the cellular production of an RNA dislocation agent containing RRE sequences would actively remove the Rev protein from the nucleus and induce its relocation in the cytoplasm where it would be unavailable for transport of viral RNA. Here the RRE sequences in the transcripts act as the affinity domain.

The many examples which follow are set forth to illustrate various aspects of the present invention, but are not intended to limit in any way the scope of the invention as more particularly set forth in the claims below.

DESCRIPTION OF THE PREFERRED EMBODIMENTS

Examples

Example 1

Preparation of a Two Segment CHENAC in which the Ligands and Chemical Modifications are Localized in One Region of One Segment (i) Description of construct A construct is prepared from one unmodified strand segment and a modified primer segment (FIG. 1*a*). The unmodified single-stranded circle is derived from a plasmid that contains the desired sequences for biological function and it also contains an F1 packaging signal. (Plasmids of this nature are available from a variety of commercial sources.). An *E. coli* host containing this plasmid is infected with M13 helper phage to obtain single-stranded DNA packaged into phage particles. DNA can then be prepared by a variety of commonly used procedures. The oligomer primer is synthesized with an allylamine phosphoramidite (prepared by the method of Cook et al., 1988) and then modified with tri-lactyl lysyl lysine as described below. The unmodified segment contains a sequence complementary to the modified primer segment. After exposure of the construct to the target cells, the galactose moieties provide binding to their natural receptor and transport the complex into the cell. In the present example, the primer is extended by DNA polymerases in the cell to convert the construct to double-stranded form. (FIG. 1*b*) which allows the construct to express sequences specifying biological function in the unmodified region of the CHENAC (designated by the solid black region in FIG. 1*b*). In this example the biological function region of the construct is separated from the region bearing the ligands and chemical modifications.

(ii) Preparation of Lactyl isothiocyanate p-Nitrophenyl-β-D lactopyranoside (Toronto Research Chemicals, Inc. Catalog # N50385) is converted into p-Isothiocyano-β-D lactopyranoside by the method described by Rafestin et al. (FEBS Letters 40 62-66, 1974).

(iii) Preparation of trilactyl derivative 0.7 g LysylLysine dihydrochloride (Sigma Chemicals) is dissolved in 30 ml of $H_2O$. 4 g of p-Isothicyano-β-D lactopyranoside (approximately 8 mMoles) from step (i) is added and the reaction is stirred for 4 hours at room temperature. During this time the pH of the mixture was adjusted to 9.0 and maintained at that value by the addition of 0.2M NaOH. At the end of the reaction, the volume is adjusted to 500 ml with $H_2O$ and loaded onto a DEAE-DE52 cellulose column (previously adjusted to pH 9.0 and then equilibrated with 0.05 M TRIS buffer, pH 9.0). Unreacted LysylLysine remained unabsorbed to the column and is removed by washing the column with 0.01 M LiCl. The product is eluted with 0.1 M LiCl and the fractions from the column are analyzed for UV absorbance at 260 nm. The peak is collected and the $H_2O$ evaporated under vacuum. The dry residue is triturated with an ethanol/ether (3:1) mixture to remove the LiCl, leaving a solid product. The yield of tri-Lactyl-LysylLysine is approximately 80%.

(iv) Activation of tri-Lactyl-LysylLysine 0.5 g of tri-Lactyl-LysylLysine (0.25 mMoles), prepared in step (iii), is dissolved in 30 ml of dry Dimethylformamide. 1 g of N-Hydroxy-succinimide is added, followed by 50 mg of Dicyclohexylcarbodiimide. The reaction is allowed to proceed overnight at room temperature. The following day it is evaporated under vacuum. The residue is triturated two times with 25 ml of isopropanol for 30 minutes each at room temperature to remove unreacted Dicyclohexylcarbodiimide and the excess of N-Hydroxysuccinimide. The product is then washed over a filter with absolute ether, the ether removed and the product used without any further purification.

(v) Lactosylation of the nucleic acid portion 1 mg of an oligomer designed to be the primer shown in FIG. 1 is dissolved in 4 ml of 0.7M LiCl, 0.1 M bicarbonate buffer (pH 7.8). 20 mg of tri-Lactyl-LsylLysine active ester (an approximately 10-fold excess of the reagent compared to the number of allylamine groups) prepared in step (iii) is dissolved in 1 ml of Dimethylformamide and added and the mixture was stirred for 6 hours at room temperature. The mixture is evaporated under vacuum and subsequently dissolved in 1 ml of $H_2O$. The solution is centrifuged to remove insoluble material and the supernatant was subjected to G50 column chromatography and the DNA fractions combined.

Example 2

A Double-Stranded Version of Example 1

The construct described in FIG. 1a from EXAMPLE 1 is again used but prior to exposing the DNA to the target cells, the primer is extended in vitro by the action of Klenow enzyme (Klenow fragment of DNA polymerase I) to convert the construct into the completely double-stranded DNA molecule shown in FIG. 1b. Primer extension is performed under appropriate conditions to avoid strand displacement, for example by carrying out the synthesis at 14° C. so that the newly synthesized strand stops at the position of the 5' end of the primer.

Example 3

Figure 2:
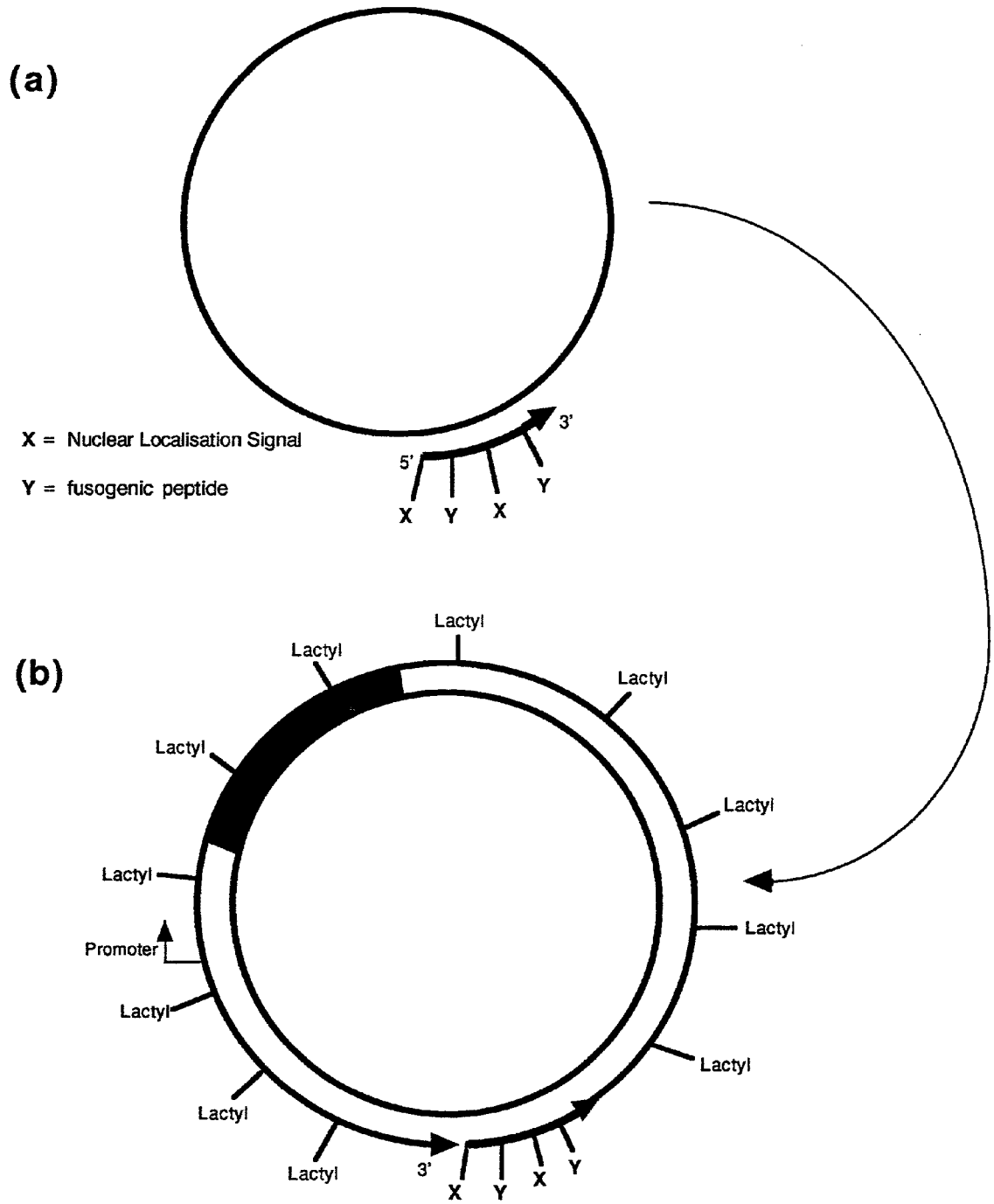
FIG. 2 depicts the dispersed attachment of ligands to a nucleic acid construct by extension from a modified nucleic acid primer.

Preparation of a Two Segment CHENAC in which One Segment Has Dispersed Ligands and Chemical Modifications (i) Description of the construct A construct is prepared from an unmodified strand segment and a modified primer segment (FIG. 2). The modified segment is a DNA oligomer prepared by chemical synthesis such that it contains allylamine deoxyuridine bases as described previously. Peptides are synthesized that contain sequences for a) a fusogenic peptide derived from influenza (Lear and DeGrado, 1987, J. Biol. Chem. 262: 6500) and b) a peptide promoting localisation to the nucleus of a cell (Kalderone et al., 1984, Cell 39: 499). The peptides are joined to the allyl amine moieties by the procedure given below. The modified primer is complementary to a region in the unmodified segment. The primer is hybridized to the unmodified segment, and extended by Klenow enzyme in the presence of a nucleoside triphosphate mixture containing lactyl-deoxyuridine triphosphate precursors (described below) using the sequence of the unmodified segment as template. Synthesis (polymerization) of the nascent strand is performed at 14° C., so that extension stops at the position of the 5' end of the primer (FIG. 2b).

(ii) Synthesis of peptides for addition into the DNA primer

The sequence coding for the Fusogenic Peptide (Gly-Phe-Phe-Gly-Ala-Ile-Ala-Gly-Phe-Leu-Glu-Gly-Gly-Trp-Glu-Gly-Met-Ile-Ala-Gly) (SEQ ID NO:1) and the sequence coding for the Nuclear Localisation Peptide are synthesized chemically with an additional cysteine group added onto the carboxy terminus of each.

(iii) Addition of peptides to allylamines

The allylamine modified nucleic acids are reacted with a 10-fold excess of 3-maleimidopropionic acid N-Hydroxy succinimide ester in 0.7 M LiCl, bicarbonate buffer (pH 7.9) and incubated at room temperature for 40 minutes. At the end of the reaction, the pH is adjusted to 6.0 with acetic acid. The unreacted NHS ester (and its hydrolysis product) are removed by extraction with n-butanol two times. The DNA is precipitated with 4 volumes of Ethanol at −70° C. The pellet is then resuspended in 0.1M sodium acetate buffer (pH 6.0) in a minimum concentration of 1 mg/ml. The derivatized DNA is mixed with the desired amount of thiol-containing fusogenic and nuclear localisation peptides from step (ii) and reacted at room temperature for 6 hours. The unreacted maleimido residues on the DNA are quenched by the addition of β-mercapto-ethanol.

iv) Synthesis of Lactyldeoxy UTP

10 μmoles allylamino deoxyUTP (Enzo Biochem, Inc.) are dissolved in 6 ml of 0.7M Lithium Chloride, 0.2M sodium bicarbonate, pH 7.8 and mixed with 20 μmoles of the lactyl-isothiocyanate (described previously) dissolved in 2 ml of Dimethylformamide. The mixture was reacted for 40 minutes at 25° C. and then diluted to 100 ml with distilled water and loaded onto a 100 ml bed volume DEAE Sephadex A25 column. The column was washed with 100 ml 0.05 M triethylammonium bicarbonate buffer (pH 7.8) and the product was eluted with a linear gradient of 0.05 M-0.6 M triethylammonium bicarbonate buffer (pH 7.8). The fractions with maximal UV absorbance at 290 nm were collected and the triethylammonium bicarbonate was removed in vacuo in the rotary evaporator at 35° C. The solid residue containing the lactyldeoxy UTP is dissolved in 10 mM tris buffer pH 8.0 and used as a substrate for DNA polymerase.

Example 4

Preparation of a Two Segment CHENAC in which One Segment Has Dispersed Ligands and Chemical Modifications Incorporated by Ribonucleotide Moieties A single-stranded DNA construct is derived as described in Example 1. A second strand made up of RNA is made by incubation of the DNA template with RNA polymerase and a mixture of ribonucleotides according to the method described in Stavrianopoulos et al. (1972, Proc. Nat. Acad. Sci. 69; 2609). Two types of modified ribonucleotides are included in this mixture; lactyl-UTP and allylamine UTP. The allylamine UTP is commercially available (ENZO Biochem, Inc.) and the lactyl-UTP is synthesized as previously described for the lactyl-deoxy-UTP in Example 1 except the ribo derivative of allylamine UTP is used as the starting material. After the RNA strand is synthesized, it is separated from the DNA template strand by melting and then the allylamine nucleotides were modified further by the addition of fusogenic peptides as described previously in Example 3. The strands were then allowed to reanneal to form the final structure shown in FIG. 3.

Example 5

Figure 4:
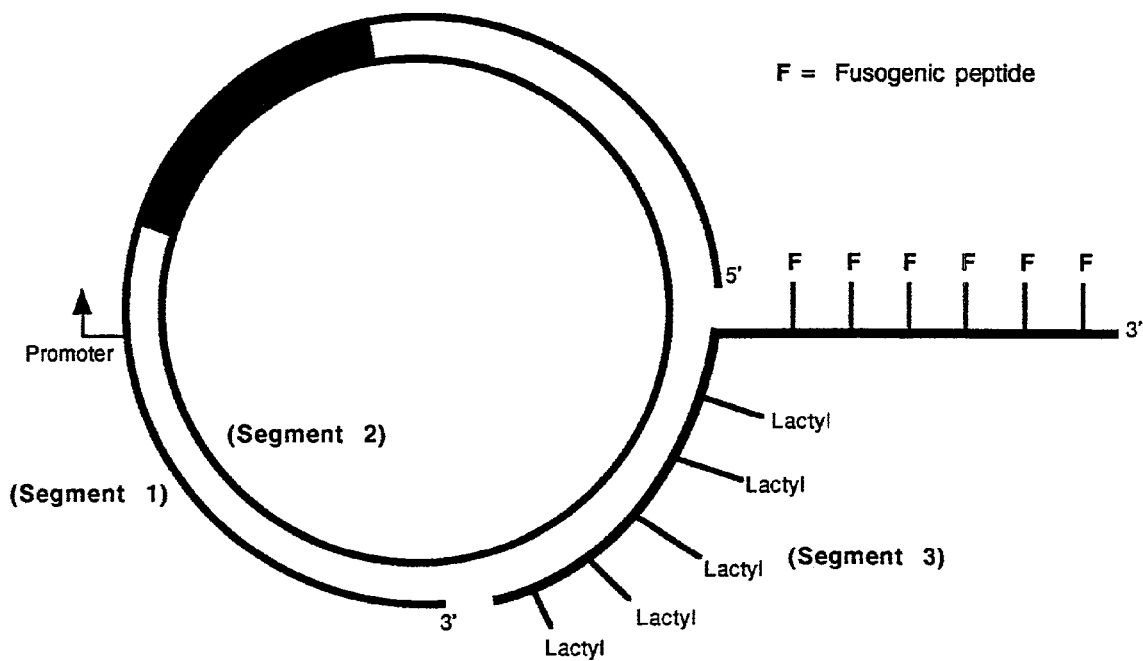
FIG. 4 illustrates the localized attachment with a nucleic acid construct by hybridization of a gapped circle with a modified nucleic acid moiety that also contains useful moieties incorporated into a 3' tail.
Figure 5:
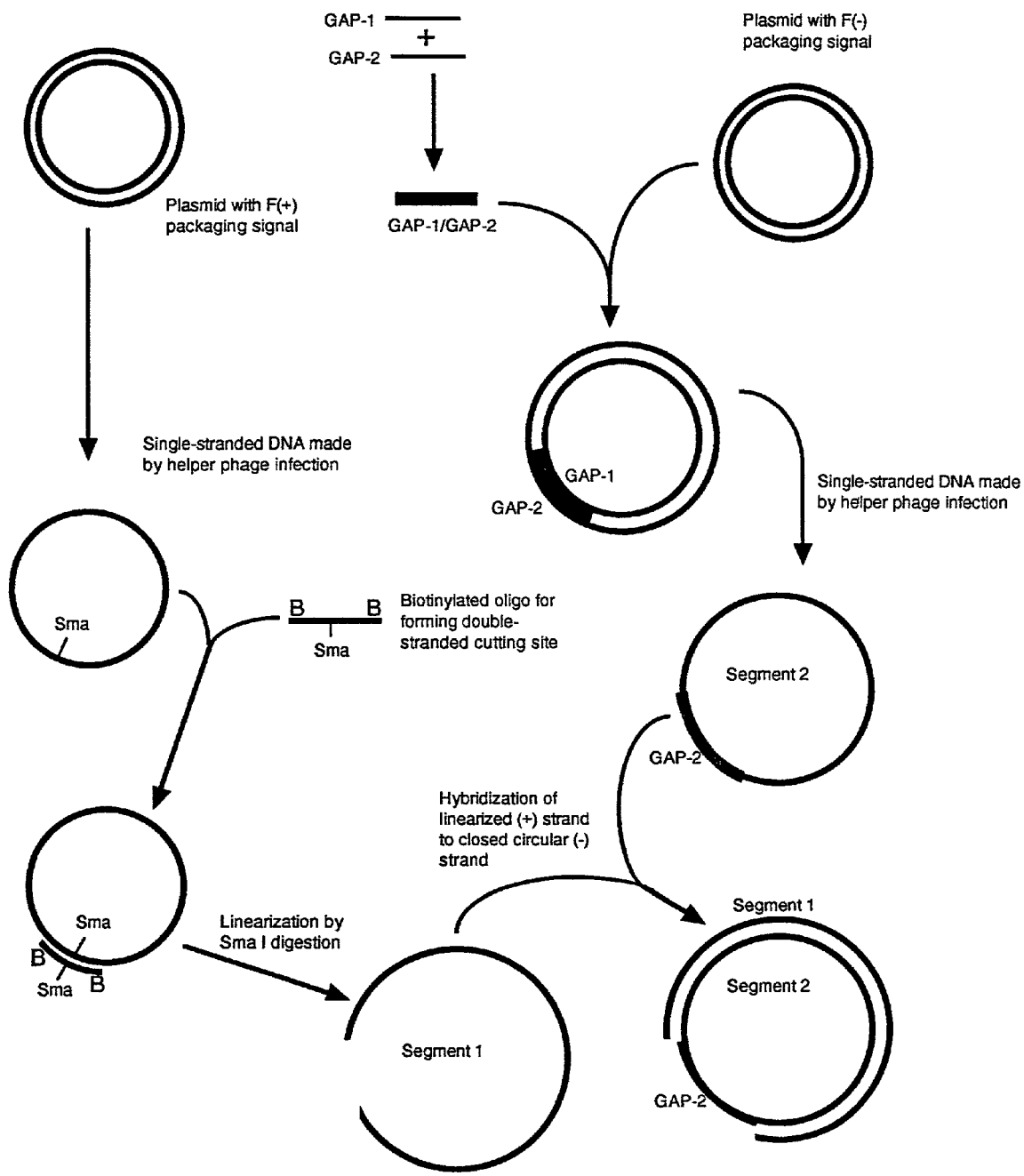
FIG. 5 illustrates the preparation of a gapped circle such as shown in FIG. 4.

Preparation of a Three Segment CHENAC Containing a Modified Single Stranded Tail (i) Description of the construct This construct is prepared from two unmodified complementary DNA segments (Segments 1 and 2) and a modified DNA segment (Segment 3). Segment 1 and Segment 2 are hybridized together to form a gapped circle with the gapped region being complementary to Segment 3. The final assembly of these segments are shown in FIG. 4. The methods for creating the individual components and assembling them into the final construct are given below (ii) Preparation of the gapped circle a) Segment 1 is prepared from plasmid DNA as described previously in Example 1. However, in this particular example, the starting plasmid contains the F(+) packaging signal. Since single-stranded DNA is not a suitable substrate for most restriction enzymes, a small portion of the circular single-stranded DNA is transformed into double-stranded form by hybridization with an oligo that is complementary to an appropriate restriction site. In this example, the restriction enzyme is Sma I and the oligo has been modified by the inclusion of biotinylated nucleotides (Cook, et al. 1988) at the ends. After digestion, the Sma I digested duplex DNA is destabilized and the biotinylated oligo has a much lower affinity. Purification of the cleaved single-stranded linear DNA is achieved by passing the digest over a strepavidin column and collecting the material that does not bind.

b) Segment 2 is prepared by preparation of two complementary oligonucleotides (GAP-1 and GAP-2) and hybridizing them together to form an unmodified double stranded oligonucleotide whose sequence will constitute the gap in the construct. The starting plasmid is the same one that was used to make Segment 1, except it contains the F(−) packaging signal. The introduced oligonucleotide (GAP-1/GAP-2) contains terminal restriction sites for the restriction enzyme Sma I in order to facilitate its insertion by restriction digestion and ligation. After cloning of a plasmid with the oligonucleotide inserted into the proper site, circular single-stranded Segment 2 DNA is obtained as shown in FIG. 5.

c) Segments 1 and 2 are annealed together to form a gapped circle where the single-stranded region contains the GAP-2 sequence. The overall process of steps ii-a, ii-b and ii-c are shown in FIG. 5

(iii) Synthesis of Segment 3

Segment 3 is prepared by synthesizing an oligomer similar to GAP-1 which differs from this oligomer in not having the Sma I sites added onto the end and also by being synthesized with allylamine moieties. After synthesis of the oligomer, the allylamine-modified nucleotides are further modified by the addition of the trilactyl lysyl lysine derivative as described previously. Segment 3 was processed further by the steps given below.

(iv) Addition of modified 3'tail to Segment 3

1 mg of the lactosylated oligomer (Segment 3) is dissolved in 10 ml of a reaction mixture containing 0.2 M cacodylate (pH 6.8), 1 mM deoxythymidine Triphosphate, 0.3 mM allylamine-deoxyuridine triphosphate, 1 mM cobalt chloride, 1 mM β-mercaptoethanol and 40,000 units of terminal transferase. The mixture is incubated for 2 hours at 35° C. and stopped by the addition of EDTA. Enzyme is removed by absorption to a phosphocellulose column at pH 6.0 and the flow-through is collected, precipitated with ethanol and redissolved in 2 ml of 0.1 mM EDTA. The final product has a poly-dT tail with approximately ¼ of the bases containing allylamine groups. Fusogenic peptides are then added onto the allylamine moieties as described previously.

(v) Final assembly

The final construct shown in FIG. 4 was formed by the hybridization of the gapped circle created in step (ii-c) with the tailed oligomer created in step (iv) through the complementary of the GAP-1 and GAP-2 sequences.

Example 6

Figure 6:
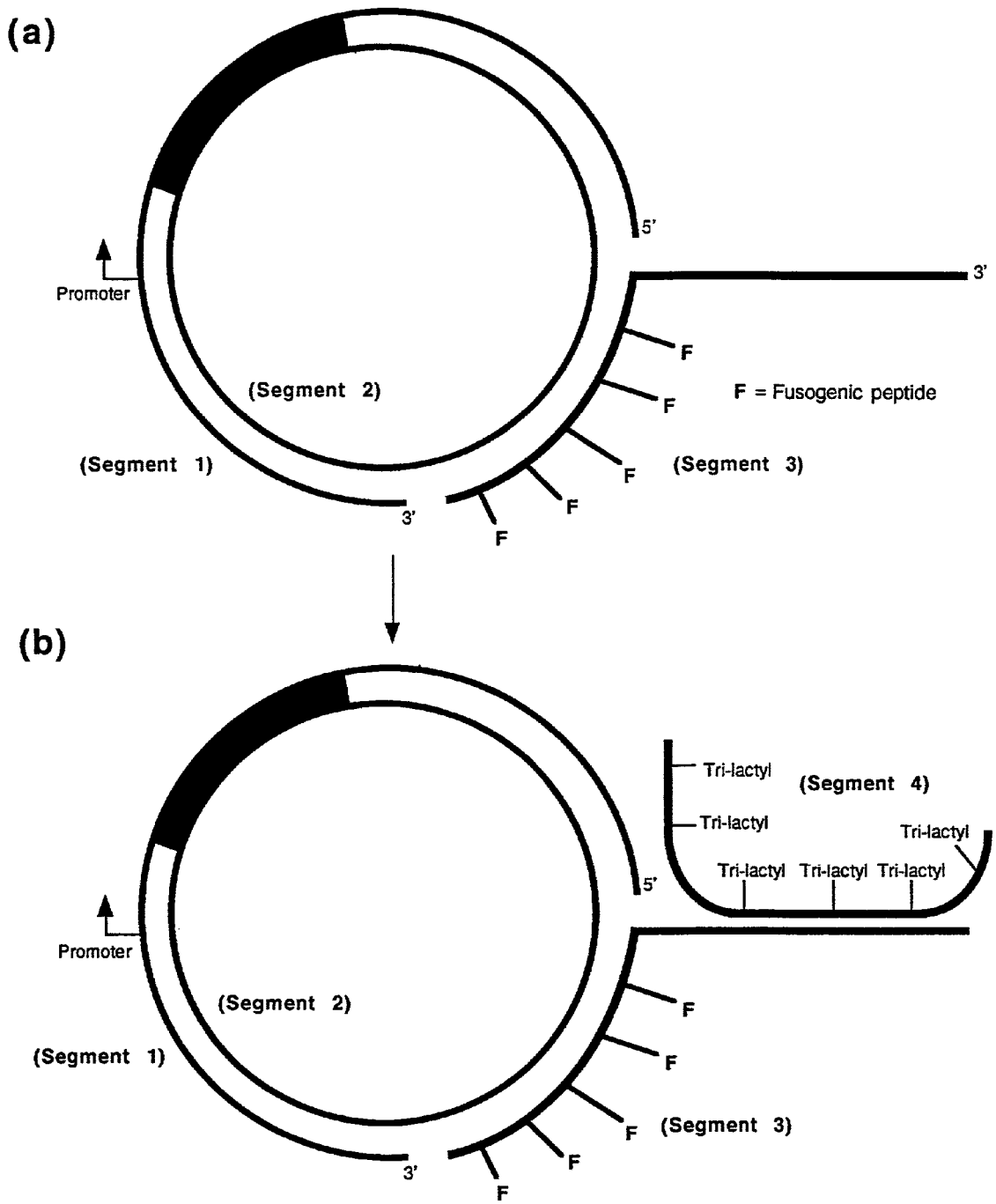
FIG. 6 illustrates the localized attachment with a nucleic acid construct by hybridization of a gapped circle with a modified nucleic acid moiety with an unmodified 3' tail to which has been hybridized a nucleic acid with useful ligands incorporated thereinto.

Preparation of a Three Segment CHENAC Containing an Unmodified Single Stranded Tail Capable of Hybridizing to Homopolymers Containing Ligands This construct was created in the same manner as the construct described in Example 5, except that after synthesis of the oligomer for Segment 3, the fusogenic peptide was added to the allylamine derivatives instead of the lactyl derivatives and the synthesis of the 3' tail was carried out in the presence of unmodified dATP. As in the previous example, Segment 1, Segment and Segment 3 were assembled together to make a double stranded circle with a 3' single-stranded tail. However, as shown in FIG. 6 a further step was added in which segment 4 was added to the complex. This segment was formed by extension of a Thymine tetranucleotide with Terminal transferase in the presence of a mixture of TTP and the lactyl-dUTP in a ratio of 3:1 using the same conditions described previously. Hybridization of Segment 4 to the complex results in the final construct shown in FIG. 6.

Example 7

Construction of an RNA Derived CHENAC

Figure 7:
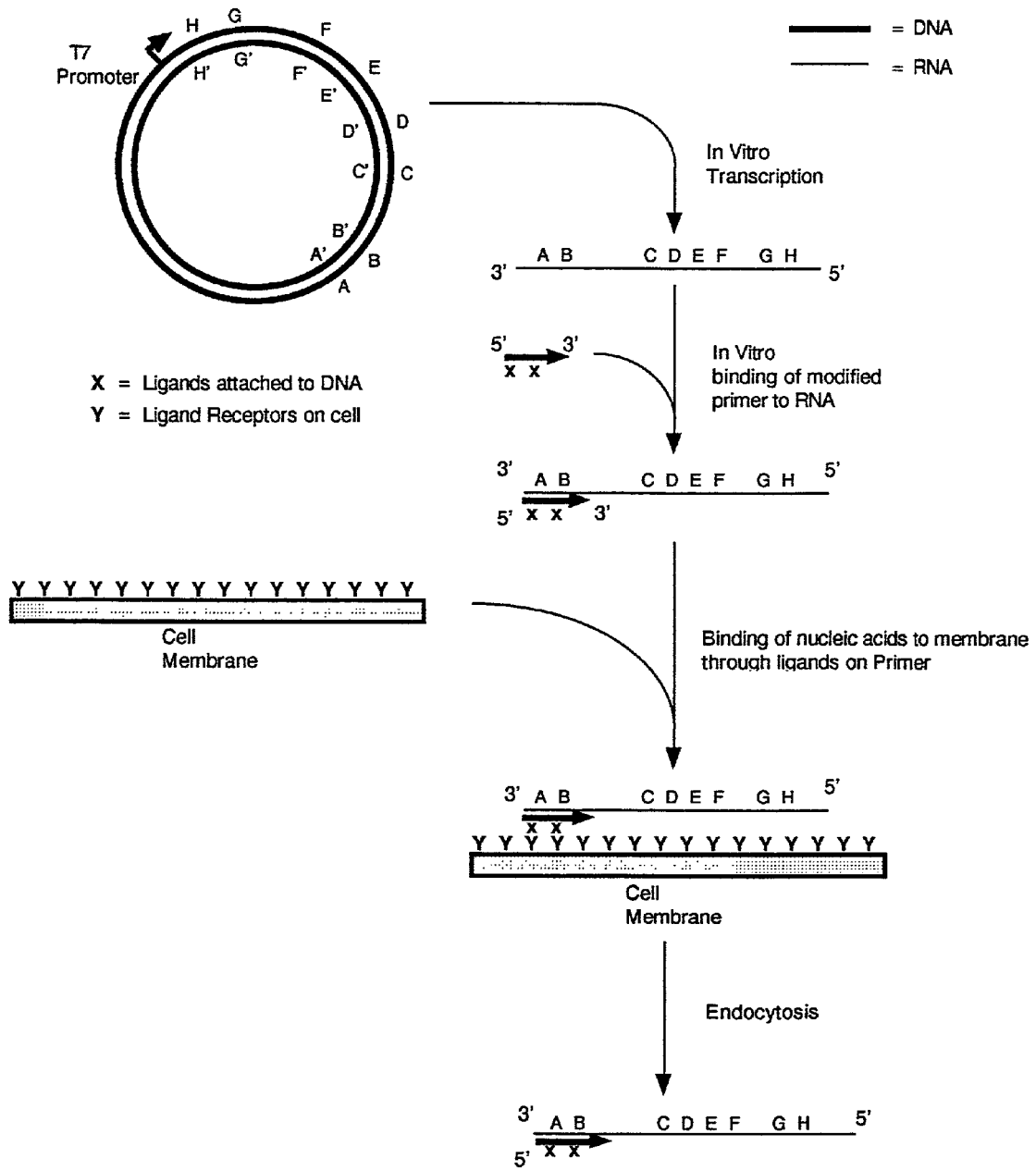
FIGS. 7 AND 8 show the process for introducing a segment of RNA into a cell by means of a modified primer whereby the RNA will be transformed in vivo into a double-stranded DNA segment.
Figure 8:
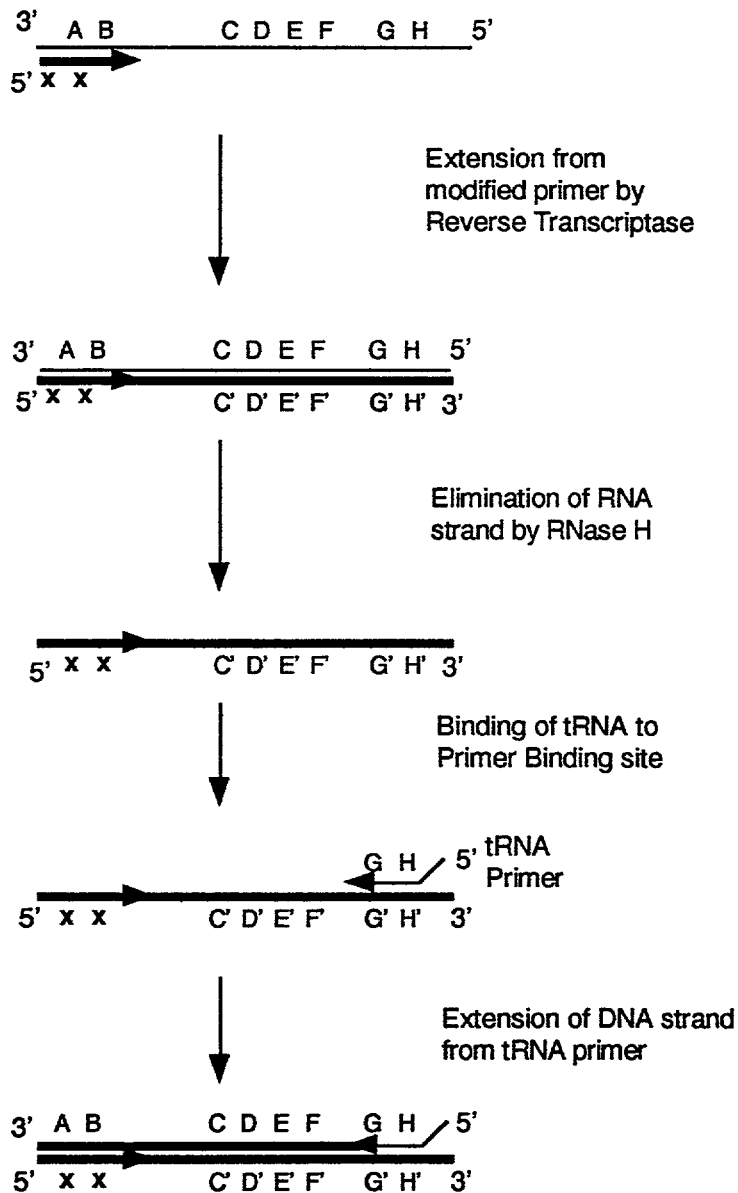

A construct is made with the appropriate structure shown in FIG. 7. Transcription is carried out in vitro by use of a T7 promoter directing the synthesis of the sequences of interest. The transcript contains a) sequence A B, which represents a sequence complementary to a lactylated DNA primer (prepared as described previously), b) sequence C D which represents a CMV promoter for directing synthesis of a transcript in vivo, c) sequence E F which represents a sequence for biological function which will be expressed after transcription by the CMV promoter and d) sequence G H which is designed such that its complementary sequence will be a primer binding site similar to the one used by HIV to bind a cellular tRNA$^{lys}$ as a primer for reverse transcriptase. After transcription of the RNA in vitro, the modified primer is annealed to the RNA to form the complex shown in FIG. 7. This complex could be used either in vivo, ex vivo or in vitro to bind the RNA to a target cell through a ligand/receptor interaction. After endocytosis, some portion of the RNA should be available in the cytoplasm for further processing and activity. FIG. 8 shows the pathway that would occur in the presence of reverse transcriptase activity. This activity can be provided either by targeting a cell that has this activity already present (either intrinsically or due to a retroviral infection) or by introducing it by any of a variety of means known to those skilled in the art. The end result of the steps shown in FIG. 8 is a double stranded linear piece of DNA which will be capable of producing transcripts that provide a desirable biological activity.

Example 8

Construction of an RNA Derived CHENAC with Multiple Primers

Figure 9:
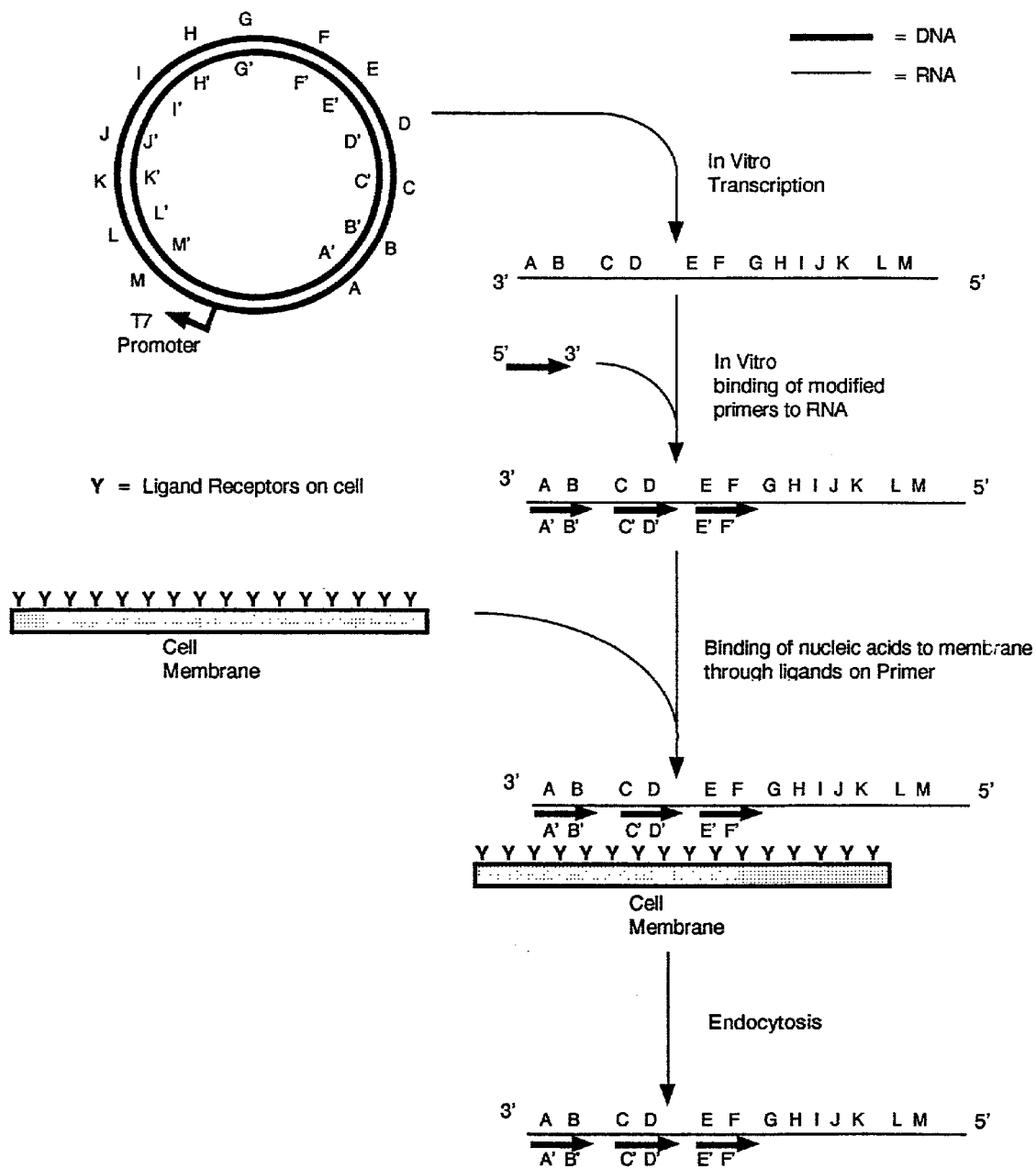
FIGS. 9 AND 10 show the process for introducing a segment of RNA into a cell by means of modified primers whereby the RNA will be transformed in vivo into double-stranded DNA segments.
Figure 10:
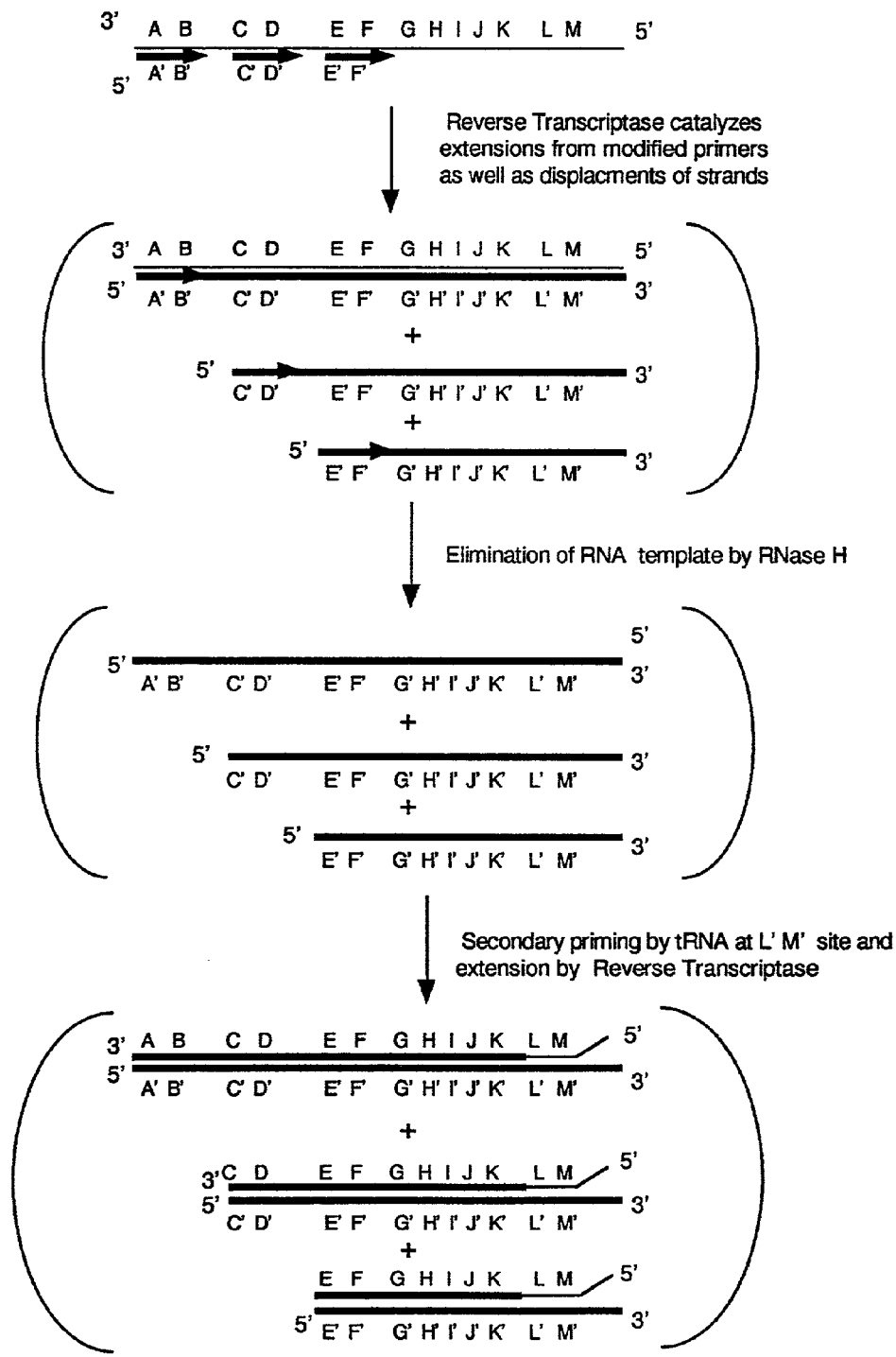

A construct is made with the appropriate structure shown in FIG. 9. Transcription is carried out in vitro by use of a T7 promoter directing the synthesis of the sequences of interest. The construct in this example is similar to the one described in Example 8 except that it is intended to produce an RNA that will be annealed with multiple primers rather than a single modified primer. One or more of these primers can be modified. In the present example, the transcript contains a) sequence A B, which represents a sequence complementary to a lactylated DNA primer (prepared as described previously), b) sequence C D, which represents a sequence complementary to a modified DNA primer that has fusogenic peptides attached (prepared as described previously) c) Sequence E F, which is an unmodified primer d) sequence G H which represents a CMV promoter for directing synthesis of a transcript in vivo, e) sequence I J K which represents a sequence for biological function which will be expressed after transcription by the CMV promoter and d) sequence L M which is designed such that its complementary sequence will be a primer Binding site similar to the one used by HIV to bind a cellular tRNA$^{lys}$ as a primer for Reverse Transcriptase. For the purposes of clarity, the appended modifications are not depicted in FIG. 10. After transcription of the RNA in vitro, the primers described above are annealed to the RNA to form the complex shown in FIG. 9. This complex could be used either in vivo, ex vivo or in vitro to bind the RNA to a target cell through a ligand/receptor interaction. The ligand modified primer will promote uptake of the complex and after endocytosis the fusogenic peptide modified primer will promote the release of the RNA from the endosomes. FIG. 10 shows the pathway that would occur in the presence of Reverse Transcriptase activity. This activity can be provided either by targeting a cell that has this activity already present (either intrinsically or due to a retroviral infection) or by introducing it by any of a variety of means known to those skilled in the art. The end result of the steps shown in FIG. 10 is a series of double stranded linear piece of DNA (each initiated from one of the primers from the complex formed in vitro) which will be capable of producing transcripts that provide a desirable biological activity.

Example 9

Construction of a One-Segment Single-Stranded CHENAC

Figure 11:
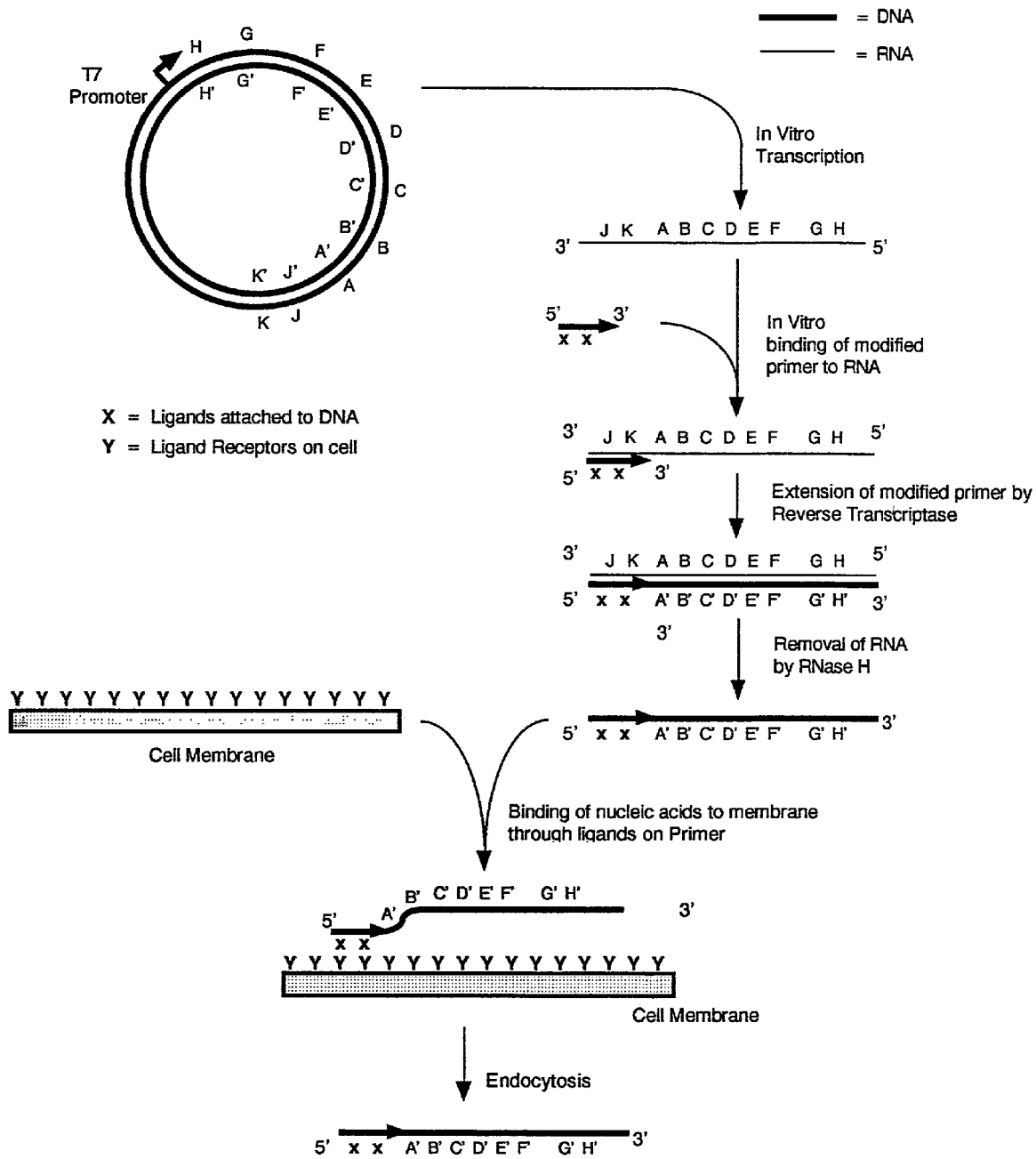
FIG. 11 illustrates a process for introducing a segment of single stranded DNA having modified nucleotides as part of its sequence.

A construct is made with the appropriate structure shown in FIG. 11. Transcription is carried out in vitro by use of a T7 promoter directing the synthesis of the sequences of interest. The transcript contains a) sequence J K, which represents a sequence complementary to a lactyl lysyl lysine modified DNA primer (prepared as described previously) as well as sequences for biological function which include a CMV promoter for directing synthesis of a transcript, a sequence for biological function which will be expressed after transcription by the CMV promoter and a sequence or sequences complimentary to tRNA binding sites. This example differs from the two previous examples in that the complementary DNA is synthesized in vitro by using Reverse Transcriptase with the tri lactyl-LysylLysine modified DNA segment as a primer. The resulting RNA/DNA double stranded molecule is treated with Rnase H to yield a single stranded DNA CHENAC.

Figure 12:
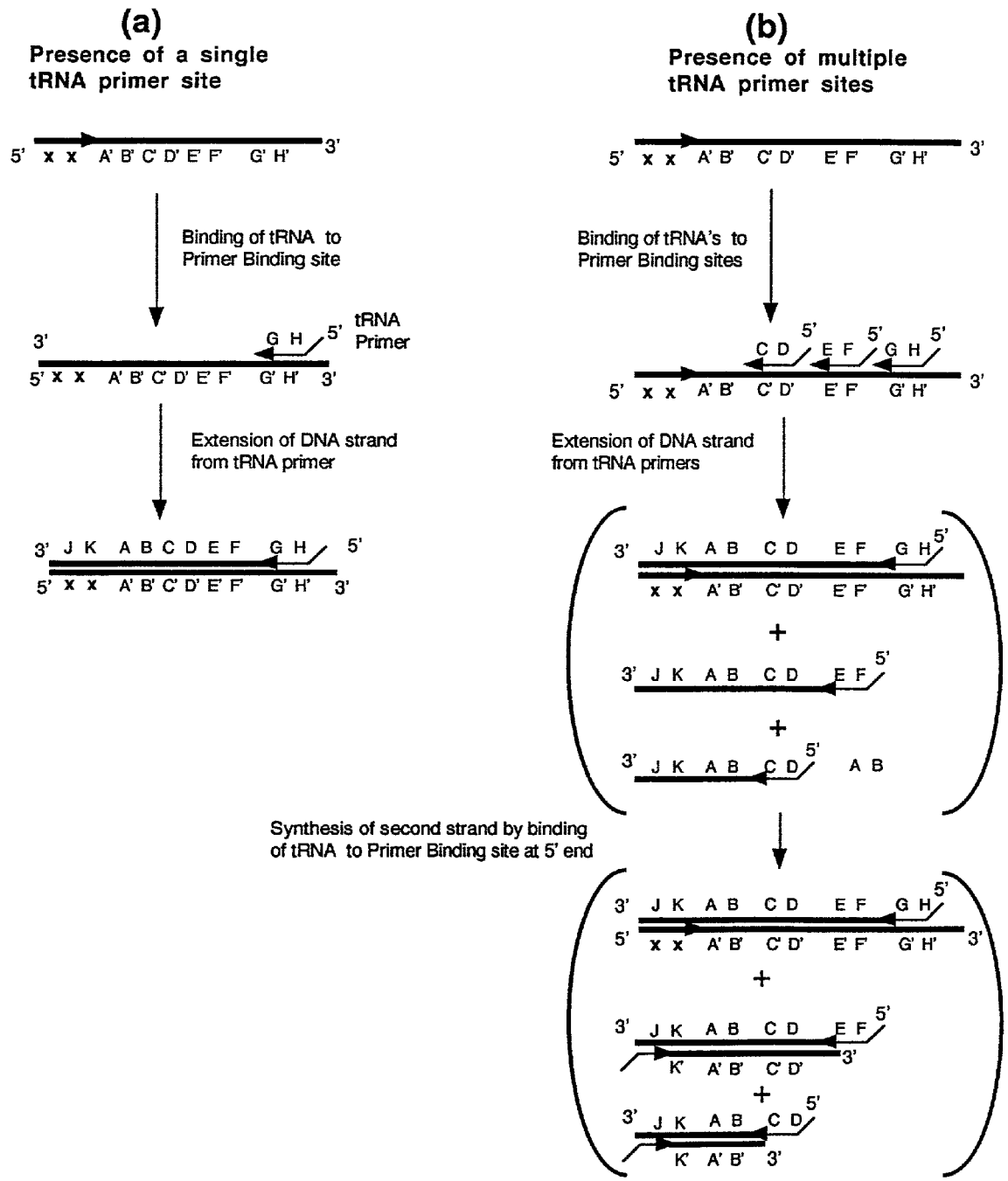
FIG. 12 illustrates the fate of the modified single-stranded DNA from FIG. 11 after it has been introduced into a cell.

This complex could be used either in vivo, ex vivo or in vitro to bind the DNA CHENAC to a target cell through a ligand/receptor interaction. After endocytosis, some portion of the DNA should be available in the cytoplasm for further processing and activity. FIG. 12 shows two possible pathways that could occur after release of DNA into the cytoplasm. FIG. 12a shows a pathway similar to that seen in FIG. 8 where the construct has been designed such that there is a single tRNA binding site at the 3' end of the DNA CNMAC. Priming and extension in vivo by cellular mechanisms result in a single double-stranded DNA molecule. FIG. 12b shows a pathway where the construct has been designed such that there are multiple tRNA binding sites at the 3' end of the CNMAC. These can either be identical or different tRNA species can be used. Extension from a CNMAC with sequence for three tRNA primers (as shown in FIG. 12b) leads to the synthesis of a double-stranded DNA molecule and two single-stranded DNA molecules. These latter two molecules can be converted into double-stranded molecules if the sequence chosen for the ligand modified primer is also similar to a tRNA primer sequence. When the construct is designed such that the pathway will be similar to that shown in FIG. 12a, the construct provide a transcript in which a) sequence J K represents a sequence complementary to the ligand modified primer b) the sequence A B represents a sequence for a CMV promoter c) the sequence C D E F represents a sequence for biological function which will be expressed after transcription by the CMV promoter and d) sequence G H which is designed such that its complementary sequence will be a primer Binding site similar to the one used by HIV to bind a cellular tRNA$^{lys}$ as a primer for Reverse Transcriptase. When the construct is designed such that the pathway will be similar to that shown in FIG. 12b, the construct provide a transcript in which a) sequence J K represents a sequence complementary to the ligand modified primer b) the sequence A represents a sequence for a CMV promoter c) the sequence B represents a sequence for biological function which will be expressed after transcription by the CMV promoter and d) and sequences C D, E F and G H represent sequences that are complementary to sequence will be primer Binding sites for tRNA's that can be used as primers. The major difference between the net result of the pathways shown in this example and previously described in Example 7 and Example 8 is that the two latter examples depended upon the in vivo presence of Reverse Transcriptase whereas the present example provides the Reverse Transcriptase activity in vitro prior to binding and uptake into target cells.

Example 10

Preparation of a Double-Stranded CHENAC Containing Moieties on Each Strand

Figure 13:
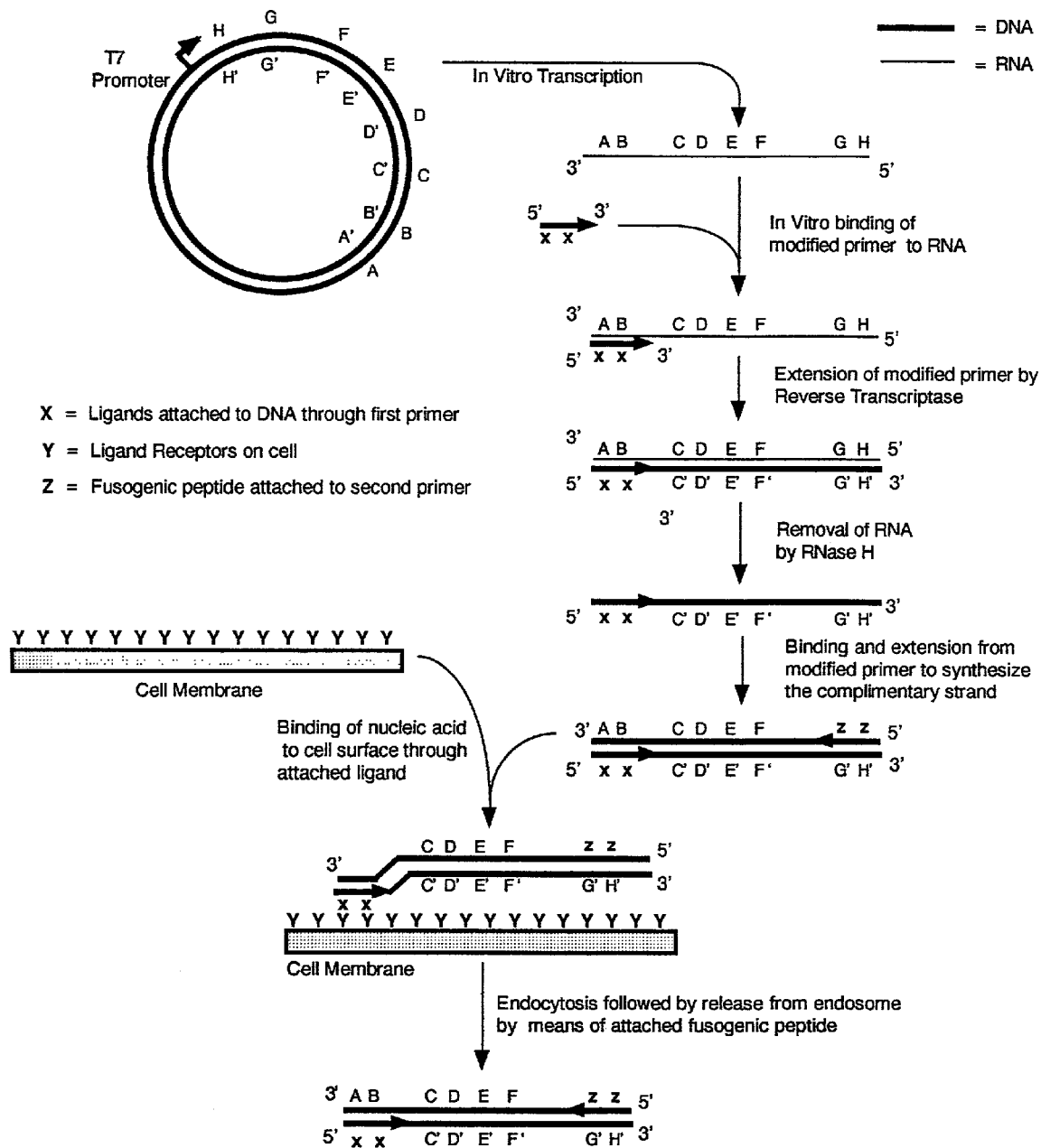
FIG. 13 illustrates a process for introducing a segment of double stranded DNA having modified nucleotides as part of the sequence on each strand.

A construct is made with the appropriate structure shown in FIG. 13. Transcription is carried out in vitro by use of a T7 promoter directing the synthesis of the sequences of interest. The transcript contains a) sequence A B, which represents a sequence complementary to a lactyl-LysylLysine modified DNA primer (prepared as described previously), b) sequence C D which represents a CMV promoter for directing synthesis of a transcript in vivo, c) sequence E F which represents a sequence for biological function which will be expressed after transcription by the CMV promoter and d) sequence G H which is identical to the sequence of a second modified primer that has fusogenic peptides attached (prepared as described previously). In FIG. 10, the lactyl ligands are depicted by X X on the first primer and the fusogenic peptides are shown as Z Z in the second primer. DNA is synthesized in vitro by using the transcript as a template for Reverse Transcriptase with the tri lactyl lysyl lysine modified DNA segment as a primer. The resulting RNA/DNA double stranded molecule is treated with Rnase H to yield single stranded DNA. The second primer containing the fusogenic peptides is then used as a primer to prepare the complimentary second strand of DNA.

This complex could be used either in vivo, ex vivo or in vitro to bind the DNA to a target cell through a ligand/receptor interaction. The ligand modified primer will promote uptake of the complex and after endocytosis the fusogenic peptide modified primer will promote the release of the DNA from the endosomes.

Example 11

A Bifunctional Binder Composed of a Bispecific Antibody

Figure 14:
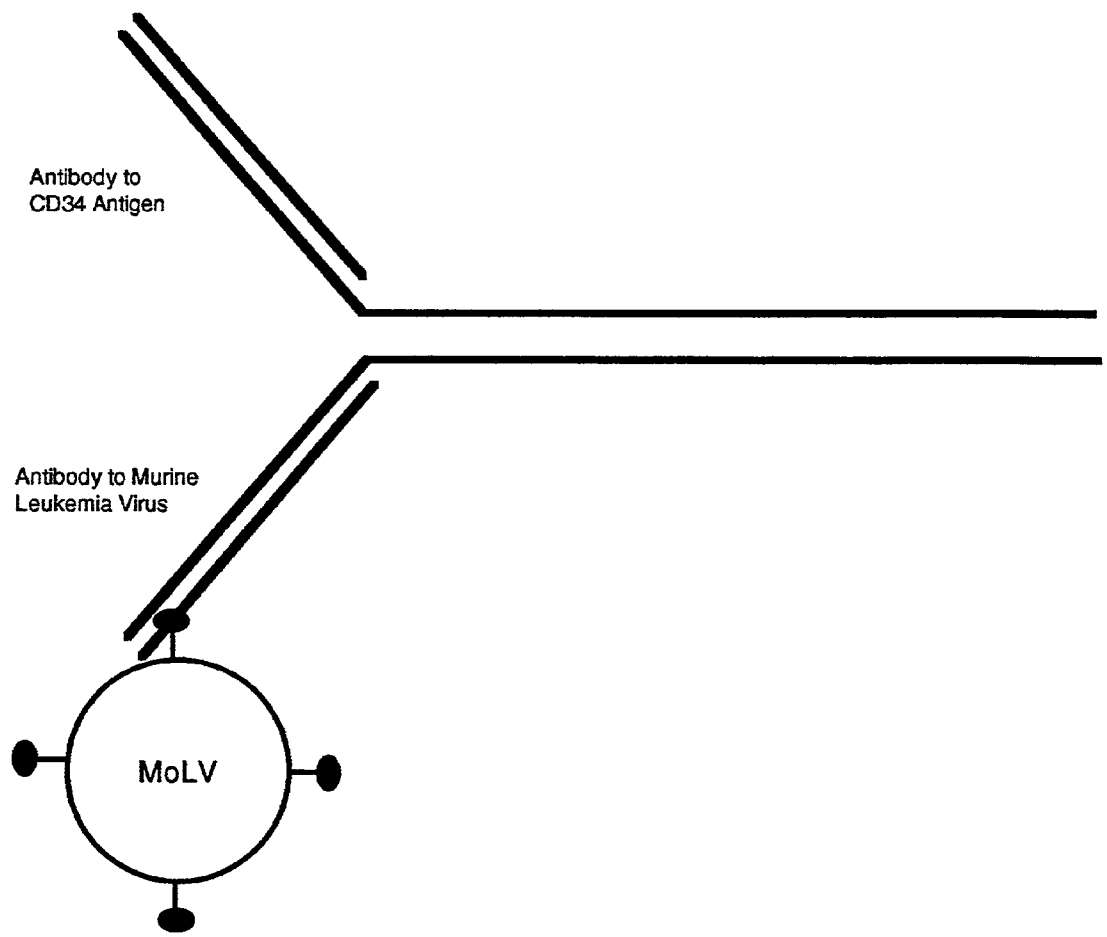
FIG. 14 illustrates a divalent antibody binder with one portion having an affinity for binding a retroviral particle, and the other portion having an affinity for binding the CD34 antigen.

The methods of recombinant DNA are used to prepare a bispecific antibody with specificities for the CD4 protein of lymphocytes and for murine leukemia virus (FIG. 14). The antibody is prepared from murine monoclonal antibodies according to the procedure of Staerz and Bevan (1985 Proc Natl Acad Sci USA 83; 1453) for the production of hybrid hybridomas.

Antibody modifications. Hydrazine groups are introduced to antibodies in the carbohydrate moieties after oxidation with periodate or galactose oxidase and subsequent reaction with hydrazine. When galactose oxidase is used for antibody oxidation, it is necessary to analyze for free galactose groups as follows. The antibody is oxidized with galactose oxidase in the presence of a peroxidase. At the end of the reaction the mixture is reacted with Lucifer Yellow CH (Aldrich) and passed through a G50 column. If the flowthrough from the column fluoresces, this is an indication that the antibody contains free galactose residue and that the galactose oxidase can be used for antibody activation.

Ten mg antibody are dissolved in 1 ml of 0.1M acetate buffer, pH 5.0, and oxidized with 1.0 umole NaIO$_4$ at 4° C. for 30 minutes. Excess period ate is removed by Sephadex G50 (Pharmacia) chromatography in 0.05M acetate buffer, pH 5.0. The protein fractions are combined and reacted with 1.0 umole hydrazine acetate, pH 5.0, for 30 minutes at room temperature. The pH is raised to 9.0 with sodium carbonate and the contents are cooled to 0° and 10 umoles sodium borohydrate are added in three portions at ten minute intervals. The reduction is continued for an additional 60 minutes and the antibody is precipitated with 55% ammonium sulfate. After 2 hr at 0° C. the reaction mixture is centrifuged for 30 minutes at 10,000×g. The pellet is dissolved in 1 ml acetate buffer, pH 5.5, and dialyzed in the cold against 0.1M acetate buffer, pH 5.5.

One umole of 3-maleimidipropionic acid N-hydroxy-succinimide ester is dissolved in 0.5 ml dimethylsulfoxide and added slowly to the dialysate and incubated for 30 minutes at room temperature. Excess maleimide is removed by G50 chromatography and the combined antibody fractions are reacted with the thiol containing ligand for 1 hr at room temperature at pH 6.5. Subsequently the conjugated antibody is separated form the unreacted ligand by molecular sieving chromatography of the appropriate pore size.

Oligonucleotides synthesized with a thiol group at the 5' end or the thiol groups were added by reaction with an allylamine residue at the 5' or 3' end of the nucleic acid with homocysteine thiolactone at pH 9.0.

Example 12

Figure 15:
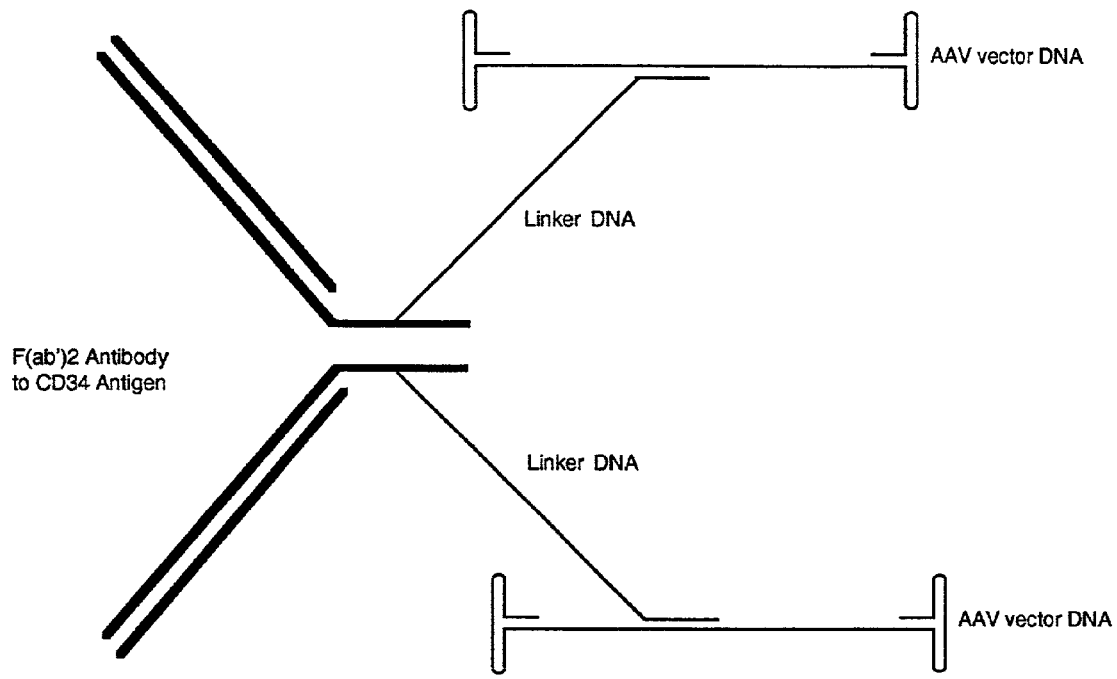
FIG. 15 shows the covalent attachment of DNA to each portion of an F(ab')2 antibody fragment with an affinity for the CD34 antigen.

A Bifunctional Binder Composed of an Antibody to the CD4 Cell Surface Protein as the Domain for the Cell and a Single Stranded DNA Molecule as the Domain for the Nucleic Acid Component (FIG. 15)

A single stranded DNA molecule 120 bases in length and containing a 5' terminal nucleotide modified by the addition of an allylamine group is prepared chemically by the method of Cook et al. (1988 Nucleic Acids Res 16; 4077). and the allylamine residue is thiolated as in Example 11. The 70 bases at the 3' end are complementary to the single stranded region of Adeno Associate Virus DNA. The single stranded DNA is attached to the F(ab')$_2$ fragment as in Example 11 and they anneal to Adeno Associated Virus as indicated in FIG. 15.

Example 13

Figure 16:
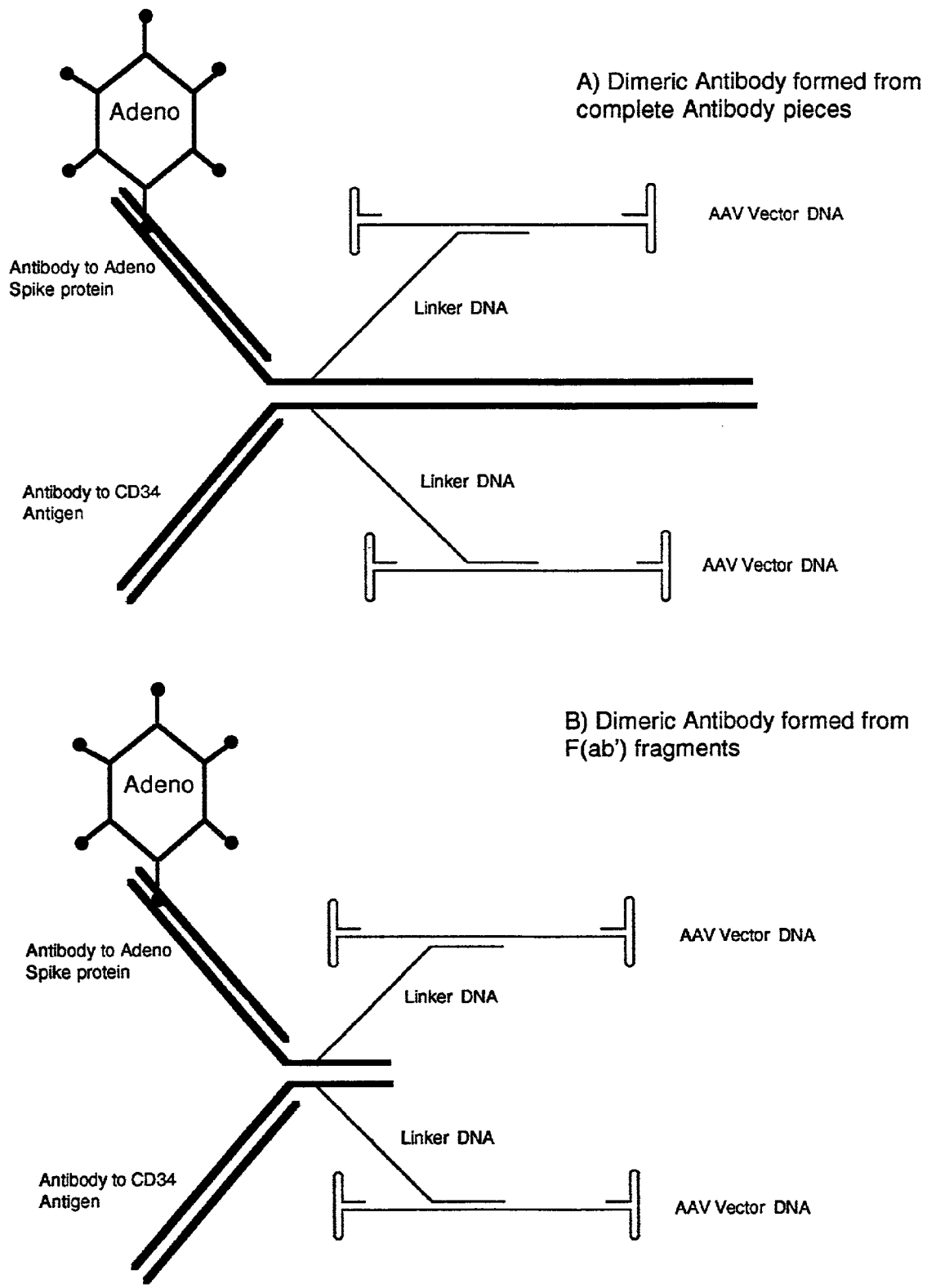
FIG. 16(A) depicts the covalent attachment of DNA to an adenovirus binding portion of a divalent antibody in order to promote the binding of an AAV vector DNA molecule to a CD34 receptor.
FIG. 16(B) is the same depiction as in FIG. 16(A) except that F(ab') fragments are used instead of complete antibody proteins.

A Binder Composed of a Bispecific Antibody (or of the F(ab')$_2$ Fragment of a Bispecific Antibody) Attached to a Single Stranded DNA Domain for the Nucleic Acid Component (FIG. 16)

A bispecific antibody is prepared as described in Example 11 from a murine monoclonal antibody to CD34 cell surface protein and a murine monoclonal antibody to adenovirus. The single stranded DNA molecule described in Example 12 is attached to the bispecific antibody (or to the F(ab')$_2$ fragment of the bispecific antibody) and annealed to the adeno associated virus. An inactivated adenovirus is bound to the antibody (Cristiano et al. 1993 Proc Natl Acad Sci USA 90; 2122: Curiel et al. 1991 Proc Natl Acad Sci USA 88; 8850) in order to facilitate cellular uptake of the complex.

Example 14

Figure 17:
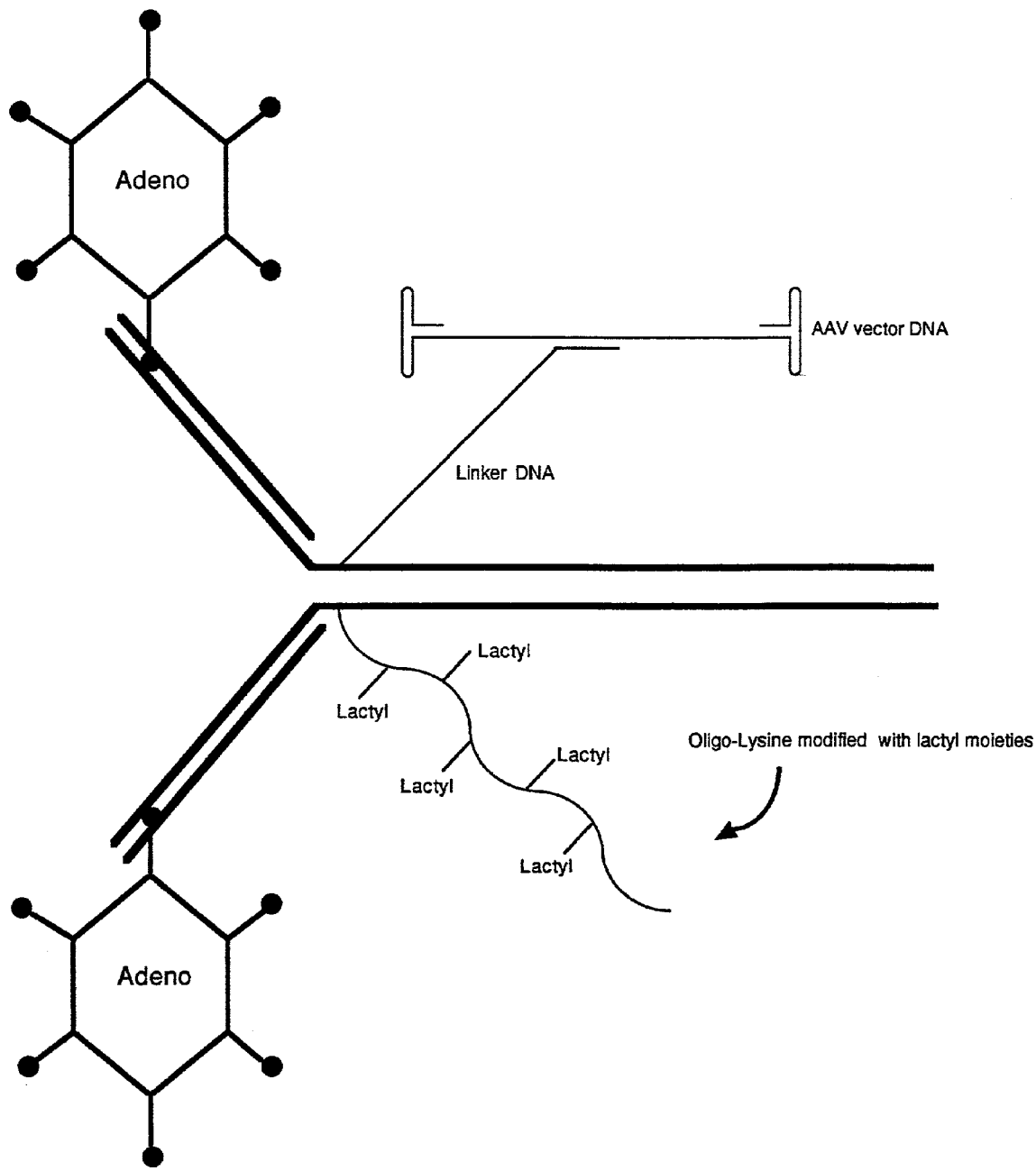
FIG. 17 illustrates a monovalent antibody to an adenovirus spike protein with one portion being modified by covalent attachment of DNA that can bind an adenovirus associated virus (AAV) vector DNA molecule through hybridization and the other portion being modified by the covalent attachment of an oligolysine modified by the attachment of lactyl groups.

A Binder composed of a Domain for Adeno Associated Virus DNA, a Domain for Binding to Liver Cells and an Inactivated Adenovirus (FIG. 17)

Preparation of lactyl oligolysine 10mer. Oligolysine is synthesized containing a cysteine residue at the carboxy terminus. The thiol group is blocked with Ellman's reagent and the amino groups are reacted with a threefold excess of lactylisothiocyanate in 0.1M bicarbonate buffer, pH 9.0, and 20% dimethylformamide for 2 hr at room temperature. The reaction mixture is chromatographed on a G50 column and the lactyl-oligolysine fractions are combined and freeze dried. The solid is dissolved in 2 ml 1 mM dithiothreitol to unblock the protected thiol group and chromatographed again on a G50 column to remove the excess dithiothreitol and the liberated Ellman's reagent. All operations are performed with argon saturated buffer to prevent thiol oxidation by air. The combined lactyl oligolysine fractions are combined and reacted immediately with the maleimide derivatized antibody (see below) or proteins in a mixture with thiol containing nucleic acid as in Example 12.

Example 15

Figure 18:
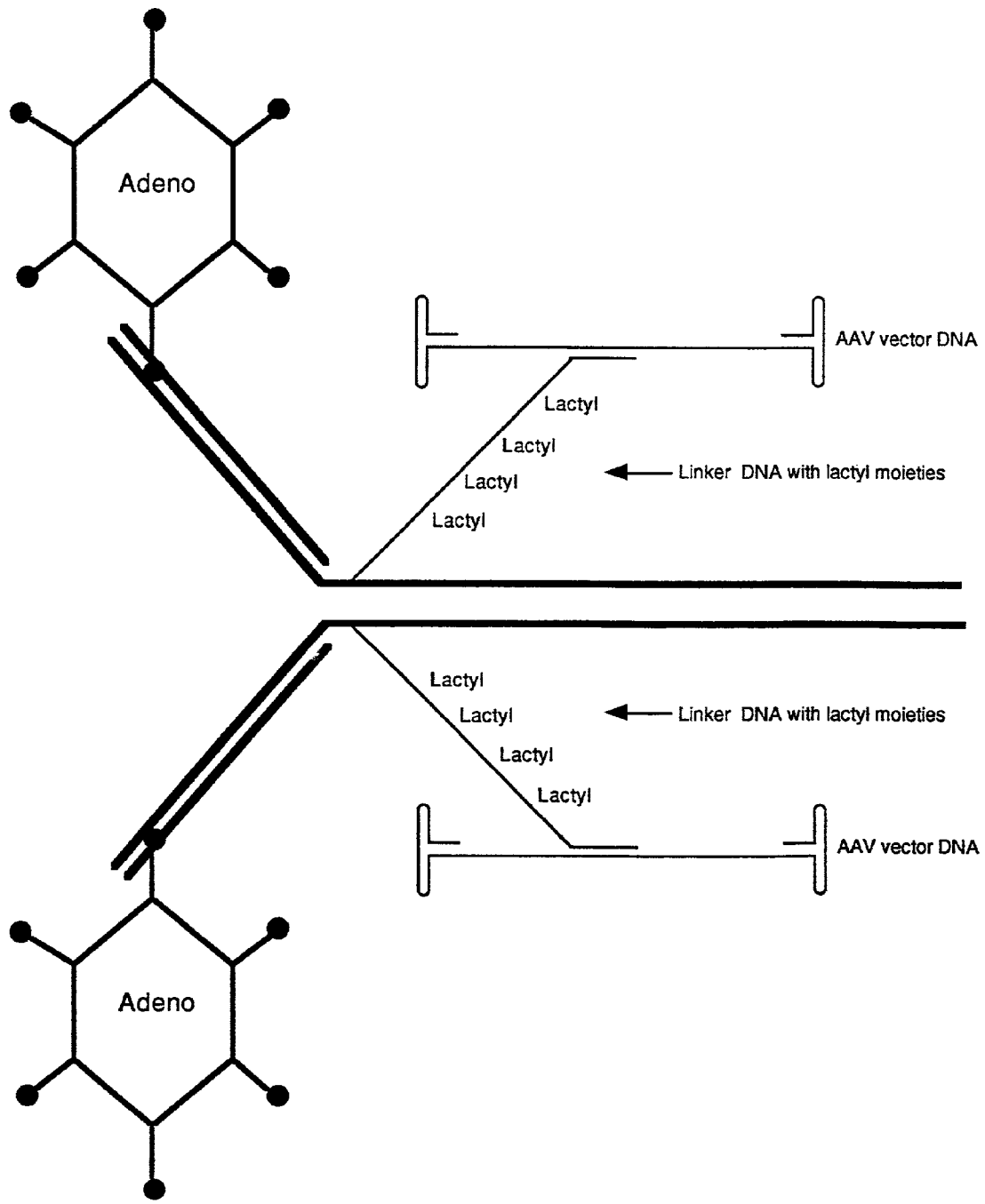
FIG. 18 shows a monovalent antibody to an adenovirus spike protein in which each portion of the antibody has been modified by the covalent attachment of lactosylated DNA molecules which are bound to an AAV vector DNA by means of hybridization.

An Antibody Binder with an Attached DNA with Domains for Adeno Associated Virus DNA and for Binding to Liver Cells (FIG. 18)

A single stranded DNA molecule 100 bases in length and with a 5' terminal nucleotide containing a thiol group is synthesized chemically Allylamine groups are interspersed at 10 base intervals along the 50 bases at the 5' end of the molecule Cook et al.) and the 50 bases at the 3' end of the molecule are homologous to adenovirus associated virus DNA. After blocking the thiol groups, the lactyl groups are added as described in Example 11. The thiol groups are then unmasked and the lactyl modified single stranded DNA is added to a murine monoclonal antibody to adenovirus and it is annealed to adenovirus associated virus DNA as described in Example 12.

Example 16

Figure 19:
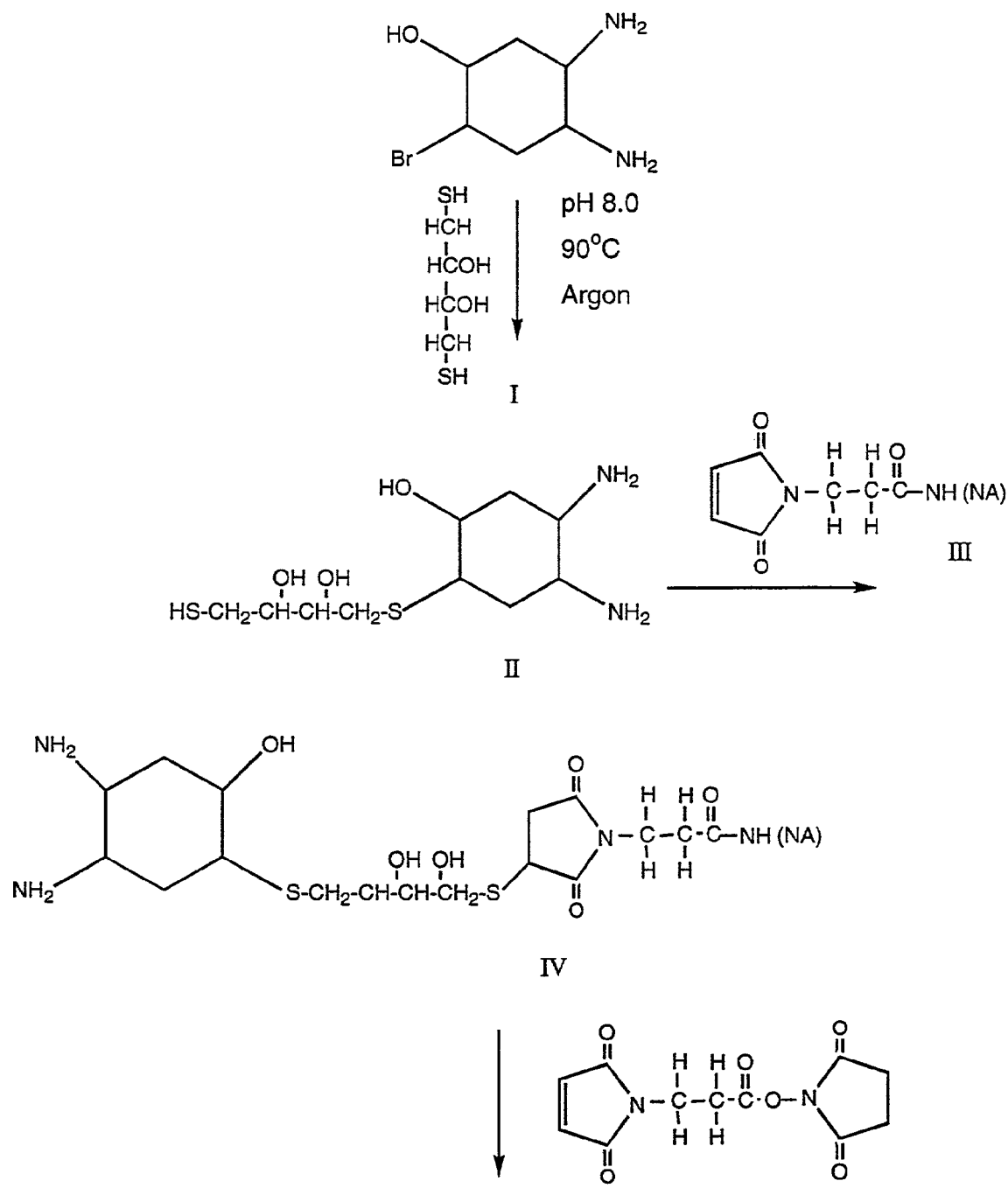
FIGS. 19 AND 20 describe the synthetic steps for producing a reagent that is useful for attaching nucleic acid moieties to an antibody.
Figure 20:
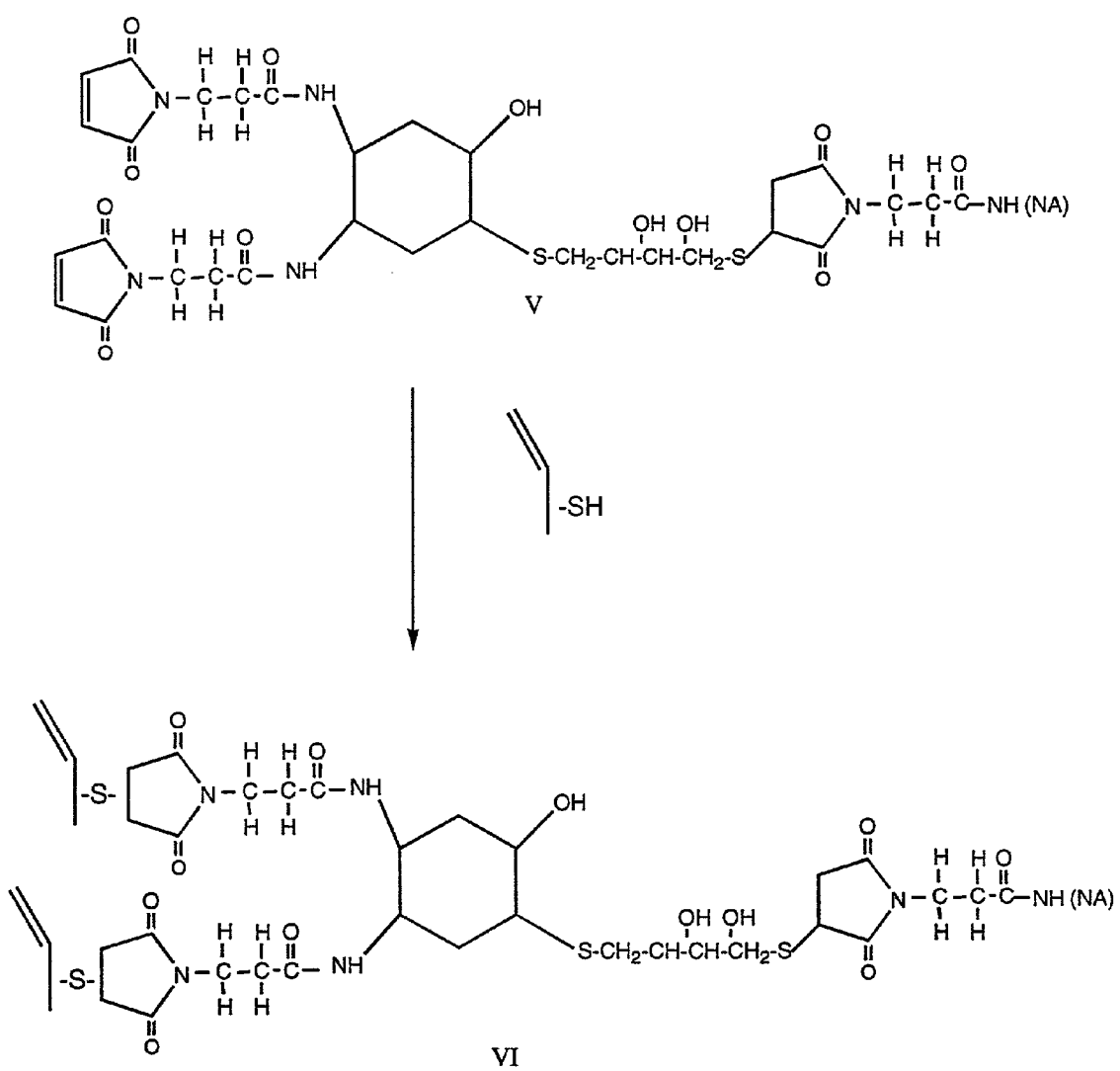

Preparation of a Multimeric Antibody by Means of Nucleic Acid Hybridization (i) Preparation of homopolymer
Oligo(dA) and oligo(dT) with an amine group at the 5' end were synthesized chemically. Longer molecules were prepared by using the amine-containing oligos as primers in a reaction with Terminal transferase and the appropriate dNTP precursors depicted as NA in FIGS. 19 and 20.
(ii) Preparation of homopolymer linker
1,2 Diamino-4-Bromo-5-Hydroxycyclohexane was prepared according to U.S. Pat. No. 4,707,440 where the product of the (11-5) reaction was reacted with N-Bromosuccinimide as in step (4-7) to yield compound I. (The various steps in this synthesis are shown in FIGS. 19 and 20). Compound I was reacted with a 5-fold excess of dithiothreitol at 90° C., pH 8.0 in argon atmosphere for 2 hours. The reaction mixture was acidified to pH 1.0 and the excess of dithiothreitol was removed by peroxide-free ether until no thiol was detected in the ether phase. The aqueous phase which contains Compound II was used for the next step.

(iii) Attachment of linker to homopolymer

The 5' amino group of the nucleic acid was reacted with 3-maleimidopropionic acid N-hydroxy succinimide ester in 0.2 M sodium bicarbonate buffer pH 7.8 and 0.7 M lithium chloride 30% dimethyl formamide for 40 minutes at 25° C. The pH of the mixture was brought to 5.5 with 2.0 M acetic acid and the excess active ester was removed by extraction with n-butanol. The product Compound III was precipitated with 4 volumes ethanol for 2 hours at −70° C. It was centrifuged and the pellet was dissolved in 0.7 M lithium chloride and reacted immediately with excess Compound II at pH 6.0 for 30 minutes at room temperature to yield Compound IV; it was separated from excess of Compound II by ethanol precipitation as in the previous step. Compound IV was reacted with excess 3-maleimidopropionic acid N-hydroxy succinimide ester (as described in the preparation of Compound III) to yield Compound V. The product was precipitated twice with 4 volumes ethanol and stored as a pellet at −70° C. until used.

(iv) Preparation of Antibody

Fab'-SH fragments were prepared by reduction of F(ab')$_2$ antibody with 0.5 M dithiothreitol at pH 7.5 (Taizo Nitta, Hideo Yagita, Takachika Azuma, Kiyoshi Sato and Ko Okumura Eur J. Immunol 1989 19: 1437-1441) under argon atmosphere. The pH was lowered to 6.0 and the antibody was separated from dithiothreitol by G50 chromatography using fully deaerated buffer under argon atmosphere to prevent oxidation to F(ab')$_2$ (v) Attachment of homopolymer to Antibody fragments The protein fractions from step (iv) were combined and reacted with Compound V (FIG. 20) from step (iii) in a 2:1 ratio to form Compound VI, always under argon atmosphere and in the presence of 2 mM EDTA to prevent nuclease action. After overnight incubation at 4° C., Ethylmaleimide was added to the reaction mixture to block any free thiol residues and the protein was precipitated with ammonium sulfate (60% of saturation). The pellet was dissolved in minimum amount tris-HCl buffer, pH 7.8 and chromatographed in a G100 column to separate the conjugate from the reaction products.

(vi) Annealing of homopolymers to obtain Antibody multimers

Figure 21:
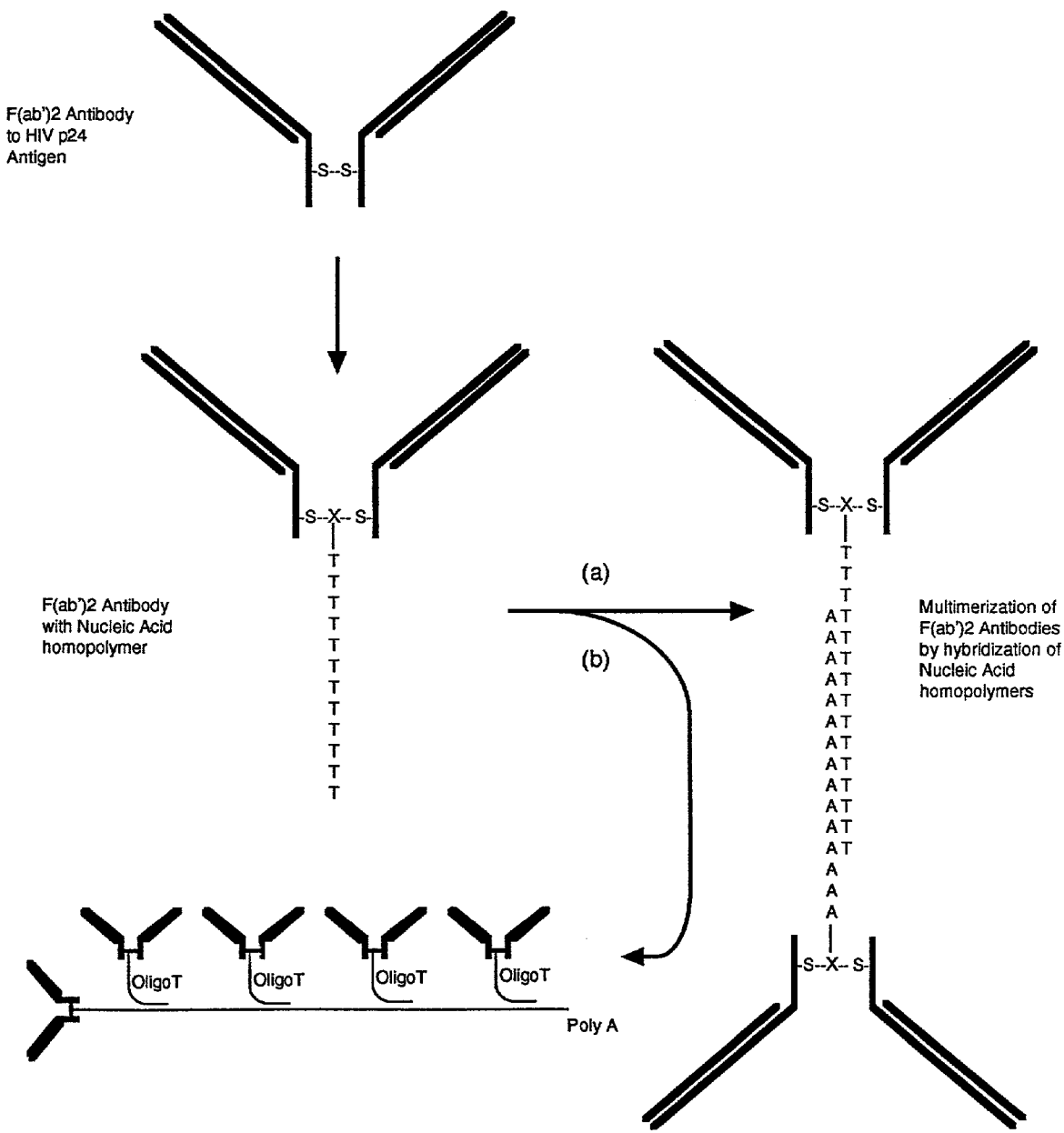
FIG. 21 depicts a process for mutlimerization of F(ab')2 antibody fragments by hybridization of nucleic acid homopolymers (polynucleotide sequences shown in SEQ ID NOS 52-54, from left to right).

Annealing is done 0.2M NaCl, 0.05M Tris HCl (pH 7.8), 1 mM EDTA. FIG. 21 shows the overall outline of the process. In the last step shown in FIG. 21, (a) shows an example where both the A homopolymer and the T homopolymer are short enough that there is essentially only one of each type of molecule binding together in a 1:1 ratio (SEQ ID NOS 52-54). The (b) diagram shows the situation where the A homopolymer was synthesized such that its much longer than the T homopolymer; in this situation, larger numbers of antibodies can be linked together into complexes.

Example 17

Preparation of a Multimeric Insulin by Means of Nucleic Acid Hybridization

Figure 22:
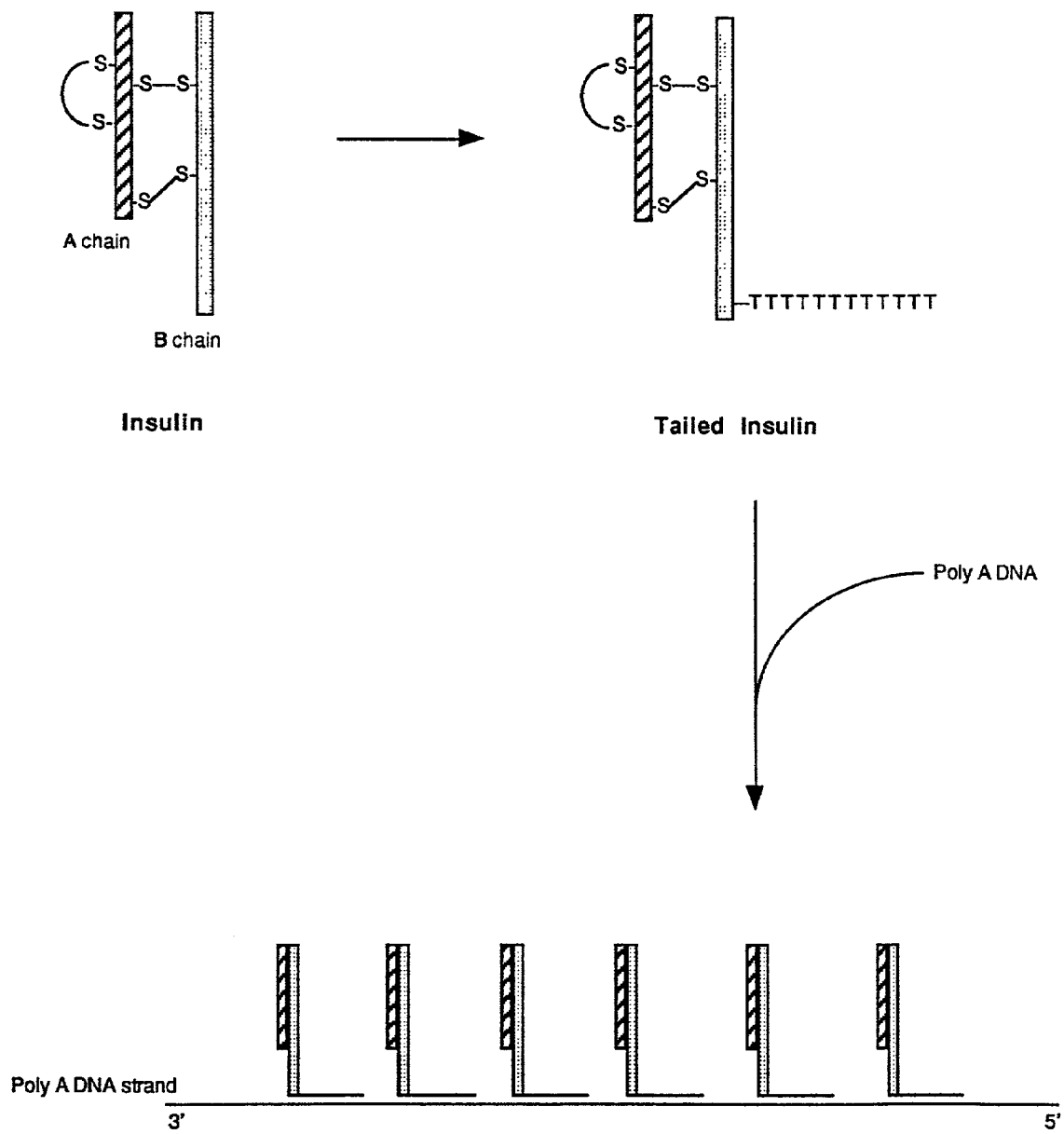
FIG. 22 depicts a process for multimerization of insulin molecules by hybridization of nucleic acid homopolymers (polynucleotide sequence shown in SEQ ID NO 52).

Oligo T with a primary amino group (prepared as described earlier) is reacted in 0.7M LiCl, 0.1M sodium bicarbonate buffer, pH 7.8 and 30% dimethyl formamide with a 3-fold excess of suberic acid bis (N-hydroxysuccinimide) ester for 15 minutes at room temperature. The pH was then lowered to 5.0 by the addition of 2M acetic acid and the excess of active ester was extracted twice with n-butanol. The nucleic acid was precipitated with 4 volumes ethanol at −70° C. and the pellet after centrifugation was dissolved in cold 0.7M LiCl in 0.1M sodium bicarbonate solution (pH 7.8), solid insulin was added in 1:1.2 ratio and the conjugation was allowed to take place at 4° C. overnight. The product is separated from the reactants by molecular sieving chromatography on G75 columns. A multimeric complex is formed by the hybridization of the T-tailed insulin molecules (SEQ ID NO 52) with a Poly A binder as described earlier. The steps in this Example are shown in FIG. 22.

Example 18

Preparation of a Multimeric Insulin by Means of Nucleic Acid Hybridization through Specific Discrete Sequences A group of nucleic acid sequences are selected from the known sequence of the single-stranded form of bacteriophage M13. These are then artificially synthesized such that they have a primary amino group on the nucleotide at the 5' end. the oligomers are individually activated and attached to insulin molecules as described in Example 17. A mixture is made of each of the oligomer/insulin complexes and mixed with M13 DNA derived from phage particles (the + strand). The product was separated from the reactants by molecule sieving chromatography. The steps in this Example are shown in FIG. 23.

Example 19

Figure 24:
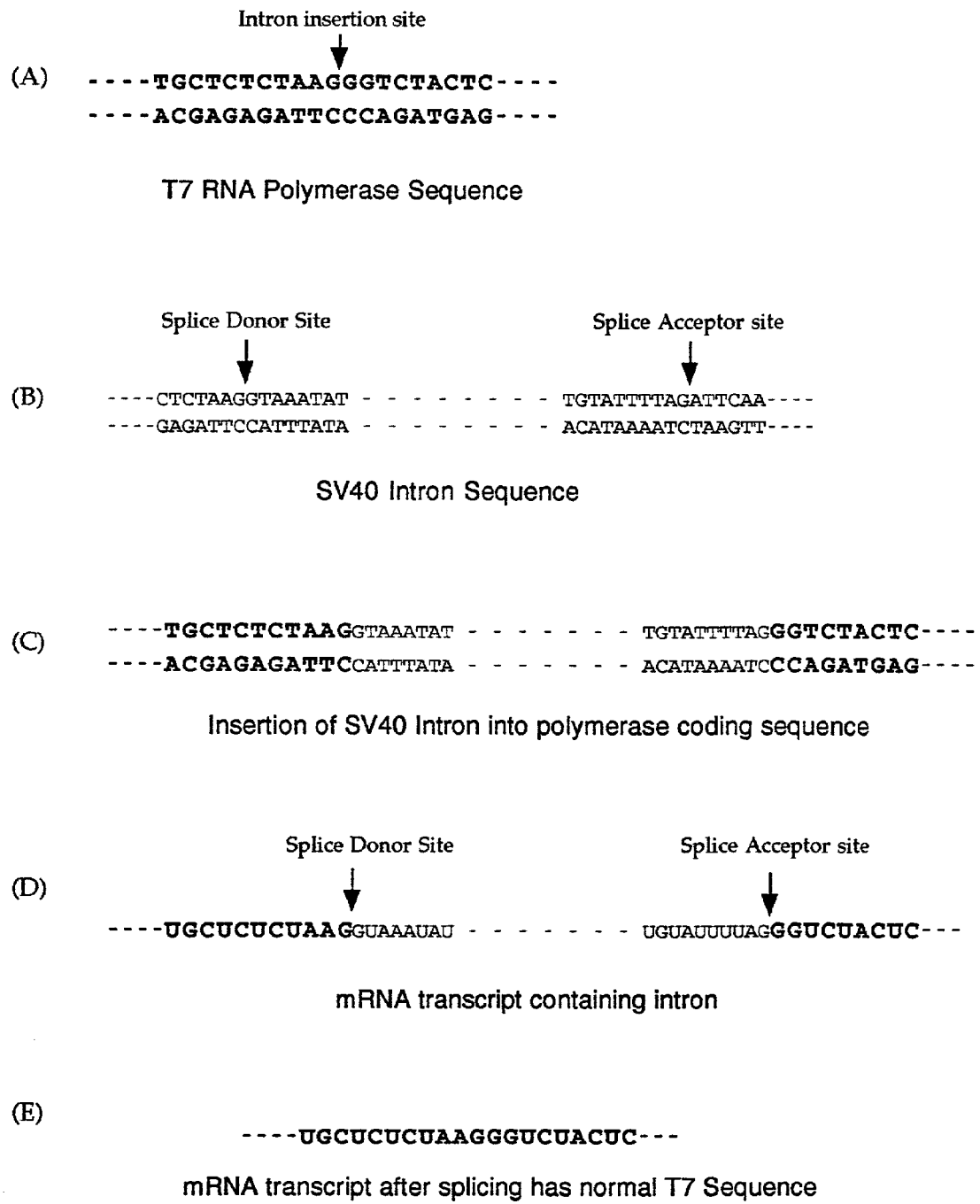
FIG. 24 shows the introduction of an SV40 intron sequence that reconstitutes appropriate signals for in vivo splicing and production of a normal mRNA transcript for T7 RNA polymerase (polynucleotide sequences shown in SEQ ID NOS 2, 55, 3, 4, 56, 57, 5, 6, 58, 59, 7, 8 and 9, respectively, in order of appearance).

Synthesis of a Eukaryotic Vector that Expresses T7 RNA Polymerase as well as Antisense Sequences Directed by a T7 Promoter (A) Intron and Intron Insertion Site The SV40 small T intron has been utilised in a number of DNA vectors and it has been chosen for this particular example due to its small size and the presence of stop codons in all three reading frames. The consensus sequences for splice donors and acceptors are partially made up by exon sequences as well as intron sequences. A computer search using the MacDNASIS program (Hitachi, Inc.) allowed the identification of 19 different sites within the T7 RNA polymerase coding sequence (Mount, 1982 Nucleic Acids Research 10, 459) that contain the sequence (C/A)AGG, which as described earlier is a consensus sequence for a post-splice junction. Any of these sites should be suitable for the intron insertion site, but for this example, a T7 site was chosen that closely resembled some of the flanking exon sequences of the SV40 intron. FIG. 24 shows the sequences surrounding this site in the T7 RNA polymerase gene sequence and the subsequent insertion of the SV40 virus intron into this site. FIG. 24 also shows the mRNA made from this fusion and the subsequent splicing out of the Intron sequence to reconstitute the normal T7 coding sequence.

(B) Fusion of intron sequences into the T7 coding sequences

Figure 25:
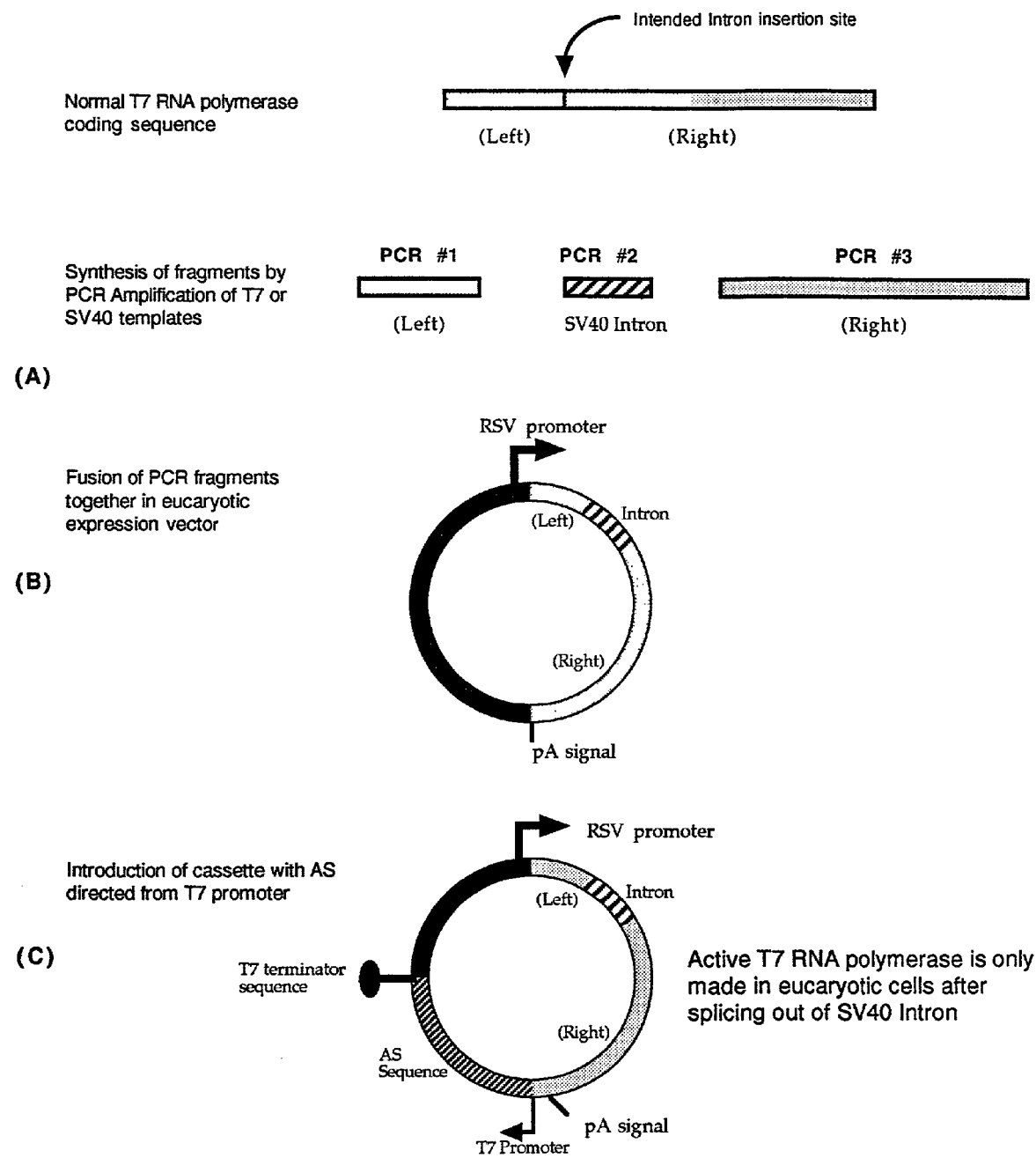
FIG. 25 shows the process of the intron introduction and subsequent construction of a T7 expression vector.

A method for introduction of the intron and production of a vector that contains the interrupted T7 RNA Polymerase as well as sequences directed from a T7 promoter is given in FIG. 25. As shown in FIG. 25, the creation of this construct can be accomplished by PCR amplifications of each segment of the T7 RNA polymerase gene (left and right of the intended intron insertion site) and PCR amplification of a eucaryotic intron. These pieces are joined together using cloning steps described below. It has previously been shown that PCR products can be fused together by a technique referred to as "Splicing by Overlap Extension" (SOE) to generate precisely joined fragments without extra sequences being added (Horton et al 1990 BioTechniques 8: 528; Horton et al., 1989 Gene 77: 61). However, in addition to the PCR reactions needed to create the different segments, the SOE method involves the use of these PCR products as primers in a secondary PCR reaction to fuse the segments. For fusions of multiple segments there would be a series of sequential PCR reactions to be carried out. Even with thermostable DNA polymerases chosen for a lower error frequency, the synthesis of the final product will require that some sequences be subject to several multicycle amplification steps thereby leading to an increased chance of undesirable mutations in the final product. For this reason, the inventors of the technique advised sequencing the final product to insure that the desired product was obtained (Horton et al., 1990). In the present example, a method was used that requires only an initial round of PCR amplification to create each segment followed by ligation of the segments together to form the final fused product. Fusions of the gene segments and intron to form the appropriate product were carried out by addition of restriction enzyme sequences onto the 5' end of the PCR primers to allow the production of "sticky ends" (Scharf et al., 1986 Science 233: 1076). To give the precisely defined end points for this fusion, restriction enzymes (Bsa I and Bsm B1) that recognize non-palindromic sequences and cut outside of their recognition sequence to leave a single stranded tail with arbitrary definition were used. This method allows joining of sequences at any point chosen by the user by the appropriate design of the PCR primers.

(C) Synthesis of the individual segments used for the fusion.

The T7 RNA polymerase is encoded by bases 3171-5822 in the T7 genome (Dunn and Studier, 1983 J. Mol. Biol. 166: 477) and this sequence is available in Genbank as Accession #'s V01146, J02518 or X00411. Based upon this information, six different oligos were synthesized. The use of these oligos and their sequences are given in FIG. 26. TSP1 (SEQ ID NO 10) and TSP 2 (SEQ ID NO 11) were annealed together by a 12 bp complimentary sequence and extended to form a completely double-stranded DNA molecule (FIG. 27). Conditions were as follows: 150 µM of TSP 1 (SEQ ID NO 10), 150 µM of TSP 2 (SEQ ID NO 11), 1*NEB Buffer #2 (New England Biolabs, Inc.), 200 uM dNTP and 13 units of Sequenase v2.0 (U.S. Biochemicals, Inc) for 75 minutes at 37° C. TSP 3 (SEQ ID NO 12) and 4 (SEQ ID NO 13) were used in a PCR reaction (Saiki et al. 1985 Science 230, 1350) with T7 genomic DNA as a template to synthesize the "Left" fragment. Reagent conditions were as follows: 100 ul volume containing 100 ng T7 template (Sigma Chemical Co.), 1 uM TSP 3 (SEQ ID NO 12), 1 uM TSP 4 (SEQ ID NO 13), 1 mM MgCl2, 1*PCR buffer, 250 uM dNTP, 2.5 units of Taq DNA Polymerase. Temperature cycling conditions were: 16 cycles of (1) 50 seconds at 94° C. (2) 25 seconds at 50° C. and (3) 3 minutes at 72° C. The same conditions were used to form the "Right" end fragment with Oligomers TSP-5 (SEQ ID NO 14) and TSP-6 (SEQ ID NO 15) except that due to the length (over 2 kb) of the expected product, 2.5 units of Taq Extender (Stratagene, Inc) was added and the Taq Extender buffer substituted for the normal PCR buffer. INT-1 (SEQ ID NO 16) and INT-2 (SEQ ID NO 17) were used together in a PCR reaction to form the Intron piece. Conditions were the same as those used for synthesizing the "Left" fragment of T7, except that a clone of SV40 was used as the template and due to the smaller size of the amplicon, the cycle conditions were only 1' at 72° C. for the extension time. FIG. 27 shows the synthesis of the short double stranded piece of DNA made by extension of oligos TSP 1 (SEQ ID NO 10) and TSP 2 (SEQ ID NO 11) and its combination with the left end of the TSP 3/TSP 4 PCR product to generate the complete (NLS+) T7 RNA polymerase (SEQ ID NOS 30-31). The resultant nucleic and amino acid sequences are given in FIG. 28 for the construct given in this example as well as the normal wild type T7 RNA polymerase sequences (SEQ ID NOS 28-29).

Thus, the modifications carried out at the 5' end during this construction process were:

a) The sequence around the ATG start codon was changed to give a Kozak consensus sequence (Kozak 1984 Cell 44: 283) to increase efficiency of translation of the gene product. This change had previously been introduced into the T7 RNA polymerase coding sequence.

b) The fusion of the TSP1/TSP2 (SEQ ID NOS 18-19) extension product to the TSP3/TSP4 PCR introduces a 9 amino acid insertion between bases 10 and 11 in the normal T7 RNA polymerase protein sequence. This sequence has previously been shown to be a signal for transportation to the nuclease by Kalderone et al. (1984 Cell 39: 499) and had been introduced into T7 RNA polymerase by Lieber et al., (1989) as a substitute for the first 10 amino acids and inserted into an artificially created EcoR1 site by Dunn et al., (1988). The method used in this Example to introduce the Nuclear Localisation Signal (NLS) was designed to minimize perturbations to the normal structure of the protein. The codons for the amino acids coding for the NLS are indicated as larger type size in FIG. 28

Figure 29:
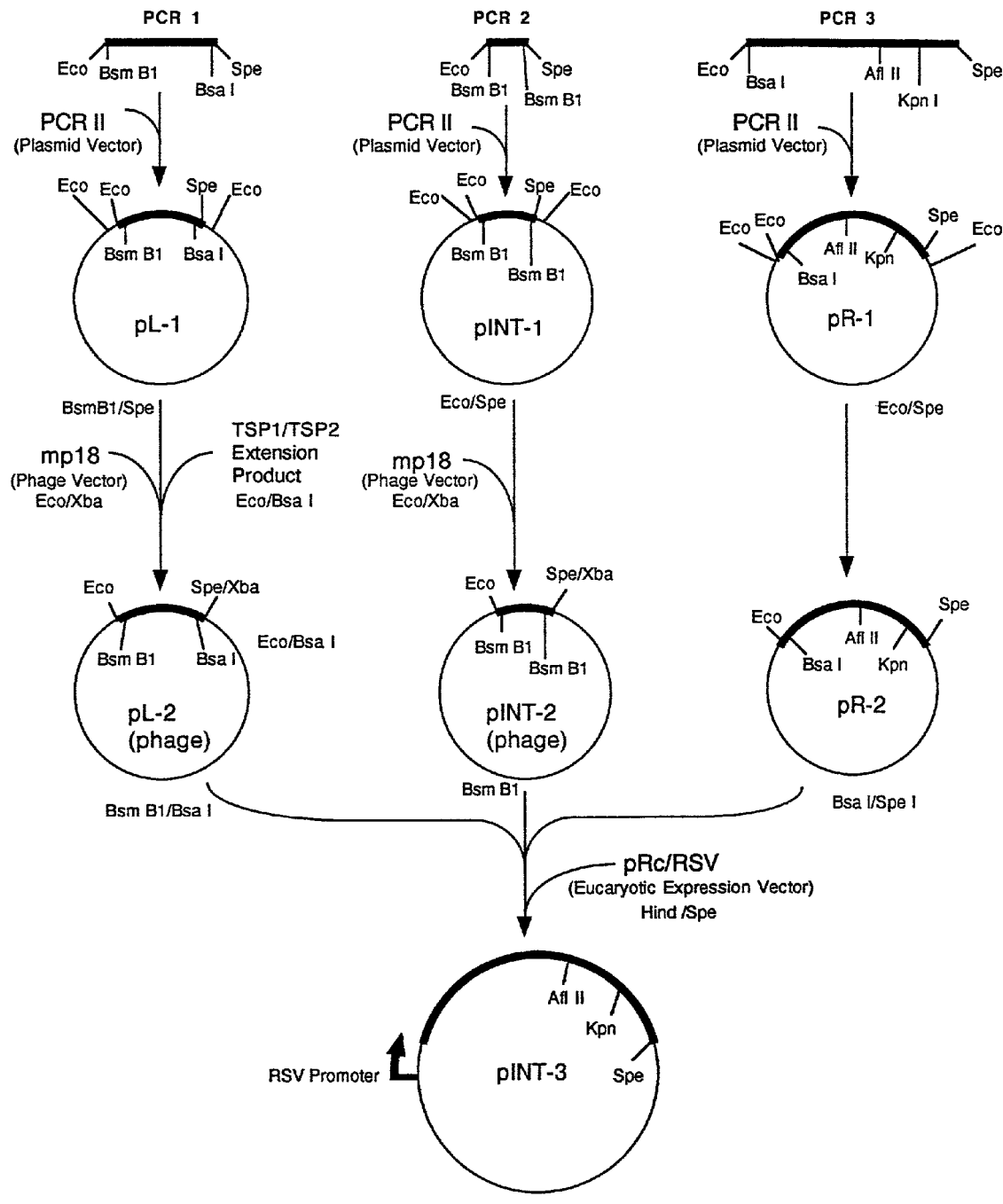
FIG. 29 shows the process for the assembly of PCR generated fragments by cloning methods to assemble a clone that directs the synthesis of an intron containing T7 RNA polymerase transcript.

(D) Combination of pieces to form the final construct of the T7 RNA polymerase gene in a eucaryotic expression vector FIG. 29 shows the various steps used for this process. For ease of use, each of the three pieces (PCR #1, PCR #2 and PCR #3) was cloned into a plasmid vector (PCR II) using the TA cloning kit and following the manufacturer's instructions (Invitrogen, Inc.).

PCR #1 (the left end of the T7 RNA polymerase) was cloned into PCR II to create pL-1 (SEQ ID NO 40). This construct was then digested with BsmB1 and Spe I to excise out the PCR product and the TSP1/TSP2 Extension product (SEQ ID NOS 18-19, shown in detail in FIG. 27) was digested with Eco R1 and Bsa I. Due to the design of the primers, the single-stranded tails created by BsmB1 and Bsa I are complimentary to each other and ligation of these pieces forms a single piece with an EcoR1 tail at one end and a Spe I tail at the other end. Digestion of the M13 vector, mp18, with EcoR1 and Xba I allows insertion of the EcoR1/Spe I piece to form pL-2 (SEQ ID NO 41). PCR #2 (the SV40 Intron) was cloned into PCR II to form pINT-1. This construct was digested with EcoR1 and Spe I and transferred into the M13 vector (mp18 digested with EcoR1 and Xba I) to form pINT-2.

PCR #3 (the right end of the T7 RNA polymerase) was cloned into PCR II to create pR-1. This construct was digested with Eco R1 and Spe I and then self-ligated to form pR-2. This step was added to eliminate extra EcoR1 and Spe I sites present in pR-1.

As described in FIG. 25, the elements in pL-2 (SEQ ID NO 41), pINT-2 and pR-2 are fused together to form the complete intron-containing T7 RNA polymerase. This was accomplished by digestion of pL-2 (SEQ ID NO 41) with BsmB1 and Bsa I; pINT-2 with BsmB1; and pR-2 with BsaI and Spe I. Ligation of these three inserts together forms a single fragment that has one end compatible with a Hind III end and the other end compatible with Spe I. This fragment was cloned in the same step into pRc/RSV (from Invitrogen, Inc.) that had been previously digested with Hind III and Spe I. As shown in FIG. 29, this final product is pINT-3. This particular eucaryotic vector was chosen since it had been shown previously that the RSV promoter is especially active in hematopoietic cell lines. Also, the ligation of the Hind III end from pRcRSV to the end created from the BsmB1 digestion of pL-2 (SEQ ID NO 41), does not reconstitute the Hind III site in pINT-3, the final product.

E) Antisense sequences

Three different targets in the HIV genome were chosen as test targets for Antisense: (A) the 5' common leader, (B) the coding sequence for Tat/Rev and (C) the splice acceptor site for Tat/Rev. Antisense to (A) was derived from a paper by Joshi et al. (1991 J. Virol. 65, 5534); Antisense to (B) was taken from Szakiel et al. (1990 Biochem Biophys Res Comm 169, 213) and the Antisense to (C) was designed by us. The sequences of the oligos and their locations in the HIV genome are given in FIG. 30. Each oligo was designed such that annealing of a pair of oligos gives a double-stranded molecule with "sticky ends" that are compatible with a Bam H1 site. The oligos were also designed such that after insertion into a Bam H1 site, only one end of the molecule would regenerate the Bam H1 site, thus orientation of the molecule could easily be ascertained. The resultant clones were termed pTS-A, pTS-B and pTS-C for the anti-HIV sequences A, B and C respectively.

F) Cloning of T7 terminator

The sequence for termination of transcription by the T7 RNA polymerase is encoded by a sequence between the end of the gene 10b protein at base number 24,159 and the start codon of the gene 11 product at base number 24,227 in the T7 genome (Dunn and Studier 1983 J. Mol. Biol. 166, 477 Genbank Accession #'s V01146, J02518 or X00411. Based upon this information, TER-1 (SEQ ID NO 38) and TER-2 (SEQ ID NO 39) were synthesized (Sequences given in FIG. 30) and used in a PCR amplification reaction to obtain a double-stranded 138 bp piece that contained the T7 sequences from 24,108 to 24,228 with an Xba I site added at one end and a Pst 1 site added to the other. The reagent conditions for amplification were as described for the TSP3/TSP4 reaction but the temperature cycling conditions were: 16 cycles of (1) 50 seconds at 94° C. (2) 25 seconds at 50° C. and (3) 1 minute at 72° C. As shown in FIG. 30, the terminator piece was cloned into the PCR II vector and then after XbaI/Pst I digestion it was transferred into an M13 vector.

G) Creation of T7 driven antisense transcription units.

The clones containing Antisense sequences (pTS-A, pTS-B and pTS-C) were digested with Eco R1 and Pst I while the clone containing the T7 terminator (pTER-2) was digested with Xba and Pst I. These were ligated together with pIBI 30 (IBI, Inc.) that had been digested with Eco R1 and Pst I to form the AntiSense transcription units shown in FIG. 30 which have Antisense sequences transcribed from a T7 promoter and then terminated by a T7 terminator. The resultant clones were termed pTS-A1, pTS-B1 and pTS-C1 for the anti-HIV sequences A, B and C respectively.

H) Transfer of Antisense Transcription Units into pINT-3

Figure 31:
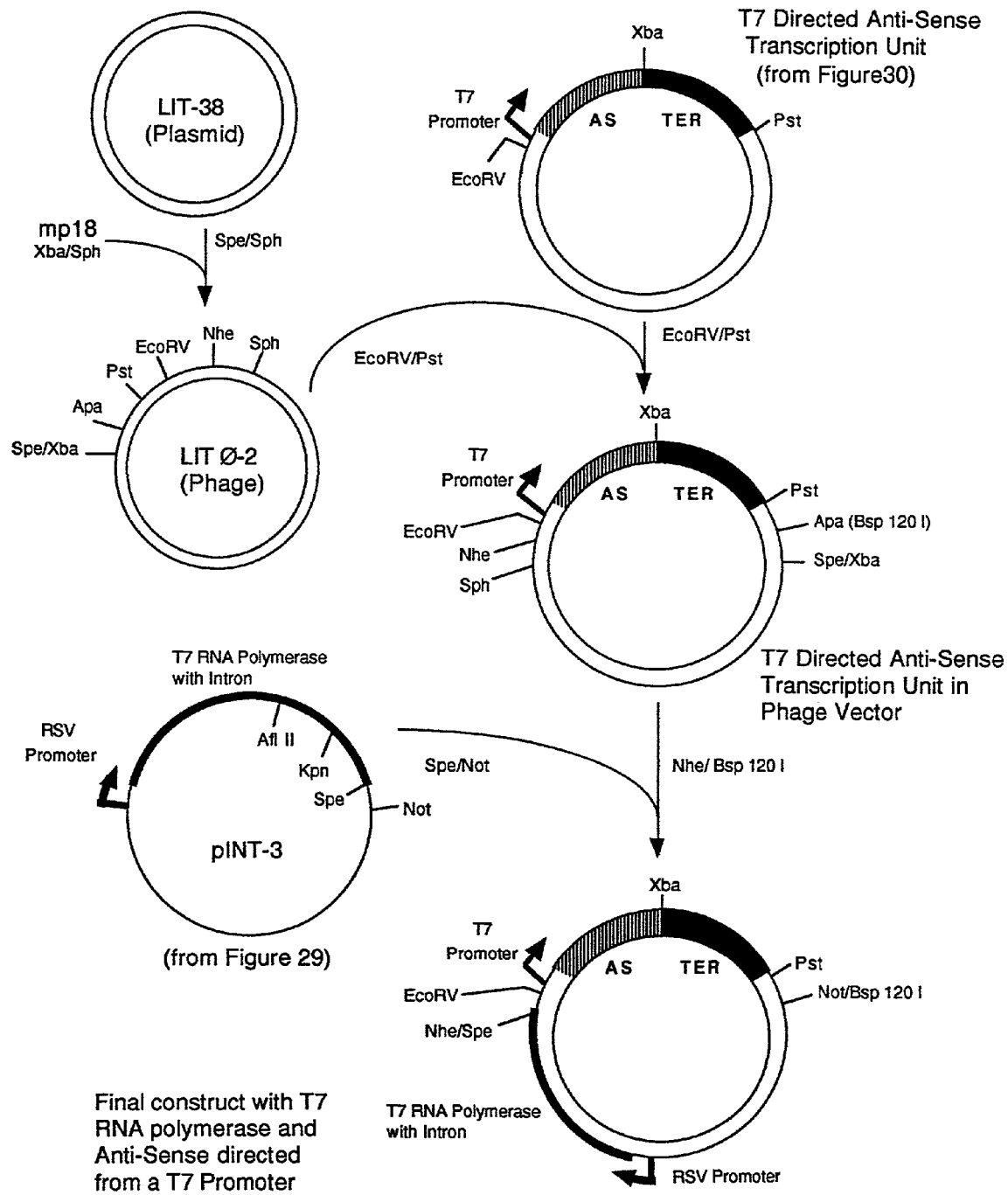
FIG. 31 shows the cloning steps for the combination of T7 directed antisense into a clone that contains the intron containing T7 RNA polymerase.

By the nature of the present invention, the T7 driven Antisense Transcriptions units can be transferred into pINT-3 to make a single construct T7 polymerase/promoter construct. This was accomplished by creating an M13 phage vector LIT Ø-2 by transferring the polylinker from the plasmid vector LIT-38 (New England Biolabs, Inc.) by digestion with Spe I and SphI and ligating the polylinker insert into mp18 that had been digested with Xba I and Sph I. This and subsequent steps are shown in FIG. 31. Clones pTS-A1, pTS-B1 and pTS-C1 which contain T7 directed Antisense sequences were digested with EcoRV and Pst I. They were then ligated to the LIT 0-2 vector which had also been digested with Eco RV and PstI. The resultant clones are phage vectors that contain T7 directed Antisense sequences and were termed pTS-A2, pTS-B2 and pTS-C2 respectfully. These clones were digested with Nhe I and Bsp 120 I and ligated to the pINT-3 vector (from FIG. 29) that had previously been digested with Spe I and Not I. the resultant clones pRT-A, pRT-B and pRT-C contain the coding sequence for the T7 RNA polymerase driven by the RSV promoter and with an SV40 intron sequence that will be spliced out to form a functional polymerase enzyme and in addition each construct contains an HIV Antisense sequence driven by a T7 promoter and terminated by a T7 terminator.

Example 20

Figure 32:
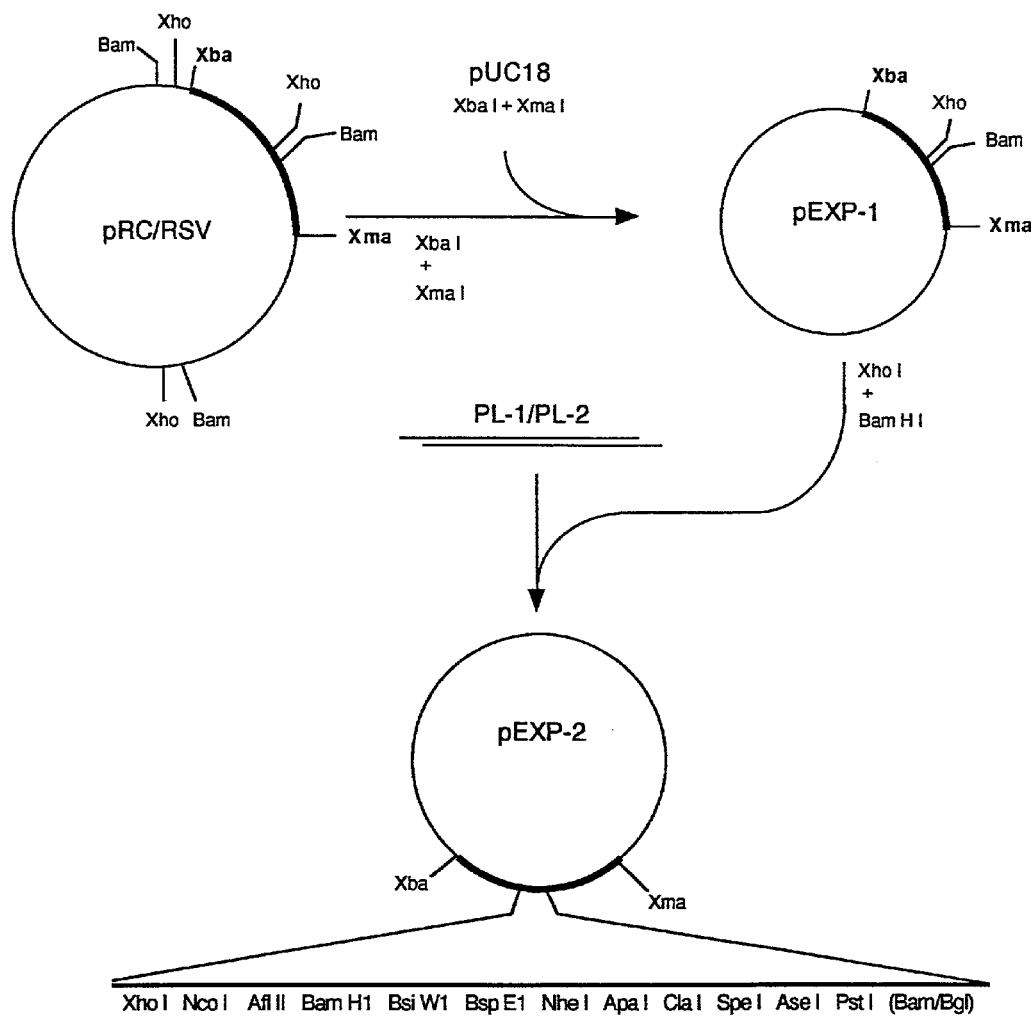
FIG. 32 shows the DNA sequences (SEQ ID NOS 40-41, respectively, in order of appearance) and subsequent cloning steps for making a protein expression vector.
Figure 33:
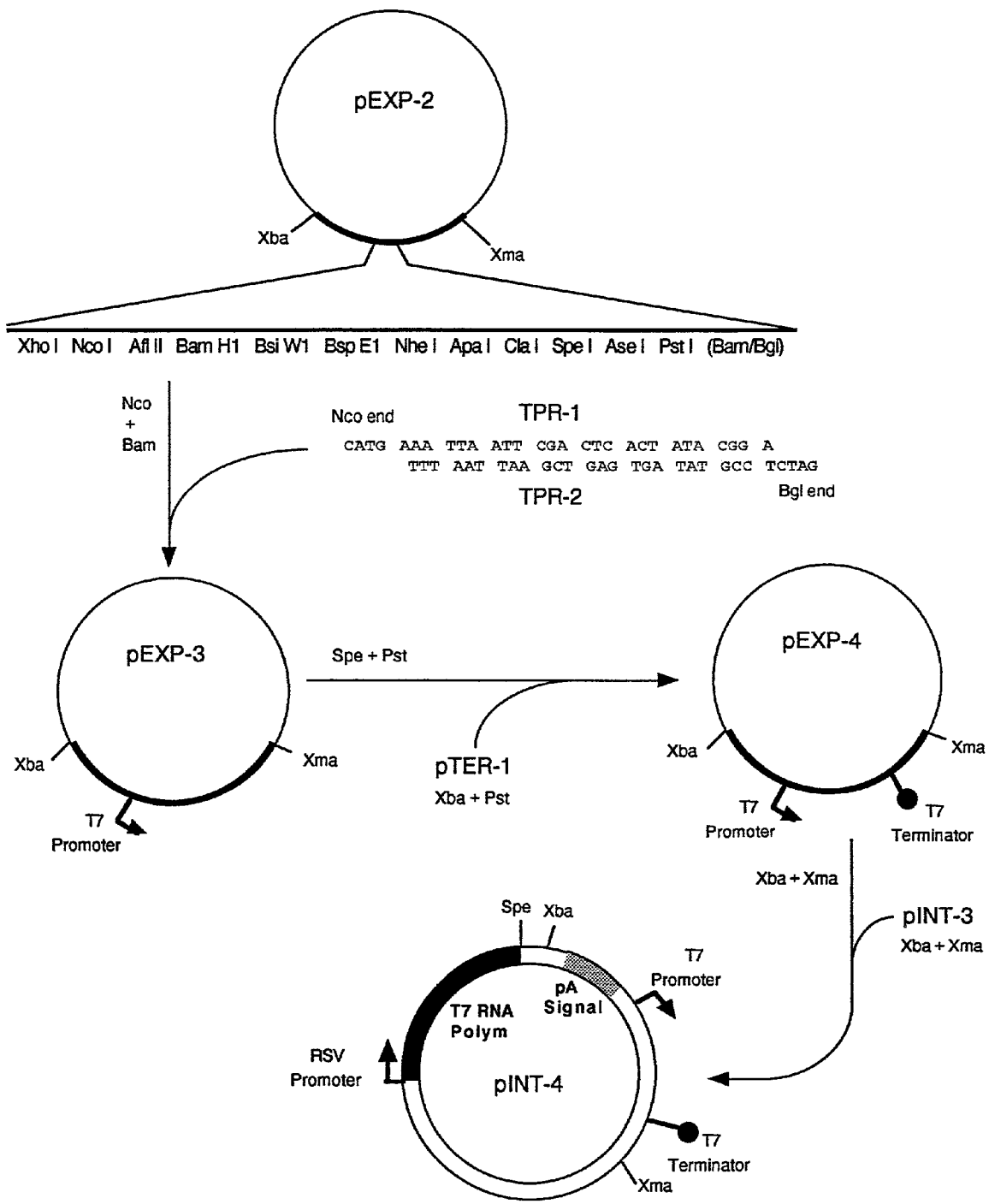
FIG. 33 shows a process for a combination of the polylinker sequence (SEQ ID NOS 42-43, respectively, in order of appearance) from FIG. 32 and a T7 promoter and a T7 terminator for making a T7 directed protein expression vector.

Expression of a Protein Made From T7 Directed Transcripts Derived From a Single Construct That Also Expresses the T7 RNA Polymerase The pINT-3 vector used in the previous example can be modified for use as an expression vector for T7 directed protein synthesis. For this purpose, the pINT-3 vector needs has a T7 promoter, a T7 terminator and a polylinker in between. The optimal site for the placement of these moieties is after the poly A signal for the T7 RNA polymerase in pINT-3 where there is an Xho I and a Bam H1 site. Since there are also other Xho I and Bam H1 sites within the vector, manipulations of this particular segment can only be done if the small segment containing this area is separated out, the appropriate nucleic acids introduced in between the Xho I and Bam H 1 sites and then the segment replaced back in. The steps used for the creation of this construct are shown in FIGS. 32 and 33.

a) Introduction of polylinker

The segment containing the Xho/Bam H1 insertion site was derived from the plasmid pRC/RSV, which was the parent of pINT-3. This was done by digesting pRC/RSV with XbaI and Xma I and transferring the appropriate fragment into the plasmid pUC18 (NewEngland Biolabs, Inc.) previously digested with Xba I and Xma I to obtain the vector pEXP-1. This in turn was digested with Xho I and Bam H1 and then a polylinker was inserted by ligation with oligomers PL-1 and PL-2 (Sequences are shown in FIG. 32). The resultant plasmid was named pEXP-2 and the restriction sites contained with the new polylinker are shown in FIG. 32.

b) Introduction of T7 promoter and T7 terminator

A promoter was inserted into pEXP-2 by digestion with Nco I and Bam H1 followed by ligation with oligomers TPR-1 and TPR-2 (Sequences are shown in FIG. B-10) to create pEXP-3. The normal T7 promoter consensus sequence (Dunn and Studier, 1983) was not used since it has been shown that it can function as a eucaryotic promoter in some cell lines (Sandig et al., 1993 Gene 131; 255) and a sequence derived from Lieber et al. (1993) was substituted since this sequence still functions well in the presence of T7 RNA Polymerase but remains silent in its absence. The vector pEXP-3 was digested with Spe I and Pst and ligated to the T7 terminator fragment derived from the pTER-1 construct described in the previous example in order to create the vector pEXP-4. The Xba/Xma segment has now been modified to contain the T7 terminator, a short polylinker and the T7 terminator. It was substituted for the unmodified segment in pINT-3 by Xba I/Xma I digestion of pINT-3 and PEXP-4 followed by ligation as shown in FIG. 33 thus creating the vector pINT-4.

c) Introduction of a protein coding sequence into the new T7 Expression vector

The gene coding for the complete lac Z sequence was obtained from pZeoSVLacZ (Invitrogen, Inc.) by digestion with Age I and Cla I. This was then ligated into pINT-4 that had been previously digested with Bsp E1 and ClaI to create pINT-LacZ (not shown). After introduction into a eucaryotic cell, the RSV promoter directs the synthesis of the T7 RNA polymerase which in turn acts upon the T7 promoter to synthesize B-galactosidase.

Example 21

Figure 34:
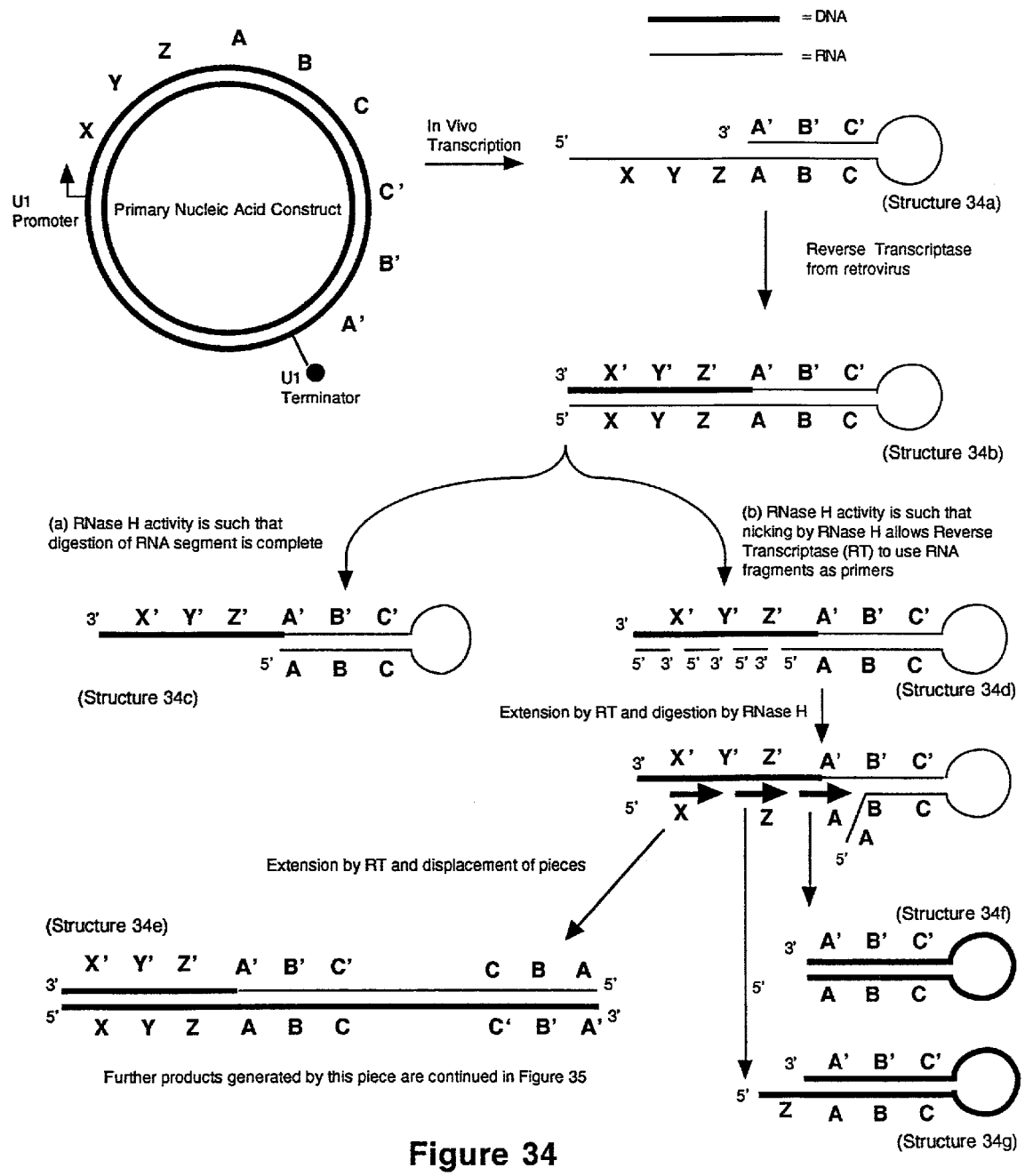

A Primary Nucleic Acid Construct that Propagates Production Centers for the Production of Produces Single-Stranded Antisense A Primary Nucleic Acid Construct is described as shown in FIGS. 34 and 35 whereby, subsequent to introduction into a cell, a series of events, including self priming, multiple priming and Rnase H and reverse transcriptase activities, leads to the production of single stranded DNA antisense molecules. In this case a Nucleic Acid Construct creates multiple copies of a Production Center, an RNA transcript with hairpin structure with a discrete 3' end (structure 34a, FIG. 34). In the presence of reverse transcriptase self priming occurs by the 3' end of the hairpin acting as primer to extend to the 5' end of the molecule resulting in a hairpin structure composed of both DNA and RNA (structure 34b). By a multiple priming process, Rnase H, either as part of the viral reverse transcriptase or from the Inherent Cellular Systems, starts degradation of the RNA bound to the DNA. Degradation can be complete if there is enough Rnase H activity, or if the reverse transcriptase activity is high enough, the initiation of RNA degradation provides RNA fragments that serve as primers for extension using the DNA portion as a template. In the former case the net result of the degradation by RNase H is a single-stranded DNA molecule with a double stranded 5' RNA terminus (structure 34c); in the latter case (structure 34d), the priming event results in a) the Production of a series of molecules such as 34f and 34g, the length of the single-stranded DNA portion depending upon the site of the priming initiation event and b) the propagation of Production Centers such as structure 34e. Structure 34g could act as a biological modifier if, for example, the sequences represented as the Z single stranded DNA region were antisense sequences. Through the activity of RNase H and reverse transcriptase, structure 34e would be processed further to produce single stranded DNA molecules (structures 351h, 35i and 35j, FIG. 35). which could act as antisense DNA if the sequences X', Y', Z' were designed with that purpose. The Production of antisense DNA molecules according to this invention represents the first demonstration of the method for the intracellular synthesis of antisense DNA.

Example 22

Figure 36:
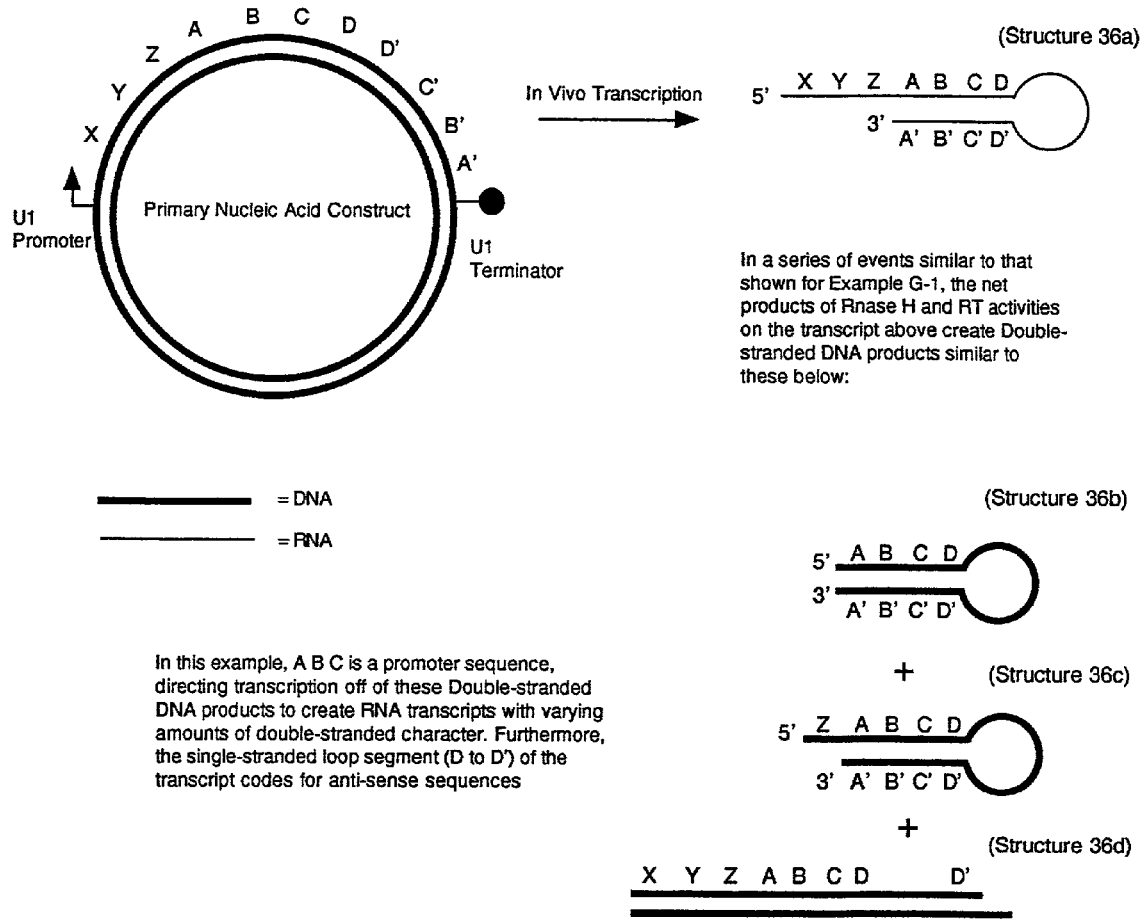
FIG. 36 depicts the design of a primary nucleic acid construct that will generate a secondary nucleic acid construct capable of directing transcription.

A Primary Nucleic Acid Construct that Propagates an RNA Production Center that is Reverse Transcribed to Create DNA Production Centers Capable of Directing Transcription In this example, the same processes of self priming and multiple priming, described in the Example 21 occur with the propagation of single stranded DNA hairpin structures (FIG. 36). As in Example 21, structures 36b, 36c and 36d (FIG. 36) act as Production Centers for the Production of single stranded RNA. In this case this represents an amplification event since reverse transcriptase and RnaseH convert a single Production Center (36a), into a double stranded DNA Production Centers (36b, 36c and 36d) which can direct the Production of multiple single stranded RNA molecules.

Example 23

Figure 37:
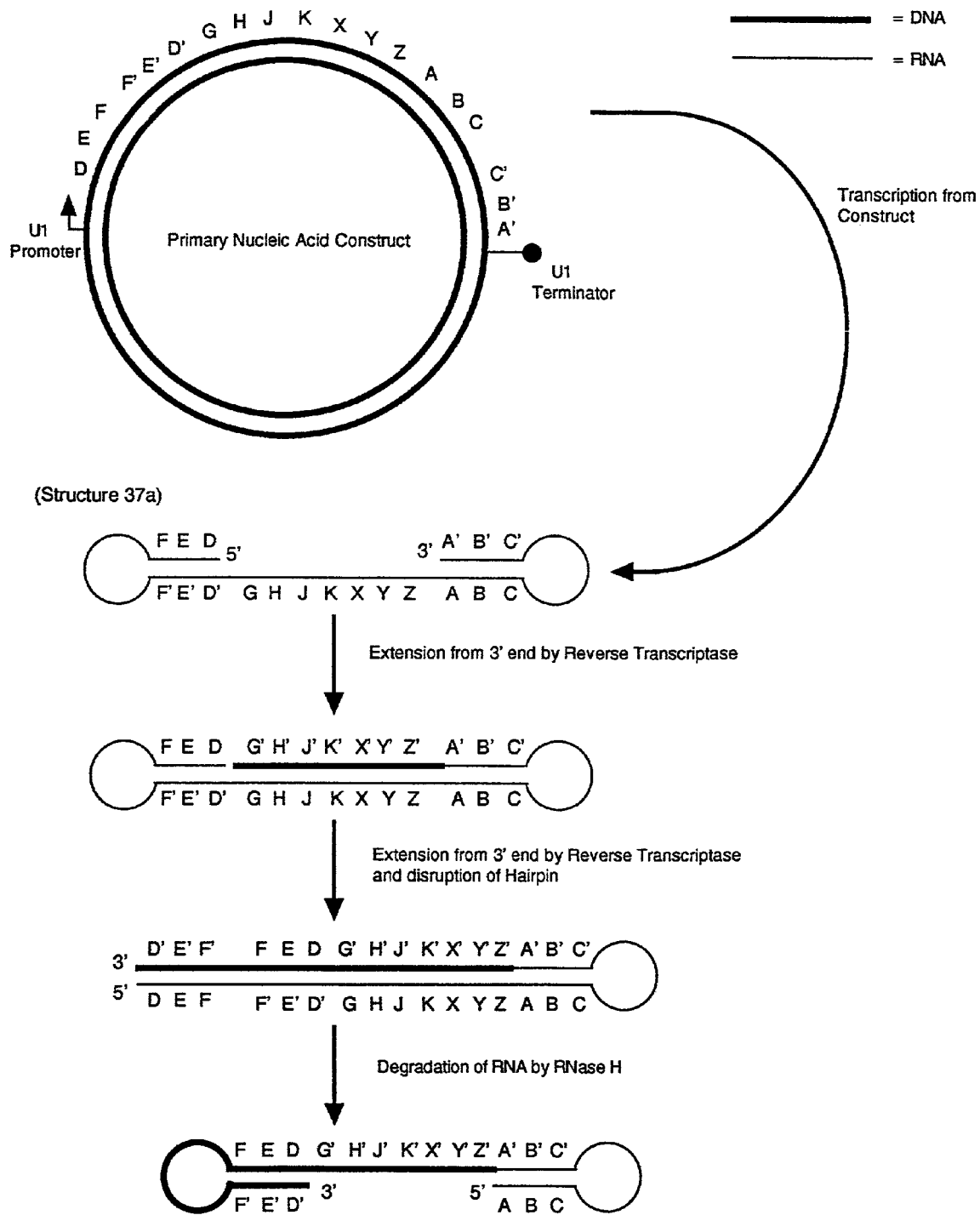
FIGS. 37 AND 38 depict the design of a primary nucleic acid construct that will generate a double hairpin production center (secondary nucleic acid construct).
Figure 38:
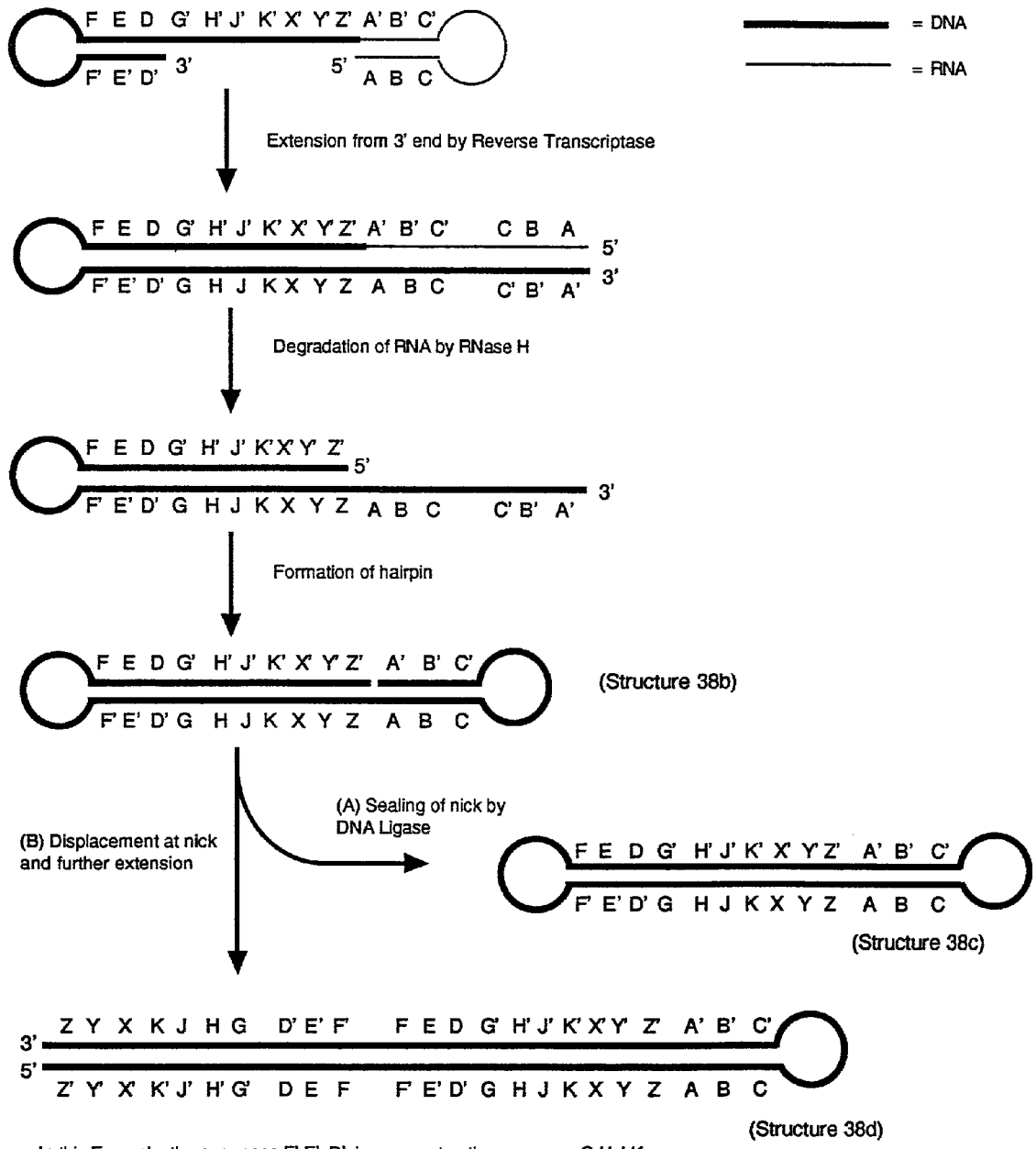

A Primary Nucleic Acid Construct which Propagates a Double Hairpin Production Center for the Production of Single Stranded RNA In this example, a double stranded DNA Primary Nucleic Acid Construct (structure 37a, FIG. 37) has been designed such that a single stranded Production Center, propagated from it, forms hairpin structures at the 5' and 3' ends. Extension by self priming from the 3' end followed by further steps catalyzed by RnaseH and reverse transcriptase result in the propagation of a double-stranded DNA molecule with single stranded hairpin ends (structure 38b, FIG. 38). This can be further processed, by the action of DNA ligase, to form a covalently closed molecule (38c) or by the action of reverse transcriptase to form a larger linear molecule (38d). The presence of promoters and coding sequences in these Production Centers provides for Production of single stranded RNA. As seen above in Example 22, this is an amplification event since each Production Center producing RNA transcripts was itself derived from a single transcript.

Example 24

Figure 39:
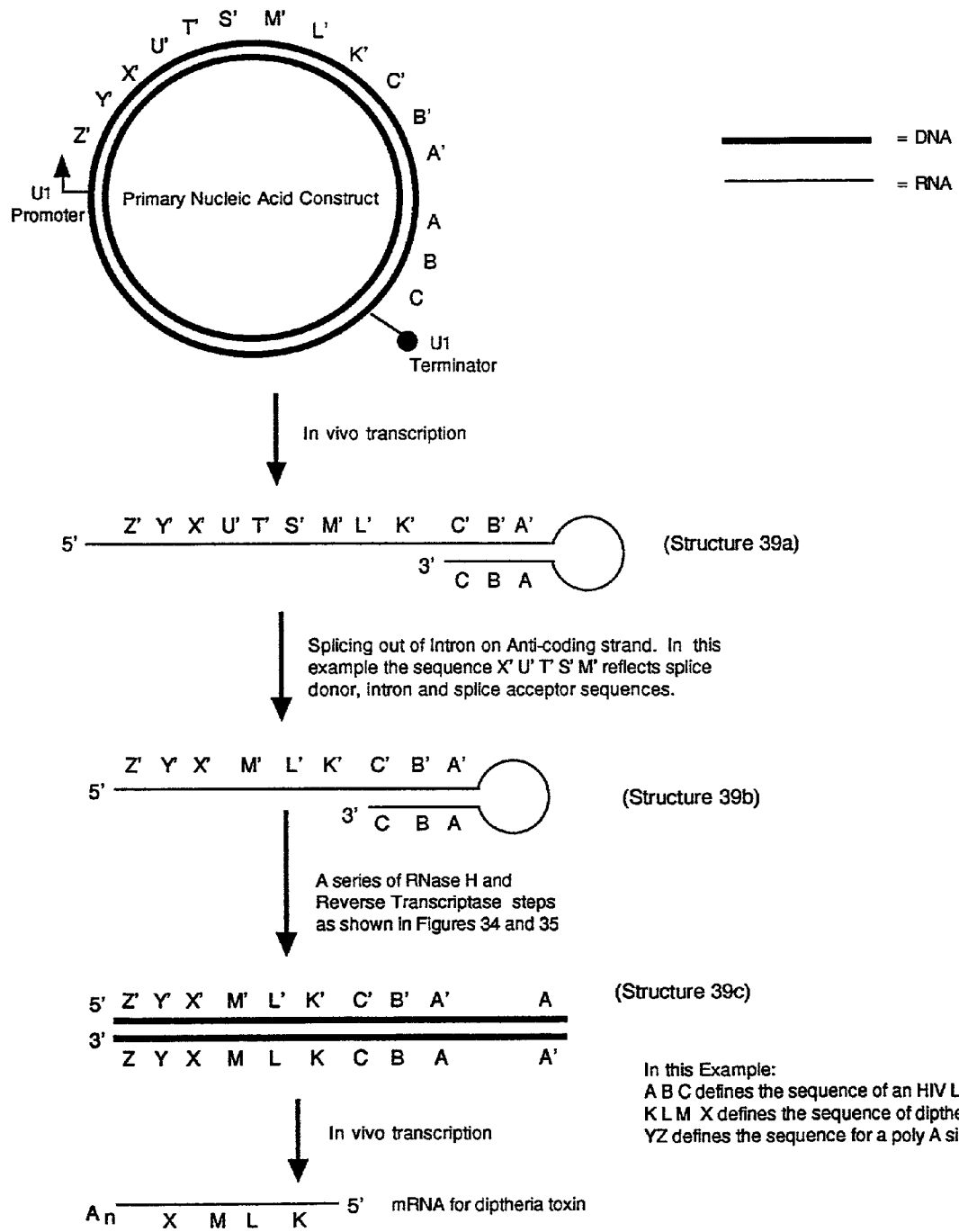
FIG. 39 depicts the design of a primary nucleic acid construct that will generate a production center (secondary nucleic acid construct) capable of inducible suicide.

A Nucleic Acid Construct which Propagates a Production Center Capable of Inducible Cell Destruction In this example (FIG. 39) provides for the production a single stranded nucleic acid as a result of the introduction into cell of an inherent cellular system. In this case, the events leading to the Propagation of a Production Center (structure 39b) are brought about by the presence of Reverse Transcriptase. Here, the single stranded nucleic acid product of a Production Center is mRNA which can be translated to produce a lethal product, diphtheria toxin, resulting in a reverse transcriptase dependent cytocidal event. Elimination of low level synthesis of a toxic gene product such as diphtheria toxin in the absence of viral infection TAT activation (as was observed by Harrison et al.) is accomplished by the use an intron artificially inserted into the non-coding strand (39a) of the segment coding for the toxin. In this way, transcription of the toxin sequence will not produce an active product. Production of active toxin only occurs when the antisense transcript is spliced and used as a template for Reverse Transcriptase.

The result of Rnase H and reverse transcriptase mediated activities is a double stranded DNA Production Center (39c) that has a template for the toxin and which has the intron sequences removed. As a further refinement, the promoter sequence in the double-stranded DNA Production Center (region designated as ABC in structure 39b) can be an HIV LTR. In this case Production of the toxin would be dependent upon two events that should be provided by viral infection.

Example 25

Figure 40:
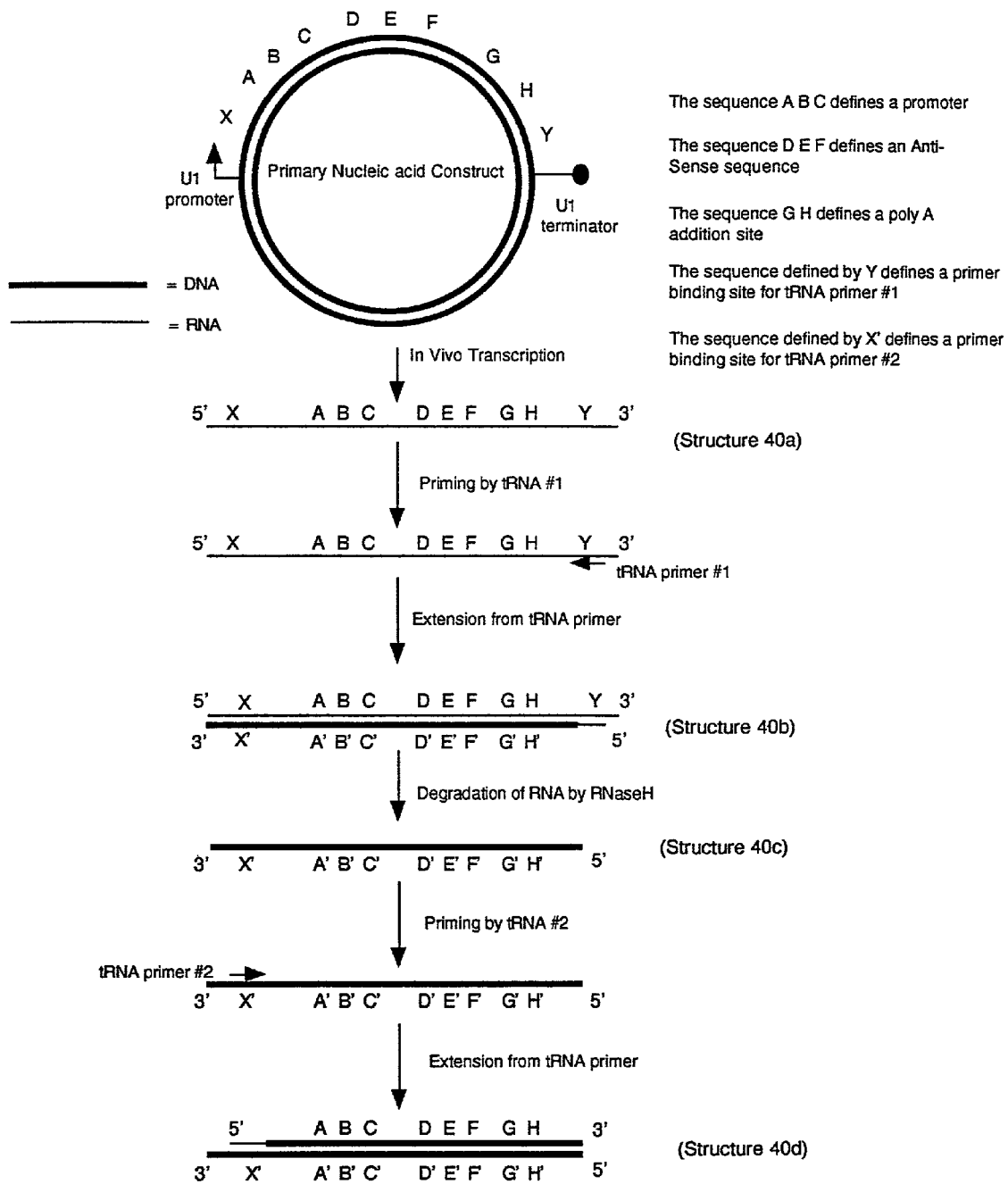
FIG. 40 depicts the design of a primary nucleic acid construct that will use tRNA primers in vivo to make secondary nucleic acid constructs capable of transcription.

Use of tRNA Primers to Create a Double-Stranded DNA Production Center for Production of Single Stranded RNA This example utilizes the presence of primer binding sites in a single stranded RNA Production Center for the Propagation of a double-stranded DNA Production Center. In this way, sequences derived from the Primer Binding Sites of retroviruses, such as the HIV primer binding site which utilizes lysyl tRNA as a primer, can be inserted near the termini (regions designated X and Y) in the RNA Production Center (FIG. 40, structures 40b and 40c) for the priming of DNA synthesis to form double stranded DNA Production Centers. The resultant Production Centers, such as structure 40d, are double stranded DNA molecules but can function as described previously to produce single stranded RNA which either can be utilized as anti-sense nucleic acid or which can be translated to produce a protein.

Example 26

Figure 42:
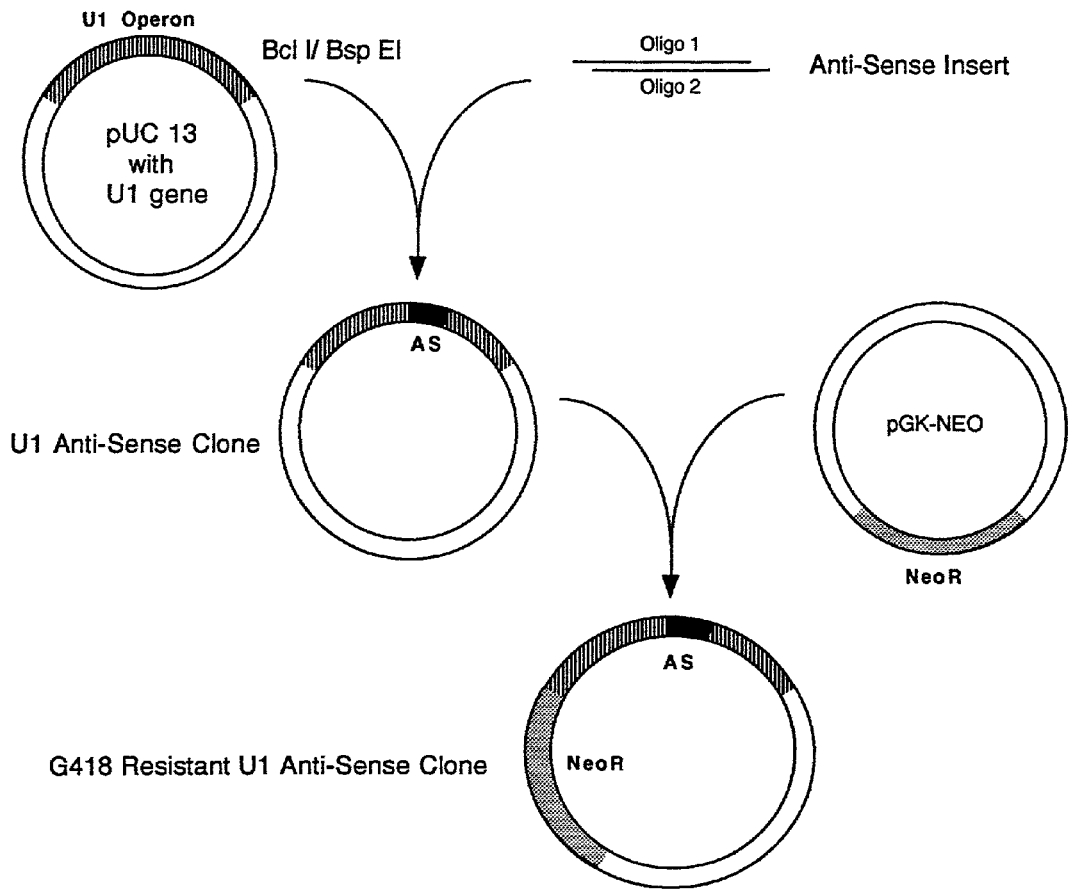
FIG. 42 shows the oligomer sequences (SEQ ID NOS 44-51, respectively, in order of appearance) for making HIV antisense sequences and the insertion of these oligomers as replacement for a portion of the U1 transcript sequence in a clone containing a U1 operon.

Construction of Plasmids with Anti-sense Segments Introduced Into the Transcript Region of the U1 Gene The overall process used in this example is depicted in FIG. 41. The gene for U1 is present in the plasmid pHSD-4 (Manser and Gesteland 1982 Cell 29; 257). Three different pairs of deoxyoligonucleotides were synthesized and the sequences are given in FIG. 42. The pairs were hybridized to form double stranded molecules with single stranded overhangs to form sites compatible with the Bcl/Bsp ends in the plasmid. The Bcl/Bsp ends in the plasmid remain after removal of the 49 base sequence from the U1 coding sequence. When each sequence is inserted into and expressed from the U1 coding region of pHSd-4 U1 it will appear as an antisense RNA sequence to a region of the HIV genome.

After digestion with Bcl 1 and Bsp E1, a 49 base pair segment is eliminated from the U1 transcript portion of the gene. The oligo pairs have been designed to form sticky ends compatible with the Bcl/Bsp ends in the plasmid. Ligation of each of the pairs of Oligos (HVA-1 (SEQ ID NO 44)+HVA-2 (SEQ ID NO 45), HVB-1 (SEQ ID NO 46)+HVB-2 (SEQ ID NO 47) and HVC-1 (SEQ ID NO 48)+HVC-2) (SEQ ID NO 49) created pDU1-A with an insertion of 72 bp, pDU1-B with an insertion of 66 bp and pDU1-C with an insertion of 65 bp. As a control, two oligomers (HVD-1 (SEQ ID NO 50) and HVD-2 (SEQ ID NO 51)) with sequences unrelated to HIV were also inserted into the U1 operon to create pDU1 which contains an insertion of 61 bp.

To allow for selection of transformants after introduction of these chimeric U1 genes, the Neomycin resistance gene was introduced by digestion of pGK-neo (McBurney et al. 1991 Nucleic Acids Research 19; 5755) with Hind III and Sma I and ligation into the pDUI series of plasmids previously digested with Hind III and Hinc II to create the pNDU1 series (pNDU1-A, pNDU1-B, pNDU1-C and pNU1-D).

Figure 43:
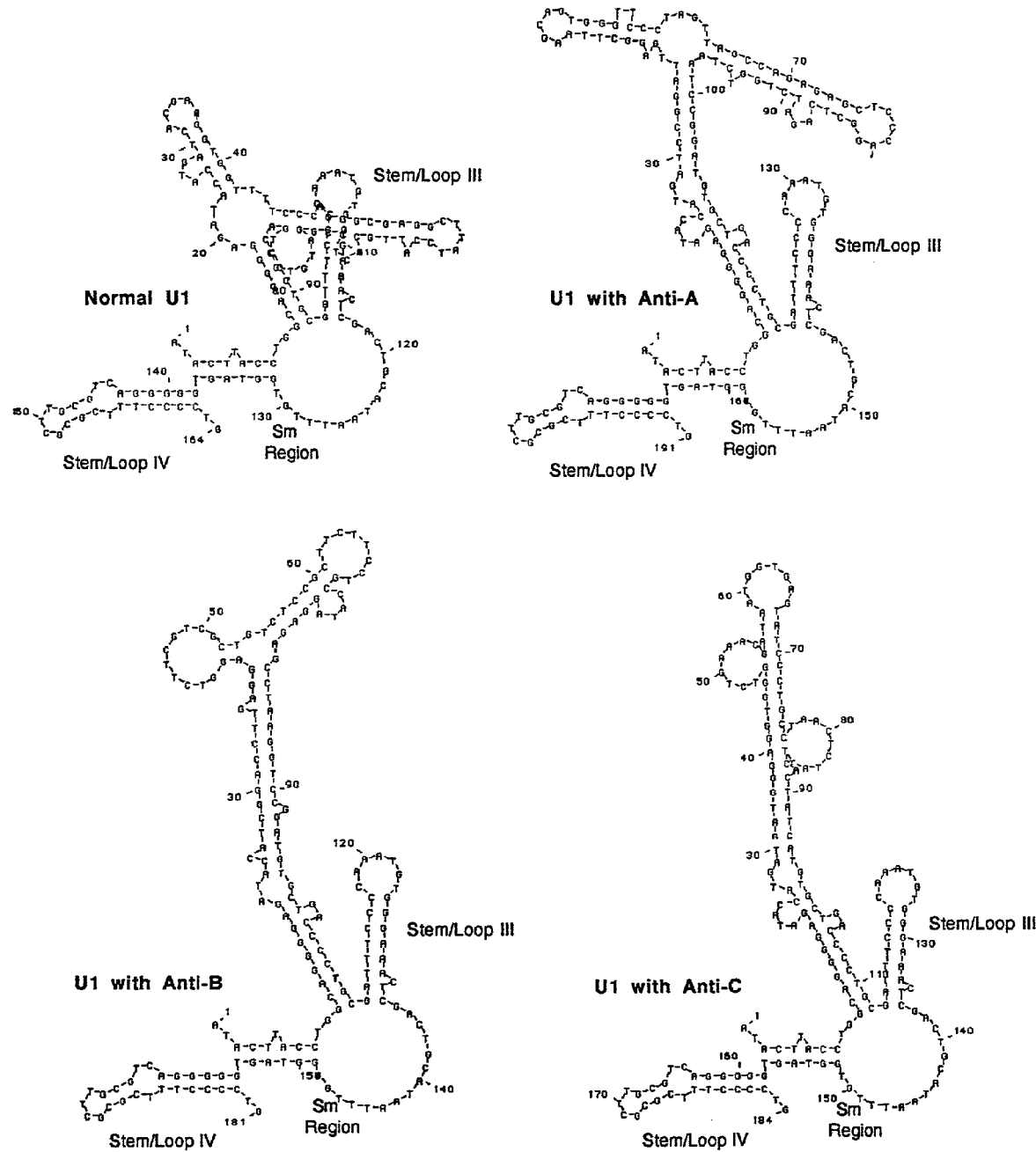
FIG. 43 is a computer generated secondary structure prediction for U1 transcripts with HIV antisense sequence substitutions (SEQ ID NOS 60-63, respectively, in order of appearance).

As described earlier, the design of the cloning method should allow the insertion of novel sequences that would still allow the utilisation of signals provided by the U1 transcript for nuclear localisation of Anti-sense sequences. To test whether the insertion of the sequences described above resulted in unintended changes in the U1 region responsible for re-importation of the U1 transcripts a computer analysis was done to compare the predicted structures for the normal U1 and the chimeric novel molecules using the MacDNASIS program (Hitachi, Inc.). In FIG. 43 it can be seen that despite changes in the 5' end (where the new sequences have been introduced) loops III and IV as well as the Sm region remain undisturbed (SEQ ID NOS 60-63).

Example 27

Figure 44:
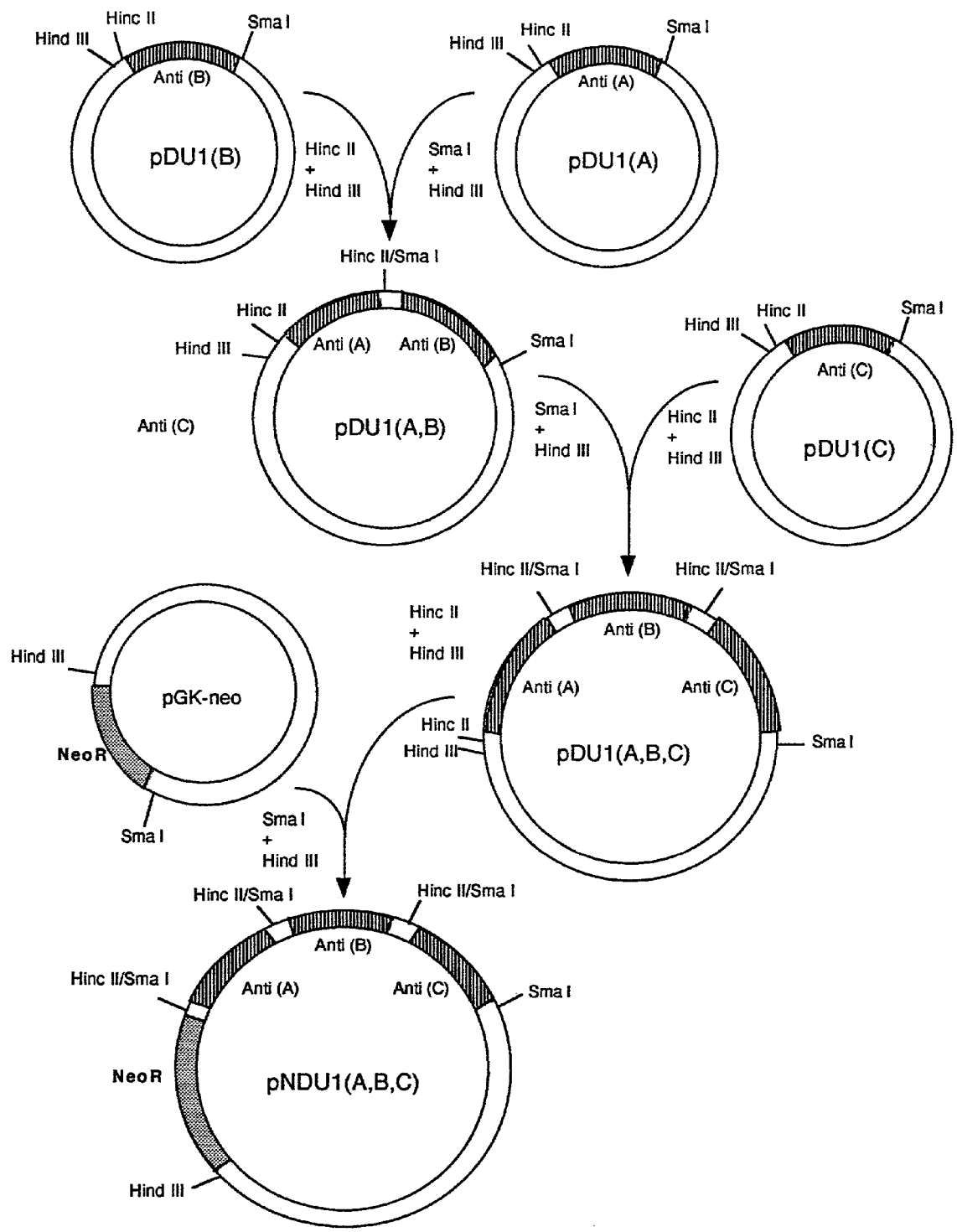
FIG. 44 depicts the cloning process for making of a clone that contains multiple HIV antisense containing U1 operons.

Construction of a Multi-Cassette Construct which Expresses Three Antisense Sequences as Part of U1 snRNA The various steps used in this example are depicted in FIG. 44. The various constructs used in this example, pDU1(A), pDU1(B), pDU1(C) and pGK-neo were described in Example 26 of this patent. The plasmid pDU1(B) with the "B" anti-sense embedded within the U1 transcript was digested with Sma I and Hind III. The segment containing the U1 operon with the "A" anti-sense was released by digestion of pDU1 (A) with Hinc II and Hind III and ligated into the pDU1 (B) plasmid to create pDU1 (A,B) which contains two separate operons for the "A" and "B" anti-sense sequences. This construct was then digested with Sma I and Hind III (to release the double operon) and ligated into pDU1(C), containing the U1 operon with the "C" anti-sense, that had previously been digested with Hinc II and Hind III. The resultant construct, pDU1(A,B,C) contains three separate operons containing the "A", "B" and "C" anti-sense sequences. To allow selection for the presence of this construct after a transfection step, the segment containing Neomycin resistance was excised from the vector pGK-neo by digestion with Hind III and Sma I and ligated into the pDU1(A,B,C) construct to create pNDU1(A,B,C). The ordering of the three operons in the pDU1(A,B,C) and pNDU1(A,B,C) constructs is given in FIG. 46.

Example 28

Figure 45:
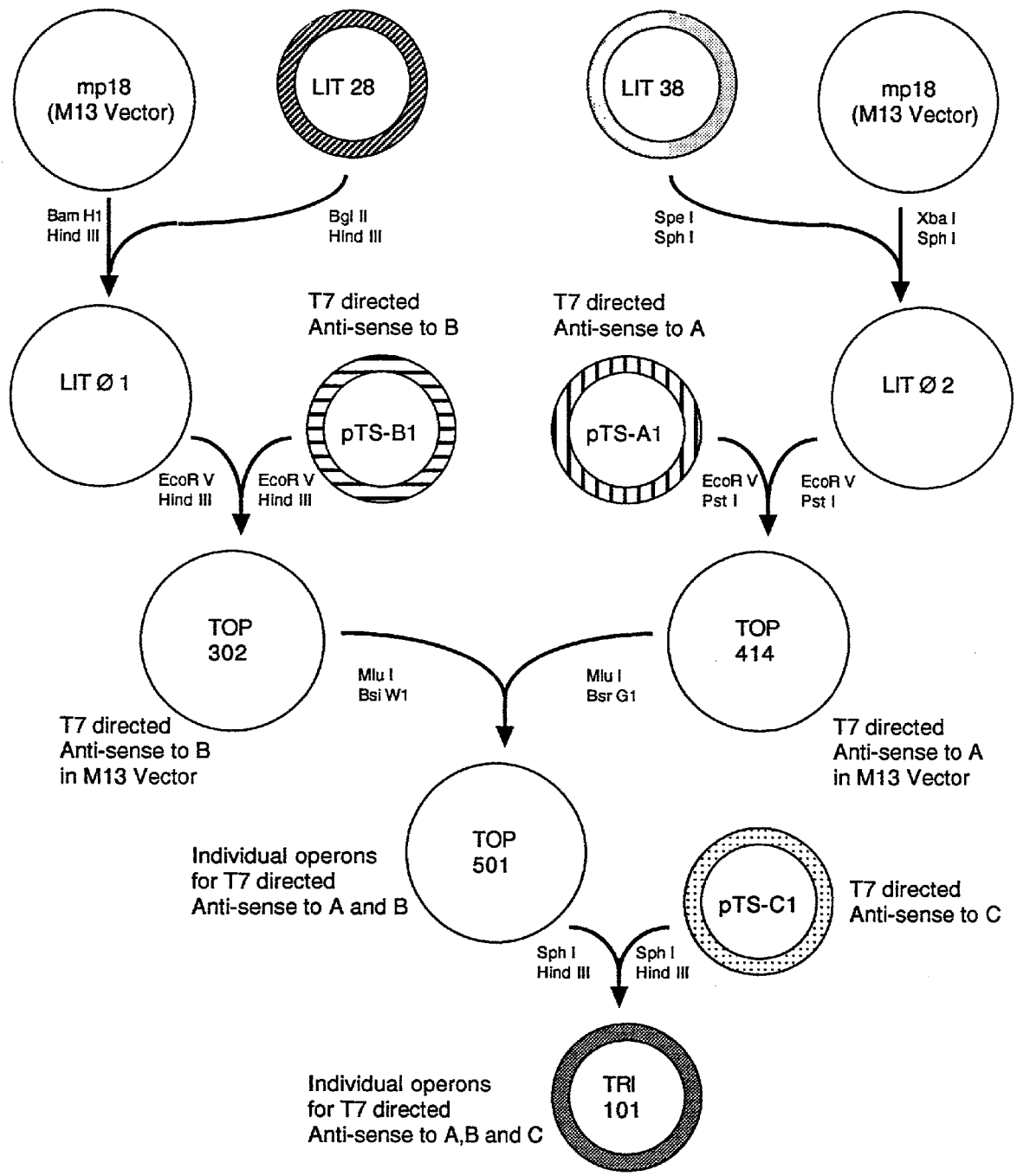
FIG. 45 depicts the cloning steps for constructing a clone that contains multiple independent HIV antisense containing T7 directed transcripts.

Construction of an Antisense Expressing Multi-Cassette Construct Containing Three T7 RNA Promoters The various steps used in this example are depicted in FIG. 45. The polylinker from plasmid LIT 28 (New England Biolabs, Inc.) was transferred into an M13 vector by digestion of the plasmid with Bgl II and Hind III and then ligating it with mp18 (New England Biolabs, Inc.) previously digested with Bam H1 and Hind III to create the phage vector LIT 01. The plasmid pTS-B (described in Example 19) containing a T7 promoter, the "B" Anti-Sense sequence and the T7 terminator, was digested with EcoRV and Hind III and then ligated to LIT 01 previously digested with EcoRV and Hind III to create TOP 302, a phage vector with the "B" Anti-sense T7 operon.

The polylinker from plasmid LIT 38 (New England Biolabs, Inc.) was transferred into an M13 vector by digestion of the plasmid with Spe I and Sph I and then ligating it with mp18 previously digested with Xba I and Sph I to create the phage vector LIT 02. The plasmid pTS-A (Example 19) containing a T7 promoter, the "A" anti-sense sequence and the T7 terminator, was digested with EcoRV and Pst I and then ligated to LIT 02 previously digested with EcoRV and Pst I to create TOP 414, a phage vector with the A Anti-sense T7 operon. The T7 operons in TOP 302 and TOP 414 were joined together by digestion of TOP 302 with Mlu I and Bsi W1 and ligating it to TOP 414 previously digested with Mlu I and Bsr G1 to form TOP 501, a phage vector which has both the "A" Anti-Sense T7 operon and the "B" Anti-Sense T7 operon.

The plasmid pTS-C (described in Example 19) containing a T7 promoter, the "C" anti-sense sequence and the T7 terminator, was digested with Sph I and Hind III. TOP 501 was then digested with SphI and Hind III and ligated to pTS-C2 to create TRI 101 which has the "A" Anti-Sense T7 operon, the "B" Anti-Sense T7 operon and the "C" Anti-Sense T7 operon in a single construct. The ordering of the three operons in the TRI 101 construct is given in FIG. 46. Co-transfection of this construct with a vector that expresses T7 RNA polymerse (The Intron containing T7 RNA Polymerase described in Example 19 could be used for this purpose) allows the in vivo production of all three Anti-Sense transcripts.

Example 29

Figure 47:
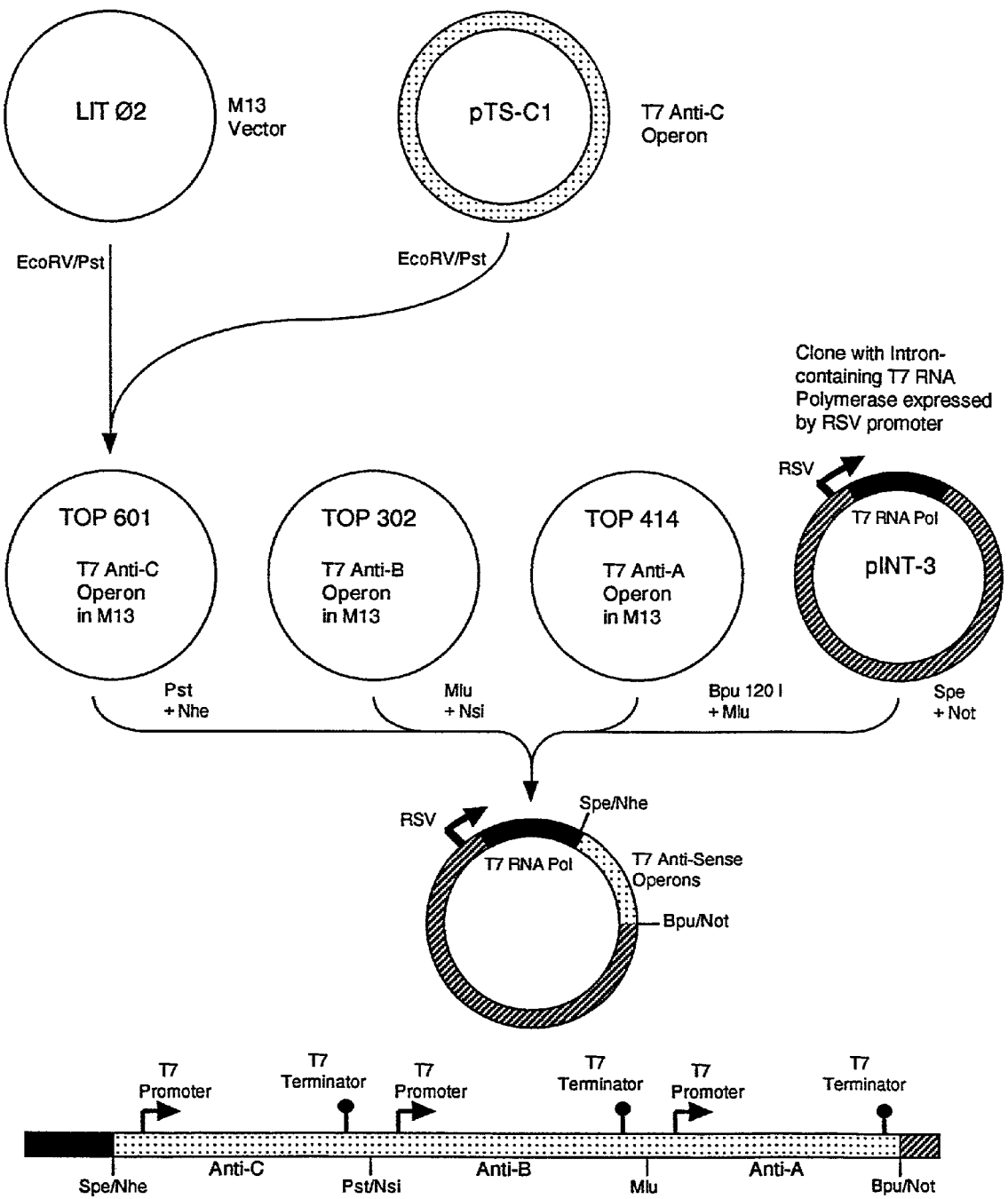
FIG. 47 depicts the cloning steps for insertion of multiple T7 antisense operons into a vector coding for the T7 intron containing RNA polymerase.

Construction of an Antisense Expressing Multi-Cassette Construct Containing Three T7 RNA Promoters and an Intron-Containing T7 RNA Polymerase Gene Although the preceding example utilises the common method of expressing T7 directed transcripts by means of cotransfection with a construct with the RNA polymerase and a second construct with a T7 promoter, an application of the current invention describes a method of carrying both entities (polymerase and promoter) on the same construct. The present example is an illustration of a single construct that contains the T7 RNA polymerase as well as multiple operons of T7 driven Anti-Sense transcripts. The various steps used in this example are depicted in FIG. 47. The plasmid pTS-C (described above) was digested with EcoRV and Pst I and ligated into the M13 vector LIT Ø2 (described above) which had previously been digested with EcoRV and Pst I, to create the TOP 601 which is a phage vector with the "C" Anti-Sense T7 operon. As described earlier, the construct pINT-3 contains the T7 RNA Polymerase with an SV40 intron inserted within the coding region; in eucaryotic cells there is expression by an RSV promoter followed by excision of the intron by means of the normal splicing machinery of the cell. To insert the T7 Anti-sense operons, it was digested with Spd I and Not I. The T7 Anti-sense operons were inserted as a triple insert by the simultaneous ligation of the Spe/Not pINT-3 DNA with TOP 601 previously digested with Pst I and Nhe I, TOP 302 previously digested with Mlu I and Nsi I and TOP 414 previously ligated with Bpu 120 1 and Mlu I. The resultant clone as well as a diagram of the positions of the different Anti-sense operons is shown in FIG. 47.

Example 30

Testing the Anti HIV U1 Constructs in Cells

Inhibition of Virus Growth
a) Creation of stable transformed cell lines:
U937 cells (Laurence, et al., 1991, J. Virol. 65: 214-219) were transformed with the various U1 constructs described above using Lipofectin (BRL Inc.) and following the manufacturer's suggested protocol. After transformation, the cultured cells were divided into 2 portions. One portion was used to obtain individual clones while the other portion was used to obtain a population of pooled clones. To obtain the individual clones, aliquots of $1 \times 10^4$ cells were seeded into separate chambers in 96 well tissue culture plates and stable transformants were selected by growth in DMEM (Gibco and BRL) medium supplemented with 10% fetal bovine serum (heat inactivated) (Gibco and BRL) in the presence of 600 microgram/ml G418 (Gibco and BRL). The G418-containing medium was replaced every 3 to 4 days, and after 3 weeks of incubation, drug resistant cells were removed from individual wells by aspiration and expanded by growth in culture dishes.

To obtain the population of pooled clones, $1 \times 10^6$ cells were seeded into T-25 flasks (Corning) and grown in the presence of G418.

b) Characterization of cell lines
RNA was isolated from either resistant clones or resistant pooled clones using hot phenol extraction (Soeiro and Darnell, 1969, J. Mol Biol 44: 551-562). This RNA was used in a dot blot analysis using the protocol accompanying the Genius System (Boehringer Mannheim). The probe used in this analysis was a riboprobe made from a clone of the three inserts (A, B, and C) in pBlueScript (Stratagene) cloned into the XmaI and BamH1 site. This clone produced insert RNA of the sense orientation. The results of this analysis showed that all cell populations that had been transformed by the U1 clone and that had demonstrated resistance to G418 that were tested expressed the antisense insert RNA. Comparable dot blot analyses were performed using RNA from the parental line U937 as well as yeast RNA (Boehringer Mannheim.) These dots showed no evidence of the antisense insert RNA. The antisense RNA synthesized in vitro using the clones pBlueScript 12, pBlueScript 34, pBlueScript 56 and pBlueScript 78, described above, showed positive hybridization using the sense probe described in this paragraph. From this we conclude that those transformed cell populations that were tested were indeed expressing antisense RNA from the HIV virus sequence.

c) HIV challenge experiment number 1:
$0.5 \times 10^6$ cells of the pooled clones transformed by the triple U1 construct were incubated with HIV virus at a multiplicity of 0.15 pfu of the virus per cell in the presence of 2 μg/ml of polybrene for 2 hours at 37° C. using the procedure of Laurence et al. (1991 J. Virol. 65: 214-219). The cells were then washed, resuspended in 1 ml of culture medium (RPMI 1640+10% fetal bovine serum, Flow Labs) and plated in duplicate (0.5 ml per well.) One-half of the culture medium was removed and replaced with fresh medium every 3-4 days. 6 days post infection, samples of these cells were tested for the extent of infection by HIV virus using a p24 ELISA antigen capture following the protocol of the manufacturer (DuPont). The control cultures for this experiment were cells transformed by clones not containing antisense sequences to HIV (see above). The results of this experiment are shown in Table 1.

TABLE 1

| Sample | [HIV-1], pg/ml | | % Inhibition of HIV p24 | |
| --- | --- | --- | --- | --- |
| | Expt A | Expt B | Expt A | Expt B |
| 2.2.78 pool control | 959 ± 49 | | — | |
| 1.9.16 pool | 780 | error | 18.7 | — |
| 2.10.16 pool | 514 | 554 | 46.4 | 42.2 |

Both of the pooled clone samples showed inhibition of production of p24 when compared to the control clones. In the instance of the pooled clone 2.10.16, the degree of inhibition when compared to the control was close to 50%. This pooled clone population of cells was examined further as described below.

At 18 days after infection, the p24 concentration in the growth medium was determined as described above. The results of this determination are reported in Table 2.

TABLE 2

| Sample | [HIV-1], pg/ml | % Inhibition of HIV p24 |
|---|---|---|
| U937 control | 200 | — |
| 2.2.78 pool control | 220 ± 2 | 0 |
| 2.10.16 pool | 12 ± 0.4 | 94.5 |

This table shows that there is approximately 95% inhibition of p24 antigen production in the pooled clone population of cells when compared with either the control pooled clone population or the parent cell line.

On day 24 after viral inoculation, when the cells were assayed by trypan blue dye exclusion the control pooled clone population were 17% viable, and contained numerous syncytia (multinucleated giant cells characteristic of HIV infection). The pooled clone population labeled as 2.10.16 were 40-60% viable and had no visible syncytia.

After day 24, the cells of the control pooled clone culture and the pooled clone culture were subjected to ficol gradient separation (Pharmacia). This procedure separates the live cells from the dead cells every 3-4 days as a routine maintenance procedure. At 35 days, there were no cells left in the control pooled clone population of cells, while the pooled clone population had viable cells. When these viable cells from the pooled clone population were then assayed for the presence of the p24 antigen, it was found that the culture line named 2.10.16 showed no evidence of the presence of p24 antigen in the culture medium above the background (0.032±0.08 OD compared with 0.039 OD). In this experiment, the HIV infected cells had a measured amount of p24 antigen that was greater than 2 OD. Thus by this time in the selection protocol, the degree of inhibition of the virus was greater than 99%.

d) HIV challenge experiment number 2:

In this experiment, the pooled clone population identified as 2.10.16 (from day 31 of the first challenge) as well as the control pooled clone population and the parent cell line U937 were infected again with the BAL strain of HIV at a multiplicity of 0.10 pfu per cell as described above. After infection, the cells were maintained as described above. At day 9 and day 12 after infection the p24 antigen was determined as described above. The results of this determination are reported in Table 3.

TABLE 3

| | HIV-1 [p24], pg/ml | |
|---|---|---|
| Cell Type | day 9 | day 12 |
| U937 | 3 | 5.1 ± 0.4 |
| 2.10.16.R1 | <1 | 14.3 ± 1.3 |

This table shows that at day 12 there is approximately 66% inhibition of p24 antigen production in the pooled clone population of cells when compared with the parent cell line.

When these cells were maintained with separation of the live from the dead cells using the ficol gradient every 3-4 days as described above it was found at day 21 that there was no evidence of p24 antigen in the 2.10.16 cell lines when compared with the parental cell line infected with HIV virus. (Here the comparison is of OD units of the 2.10.16 pooled clone population of 0.009 the same number as the control parental line without infection with >2 OD units.)

e) Further characterization of the 2.10.16 cell line after three cycles of challenge with hiv virus:

In this experiment, the pooled clone population identified as 2.10.16R1 (from day 21 of the second challenge experiment) and the parent cell line U937 were infected again with the BAL strain of HIV as described above. After infection, the cells were maintained as described above. On days 14, 27, and 42 after infection, the p24 antigen was determined as described above for the pooled clone population (now called 2.10.16R2) as well as for the parental cell line U937. The results of this determination are reported in Table 4.

TABLE 4

| | HIV-1 p24 | | | | | | | |
|---|---|---|---|---|---|---|---|---|
| | Day 9 | | Day 14 | | Day 27 | | Day 43 | |
| Sample | OD | pg/ml | OD | pg/ml | OD | pg/ml | OD | pg/ml |
| U937 | 0.527 | 122 | 0.165 | 25 | dead | | | |
| 2.10.16R2 | 0.12 | 0 | 0.009 | 0 | 0.030 | 0 | 0.026 | 0 |
| buffer | 0.013 | | | | | | | |

This table shows that by day 27 the parental cells have disappeared from the culture medium. This is consistent with the conclusion that the virus infection has led to the destruction of the cells. In the pooled clone cell population 2.10.16R2, the amount of p24 antigen detected in these supernatants is below the sensitivity of the assay procedure. Thus on the third challenge of the original pooled clone cell population there is no evidence of virus growth.

Figure 48:
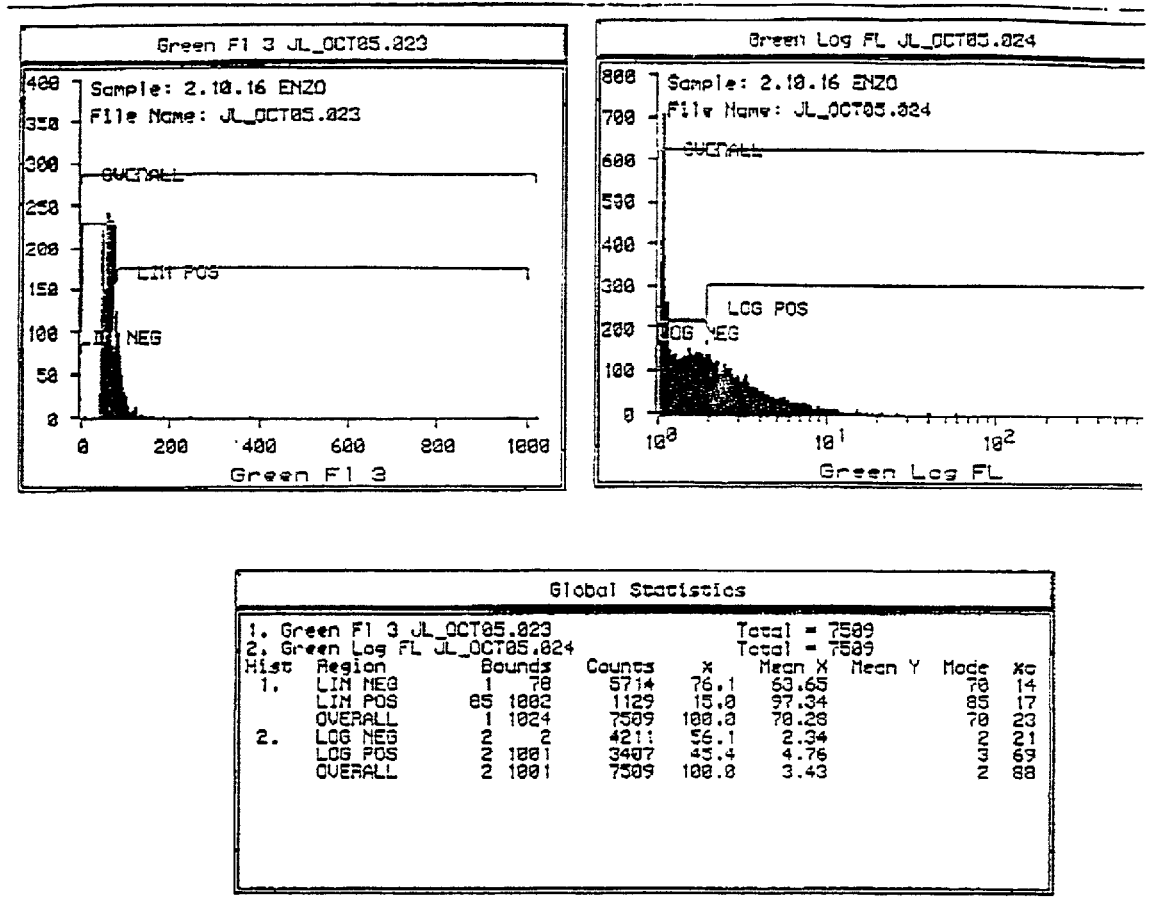
FIG. 48 represents flow cytometry data measuring binding of anti-CD4+ antibody to HIV resistant U937 cells.

The parental cell line U937 is known to contain the surface antigen CD4+. This parent strain and the strain 2.10.16R2, pooled strain after 3 cycles of selection, were assayed in a flow cytometer for the presence of the CD4+ antigen by measuring the binding of mouse CD4+ antibody (Becton Dickenson) with fluorescinated goat anti mouse (Tago). As can be seen in FIG. 48, CD4+ antigen is present on the surface of the parental strain and the 2.10.16R2-HIV resistant cell strain. This is evidence that the cells have not been selected to be resistant to infection by HIV virus through the loss of the adsorption protein, specifically the CD4+ antigen.

Figure 49:
FIG. 49 shows PCR amplification of the gag region indicating the absence of HIV in viral resistant cell line (2.10.16) after challenge.

While the evidence of virus growth based on the production of the gag antigen, p24, demonstrates that the pooled strain of cells containing the genetic antisense does not permit the growth of virus, further evidence that the virus is not present in this cell population was obtained using the DNA PCR assay for the identification of the coding region of the gag gene (the region coding for the p24 antigen) using the standard Cetus primers which detect virtually all HIV-1,-2 isolates (Applied BioSystems). As can be seen from the FIG. 49 representing UV illumination of the EtBr stained DNA, the + control (using DNA provided in the kit) gave a band of the expected size (lane 1), while several dilution of the amplification products of 2.10.16R2 DNA did not show such a band.

These data demonstrate that cell lines can be developed using antisense constructs that maintain their CD4+ phenotype. These cell lines do not support the growth of the HIV virus as measured both by the production of the p24 antigen and measured with the quick DNA PCR kit of Cetus. In addition these cell strains have been shown to survive multiple challenge from infectious HIV virus.

Example 31

Testing the anti HIV U1 Constructs in Cells

Inhibition of synthesis of beta-galactosidase activity:

a) Eukaryotic Vector Carrying Target Sequence a Upstream of the Beta-Galactosidase Gene.

Figure 50:
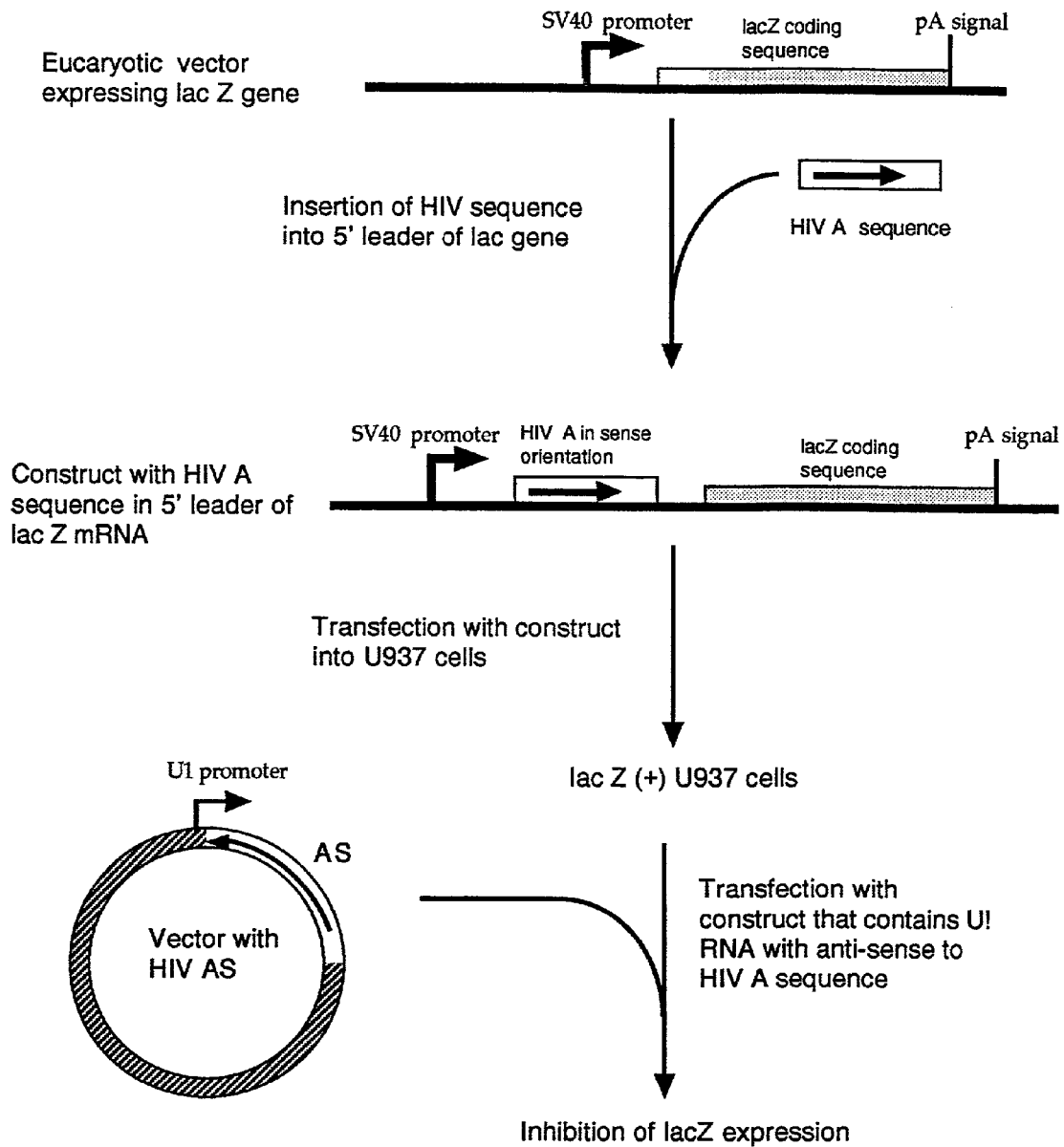
FIG. 50 depicts a model system for testing the potential inhibition of HIV antisense sequences by using beta-galactosidase activity as an indicator.

The A segment (from the tar sequence of HIV) of target DNA was isolated as described above. This segment was cloned into the Kpn1 BamH1 site of the eukaryotic vector pSV Lac Z(Invitrogen), that carries Lac Z coding sequences and SV40 enhancer and promoter and poly A signal sequences. The cloning sites is between these sequences. The cloning sequence is diagrammed in the attached figure (FIG. 50).

b) Expression of beta-galactosidase activity in stably transfected U937 cells:

U937 cells were transformed using the Lipofectin procedure described above. In this experiment positive clones were selected as zeocin resistant. 5 separate transfected cell populations were isolated. These cells were 1. U937 cells untransfected; 2. U937 cells transformed with the HIV A clone alone; 3. U937 cells transfected with the HIV A clone and then a second time with the U1 antisense A clone (see above for the description of the clone—the second transfection was selected as G418 resistant); 4. U937 cells cotransfected with the HIV A clone and the U1 antisense ABC clone (again see above for a description of the clone); and 5. U937 cells cotransfected with the HIV A clone and the U1-null DNA clone (again see above for a description of the clone).

Log phase cells of U937 (both stably transfected and untransfected) were washed free of medium with 1×PBS containing 10 mM $Mg^{++}$ and 1 mM $Ca^{++}$. The washed cells were fixed lightly (5 minutes) at room temperature in PBS containing 2% formaldehyde and 0.05% glutaraldehyde. The fixative was removed and the cells were washed free of fixative with two washes with PBS. The washed fixed cells were then suspended in staining solution (PBS containing 5 mM potassium ferrocyanide and 2 mM $MgCl_2$) containing 1 mg/ml X-gal (BRL) and incubated at 37° C. for 2 hours to overnight. The cells were examined under a microscope at 40×.

The results of this experiment are illustrated in FIG. 51 (lower set of data). The positive production of the enzyme beta-galactosidase is assayed by the production of a blue precipitate in the cytoplasm of the transfected cells. No blue is detected in cell lines 1, 3 and 4 while blue spots are detected in the cytoplasm of the cell line 2 and 5. These data demonstrate that the production of the enzyme beta-galactosidase that is shown as a blue stain in cell line 2 with the HIV A clone alone or in cell line 5 where both the HIV A clone and the null DNA control is not seen when either the antisense U1 A clone is cotransfected with the HIV A clone (cell line 3) or the antisense U1 ABC clone is cotransfected with the HIV A clone (cell line 4). Thus the presence of the antisense A sequence in the cell lines with this HIV A clone expressing the enzyme beta-galactosidase blocks the production of this enzyme.

c. Expression of beta-galactosidase activity in extracts:

To measure enzyme activity by soluble assay (FIG. 51, upper set of data) extracts were prepared from loge-phase cultures either by sonication or repeated freeze-thawing. The log-phase cells ($5 \times 10^6$ cells per ml) were washed free of medium with PBS containing 10 mM $Mg^{++}$ and 1 mM $Ca^{++}$. The washed cells were suspended in 250 mM Tris-Cl, pH 7.5 and freeze-thawed 3 times or alternatively sonicated 5 minutes at maximum output. The crude lysate was centrifuged and enzyme activity was measured in clear supernatants by hydrolysis of the lactose analog ONPG (Sigma). When this substrate is cleaved by the enzyme to make ONP a yellow colored compound produced. Thus the beta-galactosidase activity can be monitored by observing the change in absorbance at 420 nm. Extracts prepared from cells that are stably transfected with the HIV A clone produce a yellow color in 30 minutes at 37° C., whereas the extracts prepared from untransfected cells remain colorless even after incubation over night.

The 5 transfected cell lines were assayed using this soluble assay format and the results are reported in table 5. From this table it can be seen that the U1 anti-A transfected cells do not have measurable amounts of beta-galactosidase activity. (Compare line 3 with lines 2 and 5.) Also it can be seen that the U1 anti-ABC clones do not show measurable amounts of beta-galactosidase activity. (Compare line 4 with lines 2 and 5.) These results confirm the results from the in situ assay of the affect of the U1 anti A and anti ABC clones on the production of beta-galactosidase activity of clones that have the A target cloned into their sequences.

Example 32

Asymptomatic HIV positive patients are given pre-treatment evaluations including medical histories; physical examinations, blood chemistries including CBCs, differential counts, platelet counts; blood chemistries including glucose, calcium, protein, albumin, uric acid, phosphate; Blood Urea Nitrogen and creatinine; Urinalysis; electrocardiogram and chest X-ray; p24 antigen level; CD4 counts; PCR to determine viral load. The p24 antigen, CD4 counts and PCR are done at weekly intervals for 4 weeks prior to removal of cells in order to establish baseline data, and these assays are continued biweekly throughout the period of treatment.

Blood is removed from patients and the peripheral blood mononuclear cells are separated from erythrocytes and neutrophils by Ficoll-Hypaque centrifucation. After washing, the PBMCs are depleted of CD8+ cells by the use of murine anti-human CD8-coated flasks (CELLector™ Flasks, Applied Immune Sciences). Cells which do not adhere to the surface of the flasks are cells assayed for cellular phenotype by flow cytometry and then activated with OKT3 antibody in serum-free medium.

The OKT3-activated cells are resuspended at a concentration of $1-2 \times 10^5$ cells/ml in fresh medium containing 60 units/ml of IL-2. The cells are expanded to about $2 \times 10^6$/ml.

A retrovirus vector containing sequences for the expression of antisense RNA directed at HIV is grown in a packaging cell line. A DNA construct (described in Example F1 is introduced into retrovirus vector LNL6, which contains a neomycin resistance marker. The cells are transduced by resuspension in culture medium to a concentration of approximately $10^5$ cells/ml and mixing with culture supernatant from the retrovirus vector infected cells to provide an MOI of approximately 1.0. Five mg/ml protamine sulfate are added and the mixture is incubated at 37° C. for 6 hours. The cells are washed three times and placed in G418 containing culture medium. This transduction procedure is repeated daily for three consecutive days.

After 7 days in G418 selection medium the G418 is removed and the cells are expanded in the presence of growth factors (as described above). When sufficient cells are produced, they are harvested, washed and resuspended in physiological saline for infusion into the patient. Cellular phenotype is measured by flow cytometry measurements.

This antisense treatment is supplemented by treatment with soluble CD4 protein. Administration commences immediately after the administration of HIV therapy according to the method of (Husson et al., 1992).

This supplemented gene therapy is further supplemented by concurrent administration of AZT.

Many obvious variations might be suggested to those of ordinary skill in the art in light of the above detailed description of the invention. All such variations are fully embraced by the scope and spirit of the present invention as set forth in the claims which now follow.

What is claimed is:

1. A chemically modified nucleic acid construct, said construct comprising
   (i) at least one nucleic acid strand consisting of unmodified nucleotides; and
   (ii) one or more nucleic acid strands comprising one or more modified nucleotides or nucleotide analogs, wherein
   at least one modified nucleotide or nucleotide analog comprises a fusogenic peptide,
   at least one modified nucleotide or nucleotide analog comprises a ligand to a cell receptor, and
   at least one modified nucleotide or nucleotide analog comprises a non-nucleic acid entity that confers nuclear localization,
   and wherein said at least one nucleic acid strand consisting of unmodified nucleotides is a template for the synthesis of a nucleic acid product comprising RNA and having biological activity.

2. The construct of claim 1, wherein at least a portion of said construct is linear, and at least a portion of said construct is circular.

3. The construct of claim 1, wherein at least a portion of said construct is a first polynucleotide sequence comprising a gapped circle.

4. The construct of claim 3, wherein said gapped portion of said gapped circle is hybridized to a second polynucleotide sequence comprising the fusogenic peptide.

5. The construct of claim 1, having at least one 3' terminus, said terminus comprising a polynucleotide tail.

6. The construct of claim 5, wherein said polynucleotide tail is hybridized to a complementary polynucleotide sequence.

7. The construct of claim 1, wherein said construct comprises DNA.

8. The construct of claim 1, wherein at least one of said modified nucleotide or nucleotide analog has been modified at least on the sugar moiety.

9. The construct of claim 6, wherein said ligand to a cell receptor is attached to the complementary polynucleotide sequence.

10. The construct of claim 1, wherein said ligand to a cell receptor is a hormone, lectin, protein, polysaccharide, polysaccharide, asialoorosomucoid, transferrin or a tri-lactyl lysyl lysine.

11. A chemically modified nucleic acid construct, said construct comprising a modified nucleotide or a nucleotide analog, which construct when present in a cell is used as a template for the synthesis of a nucleic acid product comprising RNA and having biological activity, wherein
    said modified nucleotide or nucleotide analog comprises at least one non-nucleic acid entity conferring cell targeting,
    wherein said construct further comprises at least three strands, wherein
        the first strand is a template strand comprising a promoter,
        the second strand
            (a) has at least one terminus, said terminus comprising a polynucleotide tail and
            (b) comprises two segments, wherein the first segment is complementary and hybridizes to a portion of the first strand and the second segment lacks said complementarity and comprises said polynucleotide tail, and
        the third strand comprises (i) said modified nucleotide or nucleotide analog comprising said non-nucleic acid entity conferring cell targeting, and (ii) a polynucleotide sequence hybridized to a complementary sequence in said polynucleotide tail.

12. The construct of claim 1, wherein said construct further comprises a modified nucleotide or nucleotide analog comprising a non-nucleic acid entity comprising a nuclear localization signal.

13. The construct of claim 1, wherein at least one of said modified nucleotide or nucleotide analog has been modified at least on the base moiety.

14. The construct of claim 1, wherein at least one of said modified nucleotide or nucleotide analog has been modified at least on the phosphate moiety.

15. The construct of claim 11, further comprising a modified nucleotide or nucleotide analog that comprises a non-nucleic acid entity that confers nuclear localization.

16. The construct of claim 11, further comprising a modified nucleotide or nucleotide analog that comprises a non-nucleic acid entity that confers nuclear localization.

17. The construct of claim 1, wherein said construct comprises RNA.

18. The construct of claim 11, wherein the first strand comprises a gapped circle having a double stranded portion and a single stranded portion, wherein said complementary portion of the second strand is hybridized to the single stranded portion.

* * * * *